US007939527B2

(12) United States Patent  
Bacani et al.

(10) Patent No.: US 7,939,527 B2
(45) Date of Patent: May 10, 2011

(54) THIAZOLOPYRIDIN-2-YLOXY-PHENYL AND THIAZOLOPYRAZIN-2-YLOXY-PHENYL AMINES AS MODULATORS OF LEUKOTRIENE A4 HYDROLASE

(75) Inventors: Genesis M. Bacani, San Diego, CA (US); Diego Broggini, Zurich (CH); Eugene Y. Cheung, Waltham, MA (US); Christa C. Chrovian, San Diego, CA (US); Xiaohu Deng, San Diego, CA (US); Laurent Gomez, San Diego, CA (US); Cheryl A. Grice, Carlsbad, CA (US); Aaron M. Kearney, Lakeside, CA (US); Adrienne M. Landry-Bayle, Carlsbad, CA (US); Alice Lee-Dutra, San Diego, CA (US); Jimmy T. Liang, San Diego, CA (US); Susanne Lochner, Singen (DE); Neelakandha S. Mani, San Diego, CA (US); Alejandro Santillán, Jr., San Diego, CA (US); Kathleen Sappey, San Diego, CA (US); Kia Sepassi, San Diego, CA (US); Virginia M. Tanis, San Diego, CA (US); Alvah T. Wickboldt, New Orleans, LA (US); John J. M. Wiener, La Jolla, CA (US); Hartmut Zinser, Schaffhausen (CH)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 12/421,406

(22) Filed: Apr. 9, 2009

(65) Prior Publication Data

US 2009/0258854 A1    Oct. 15, 2009

Related U.S. Application Data

(60) Provisional application No. 61/044,349, filed on Apr. 11, 2008, provisional application No. 61/149,129, filed on Feb. 2, 2009.

(51) Int. Cl.
*A61K 31/5355* (2006.01)
*A61K 31/4985* (2006.01)
*A61K 31/516* (2006.01)
*A61K 31/497* (2006.01)
*A61K 31/4365* (2006.01)
*C07D 413/14* (2006.01)
*C07D 239/34* (2006.01)
*C07D 513/04* (2006.01)

(52) U.S. Cl. ........... 514/234.2; 514/249; 514/253.04; 514/274; 514/300; 514/301; 544/127; 544/318; 544/350; 544/362; 546/114; 546/122

(58) Field of Classification Search .......... None
See application file for complete search history.

(56) References Cited

U.S. PATENT DOCUMENTS

| 4,273,778 A | 6/1981 | Hadley |
|---|---|---|
| 4,321,378 A | 3/1982 | Dostert |
| 4,329,466 A | 5/1982 | Dostert |
| 4,336,259 A | 6/1982 | Hadley |
| 4,352,802 A | 10/1982 | Blaney |
| 4,410,535 A | 10/1983 | Watts |
| 4,424,358 A | 1/1984 | Dostert |
| 4,432,983 A | 2/1984 | Riley |
| 4,471,120 A | 9/1984 | Dostert |
| 4,536,580 A | 8/1985 | Dostert |
| 4,544,660 A | 10/1985 | Hadley |
| 4,599,420 A | 7/1986 | Hadley |
| 4,705,858 A | 11/1987 | Hadley |
| 5,585,492 A | 12/1996 | Chandrakumar et al. |
| 5,700,816 A | 12/1997 | Isakson et al. |
| 5,719,306 A | 2/1998 | Chandrakumar et al. |
| 5,723,492 A | 3/1998 | Chandrakumar et al. |
| 5,990,148 A | 11/1999 | Isakson |
| 6,110,944 A | 8/2000 | Chen et al. |
| 6,316,490 B1 | 11/2001 | Vernier |
| 6,407,140 B1 | 6/2002 | Gregory et al. |
| 6,432,976 B1 | 8/2002 | Thompson |
| 6,506,876 B1 | 1/2003 | Chandrakumar et al. |
| 6,559,140 B2 | 5/2003 | Bennani et al. |
| 6,632,823 B1 | 10/2003 | Vernier |
| 2003/0004191 A1 | 1/2003 | Gregory et al. |
| 2005/0043355 A1 | 2/2005 | Gregory et al. |
| 2005/0043378 A1 | 2/2005 | Bembenek et al. |
| 2005/0043379 A1 | 2/2005 | Bembenek et al. |
| 2006/0074121 A1 | 4/2006 | Chen et al. |
| 2006/0223792 A1 | 10/2006 | Butler et al. |
| 2007/0079078 A1 | 4/2007 | Fujita et al. |

(Continued)

FOREIGN PATENT DOCUMENTS

EP    0266576    5/1988

(Continued)

OTHER PUBLICATIONS

Alestas, T. et al. Enzymes involved in the biosynthesis of leukotriene B4 and prostaglandin E2 are active in sebaceous glands. J. Mol. Med. 2006, 84(1), 75-87.

Andoh, T. et al. Intradermal leukotriene B4, but not prostaglandin E2, induces itch-associated responses in mice. Eur. J. Pharmacol. 1998, 353(1), 93-96.

Andoh, T. et al. Involvement of blockade of leukotriene B4 action in anti-pruritic effects of emedastine in mice. Eur. J. Pharmacol. 2000, 406(1), 149-152.

Andoh, T. et al. Involvement of leukotriene B4 in substance P-induced itch-associated response in mice. J. Investigativ. Dermatol. 2001, 117(6), 1621-1626.

(Continued)

*Primary Examiner* — Yong Chu
*Assistant Examiner* — Alicia L Otton

(57) ABSTRACT

Thiazolopyridin-2-yloxy-phenyl and thiazolopyrazin-2-yloxy-phenyl amine compounds are described, which are useful as LTA4 hydrolase (LTA4H) modulators. Such compounds may be used in pharmaceutical compositions and methods for modulation of LTA4H and for the treatment of disease states, disorders, and conditions mediated by LTA4 hydrolase activity.

37 Claims, No Drawings

U.S. PATENT DOCUMENTS

| | | |
|---|---|---|
| 2007/0155726 A1 | 7/2007 | Arnaiz et al. |
| 2007/0167425 A1 | 7/2007 | Nakade et al. |
| 2008/0057074 A1 | 3/2008 | Takaoka |
| 2008/0194630 A1 | 8/2008 | Barchuk et al. |
| 2009/0111794 A1* | 4/2009 | Bacani et al. ............ 514/214.02 |

FOREIGN PATENT DOCUMENTS

| | | |
|---|---|---|
| EP | 416521 | 9/1990 |
| EP | 623621 | 4/1994 |
| FR | 2446823 | 1/1979 |
| JP | 63170356 | 7/1988 |
| WO | WO 96/11192 | 4/1996 |
| WO | WO 96/41625 | 12/1996 |
| WO | WO 97/29774 | 8/1997 |
| WO | WO 01/81347 | 1/2001 |
| WO | WO 03/037904 | 5/2003 |
| WO | WO 2004/103959 | 12/2004 |
| WO | WO 2006/002133 | 1/2006 |
| WO | WO 2006/004475 | 1/2006 |
| WO | WO 2006/133802 | 12/2006 |
| WO | WO 2007/007069 | 1/2007 |
| WO | WO 2007/079078 | 7/2007 |
| WO | WO 2008/016811 | 2/2008 |

OTHER PUBLICATIONS

Andoh, T. et al. Intradermal nociceptin elicits itch-associated responses through leukotriene B4 in mice. J. Investigativ. Dermatol. 2004, 123(1), 196-201.

Andoh, T. et al. Suppression by bepotastine besilate of substance P-induced itch-associated responses through the inhibition of the leukotriene B4 action in mice. Eur. J. Pharmacol. 2006, 547(1-3), 59-64.

Barnes, P.J. Future Advances in COPD Therapy. Respiration 2001, 68(5), 441-448.

Bagshawe et al. Antibody-Directed Enzyme Prodrug Therapy: A Review Drug Dev. Res. 1995, 34, 220-230.

Barone, F.C. et al. Time-related changes in myeloperoxidase activity and leukotriene B4 receptor binding reflect leukocyte influx in cerebral focal stroke. Mol. Chem. Neuropathol. 1995, 24(1), 13-30.

Benoist, C. and D. Mathis. Mast Cells in Autoimmune Disease. Nature 2002, 420(6917), 875-878.

Berge et al. Pharmaceutical Salts Journal of Pharmaceutical Sciences 1977, 66(1), 1-19.

Bertolini et al. A New Rational Hypothesis for the Pharmacophore of the Active Metabolite of Leflunomide, A Potent Immunosuppressive Drug. J Med Chem 1997, 40, 2011-2016.

Bodor et al. Novel Approaches to the Design of Safer Drugs: Soft Drugs and Site-Specific Chemical Delivery Systems Advances in Drug Research 1984, 13, 224-331.

Byrum, R.S. et al. Determination of the Contribution of Cysteinyl Leukotrienes and Leukotriene $B_4$ in Acute Inflammatory Responses Using 5-Lipoxygenase- and Leukotriene $A_4$ Hydrolase-Deficient Mice. J. Immunol. 1999, 163(12), 6810-6819.

Camp, R.D.R. et al. Responses of Human Skin to Intradermal Injection of Leukotrienes $C_4$, $D_4$ and $B_4$. Br. J. Pharmacol. 1983, 80(3), 497-502.

Camp, R. et al. Production of Intraepidermal Microabscesses by Topical Application of Leukotriene $B_4$. J. Invest. Dermatol. 1984, 82(2), 202-204.

Carpagnano, G.E. et al. Increased leukotrien B4 and interleukin-6 in exhaled breath condensate in cystic fibrosis. Am. J. Respir. Crit. Care Med. 2003, 167(8), 1109-1112.

Chen, X. et al. Leukotriene A4 hydrolase in rat and human esophageal adenocarcinomas and inhibitory effects of bestatin. J. Natl. Cancer Inst. 2003, 95(14), 1053-1061.

Chen, X. et al. Leukotriene A4 hydrolase as a target for cancer prevention and therapy. Curr. Cancer Drug Targets 2004, 4(3), 267-283.

Cohen, J. The Immunopathogenesis of Sepsis. Nature (London) 2002, 420(6917), 885-891.

Coussens, L.M. et al. Inflammation and Cancer. Nature (London) 2002, 420(6917), 860-867.

Crooks, S.W. and R.A. Stockley. Leukotriene $B_4$. Int. J. Biochem. Cell Biol. 1998, 30(2), 173-178.

Cunha, J.M. et al. The critical role of leukotriene B4 in antigen-induced mechanical hyperalgesia in immunised rats. Br. J. Pharmacol. 2003, 139(6), 1135-1145.

Ellis, C.N. et al. Cost of atopic dermatitis and eczema in the United States. J. Am. Acad. Dermatol. 2002, 46, 361-370.

Emingil, G. et al. Levels of leukotriene B4 in gingival crevicular fluid and gingival tissue in specific periodontal diseases. J. Periodontol. 2001, 72(8), 1025-1031.

Fitzpatrick, F.A. et al. Effects of Leukotriene $A_4$ on Neutrophil Activation. Ann. N.Y. Acad. Sci. 1994, 714, 64-74.

Ford-Hutchinson, A.W. et al. 5-Lipoxygenase. Ann. Rev. Biochem. 1994, 63, 383-417.

Fleisher, D. et al. Improved oral drug delivery: solubility limitations overcome by the use of prodrugs. Advanced Drug Delivery Reviews, 1996, 19, 115-130.

Friedrich E.B. et al. Mechanisms of leukotriene $B_4$-triggered monocyte adhesion. Arterioscler Thromb Vasc Biol 2003, 23, 1761-1767.

Funk et al. Molecular Cloning and Amino Acid Sequence of Leukotriene A4 Hydrolase. PNAS 1987, 84, 6677-6681.

Gelfand, E.W. et al. CD8+ T lymphocytes and leukotriene B4: novel interactions in the persistence and progression of asthma. J. Allergy Clin. Immunol. 2006, 117(3), 577-582.

Gierse et al. High level Experssion and Purification of Human Leukotriene A4 Hydrolase from Insect Cells Infected with a Baculovirus Vector. Protein Expression and Purification, 1993, 4, 358-366.

Gompertz, S. et al. Changes in bronchial inflammation during acute exacerbations of chronic bronchitis. Eur. Respir. J. 2001, 17(6), 1112-1119.

Goodarzi, K. et al. Leukotriene $B_4$ and BLT1 Control Cytotoxic Effector T Cell Recruitment to Inflamed Tissues. Nat. Immunol. 2003) 4(10), 965-973.

Griffiths, R.J. et al. Leukotriene $B_4$ Plays a Critical Role in the Progression of Collagen-Induced Arthritis. PNAS 1995, 92(2), 517-521.

Hakonarson, H. et al. Effects of a 5-lipoxygenase-activating protein inhibitor on biomarkers associated with risk of myocardial infarction. A randomized trial. JAMA 2005, 293(18), 2245-2256.

Hanifin, J.M. et al. Guidelines of care for atopic dermatitis, developed in accordance with the American Academy of Dermatology (AAD)/ American Academy of Dermatology Association Administrative Regulations for Evidence-Based Clinical Practice Guidelines. J. Am. Acad. Dermatol. 2004, 50, 391-404.

Helgadottir, A. et al. The Gene Encoding 5-Lipoxygenase Activating Protein Confers Risk of Myocardial Infarction and Stroke. Nat. Genet. 2004, 36(3), 233-239.

Helgadottir A. et al. A variant of the gene encoding leukotriene A4 hydrolase confers ethnicity-specific risk of myocardial infarction. Nat Genet. 2006, 38, 68-74.

Huang L, et al. Molecular and Biological Characterization of the Murine Leukotriene B4 Receptor Expressed on Eosinophils. J. Exp. Med. 1998, 188(6), 1063-1074.

Hwang, S.W. et al. Direct activation of capsaicin receptors by products of lipoxygenases: endogenous capsaicin-like substances. Proc. Natl. Acad. Sci. USA 2000, 97(11), 6155-6160.

Ikai, K. Psoriasis and the Arachidonic Acid Cascade, Jour. Of Derm. Sci., 1999, 21, 135-146.

Jala, V.R. et al. Leukotrienes and Atherosclerosis: New Role for Old Mediators. Trends Immunol. 2004, 25(6), 315-322.

Kachur, J.F. et al. Pharmacological Characterization of SC-57461A (3-[Methyl[3-[4-(phenylmethyl)phenoxy]propyl]amino]propanoic acid HCl), a Potent and Selective Inhibitor of Leukotriene $A_4$ Hydrolase II: In Vivo Studies. J. Pharmacol. Exp. Ther. 2002, 300(2), 583-587.

Klein, A. et al. Stem Cell Factor Plays a Major Role in the Recruitment of Eosinophils in Allergic Pleurisy in Mice via the Production of Leukotriene $B_4$. J. Immunol. 2000, 164(8), 4271-4276.

Laughter, D. et al. The prevalence of atopic dermatitis in Oregon schoolchildren. J. Am. Acad. Dermatol. 2000, 43, 649-655.

Liao, T. et al. Blockade of the interaction of leukotriene B4 with its receptor prevents development of autoimmune uveitis. Invest. Ophthalmol. Vis. Sci. 2006, 47(4), 1543-1549.

Libby, P. Inflammation in Atherosclerosis. Nature (London) 2002, 420(6917), 868-874.

Miyahara N. et al. Role of the LTB4/BLT1 pathway in allergen-induced airway hyperresponsiveness and inflammation. Allergy Intl. 2006, 55(2), 91-97.

Munafo, D.A. et al. Leukotriene A4 Hydrolase in Human Bronchoalveolar Lavage Fluid. J. Clin. Invest. 1994, 93(3), 1042-1050.

Nakae, H. et al. Relationship between cytokines and leukotriene B4 in sepsis. Res. Commun. Chem. Pathol. Pharmacol. 1994, 83(2), 151-156.

Nathan, C. Points of Control in Inflammation. Nature (London) 2002, 420(6917), 846-852.

Message et al., "The Immunology of Virus Infection in Asthma" 2001, European Respiratory Journal, vol. 18:1013-1025.

Schimmer et al., Adrenocorticotropic Hormone; Adrenocortical Steroids and Their Synthetic Analogs; Inhibitors of the Synthesis and Action of Adrenocortical Hormones 2001; in Hardman JG, Limbird LE; eds. Goodman and Gilman's The Pharmacological Basis of Therapeutics, 10th ed. New York: McGraw-Hill; 1666-1668.

International Search Report dated Jan. 22, 2010 for International Application No. PCT/US2009/040070.

Ott, V.L. et al. Cell-Dependent Migration of Effector CD8+ T Cells Through Production of Leukotriene B4. Nat. Immunol. 2003, 4(10), 974-981.

Penning, T.D. Inhibitor of Leukotriene A4 (LTA4) Hydrolase as Potential Anti-Inflammatory Agents. Curr. Pharm. Des. 2001, 7(3), 163-179.

Reid, G.K. et al. Correlation Between Expression of 5-Lipoxygenase-Activating Protein, 5-Lipoxygenase, and Cellular Leukotriene Synthesis. J. Biol. Chem. 1990, 265(32), 19818-19823.

Robinson, R. et al. Discovery of the Hemifumarate and (α-L-Alanyloxy) methyl Ether as Prodrugs of an Antirheumatic Oxindole: Prodrugs for the Enolic OH Group. J. Med Chem. 1996, 39, 10-18.

Samuelsson, B. et al. Leukotrienes: Mediators of Immediate Hypersensitivity Reactions and Inflammation. Science (Washington, D.C.) 1983, 220 (4597), 568-575.

Samuelsson, B et al. Enzymes Involved in the Biosynthesis of Leukotriene B4. J. Biol. Chem. 1989, 264(33), 19469-19472.

Shan et al. Prodrug strategies based on intramolecular cyclization reactions. Journal of Pharmaceutical Sciences 1997, 86(7), 765-767.

Sharon, P. et al. Enhanced Synthesis of Leukotriene B4 by Colonic Mucosa in Inflammatory Bowel Disease. Gastroenterology 1984, 86(3), 453-460.

Sidbury, R. et al. Old, new, and emerging therapies for atopic dermatitis. Dermatol. Clin. 2000, 18(1), 1-11.

Steinberg, D. Atherogenesis in Perspective: Hypercholesterolemia and Inflammation as Partners in Crime. Nat. Med. 2002, 8(11), 1211-1217.

Su, J.C. et al. Atopic eczema: its impact on the family and financial cost. Arch. Dis. Child 1997, 76, 159-162.

Subbarao, K. et al. Role of Leukotriene B4 Receptors in the Development of Atherosclerosis: Potential Mechanisms. Arterioscler. Thromb. Vasc. Biol. 2004, 24, 369-375.

Tager, A.M. et al. Leukotriene B4 Receptor BLT1 Mediates Early Effector T Cell Recruitment. Nat. Immunol. 2003, 4(10), 982-990.

Takakuwa, T. et al. Relationships between plasma levels of type-II phospholipase A2, PAF-acetylhydrolase, leukotriene B4, complements, endothelin-1 and thrombomodulin in patients with sepsis. Res. Commun. Chem. Pathol. Pharmacol. 1994, 84(3), 271-281.

Terawaki K. et al. Absence of leukotriene $B_4$ receptor 1 confers resistance to airway hyperresponsiveness and Th2-type immune responses. J Immunol. 2005, 17(7), 4217-4225.

Tracey, K.J. The Inflammatory Reflex. Nature (London) 2002, 420(6917), 853-859.

Tsuji F. et al. Involvement of Leukotriene B4 in Arthritis Models. Life Sci. 1998, 64(3), L51-L56.

Wang, S. et al. A Novel Hepatointestinal Leukotriene B4 Receptor. Cloning and Functional Characterization. J. Biol. Chem. 2000, 275(52), 40686-40694.

Weiner, H.L., et al. Inflammation and Therapeutic Vaccination in CNS Diseases. Nature (London) 2002, 420(6917), 879-884.

Willemsen M.A. et al. Clinical and biochemical effects of zileuton in patients with the Sjogren-Larsson syndrome. Eur J Pediatr. 2001,160, 711-717.

Woodmansee D.P. et al. Simon RA. A pilot study examining the role of zileuton in atopic dermatitis. Ann Allergy Asthma Immunol. 1999, 83, 548-552.

Yokomizo, T. et al. Leukotriene A4 Hydrolase and Leukotriene B4 Metabolism. J. Lipid Mediat. Cell Signal. 1995, 12(2-3), 321-332.

Yokomizo, T. et al. A Second Leukotriene B4 Receptor, BLT2: A New Therapeutic Target in Inflammation and Immunological Disorders. J. Exp. Med. 2000, 192(3), 421-431.

Yokomizo, T. et al. Co-expression of two LTB4 Receptors in Human Mononuclear Cells. Life Sci. 2001, 68(19-20), 2207-2212.

Yokomizo, T. et al. Leukotriene B4: Metabolism and Signal Transduction. Arch. Biochem. Biophys. 2001, 385(2), 231-241.

Zhu, Y.I. et al. Preview of Potential Therapeutic Applications of Leukotriene B4 Inhibitors in Dermatology. Skin Pharmacol. Appl. Skin Physiol. 2000, 13(5), 235-245.

Zhu, L. et al. A convenient synthesis of 2-mercapto and 2-chlorobenzotniazoles. J. Heterocyclic Chem. 2005, 42, 727-730.

Zouboulis, Ch.C. et al. Zileuton, an Oral 5-Lipoxygenase Inhibitor, Directly Reduces Sebum Production. Dermatology 2005, 210(1), 36-38.

Zouboulis, Ch.C. et al. A new concept for acne therapy: a pilot study with zileuton, an oral 5-lipoxygenase inhibitor. Arch. Dermatol. 2003, 139(5), 668-670.

Dostert, P. et al., Studies on the Neuropleptic Benzamides. III— Synthesis and Antidopaminergic Properties of New 3-nortropane Derivatives, Eur. J. Med. Chem. vol. 19, No. 2, 1984, 105-110.

Szefler et al., Am. J. Respir. Crit. Care Med. Feb. 1, 2003; 176(3):290-291.

Vippagunta et al., "Crystalline Solids", Advanced Drug Delivery Reviews, 2001 vol. 48, 3-26.

Gavezzotti, "Are Crystal Structures Predictable?"? Accounts of Chemical Research, 1994 vol. 27, 309-314.

Penning et al., "Pyrrolidine and Piperidine Analogues of SC-57461A as Potent, orally Active Inhibitors of Leukotriene A4 Hydrolase" Bioorganic & Medicinal Chemistry Letters 2002, 12, 3383-3386.

Morisseau et al., "Potent Urea and Carbamate Inhibitors of Soluble Epoxide Hydrolases" Proceedings of the National Academy of Sciences 1999, 96, 8849-8854.

Wolff, M.E. Burger's Medicinal Chemistry $4^{th}$ Ed. Par I, Wiley: New York, 1979 336-337.

West, Anthony R., Solid State Chemistry and its Applications, Wiley, New York, 1988, pp. 358 &35565.

Patani et al.: "Biosoterism: A Rational Approach in Drug Design" 1996; Chem. Rev.; 96:3147-3176.

Agner, T. "Compliance Among Patients with Atopic Eczema", Acta Derm. Venereol. 2005; Suppl. 215; 33-35.

Ahmadzadeh et al., "Relationship Betweetn Leukotriene $B_4$ and Immunological Parameters in Rhematoid Synovial Fluids", 1991, Inflammation, vol. 15:497-503.

Ahluwalia et al., Inhibited Aortic Aneurysm Formation in BLT1-Deficient Mice, 2007, Journal of Immunology vol. 179:691-697.

Allen et al., "Inhaled Corticosteroids: Past Lessons and Future Issues" 2003 Allergy Clin. Immunol. vol. 112,3:S1-S40.

Bellamy et al., "Poor Perceptions and Expectations of Asthma Control: Results of the International Control of Asthma Symptoms (ICAS) Survey of Patients and General Practitioners" 2005, Primary Care Respiratory Journal, vol. 14:252-258.

Biernacki, et al., "Increased Leukotriene $B_4$ and 8-Isoprostane in Exhaled Breath Condensate of Patients with Exacerbations of COPD" 2003, Thorax.

Busse et al., "Advances in Immunology" 2001, New England Journal of Medicine, vol. 344:350-362.

Collin, "Structural Requirements of D-2 Antidopaminergic Genzamides. Comparison with 5HT-3 Antiserotoninergic Orthopramides", 1991, Pharmacie de Belgique, vol. 46 Issue 1:55-66.

Dahlen et al., "Treatment of Asthma with Antileukotrienes: First Line or Last Resort Therapy" 2006, European Journal of Pharmacology, 533:40-56.

Fitzgerald et al., "Asthma Control in Canada Remains Suboptimal: The Reality of Asthma Control (TRAC) Study" 2006, Can Resp. J. vol. 13, No. 5:253.

Frieri et al., "Allergen-Stimulated Leukotriene $B_4$ and Interleukin-8 Levels in Patients with Asthma and Allergic Rhinitis-Modulation by a Lipid Pathway Inhibitor" 1998, Ann. Allergy Asthma Immunol. vol. 81:331.

Koro et al., Chemical Mediators in Atopic Dermatitis: Involvement of Leukotriene $B_4$ Released by a Type I Allergic Reaction in the Pathogenesis of topic Dermatitis, J. Allergy Clin. Immunol. (1999) vol. 103:663-670.

Mathis et al., "Role of Leukotriene $B_4$ Receptors iin Rheumatoid Arthritis" 2007 Autoimmunity Reviews, vol. 7:12-17.

Milgrom et al., "Noncompliance and Treatment Failure in Children with Asthma" 1996, J. Allergy Clin. Immunol. vol. 98:1051-1057.

Moore et al., "Severe Asthma: An Overview" 2006 American Academy of Allergy, Asthma and Immunology, vol. 117:487-494.

Neu et al., "Leukotrienes in Patients with Clinically Active Multiple Sclerosis", 2002 Acta Neurol. Scand, vol. 105:63-66.

Rabier, et al., "Neuropeptides Modulate Leukotriene $B_4$ Mitogenicity Toward Cultured Human Keratinocytes", 1993 J. Invest. Deermatol. vol. 110:132-136.

Ruzicka et al., "Skin Levels of Arachidonic Acid-Derived Inflammatory Mediators and Histamine in Atopic Dermatitis and Psoriasis" 1986, J. Invest. Dermatol. vol. 86:105-108.

Seggev et al., "Serum Leukotriene $B_4$ Levels in Patients with Obstructive Pulmonary Disease" 1991, Chest. vol. 99-289-291.

Turner et al., "In Vitro and In Vivo Effects of Leukotriene $B_4$ Antagonism in a Primate Model of Asthma" 1996, J. Clin. Invest., vol. 97-381-387.

Wedi et al., Pathophysiological Role of Leukotrienes in Dermatological Diseases, 2001, BioDrugs vol. 15(11):729-743.

Wenzel et al., "Bronchoscopic Evaluation of Severe Asthma" 1997, American Journal of Respiratory and Critical Care Medicine, vol. 156:737-743.

Whatling et al., "The Potential Link Between Atherosclerosis and the 5-Lipoxygenase Pathway Investigational Agents with New Implications for the Cardiovascular Field" 2007, Informa Healthcare, vol. 16:1879-1893.

Whittle et al., "Attenuation of Inflammation and Cytokine Production in Rat Colitis by a Novel Selective Inhibitor of Leukotriene $A_4$ Hydrolase" 2008, British Journal of Pharmacology, vol. 153:983-991.

Willemsen et al., "Deffective Metabolism of Leukotriene $B_4$ in the Sjogren-Larsson Syndrome" 2001, Journal of the Neurological Sciences vol. 183:61-67.

Lundeen et al., "Leukotriene $B_4$ Receptors BLT1 and BLT2: Expression and Function in Human and Murine Mast Cells" 2006, The Journal of Immunology, vol. 177:3439-3447.

Rao et al., "Anti-Inflammatory Activity of A potent, Selective Leukotriene $A_4$ Hydrolase Inhibitor in Comparison with the 5-Lipoxygenase Inhibitor Zileuton", 2007, vol. 321, No. 3:1154-1160.

Grice et al., Discovery of Potent and Selective Leukotriene A4 Hydrolase Inhibitors Abstracts of Papers, 234th ACS National Meeting, Boston, MA, US Aug. 19, 2007.

Suzuki et al., A Practical Procedure for Preparation of N-(endo-8-(3-Hydroxy)Propyl-8-Azabicyclo[3.2.1.]Oct-3-YL)-1-Isopropyl-2-Oxo-1,2-Dihydro-3-Quinoline-Carboxamide (TS-951) 2000, Heterocycles, vol. 53, No. 11 pp. 2471-2485.

\* cited by examiner

THIAZOLOPYRIDIN-2-YLOXY-PHENYL AND THIAZOLOPYRAZIN-2-YLOXY-PHENYL AMINES AS MODULATORS OF LEUKOTRIENE A4 HYDROLASE

This application claims the benefit of U.S. Provisional Applications 61/044,349, filed Apr. 11, 2008, and 61/149,129, filed Feb. 2, 2009.

FIELD OF THE INVENTION

The present invention relates to certain thiazolopyridin-2-yloxy-phenyl and thiazolopyrazin-2-yloxy-phenyl amine compounds, pharmaceutical compositions containing them, and methods of using the compounds and pharmaceutical compositions for leukotriene A4 hydrolase (LTA4H) modulation and for the treatment of disease states, disorders, and conditions mediated by leukotriene A4 hydrolase (LTA4H) activity.

BACKGROUND OF THE INVENTION

Inflammation is normally an acute response by the immune system to invasion by microbial pathogens, chemicals or physical injury. In some cases, however, the inflammatory response can progress to a chronic state, and be the cause of inflammatory disease. Therapeutic control of this chronic inflammation in diverse diseases is a major medical need.

Leukotrienes (LT) are biologically active metabolites of arachidonic acid (B. Samuelsson, Science 1983, 220(4597): 568-575) that have been implicated in inflammatory diseases, including asthma (D. A. Munafo et al., J. Clin. Invest. 1994, 93(3): 1042-1050; N. Miyahara, et al., Allergol Int., 2006, 55(2): 91-7; E. W. Gelfand, et al., J. Allergy Clin. Immunol. 2006, 117(3): 577-82; K. Terawaki, et al., J. Immunol. 2005, 175(7): 4217-25), inflammatory bowel disease (IBD) (P. Sharon and W. F. Stenson, Gastroenterology 1984, 86(3): 453-460), chronic obstructive pulmonary disease (COPD) (P. J. Barnes, Respiration 2001, 68(5): 441-448), arthritis (R. J. Griffiths et al., Proc. Natl. Acad. Sci. U.S.A. 1995, 92(2): 517-521; F. Tsuji et al., Life Sci. 1998, 64(3): L51-L56), psoriasis (K. Ikai, J. Dermatol. Sci. 1999, 21(3): 135-146; Y. I. Zhu and M. J. Stiller, Skin Pharmacol. Appl. Skin Physiol. 2000, 13(5): 235-245) and atherosclerosis (Friedrich, E. B. et al. Arterioscler Thromb Vasc Biol 23, 1761-7 (2003); Subbarao, K. et al. Arterioscler Thromb Vasc Biol 24, 369-75 (2004); Helgadottir, A. et al. Nat Genet. 36, 233-9 (2004); Jala, V. R. et al Trends in Immun. 25, 315-322 (2004)). The synthesis of leukotrienes is initiated by the conversion of arachidonic acid to an unstable epoxide intermediate, leukotriene A4 (LTA4), by 5-lipoxygenase (5-LO) (A. W. Ford-Hutchinson et al., Annu. Rev. Biochem. 1994, 63: 383-347). This enzyme is expressed predominantly by cells of myeloid origin, particularly neutrophils, eosinophils, monocytes/macrophages and mast cells (G. K. Reid et al., J. Biol. Chem. 1990, 265(32): 19818-19823). LTA4 can either be conjugated with glutathione by leukotriene C4 (LTC4) synthase to produce the cysteinyl leukotriene, LTC4, or hydrolyzed to the diol, leukotriene B4 (LTB4) (B. Samuelsson, Science 1983, 220(4597): 568-575). LTC4 and its metabolites, LTD4 and LTE4, induce smooth muscle contraction, broncho-constriction and vascular permeability, while LTB4 is a potent chemo-attractant and activator of neutrophils, eosinophils, monocytes/macrophages, T cells and mast cells.

The stereospecific hydrolysis of LTA4 to LTB4 is catalyzed by leukotriene A4 hydrolase (LTA4H), a zinc-containing, cytosolic enzyme. This enzyme is ubiquitously expressed, with high levels in small intestinal epithelial cells, lung, and aorta (B. Samuelsson and C. D. Funk, J. Biol. Chem. 1989, 264(33): 19469-19472). Moderate expression of LTA4H is observed in leukocytes, particularly neutrophils (T. Yokomizo et al., J. Lipid Mediators Cell Signalling 1995, 12(2,3): 321-332).

Leukotriene B4 is a key pro-inflammatory lipid mediator, able to recruit and activate inflammatory cells, such as neutrophils, eosinophils, monocytes/macrophages, T cells and mast cells (F. A. Fitzpatrick et al., Ann. N.Y. Acad. Sci. 1994, 714: 64-74; S. W. Crooks and R. A. Stockley, Int. J. Biochem. Cell Biol. 1998, 30(2): 173-178; A. Klein et al., J. Immunol. 2000, 164: 4271-4276). LTB4 mediates its pro-inflammatory effects by binding to G protein-coupled receptors, leukotriene B4 receptor 1 (BLT1) and leukotriene B4 receptor 2 (BLT2) (T. Yokomizo et al., Arch. Biochem. Biophys. 2001, 385(2): 231-241). The receptor first identified, BLT1, binds LTB4 with high affinity, leading to intracellular signaling and chemotaxis. BLT1 is expressed mainly in peripheral leukocytes, particularly neutrophils, eosinophils, macrophages (Huang, W. W. et al. J Exp Med 188, 1063-74 (1998)) and monocytes (Yokomizo, T., Izumi, T. & Shimizu, T. Life Sci 68, 2207-12 (2001)). The murine receptor is also expressed on effector T cells and was recently shown to mediate LTB4-dependent migration of effector $CD8^+$ T cells (Goodarzi, K., Goodarzi, M., Tager, A. M., Luster, A. D. & von Andrian, U. H. Nat Immunol 4, 965-73 (2003); Ott, V. L., Cambier, J. C., Kappler, J., Marrack, P. & Swanson, B. J. Nat Immunol 4, 974-81 (2003)), early effector $CD4^+$ T helper type 1 ($T_H1$) and $T_H2$ chemotaxis and adhesion to endothelial cells, as well as early effector $CD4^+$ and $CD8^+$ T cell recruitment in an asthma animal model (Tager, A. M. et al., Nat Immunol 4, 982-90 (2003)). LTB4 receptor BLT2 (S. Wang et al., J. Biol. Chem. 2000, 275(52): 40686-40694; T. Yokomizo et al., J. Exp. Med. 2000, 192(3): 421-431) shares 42% amino acid homology with BLT1, but is more broadly expressed, including in peripheral tissues such as the spleen, ovary and liver, as well as in leukocytes. BLT2 binds LTB4 with lower affinity than BLT1 does, mediates chemotaxis at higher concentrations of LTB4, and differs from BLT1 in its affinity for certain antagonists. While LTB4 receptor antagonists may differ in their affinity for BLT1 versus BLT2, blocking the production of LTB4 using LTA4H inhibitors would be expected to inhibit the downstream events mediated through both BLT1 and BLT2.

Studies have shown that introduction of exogenous LTB4 into normal tissues can induce inflammatory symptoms (R. D. R. Camp et al., Br. J. Pharmacol. 1983, 80(3): 497-502; R. Camp et al., J. Invest. Dermatol. 1984, 82(2): 202-204). Increased production of LTB4 is considered important for the inflammatory component in a number of diseases, including atopic dermatitis (O. Koro et al. J. Allergy Clin. Immunol. 1999, 103, 663-670), asthma (M. Frieri et al., Ann. Allergy Asthma Immunol. 1998, 81, 331-336), inflammatory bowel disease, chronic obstructive pulmonary disease (W. A. Biernacki et al. Thorax 2003, 58, 294-298; J. S. Seggev et al., Chest 1991, 99, 289-291), atherosclerosis and cardiovascular disease, multiple sclerosis (I. S. Neu et al., Acta Neurol. Scand. 2002, 105, 63-66), psoriasis (D. M. Reilly, Acta Derm. Venereol. 2000, 80, 171-174), cystic fibrosis (J. T. Zakrzewski, et al., Br J Clin Pharmacol 1987, 23:19-27), and rheumatoid arthritis (N. Ahmadzadeh, Inflammation 1991, 15, 497-503). Therefore, inhibitors of LTB4 production should have therapeutic value as anti-inflammatory agents for these conditions. Thus, reduction of LTB4 production by an inhibitor of LTA4H activity would be predicted to have therapeutic potential in a wide range of diseases.

This idea is supported by a study of LTA4H-deficient mice that, while otherwise healthy, exhibited markedly decreased neutrophil influx in arachidonic acid-induced ear inflammation and zymosan-induced peritonitis models (R. S. Byrum et al., J. Immunol. 1999, 163(12): 6810-6819). LTA4H inhibitors have been shown to be effective anti-inflammatory agents in pre-clinical studies. For example, oral administration of LTA4H inhibitor SC57461 caused inhibition of ionophore-induced LTB4 production in mouse blood ex vivo, and in rat peritoneum in vivo (J. K. Kachur et al., J. Pharm. Exp. Ther. 2002, 300(2), 583-587). Eight weeks of treatment with the same inhibitor compound significantly improved colitis symptoms in cotton top tamarins (T. D. Penning, Curr. Pharm. Des. 2001, 7(3): 163-179). The spontaneous colitis that develops in these animals is very similar to human IBD. The results therefore indicate that LTA4H inhibitors would have therapeutic utility in this and other human inflammatory diseases.

Events that elicit the inflammatory response include the formation of the pro-inflammatory mediator leukotriene B4. Hydrolase LTA4H catalyzes the formation of this mediator, and LTA4H inhibitors block the production of the pro-inflammatory mediator LTB4, thus providing the ability to prevent and/or treat leukotriene-mediated conditions, such as inflammation. The inflammatory response is characterized by pain, increased temperature, redness, swelling, or reduced function, or by a combination of two or more of these symptoms. Regarding the onset and evolution of inflammation, inflammatory diseases or inflammation-mediated diseases or conditions include, but are not limited to, acute inflammation, allergic inflammation, and chronic inflammation.

Compounds of the present invention were shown to inhibit LTA4H in in vitro assays. Inhibition was shown in a recombinant enzymatic assay and in a cellular assay using murine (diluted 1 in 15) or human whole blood (diluted 1:1). Embodiments of the invention were also shown to inhibit murine ex vivo LTB4 production in whole blood (diluted 1:1), as well as arachidonic acid-induced neutrophil influx in murine ear tissue.

Atopic dermatitis (AD) is a chronic inflammatory skin disease that usually occurs in individuals with a personal or family history of atopy. The major features are pruritus and chronic or relapsing eczematous lesions. Complications include bacterial, fungal and viral infections as well as ocular disease. Atopic dermatitis is the most common inflammatory skin disease in children and affects more than 15% of children in the US (Laughter, D., et al., J. Am. Acad. Dermatol. 2000, 43, 649-655). Atopic dermatitis may persist in 60% of adults who were affected as children (Sidbury, R., et al., Dermatol. Clin. 2000, 18(1), 1-11).

Atopic dermatitis has significant societal impact. The family stress related to caring for children with moderate to severe AD may be comparable to the stress seen in families of children with type I diabetes mellitus (Su, J. C., et al., Arch. Dis. Child 1997, 76, 159-162). In the US, the annual cost of medical services and prescription drugs for the treatment of AD/eczema is similar to those for emphysema, psoriasis and epilepsy (Ellis, C. N., et al., J. Am. Acad. Dermatol. 2002, 46, 361-370).

Several lines of evidence support the role of LTB4 in AD. LTB4 levels are elevated in skin lesions (K. Fogh et al., J. Allergy Clin. Immunol. 1989, 83, 450-455; T. Ruzicka et al., J. Invest. Dermatol. 1986, 86, 105-108) and plasma in AD, and contribute to the inflammation through chemotactic effects on inflammatory cells (Wedi and Kapp BioDrugs. 2001; 15, 729-743. Reported in vivo and in vitro studies have shown that leukotrienes, especially LTB4, contribute to the inflammation of the skin in AD through their chemotactic effect on inflammatory cells. LTB4 receptors are expressed on mast cells, T cells, eosinophils, dendritic cells and macrophages, all of which accumulate in AD lesions. LTB4 itself is a pruritic agent, and has also been shown to mediate substance P-induced pruritus (T. Andoh et al., J. Invest. Dermatol. 2001, 117, 1621-1626), a key component of the itching in AD (T. Ohmura et al., Eur. J. Pharmacol. 2004, 491, 191-194). LTB4 induces proliferation of keratinocytes, an effect that is further potentiated by substance P (M. J. Rabier et al., J. Invest. Dermatol. 1993, 110, 132-136). Recent reports indicate a role for LTB4 in development of a Th2 immune response and IgE production. The role of LTB4 in AD is supported by beneficial effects of the 5-lipoxygenase inhibitor, zileuton, in a small, open-label clinical trials of AD (Woodmansee, D. P., et al., Ann. Allergy Asthma Immunol. 1999, 83, 548-552) and in relieving the pruritus in Sjogren-Larsson syndrome patients who have elevated LTB4 due to an impairment in its degradation (Willemsen, M. A., et al., Eur. J. Pediatr. 2001, 160, 711-717).

While AD that is mild to moderate in severity generally responds to topical therapy, correct use of these therapies and compliance remain a major issue in the clinic (T. Agner, Acta Derm. Verereol. Suppl. (Stockh) 2005, 213, 33-35). Topical corticosteroids and emollients are the standard of care in the treatment of AD. However, systemic immunomodulatory therapies and potent topical corticosteroids used to treat severe AD are associated with significant cutaneous side effects, such as striae, atrophy and telangeictasia that limit the long-term use of these agents (Hanifin, J. M., et al., J. Am. Acad. Dermatol. 2004, 50, 391-404).

Emollients have a steroid-sparing effect and are useful for both prevention and maintenance therapy. Crude coal tar and preparations containing coal tar derivatives have also been used for many years in the treatment of AD and have significant cosmetic disadvantages that influence compliance (Hanifin, et al., 2004). Topical doxepin may be a useful short-term adjunctive therapy for the relief of pruritus but sedation and contact dermatitis may complicate its use (Hanifin, et al., 2004).

The topical calcineurin inhibitors tacrolimus (Protopic®) and pimecrolimus (Elidel®) have been shown to reduce the extent, severity and symptoms of AD in adults and children and are approved for use as second-line therapy of AD. However, the recent addition of boxed warnings to the product labels regarding rare cases of malignancy reported in patients treated with topical calcineurin inhibitors limits long term use of these agents in the treatment of AD (Food and Drug Administration [FDA]/Center for Drug Evaluation and Research [CDER] resources page).

Antibiotics are used in the treatment of *Staphylococcus aureus* infections in patients with AD but have a minimal effect on the dermatitis (Hanifin, et al., 2004). Although sedating antihistamines may be useful if sleep disruption is present, oral antihistamines are generally not effective in treating AD-associated pruritus (Hanifin, et al., 2004). Ultraviolet (UV) phototherapy, including photochemotherapy with psoralen is well established in the treatment of AD but relapse upon cessation of therapy frequently occurs (Hanifin, et al., 2004).

Systemic immunomodulatory therapy with cyclosporine and corticosteroids is effective but can be associated with severe side effects and is generally reserved for patients with severe disease. Systemic corticosteroids are associated with growth retardation in children, avascular necrosis of bone, osteopenia, increased risk of infection, poor wound healing, cataracts, hyperglycemia and hypertension. Cyclosporine is nephrotoxic in a majority of patients and is associated with tremor, hirsutism, hypertension, hyperlipidemia and gum hyperplasia.

While AD that is mild to moderate in severity generally responds to topical therapy, correct use of these therapies and compliance remain a major issue in the clinic. An oral or topical agent lacking the risks associated with corticosteroids and the calcineurin inhibitors would be a welcome addition to the armamentarium of treatments for AD that is mild to moderate in severity. An effective oral or topical therapy with fewer side effects than systemic immunomodulatory therapies and potent topical corticosteroids would fill an unmet medical need in the treatment of AD.

Sjogren-Larsson syndrome is an autosomal recessive neurocutaneous disorder with severe ichthyosis. It is caused by mutation of the gene encoding microsomal fatty aldehyde dehydrogenase (FALDH) leading to a defect in fatty alcohol metabolism. FALDH catalyzes the oxidation of medium- to long-chain fatty aldehydes to their corresponding carboxylic acids. LTB4, a pro-inflammatory mediator synthesized from arachidonic acid, is inactivated by microsomal omega-oxidation, successively yielding 20-OH-LTB4, 20-CHO-LTB4 and 20-COOH-LTB4. The urine of Sjogren-Larsson syndrome patients contains highly elevated levels of LTB4 and 20-OH-LTB4. Defective LTB4 degradation in Sjogren-Larsson syndrome patients is now considered to be shown with "unambiguous evidence". (Willemsen, M. A., et al., J. Neurol. Sci. 2001, 183(1), 61-7). Sjogren syndrome is an autoimmune disease that features inflammation in some glands. Sjogren syndrome may feature also extraglandular manifestations. When the gland inflammation is not associated with another connective tissue disease, then the syndrome is referred to as primary Sjogren syndrome. When it is associated with a connective tissue disease, such as rheumatoid arthritis, systemic lupus erythematosus or scleroderma, then it is referred to as secondary Sjogren syndrome. The term "Sjogren syndrome" herein refers to any one of the primary and secondary Sjogren syndromes. No cure is currently known for this syndrome. The current treatments usually focus on the specific area of the body that is affected and also in the treatment of associated complications. Immuno-suppressants such as cortisones, azathioprine and cyclophosphamide are sometimes used to threat some serious complications, and antibiotics are also used to treat associated infections.

Embodiments of this invention have shown dose-dependent inhibition of dermal inflammation in the arachidonic acid-induced murine ear inflammation model. Oral administration of embodiments of this invention dose-dependently inhibited neutrophil influx and edema, and were shown to inhibit the ex vivo ionophore-stimulated LTB4 production at doses between 0.3 and 30 mg/kg.

LTA4H inhibitors are hypothesized to specifically block the production of LTB4 from LTA4, without affecting the biosynthesis of lipoxins, which are also produced from LTA4. Increasing or maintaining lipoxin $A_4$ ($LXA_4$) production may have beneficial therapeutic effects in dermal inflammation as it has been reported that topical application of a stable lipoxin analogue inhibits edema, granulocyte infiltration and epidermal hyperproliferation in murine skin inflammation models. 5-LO inhibitors block the pathway upstream of LTA4. This would be expected to lead to a block in not only synthesis of LTA4, LTB4 and cysteinyl leukotrienes (CysLT), but also $LXA_4$.

Embodiments of this invention have been studied in in vivo inflammation models including arachidonic acid-induced ear inflammation and allergic lung inflammation, including an ovalbumin (OVA) sensitization and airway challenge model and a rat ionophore-induced lung inflammation model. For example, embodiments of the invention show dose-dependent inhibition of the accumulation of inflammatory cells in the lungs in an ovalbumin-induced allergic airway inflammation model, a common animal model for human allergic inflammation.

Asthma is a chronic disease characterized by a variable degree of airflow obstruction, bronchial hyperresponsiveness and airway inflammation (Busse & Lemanske, 2001). Immunohistopathologic features include denudation of airway epithelium, collagen deposition beneath basement membrane, edema, mast cell activation, and inflammatory cell infiltration by neutrophils (especially in sudden-onset, fatal asthma exacerbations), eosinophils, and Th2 lymphocytes (W. W. Busse et al., N. Engl. J. Med. 2001, 344, 350-362). Airway inflammation contributes to the airway hyperresponsiveness, airflow limitation (acute bronchoconstriction, airway edema, mucus plug formation and airway wall remodeling, leading to bronchial obstruction), respiratory symptoms and disease chronicity (NIH Guidelines for the Diagnosis and Management of Asthma 1997).

Current therapy for asthma is directed at controlling acute bronchoconstrictive symptoms with beta2-adrenergic receptor agonists and managing underlying airway inflammation with inhaled corticosteroids, chromates such as cromolyn sodium and nedocromil, and antileukotriene agents, such as the cysteinyl leukotriene receptor antagonists montelukast and zafirlukast and the 5-lipoxygenase inhibitor zileuton. Systemic steroids are used in severe disease and acute exacerbations of asthma. The humanized monoclonal anti-IgE antibody omalizumab was approved for the treatment of patients with moderate-to-severe persistent asthma who have a positive skin test or in vitro reactivity to a perennial aeroallergen and whose symptoms are inadequately controlled with inhaled corticosteroids (XOLAIR® [omalizumab] July 2007).

The inflammatory component of mild persistent and moderate asthma can generally be controlled with inhaled corticosteroids, but patient compliance remains a major issue in disease management (H. Milgrom et al., J. Allergy Clin. Immunol. 1996, 98, 1051-1057). Despite optimum therapy, including long-acting beta-agonists and inhaled corticosteroids, many patients have poorly controlled asthma (J. M. Fitzgerald et al., Can. Respir. J. 2006, 13, 253-259; D. Bellamy et al., Prim. Care Respir. J. 2005, 14, 252-258). Severe asthma requires treatment with high-dose inhaled steroids or the frequent use of oral corticosteroids (W. Moore et al., J. Allergy Clin. Immunol. 2006, 117, 487-494), both of which can be associated with negative side effects such as osteopenia and growth retardation in children (D. Allen et al., Suppl. J. Allergy Clin. Immunol. 2003, 112, S1; P. Schimmer et al., Adrenocorticotropic Hormone; Adrenocortical Steroids and Their Synthetic Analogs; Inhibitors of the Synthesis and Action of Adrenocortical Hormones in Hardman J G, Limbird L E; eds. Goodman and Gilman's The Pharmacological Basis of Therapeutics, 10th ed. New York: McGraw-Hill; 2001; 1666-1668). An oral therapy that could effectively treat moderate-to-severe asthma and reduce corticosteroid requirements would address unmet medical needs.

Leukotrienes are important mediators in asthma pathogenesis and comprise two classes—the cysteinyl leukotrienes (LTC4, LTD4 and LTE4) and LTB4. Leukotriene receptor antagonists, such as montelukast or zafirlukast, target only the cysteinyl leukotrienes, while 5-lipoxygenase inhibitors, such as zileuton, inhibit the pathway upstream of both classes, and thus decrease formation of both the cysteinyl leukotrienes and LTB4. LTA4H inhibitors selectively inhibit LTB4 synthesis and do not impact cysteinyl leukotriene (CysLT) synthesis. Both classes of leukotrienes are elevated in asthma, and LTB4 is more significantly increased in severe asthma, which is associated with increased neutrophilic inflammation.

Several preclinical and clinical findings suggest that inhibition of LTB4 synthesis by LTA4H inhibitors will have therapeutic benefit in asthma. Studies in mice lacking LTB4 receptors have shown that LTB4 plays a role in eosinophil and effector T cell recruitment, IL-13 production, goblet cell hyperplasia and mucus secretion, IgE production and airway hyperreactivity (Miyahara et al., Allergy Intl. 2006, 55, 91-97). The importance of LTB4 in development in airway hyperreactivity is supported by data with the LTB4 receptor antagonist (CP-105,696), which reduced airway hyperresponsiveness induced by multiple antigen challenges in a primate model (C. R. Turner et al., J. Clin. Invest. 1996, 97, 381-387). Furthermore, the reduction of bronchial hyperresponsiveness in human asthma by the 5-LO inhibitor, zileuton, has been attributed to its inhibition of LTB4 synthesis (S. E. Dahlen et al., Eur. J. Pharmacol. 2006, 533(1-3), 40-56). Inhibition of LTB4 may also be beneficial in severe asthma (S. E. Wenzel et al., Am. J. Respir. Crit. Care Med. 1997, 156, 737-743) and viral exacerbations of asthma (S. D. Message, Eur. Respir. J. 2001, 18, 1013-1025), where neutrophilic inflammation is more prominent. CysLT antagonists and steroids have limited efficacy in severe asthmatics, while zileuton has been shown to significantly improve quality of life in these patients (R. Menendez et al., American Thoracic Society Meeting, San Diego, 2006).

An allergy is an abnormal reaction to an allergen (an ordinarily harmless substance) that triggers an abnormal response in a sensitized individual. Allergic rhinitis is an inflammation of the mucus membranes of the nose that occurs in response to an airborne antigen (allergen). Allergic rhinitis, also called allergic rhinoconjunctivitis, is characterized by frequent or repetitive sneezing, runny or congested nose, and pruritus of the nose, eyes and throat. It may also be associated with other symptoms such as headache, impaired smell, postnasal drip, conjunctival symptoms (e.g., itchy watery eyes), sinusitis and other complicating respiratory symptoms. Depending upon the time of exposure, allergic rhinitis can be classified as perennial, seasonal or occupational.

Embodiments of this invention have shown dose-dependent inhibition of lung inflammation in pre-clinical models, Based upon the well-described leukotriene biosynthesis pathway, LTA4H inhibitors are hypothesized to specifically block the production of LTB4 from LTA4, without affecting the biosynthesis of lipoxins, which are also produced from LTA4. Lipoxins, such as $LXA_4$, have been the focus of intense study and are known to play a key role as natural anti-inflammatory agents and key mediators of the natural process of resolving an inflammatory response. Furthermore, production of endogenous $LXA_4$ has been described in a variety of inflammatory diseases and lower levels of $LXA_4$ have been found in patients with severe versus moderate asthma. These data are consistent with the proposition that $LXA_4$ plays an important role in resolution of acute inflammation. Unlike LTA4H inhibitors, 5-LO inhibitors block this pathway upstream of LTA4. This would lead to a block in not only synthesis of LTA4, LTB4 and cysteinyl leukotrienes, but also $LXA_4$. Furthermore, there is a possibility that LTA4H inhibitors result in a buildup of LTA4, and pathway shunting to pro-inflammatory cysteinyl leukotrienes, although to date there is no known data to support this possibility.

Neutrophil infiltration is a prominent feature of severe asthma. Zileuton (Zyflo®), which targets both LTB4 and cysteinyl leukotrienes, has been suggested to be efficacious in severe asthma patients, while CysLT antagonists (for example, Montelukast/Singulair®), which target only cysteinyl leukotrienes, show limited efficacy. Combination of an LTA4H inhibitor and at least one of a CysLT receptor antagonist and LTC4 synthase inhibitor would target both LTB4 and cysteinyl leukotrienes, while leaving production of the anti-inflammatory lipoxins intact. Embodiments of this invention reduced inflammatory responses to airway allergen challenge in sensitized mice, leading to dose-dependent decreases airway recruitment of inflammatory cells.

Embodiments of this invention are expected to find utility in treating inflammatory bowel disease. In trinitrobenzene sulfonic acid (TNBS)-induced colitis in rats, LTA4H inhibition had significant inhibitory effects on colonic inflammation, including macroscopic colonic injury, inflammatory cell content, and levels of tumor necrosis factor alpha (TNF-α), LTB4, and IL-6. Whittle et al. (Br J. Pharmacol. 2008, 153, 983-991). LTA4H inhibition also significantly attenuated the joint inflammation and swelling associated with the destruction of collagen in murine models of arthritis. Mice deficient in receptors for LTB4 or lacking LTA4H do not develop arthritis in murine models (Mathis, S., et al. Role of leukotriene B4 receptors in rheumatoid arthritis, Autoimmun. Rev. 2007 November, 7(1):12-7). Embodiments of this invention are thus expected to find utility in treating arthritis, including, but not limited to, rheumatoid arthritis.

Abdominal aortic aneurysm (AAA) is a localized dilatation of the abdominal aorta that exceeds the normal diameter (2 cm) by more than 50%. It is caused by a degenerative process of the aortic wall. An aortic aneurysm may also occur in the thorax. Surgery is eventually required to prevent the progression to AAA rupture, which is most often a fatal event. Thus therapeutics which delay or prevent the need for surgery are an unmet medical need.

Recent genetic studies in humans as well as studies in mice and rabbits have implicated the leukotriene synthesis pathway in cardiovascular disease (reviewed in Whatling et al., *Expert Opin Investig Drugs* 2007, 16(12), 1879-93). In a well-established murine abdominal aortic aneurysm (AAA) model, mice that lack the receptor for LTB4 exhibit a reduced incidence of AAA formation (Ahluwalia et al., *J. Immunol.* 2007, 179(1), 691-7). Diminished AAA formation in LTB4-receptor-deficient mice was associated with significant reductions in mononuclear cell chemoattractants and leukocyte accumulation in the vessel wall, as well as striking reductions in the production of matrix metalloproteinases-2 and -9. Thus, it has been shown that signaling by LTB4 through its receptor contributes to the frequency and size of abdominal aortic aneurysms in mice, and prevention of LTB4 signaling by deletion of the gene coding for the LTB4 receptor in turn inhibits proinflammatory circuits and enzymes that modulate vessel wall integrity. Thus LTB4 signaling is a target for intervention in modulating development of aortic aneurysms. Inhibitors of LTA4H in the context of this invention are expected to have utility in inhibition of aortic aneurysms.

Embodiments of this invention are expected to find utility in treating also any one or a combination of atopic dermatitis, contact dermatitis, acne (T. Alestas, et al., *J. Mol. Med.* 2006, 84(1): 75-87; Ch. C. Zouboulis, et al., *Dermatology,* 2005, 210(1): 36-8; *Arch. Dermatol.* 2003, 139(5): 668-70), myocardial infarction (A. Helgadottir, et al., *Nat. Genet.* 2006, 38(1): 68-74; *Nat. Genet.* 2004, 36(3): 233-9; H. Hakonarson, et al., *JAMA* 2005, 293(18): 2245-56), stroke (A. Helgadottir, et al., *Nat. Genet.* 2004, 36(3): 233-9; F. C. Barone, et al., *Mol. Chem. Neuropathol.* 1995, 24(1): 13-30), pain (J. M. Cunha, et al., *Br. J. Pharmacol.* 2003, 139(6): 1135-45; S. W. Hwang, et al., *Proc. Natl. Acad. Sci. USA* 2000, 97(11): 6155-60), itch (T. Andoh, et al., *Eur. J. Pharmacol.* 2006, 547(1-3): 59-64, 2000, 406(1): 149-152, 1998, 353(1): 93-96); *J. Investigativ. Dermatol.* 2004, 123(1): 196-201, 2001, 117(6): 1621-26; gingivitis (G. Emingil, et al., *J. Periodontol.* 2001, 72(8): 1025-31), uveitis (T. Liao, et al., *Invest. Opthalmol. Vis. Sci.* 2006, 47(4): 1543-9), bronchitis (S. Gompertz, et al., *Eur. Respir. J.* 2001, 17(6): 1112-9), allergic rhinitis, cystic fibrosis (G. E. Carpagnano, et al., *Am. J. Respir. Crit. Care Med.* 2003, 167(8): 1109-12), upper gastrointestinal cancer (X. Chen, et al., *Curr. Cancer Drug Targets* 2004, 4(3): 267-83; *J. Natl. Cancer Inst.* 2003, 95(14): 1053-61), and sepsis (H. Nakae, et al., *Res. Commun. Chem. Pathol. Pharmacol.* 1994, 83(2): 151-6, and 84(3): 271-81), Sjogren Larsson syndrome, Sjogren syndrome, and skin burns, such as those due to sunburn or some other agent.

Examples of textbooks on the subject of inflammation include: 1) Gallin, J. I.; Snyderman, R., *Inflammation: Basic Principles and Clinical Correlates*, 3rd ed.; Lippincott Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al. *Textbook Of Medicine*, 18th ed.; W.B. Saunders Co., 1988; and 4) Stedman's Medical Dictionary.

Background and review material on inflammation and conditions related with inflammation can be found in articles such as the following: C. Nathan, Points of control in inflammation, *Nature* 2002, 420: 846-852; K. J. Tracey, The inflammatory reflex, *Nature* 2002, 420: 853-859; L. M. Coussens and Z. Werb, Inflammation and cancer, *Nature* 2002, 420: 860-867; P. Libby, Inflammation in atherosclerosis, *Nature* 2002, 420: 868-874; C. Benoist and D. Mathis, Mast cells in autoimmune disease, *Nature* 2002, 420: 875-878; H. L. Weiner and D. J. Selkoe, Inflammation and therapeutic vaccination in CNS diseases, *Nature* 2002, 420: 879-884; J. Cohen, The immunopathogenesis of sepsis, *Nature* 2002, 420: 885-891; D. Steinberg, Atherogenesis in perspective: Hypercholesterolemia and inflammation as partners in crime, *Nature Medicine* 2002, 8(11): 1211-1217.

Inflammation is due to or associated with any one of a plurality of conditions, such as asthma, chronic obstructive pulmonary disease (COPD), atherosclerosis, rheumatoid arthritis, multiple sclerosis, inflammatory bowel diseases (including Crohn's disease and ulcerative colitis), psoriasis, atopic dermatitis, contact dermatitis, acne, myocardial infarction, stroke, pain, itch (pruritus), gingivitis, uveitis, bronchitis, allergic rhinitis, cystic fibrosis, upper gastrointestinal cancer, sepsis, Sjogren syndrome, Sjogren-Larssen syndrome, and skin burns, which are each characterized by excessive or prolonged inflammation at some stage of the disease.

Organ transplant rejection and autoimmune disease treatment with a cyclooxygenase-2 inhibitor and an LTA4H inhibitor are disclosed in WO1997/29774, U.S. Patent Appl. Publ. Nos. US2003/004191 and US2005/043355, and in U.S. Pat. Nos. 5,700,816, 6,407,140. LTA4H inhibitors are disclosed in U.S. Pat. Nos. 5,719,306, 6,506,876, 5,723,492, 5,585,492, and publication WO1996/11192. Cyclic and bicyclic diamino histamine-3 receptor antagonists are disclosed in U.S. Pat. No. 6,559,140. Benzothiazole and benzoxazole LTA4H modulators have been described in U.S. Patent Appl. Publ. Nos. US2005/0043378 and US2005/0043379, and by Grice et al. (Abstracts of Papers, 234th ACS National Meeting, Boston, Mass., United States, Aug. 19-23, 2007), Rao et al. (*J. Pharmacol. Exp. Ther.* 2007, 321(3), 1154-1160) and Whittle et al. (Br J. Pharmacol. 2008, 153, 983-991). In addition, diamine derivatives are described as LTA4H inhibitors in U.S. Patent Appl. Publ. No. 2007/0155726 and Intl. Patent Appl. Publ. No. WO2007/079078. Aryl-substituted bridged diamines are disclosed as LTA4H modulators in U.S. Provisional Pat. Appl. No. 60/984,126. Combinations of a cyclooxygenase-2 inhibitor and an LTA4H inhibitor for the treatment of inflammation and inflammation-related disorders are disclosed in U.S. Pat. No. 5,990,148 and in publication WO1996/41625. Nitrogeneous derivatives have been disclosed in patent-related as well as in nonpatent-related publications, such as WO2008/016811; US2008/0057074; WO2006/002133; U.S. Pat. No. 6,316,490; U.S. Pat. No. 6,632,823; U.S. Pat. No. 6,432,976; WO2006/133802; WO2003/037904; EP 623621; EP 416521; S. Collin, *J Pharmacie de Belgique*, 1991, 46(1) 55-66; P. Dostert, et al., *European. J. Med. Chem.*, 1984, 19(2) 105-110; FR 2446823; U.S. Pat. No. 4,410,535; U.S. Pat. No. 4,352,802; U.S. Pat. No. 4,471,120; U.S. Pat. No. 4,424,358; U.S. Pat. No. 4,321,378; U.S. Pat. No. 4,329,466; U.S. Pat. No. 4,536,580; U.S. Pat. No. 4,273,778; U.S. Pat. No. 4,336,259; U.S. Pat. No. 4,544,660; U.S. Pat. No. 4,599,420; and U.S. Pat. No. 4,705,858. However, there remains a need for potent LTA4H modulators with desirable pharmaceutical properties.

Certain thiazolopyridin-2-yloxy-phenyl and thiazolopyrazin-2-yloxy-phenyl amine derivatives have been found in the context of this invention to have LTA4H-modulating activity. References cited throughout the written description are incorporated herein by reference.

SUMMARY OF THE INVENTION

In one aspect the invention relates to chemical entities selected from compounds of Formula (I), pharmaceutically acceptable salts of compounds of Formula (I), pharmaceutically acceptable prodrugs of compounds of Formula (I), solvates of compounds of Formula (I), and pharmaceutically active metabolites of compounds of Formula (I):

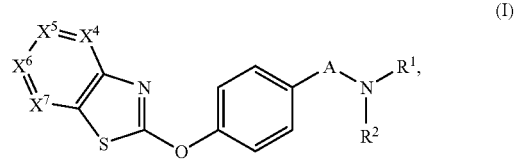

wherein
$X^4$, $X^5$, $X^6$, and $X^7$ are defined as one of the following a) and b):
  a) one of $X^4$, $X^5$, $X^6$ and $X^7$ is N and the others are $CR^a$; where each $R^a$ is independently H, methyl, chloro, fluoro, or trifluoromethyl; and
  b) each of $X^4$ and $X^7$ is N and each of $X^5$ and $X^6$ is CH;
each of $R^1$ and $R^2$ is independently H, —$(CH_2)_{2-3}OCH_3$, —$CH_2C(O)NH_2$, —$(CH_2)_3NH_2$, —$(CH_2)_{1-2}CO_2H$, —$CH_2CO_2CH_2CH_3$, benzyl, 3-(2-oxo-pyrrolidin-1-yl)-propyl, 1-acetyl-azetidin-3-ylmethyl, monocyclic cycloalkyl, 1-methyl-4-piperidinyl, or —$C_{1-4}$alkyl unsubstituted or substituted with phenyl, monocyclic cycloalkyl, OH, or $NR^bR^c$C;
  where $R^b$ and $R^c$ are each independently H, —$C(O)CH_3$, or $C_{1-4}$alkyl, or $R^b$ and $R^c$ taken together with the nitrogen to which they are attached form a saturated monocyclic heterocycloalkyl ring; or
$R^1$ and $R^2$ taken together with the nitrogen to which they are attached form:

i) a saturated monocyclic heterocycloalkyl ring, optionally fused to a phenyl ring, and unsubstituted or substituted with one or two $R^d$ substituents;

where each $R^d$ substituent is independently $C_{1-4}$alkyl unsubstituted or substituted with —OH; —OH; =O; —(CH$_2$)$_{0-2}$N(CH$_3$)$_2$; —CF$_3$; halo; —CO$_2$C$_{1-4}$alkyl; —(CH$_2$)$_{0-2}$CO$_2$H; —C(O)NH$_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —C(O)NR$^f$C$_{1-4}$alkyl; —C(O)NHC(CH$_3$)$_2$CH$_2$OH; —O-pyridinyl, —O-pyrimidinyl; —S-phenyl; (4-methylphenyl)sulfanyl; —S-pyridinyl; —C(O)—C$_{1-4}$alkyl; —C(O)-saturated monocyclic cycloalkyl; —C(O)—(CH$_2$)$_{0-1}$-2-thiophene-yl; —C(O)-2-furanyl; —C(O)-4-morpholinyl; —C(O)-pyridyl; —C(O)-1-pyrrolidinyl; —C(O)-phenyl optionally substituted with a chloro; —C(O)-1-piperazinyl optionally substituted with C$_{1-4}$alkyl; —(CH$_2$)$_{0-1}$NHC(O)—C$_{1-4}$alkyl; —NHC(O)-saturated monocyclic cycloalkyl; —NHS(O)(O)CH$_3$; —NHC(O)—CH$_2$OCH$_3$; —NHC(O)-pyridinyl; or —NHC(O)-2-thiophene-yl, where each phenyl in $R^d$ is unsubstituted or substituted with —CF$_3$, halo, or methoxy; or ii) one of the following moieties:

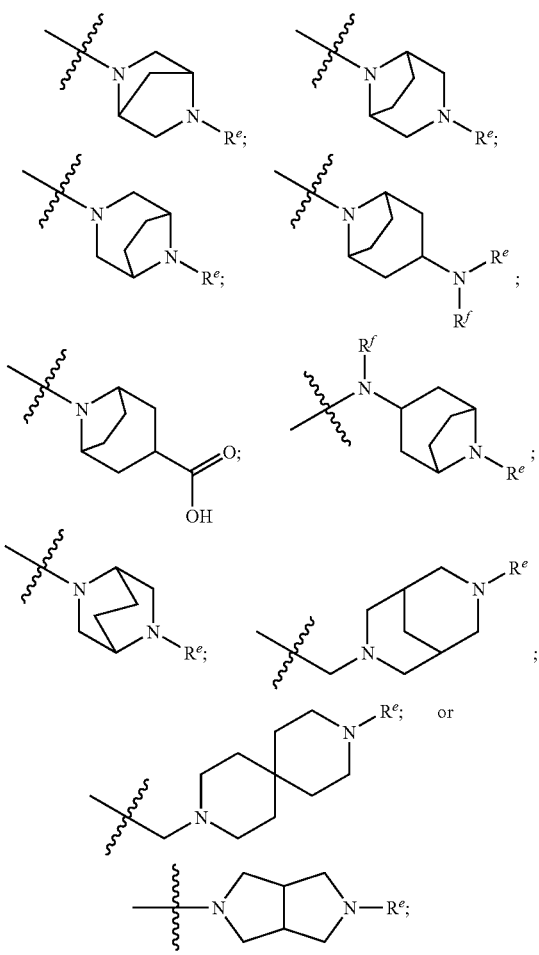

where $R^e$ is —C$_{1-4}$alkyl, C(O)C$_{1-4}$alkyl, —SO$_2$CH$_3$, —C(O)CH$_2$NH$_2$, or C(O)NH$_2$;

$R^f$ is H or —CH$_3$; and

A is —CH$_2$—, —CH$_2$CH$_2$—, or —OCH$_2$CH$_2$—.

In certain embodiments, the compound of Formula (I) is a compound selected from those species described or exemplified in the detailed description below.

In a further aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), solvates of compounds of Formula (I), and pharmaceutically active metabolites of Formula (I). Pharmaceutical compositions according to the invention may further comprise a pharmaceutically acceptable excipient.

In another aspect, embodiments of the invention are useful as LTA4H modulators. Thus, the invention is directed to a method for modulating LTA4H activity, comprising exposing LTA4H to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit LTA4H activity.

In another aspect, the invention is directed to a method of treating a subject suffering from or diagnosed with a disease, disorder, or medical condition mediated by LTA4H activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is inflammation, atopic dermatitis, or asthma.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION AND ITS PREFERRED Embodiments

For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle.

Illustrative examples of cycloalkyl groups include the following entities, in the form of properly bonded moieties:

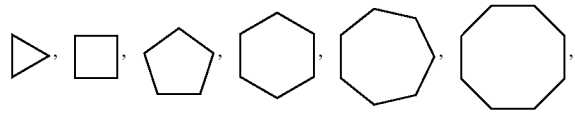

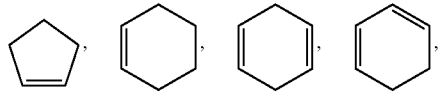

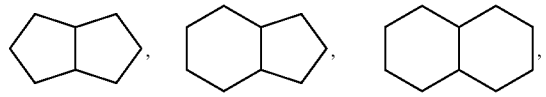

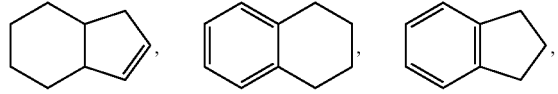

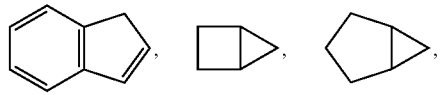

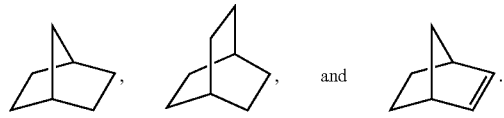

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

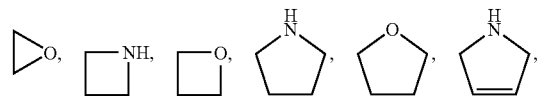

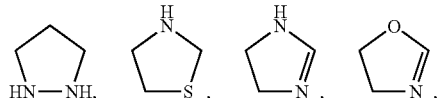

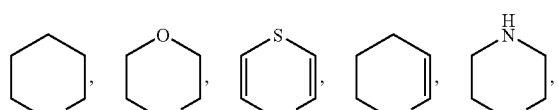

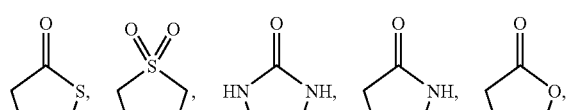

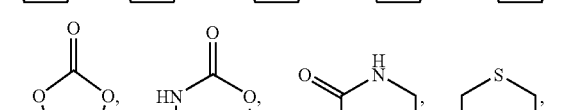

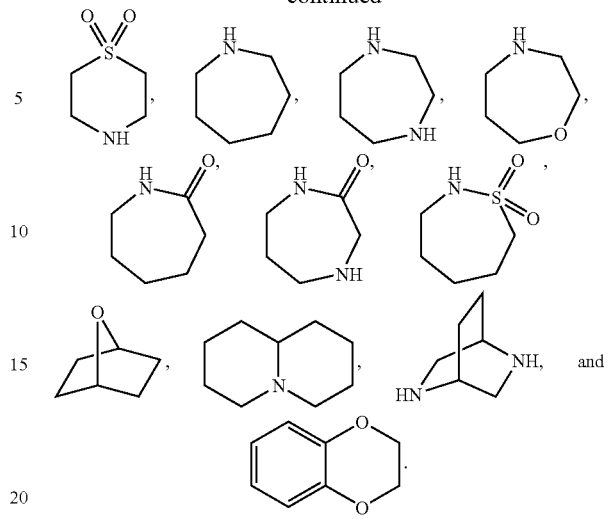

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

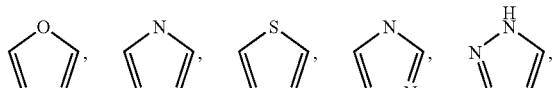

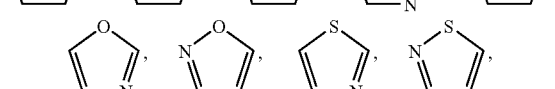

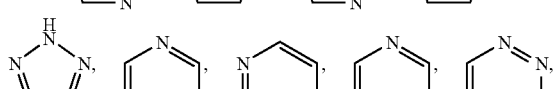

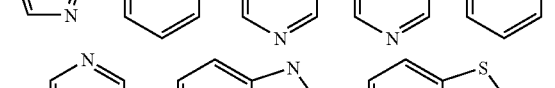

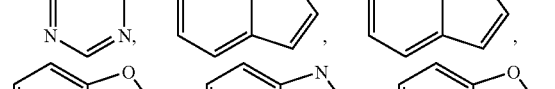

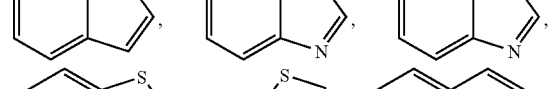

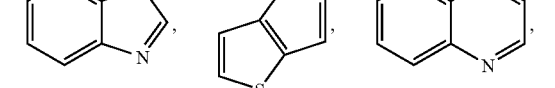

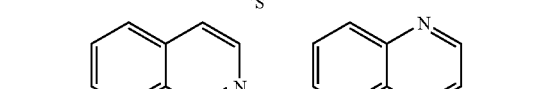

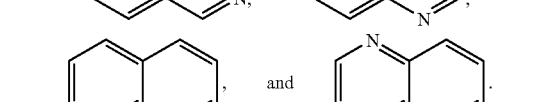

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

Certain formulae given herein are meso compounds, which are compounds that possess asymmetric centers (in this case, asymmetric carbons), but which are achiral molecules. Such compounds are named herein as meso compounds. In some cases, meso compounds are depicted and named herein with a specific stereochemical configuration. However, one skilled in the art will recognize the meso nature of such compounds. Examples include meso-3,8-diazabicyclo[3.2.1]octane-3-carboxamide and meso-1-[(3-endo)-8-azabicyclo[3.2.1]oct-3-yl]urea.

Compounds that incorporate amines such as ExA, ExB, ExC, and ExD, which are listed below, are described as "endo" or "exo" in their chemical name to denote the orientation of the two-methylene bridge with respect to the functionalized exocyclic amine. One skilled in the art will recognize that ExA and ExB are equivalent and that ExC and ExD are equivalent. Furthermore, stereochemical labels for stereocenters (e.g., R and/or S) in meso compounds have been omitted since such labels are extraneous due to the plane of symmetry.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and then the solvates are hydrates. Hydrates, such as the monohydrate, of compounds of formula (I) were obtained. Solvates of salts of compounds of formula (I) were obtained in solvated, including hydrated, forms. Solvated salts included, for example, hydrocholorides, phosphates, benzoates, and sulfates. Solvates included hydrates and methanolates. Some embodiments of solvates were mono-solvates, such as monohydrates and monomethanolates. Other embodiments of solvates were hemisolvates, such as hemihydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, pharmaceutically acceptable salts of compounds of Formula (I) were obtained in a crystalline form. Compounds of formula (I) and salts thereof exist in a plurality of forms, which can be isolated according to a plurality of methods. In some embodiments, crystals of compounds of formula (I) and their salts were obtained by crystallization from a ketone-based medium, such as from 2-butanone, acetone, and a methanol/methyl ethyl ketone mixture. In some embodiments, crystals in other forms of compounds of formula (I) and their salts were obtained by crystallization from an acidic medium, such as from methanol with lactic acid. In still other embodiments, crystals in other forms of compounds of formula (I) and their salts were obtained by crystallization from an acetonitrile-based medium, such as from a methanol/acetonitrile mixture. Other solvents from which embodiments of salts according to this invention were crystallized include anisole/pyridine mixtures, m-xylene/pyridine mixtures, dimethyl sulfoxide (DMSO)/m-xylene mixtures, methanol/methyl-t-butyl ester (MTBE) mixtures, m-xylene/N-methylpyrrolidone (NMP) mixtures, and chloroform/NMP mixtures. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the

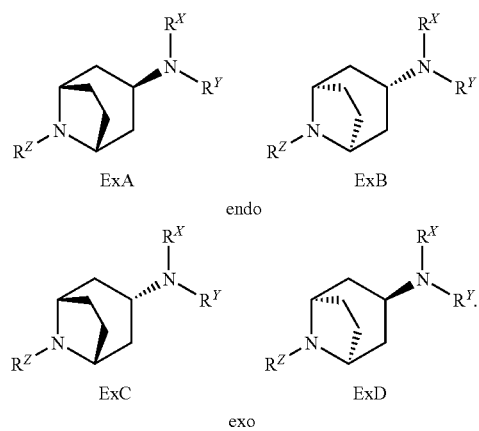

medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—OOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological merest (ChEBI) dictionary of molecular entities. (See, for example its on line version at http://www.ebi.ac.uk/chebi/init.do). As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art.

Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{32}P$, $^{33}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, and $R^e$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, and $R^e$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formula (I), $X^4$ is N and each of $X^5$, $X^6$, and $X^7$ is $CR^a$, with $R^a$ independently chosen for $X^5$, $X^6$, and $X^7$, where $R^a$ is H, methyl, chloro, or fluoro. In other embodiments, $X^5$ is N and each of $X^4$, $X^6$, and $X^7$ is CH. In still other embodiments, each of $X^4$, $X^5$, and $X^7$ is CH and $X^6$ is N. In still other embodiments, each of $X^4$ and $X^7$ is N and each of $X^5$ and $X^6$ is CH. In some embodiments, $R^a$ is H.

In some embodiments, each of $R^1$ and $R^2$ is independently H, cyclopropyl, methyl, ethyl, propyl, hydroxyethyl, cyclopropylmethyl, benzyl, 1-phenylethyl, or 2-piperidin-1-ylethylamino. In other embodiments, $R^1$ and $R^2$ taken together with the nitrogen to which they are attached form pyrrolidine, piperidine, morpholine, piperazine, dihydroisoindole, tetrahydroquinoline, or tetrahydroisoquinoline, unsubstituted or substituted with one or two $R^d$ substituents. In some embodiments, each $R^d$ substituent is independently hydroxy, methyl, trifluoromethyl, hydroxymethyl, 1-hydroxy-1-methylethyl, fluoro, ethoxycarbonyl, carboxy, carbamoyl, phenyl, 3-trifluoromethylphenyl, 2-methoxyphenyl, 4-chlorophenyl, benzyl, pyridin-4-yl, pyridin-2-yl, pyrimidin-2-yloxy, pyridin-3-yloxy, phenoxy, phenylsulfanyl, 4-chlorophenylsulfanyl, pyridin-2-yloxy, pyridin-4-yloxy, or pyrrolidin-2-onyl.

In some embodiments, $R^1$ and $R^2$ taken together with the nitrogen to which they are attached form 2,5-diaza-bicyclo[2.2.1]hept-2-yl, hexahydro-pyrrolo[3,4-c]pyrrol-2(1H)-yl, 3,8-diaza-bicyclo[3.2.1]oct-8-yl, or 3-amino-8-aza-bicyclo[3.2.1]oct-8-yl, each substituted with $R^e$. In some embodiments, $R^e$ is acetyl or carbamoyl.

In some embodiments, A is —$CH_2$—. In other embodiments, A is —$CH_2CH_2$—. In still other embodiments, A is —$OCH_2CH_2$—.

In some embodiments, chemical entities of the present invention are selected from the group consisting of:

| Ex. | Chemical Name |
|---|---|
| 1 | 2-(4-{2-[4-(Pyrimidin-2-yloxy)piperidin-1-yl]ethoxy}phenoxy)[1,3]thiazolo[4,5-b]pyridine; |
| 2 | 2-{4-[2-(1,3-Dihydro-2H-isoindol-2-yl)ethoxy]phenoxy}[1,3]thiazolo[4,5-b]pyridine; |
| 3 | 2-(4-{2-[4-(Phenylsulfanyl)piperidin-1-yl]ethoxy}phenoxy)[1,3]thiazolo[4,5-b]pyridine; |
| 4 | 2-(4-{2-[4-(Pyridin-3-yloxy)piperidin-1-yl]ethoxy}phenoxy)[1,3]thiazolo[4,5-b]pyridine; |
| 5 | 4-Pyridin-2-yl-1-{2-[4-([1,3]thiazolo[4,5-b]pyridin-2-yloxy)phenoxy]ethyl}piperidin-4-ol; |
| 6 | 2-{2-[4-([1,3]Thiazolo[4,5-b]pyridin-2-yloxy)phenoxy]ethyl}-1,2,3,4-tetrahydroisoquinoline; |
| 7 | 1-{2-[4-([1,3]Thiazolo[4,5-b]pyridin-2-yloxy)phenoxy]ethyl}-1,2,3,4-tetrahydroquinoline; |
| 8 | 2-{4-[2-(4-Phenoxypiperidin-1-yl)ethoxy]phenoxy}[1,3]thiazolo[4,5-b]pyridine; |
| 9 | 2-[4-(2-Pyrrolidin-1-ylethoxy)phenoxy][1,3]thiazolo[4,5-b]pyridine; |
| 10 | 2-[4-(2-Piperidin-1-ylethoxy)phenoxy][1,3]thiazolo[4,5-b]pyridine; |
| 11 | 2-[4-(2-Morpholin-4-ylethoxy)phenoxy][1,3]thiazolo[4,5-b]pyridine; |
| 12 | 2-(4-{2-[4-(Pyridin-2-yloxy)piperidin-1-yl]ethoxy}phenoxy)[1,3]thiazolo[4,5-b]pyridine; |
| 13 | 2-(4-{2-[4-(Pyridin-4-yloxy)piperidin-1-yl]ethoxy}phenoxy)[1,3]thiazolo[4,5-b]pyridine; |
| 14 | 2-(4-{2-[(1S,4S)-5-Acetyl-2,5-diazabicyclo[2.2.1]hept-2-yl]ethoxy}phenoxy)[1,3]thiazolo[4,5-b]pyridine; |
| 15 | (1S,4S)-5-{2-[4-([1,3]Thiazolo[4,5-b]pyridin-2-yloxy)phenoxy]ethyl}-2,5-diazabicyclo[2.2.1]heptane-2-carboxamide; |
| 16 | meso-N-[(3-endo)-8-{2-[4-([1,3]Thiazolo[4,5-b]pyridin-2-yloxy)phenoxy]ethyl}-8-azabicyclo[3.2.1]oct-3-yl]acetamide; |
| 17 | meso-N-[(3-exo)-8-{2-[4-([1,3]Thiazolo[4,5-b]pyridin-2-yloxy)phenoxy]ethyl}-8-azabicyclo[3.2.1]oct-3-yl]acetamide; |
| 18 | 2-{4-[2-(5-Acetylhexahydropyrrolo[3,4-c]pyrrol-2(1H)-yl)ethoxy]phenoxy}[1,3]thiazolo[4,5-b]pyridine; |

-continued

| Ex. | Chemical Name |
|---|---|
| 19 | 5-{2-[4-([1,3]Thiazolo[4,5-b]pyridin-2-yloxy)phenoxy]ethyl}hexahydropyrrolo[3,4-c]pyrrole-2(1H)-carboxamide; |
| 27 | 4-Phenyl-1-{2-[4-([1,3]thiazolo[4,5-b]pyridin-2-yloxy)phenoxy]ethyl}piperidin-4-ol; |
| 28 | 2-{4-[2-(4-Benzylpiperidin-1-yl)ethoxy]phenoxy}[1,3]thiazolo[4,5-b]pyridine; |
| 29 | 2-{4-[2-(4-Pyridin-4-ylpiperidin-1-yl)ethoxy]phenoxy}[1,3]thiazolo[4,5-b]pyridine; |
| 30 | 4-(4-Chlorophenyl)-1-{2-[4-([1,3]thiazolo[4,5-b]pyridin-2-yloxy)phenoxy]ethyl}piperidin-4-ol; |
| 31 | 1-{2-[4-([1,3]Thiazolo[4,5-b]pyridin-2-yloxy)phenoxy]ethyl}piperidine-4-carboxamide; |
| 32 | 1-(1-{2-[4-([1,3]Thiazolo[4,5-b]pyridin-2-yloxy)phenoxy]ethyl}piperidin-4-yl)pyrrolidin-2-one; |
| 33 | 1-{2-[4-([1,3]Thiazolo[4,5-b]pyridin-2-yloxy)phenoxy]ethyl}-4-[3-(trifluoromethyl)phenyl]piperidin-4-ol; |
| 34 | 2-{4-[2-(4-Pyridin-2-ylpiperidin-1-yl)ethoxy]phenoxy}[1,3]thiazolo[4,5-b]pyridine; |
| 36 | N-Benzyl-N-methyl-2-[4-([1,3]thiazolo[4,5-b]pyridin-2-yloxy)phenoxy]ethanamine; |
| 45 | (1S,4S)-5-{2-[4-([1,3]Thiazolo[4,5-b]pyridin-2-yloxy)phenyl]ethyl}-2,5-diazabicyclo[2.2.1]heptane-2-carboxamide; |
| 46 | 1-(1-{2-[4-([1,3]Thiazolo[4,5-b]pyridin-2-yloxy)phenyl]ethyl}piperidin-4-yl)pyrrolidin-2-one; |
| 47 | 4-(4-Chlorophenyl)-1-{2-[4-([1,3]thiazolo[4,5-b]pyridin-2-yloxy)phenyl]ethyl}piperidin-4-ol; |
| 48 | 2-{4-[2-(4-Pyridin-2-ylpiperidin-1-yl)ethyl]phenoxy}[1,3]thiazolo[4,5-b]pyridine; |
| 49 | meso-N-[(3-exo)-8-{2-[4-([1,3]Thiazolo[4,5-b]pyridin-2-yloxy)phenyl]ethyl}-8-azabicyclo[3.2.1]oct-3-yl]acetamide; |
| 50 | meso-1-[(3-exo)-8-{2-[4-([1,3]Thiazolo[4,5-b]pyridin-2-yloxy)phenyl]ethyl}-8-azabicyclo[3.2.1]oct-3-yl]urea; |
| 54 | meso-8-{2-[4-([1,3]Thiazolo[4,5-b]pyridin-2-yloxy)phenyl]ethyl}-3,8-diazabicyclo[3.2.1]octane-3-carboxamide; |
| 55 | meso-2-(4-{2-[3-Acetyl-3,8-diazabicyclo[3.2.1]oct-8-yl]ethyl}phenoxy)[1,3]thiazolo[4,5-b]pyridine; |
| 56 | 2-(Ethyl{2-[4-([1,3]thiazolo[4,5-b]pyridin-2-yloxy)phenyl]ethyl}amino)ethanol; |
| 57 | N-(Cyclopropylmethyl)-N-{2-[4-([1,3]thiazolo[4,5-b]pyridin-2-yloxy)phenyl]ethyl}propan-1-amine; |
| 58 | (1R)—N-Methyl-1-phenyl-N-{2-[4-([1,3]thiazolo[4,5-b]pyridin-2-yloxy)phenyl]ethyl}ethanamine; |
| 59 | 2-[4-(2-Morpholin-4-ylethyl)phenoxy][1,3]thiazolo[4,5-b]pyridine; |
| 60 | 2-[4-(2-Piperidin-1-ylethyl)phenoxy][1,3]thiazolo[4,5-b]pyridine; |
| 61 | 2-[4-(2-Pyrrolidin-1-ylethyl)phenoxy][1,3]thiazolo[4,5-b]pyridine; |
| 62 | 4-Phenyl-1-{2-[4-([1,3]thiazolo[4,5-b]pyridin-2-yloxy)phenyl]ethyl}piperidin-4-ol; |
| 63 | 2-{4-[2-(4-Benzylpiperidin-1-yl)ethyl]phenoxy}[1,3]thiazolo[4,5-b]pyridine; |
| 64 | 1-{2-[4-([1,3]Thiazolo[4,5-b]pyridin-2-yloxy)phenyl]ethyl}-4-[3-(trifluoromethyl)phenyl]piperidin-4-ol; |
| 65 | 2-{4-[2-(4-Pyridin-4-ylpiperidin-1-yl)ethyl]phenoxy}[1,3]thiazolo[4,5-b]pyridine; |
| 66 | 1-{2-[4-([1,3]Thiazolo[4,5-b]pyridin-2-yloxy)phenyl]ethyl}piperidine-4-carboxamide; |
| 73 | 2-{4-[2-(5-Acetylhexahydropyrrolo[3,4-c]pyrrol-2(1H)-yl)ethyl]phenoxy}[1,3]thiazolo[4,5-b]pyridine; |
| 74 | 5-{2-[4-([1,3]Thiazolo[4,5-b]pyridin-2-yloxy)phenyl]ethyl}hexahydropyrrolo[3,4-c]pyrrole-2(1H)-carboxamide; |
| 75 | 2-(4-{2-[(1S,4S)-5-Acetyl-2,5-diazabicyclo[2.2.1]hept-2-yl]ethyl}phenoxy)[1,3]thiazolo[4,5-b]pyridine; |
| 76 | meso-N-[(3-endo)-8-{2-[4-([1,3]Thiazolo[4,5-b]pyridin-2-yloxy)phenyl]ethyl}-8-azabicyclo[3.2.1]oct-3-yl]acetamide; |
| 77 | meso-1-[(3-endo)-8-{2-[4-([1,3]Thiazolo[4,5-b]pyridin-2-yloxy)phenyl]ethyl}-8-azabicyclo[3.2.1]oct-3-yl]urea; |
| 79 | 2-(4-{2-[(1R,4R)-5-Acetyl-2,5-diazabicyclo[2.2.1]hept-2-yl]ethyl}phenoxy)[1,3]thiazolo[4,5-b]pyridine; |
| 80 | (1R,4R)-5-{2-[4-([1,3]Thiazolo[4,5-b]pyridin-2-yloxy)phenyl]ethyl}-2,5-diazabicyclo[2.2.1]heptane-2-carboxamide; |
| 81 | 1-{2-[4-([1,3]Thiazolo[4,5-b]pyridin-2-yloxy)phenyl]ethyl}piperidine-4-carboxylic acid; |
| 82 | {4-[4-([1,3]Thiazolo[4,5-b]pyridin-2-yloxy)benzyl]morpholin-2-yl}methanol; |
| 83 | 1-{1-[4-([1,3]Thiazolo[4,5-b]pyridin-2-yloxy)benzyl]piperidin-4-yl}pyrrolidin-2-one; |
| 84 | 2-[4-(Pyrrolidin-1-ylmethyl)phenoxy][1,3]thiazolo[4,5-b]pyridine; |
| 85 | 2-[4-(Piperidin-1-ylmethyl)phenoxy][1,3]thiazolo[4,5-b]pyridine; |
| 86 | 2-[4-(Morpholin-4-ylmethyl)phenoxy][1,3]thiazolo[4,5-b]pyridine; |
| 87 | 2-(4-{[(3R)-3-Fluoropyrrolidin-1-yl]methyl}phenoxy)[1,3]thiazolo[4,5-b]pyridine; |
| 88 | 2-(4-{[(3S)-3-Methylmorpholin-4-yl]methyl}phenoxy)[1,3]thiazolo[4,5-b]pyridine; |

-continued

| Ex. | Chemical Name |
|---|---|
| 89 | 2-{1-[4-([1,3]Thiazolo[4,5-b]pyridin-2-yloxy)benzyl]piperidin-4-yl}propan-2-ol; |
| 90 | 2-(4-{[(2S)-2-Methylpiperidin-1-yl]methyl}phenoxy)[1,3]thiazolo[4,5-b]pyridine; |
| 91 | 2-Piperidin-1-yl-N-[4-([1,3]thiazolo[4,5-b]pyridin-2-yloxy)benzyl]ethanamine; |
| 92 | 2-(4-{[4-(Trifluoromethyl)piperidin-1-yl]methyl}phenoxy)[1,3]thiazolo[4,5-b]pyridine; |
| 93 | 2-{4-[(3,3-Difluoropyrrolidin-1-yl)methyl]phenoxy}[1,3]thiazolo[4,5-b]pyridine; |
| 94 | (3R)-1-[4-([1,3]Thiazolo[4,5-b]pyridin-2-yloxy)benzyl]pyrrolidin-3-ol; |
| 95 | {1-[4-([1,3]Thiazolo[4,5-b]pyridin-2-yloxy)benzyl]piperidin-4-yl}methanol; |
| 96 | 2-{4-[(4-Fluoropiperidin-1-yl)methyl]phenoxy}[1,3]thiazolo[4,5-b]pyridine; |
| 97 | 2-{4-[(4-Methylpiperidin-1-yl)methyl]phenoxy}[1,3]thiazolo[4,5-b]pyridine; |
| 98 | 2-(4-{[4-(Pyridin-3-yloxy)piperidin-1-yl]methyl}phenoxy)[1,3]thiazolo[4,5-b]pyridine; |
| 99 | 2-(4-{[4-(Pyrimidin-2-yloxy)piperidin-1-yl]methyl}phenoxy)[1,3]thiazolo[4,5-b]pyridine; |
| 100 | 1-[4-([1,3]Thiazolo[4,5-b]pyridin-2-yloxy)benzyl]piperidine-4-carboxamide; |
| 101 | 4-Pyridin-2-yl-1-[4-([1,3]thiazolo[4,5-b]pyridin-2-yloxy)benzyl]piperidin-4-ol; |
| 102 | 2-{4-[(4-Benzylpiperidin-1-yl)methyl]phenoxy}[1,3]thiazolo[4,5-b]pyridine; |
| 103 | 1-[4-([1,3]Thiazolo[4,5-b]pyridin-2-yloxy)benzyl]-4-[3-(trifluoromethyl)phenyl]piperidin-4-ol; |
| 104 | 4-(4-Chlorophenyl)-1-[4-([1,3]thiazolo[4,5-b]pyridin-2-yloxy)benzyl]piperidin-4-ol; |
| 105 | 4-Phenyl-1-[4-([1,3]thiazolo[4,5-b]pyridin-2-yloxy)benzyl]piperidin-4-ol; |
| 106 | (1S,4S)-5-[4-([1,3]Thiazolo[4,5-b]pyridin-2-yloxy)benzyl]-2,5-diazabicyclo[2.2.1]heptane-2-carboxamide; |
| 107 | meso-2-(4-{[3-Acetyl-3,8-diazabicyclo[3.2.1]oct-8-yl]methyl}phenoxy)[1,3]thiazolo[4,5-b]pyridine; |
| 108 | {(2S)-1-[4-([1,3]Thiazolo[4,5-b]pyridin-2-yloxy)benzyl]pyrrolidin-2-yl}methanol; |
| 109 | meso-N-{(3-exo)-8-[4-([1,3]Thiazolo[4,5-b]pyridin-2-yloxy)benzyl]-8-azabicyclo[3.2.1]oct-3-yl}acetamide; |
| 110 | meso-1-{(3-exo)-8-[4-([1,3]Thiazolo[4,5-b]pyridin-2-yloxy)benzyl]-8-azabicyclo[3.2.1]oct-3-yl}urea; |
| 111 | N-Ethyl-N-[4-([1,3]thiazolo[4,5-b]pyridin-2-yloxy)benzyl]ethanamine; |
| 116 | meso-N-{(3-endo)-8-[4-([1,3]Thiazolo[4,5-b]pyridin-2-yloxy)benzyl]-8-azabicyclo[3.2.1]oct-3-yl}acetamide; |
| 117 | meso-8-[4-([1,3]Thiazolo[4,5-b]pyridin-2-yloxy)benzyl]-3,8-diazabicyclo[3.2.1]octane-3-carboxamide; |
| 121 | 2-(4-{[(1S,4S)-5-Acetyl-2,5-diazabicyclo[2.2.1]hept-2-yl]methyl}phenoxy)-6-methyl[1,3]thiazolo[4,5-b]pyridine; |
| 122 | 2-(4-{[(1S,4S)-5-Acetyl-2,5-diazabicyclo[2.2.1]hept-2-yl]methyl}phenoxy)-6-chloro[1,3]thiazolo[4,5-b]pyridine; |
| 125 | 2-(4-{[(1S,4S)-5-Acetyl-2,5-diazabicyclo[2.2.1]hept-2-yl]methyl}phenoxy)-7-methyl[1,3]thiazolo[4,5-b]pyridine; |
| 126 | 2-(4-{[(1S,4S)-5-Acetyl-2,5-diazabicyclo[2.2.1]hept-2-yl]methyl}phenoxy)-5-methyl[1,3]thiazolo[4,5-b]pyridine; |
| 127 | 1-{(1S,4S)-5-[4-([1,3]Thiazolo[4,5-b]pyridin-2-yloxy)benzyl]-2,5-diazabicyclo[2.2.1]hept-2-yl}ethanone; |
| 128 | 2-(4-{[(1S,4S)-5-Acetyl-2,5-diazabicyclo[2.2.1]hept-2-yl]methyl}phenoxy)-6-fluoro[1,3]thiazolo[4,5-b]pyridine; |
| 129 | 6-Fluoro-2-[4-(piperidin-1-ylmethyl)phenoxy][1,3]thiazolo[4,5-b]pyridine; |
| 130 | Ethyl 1-[4-([1,3]thiazolo[4,5-b]pyridin-2-yloxy)benzyl]piperidine-4-carboxylate; |
| 131 | 1-[4-([1,3]Thiazolo[4,5-b]pyridin-2-yloxy)benzyl]piperidine-4-carboxylic acid; |
| 135 | 2-(4-{2-[4-(2-Methoxyphenyl)piperazin-1-yl]ethoxy}phenoxy)[1,3]thiazolo[4,5-b]pyridine; |
| 136 | 2-[4-(2-{4-[(4-Chlorophenyl)sulfanyl]piperidin-1-yl}ethoxy)phenoxy][1,3]thiazolo[4,5-b]pyridine; |
| 137 | 1-[4-([1,3]Thiazolo[4,5-b]pyridin-2-yloxy)benzyl]piperidin-4-ol; |
| 138 | 7-Methyl-2-[4-(piperidin-1-ylmethyl)phenoxy][1,3]thiazolo[4,5-b]pyridine; |
| 139 | N-{2-[4-([1,3]Thiazolo[4,5-b]pyridin-2-yloxy)phenoxy]ethyl}cyclopropanamine; |
| 140 | 2-Methyl-N-[1-(2-{4-[(6-methyl[1,3]thiazolo[4,5-b]pyridin-2-yl)oxy]phenoxy}ethyl)piperidin-4-yl]propanamide; |
| 141 | meso-2-{4-[2-(3-Acetyl-3,8-diazabicyclo[3.2.1]oct-8-yl)ethoxy]phenoxy}[1,3]thiazolo[4,5-b]pyridine; |
| 142 | meso-1-[(3-exo)-8-{2-[4-([1,3]Thiazolo[4,5-b]pyridin-2-yloxy)phenoxy]ethyl}-8-azabicyclo[3.2.1]oct-3-yl]urea; |
| 143 | 7-Methyl-2-(4-{2-[4-(pyridin-4-ylcarbonyl)piperazin-1-yl]ethoxy}phenoxy)[1,3]thiazolo[4,5-b]pyridine; |
| 145 | 6-Methyl-2-(4-{2-[4-(morpholin-4-ylcarbonyl)piperidin-1-yl]ethoxy}phenoxy)[1,3]thiazolo[4,5-b]pyridine; |
| 146 | 2-(4-{2-[5-(Cyclobutylcarbonyl)hexahydropyrrolo[3,4-c]pyrrol-2(1H)-yl]ethoxy}phenoxy)-7-methyl[1,3]thiazolo[4,5-b]pyridine; |

-continued

| Ex. | Chemical Name |
|---|---|
| 147 | 6-Chloro-2-(4-{2-[4-(furan-2-ylcarbonyl)piperazin-1-yl]ethoxy}phenoxy)[1,3]thiazolo[4,5-b]pyridine; |
| 149 | meso-3-{2-[4-([1,3]Thiazolo[4,5-b]pyridin-2-yloxy)phenoxy]ethyl}-3,8-diazabicyclo[3.2.1]octane-8-carboxamide; |
| 154 | N-[1-(2-{4-[(6-Methyl[1,3]thiazolo[4,5-b]pyridin-2-yl)oxy]phenoxy}ethyl)piperidin-4-yl]acetamide; |
| 155 | 1-{3-[(2-{4-[(6-Chloro[1,3]thiazolo[4,5-b]pyridin-2-yl)oxy]phenoxy}ethyl)(methyl)amino]propyl}pyrrolidin-2-one; |
| 158 | 1-(2-{4-[(7-Methyl[1,3]thiazolo[4,5-b]pyridin-2-yl)oxy]phenoxy}ethyl)-4-pyridin-2-ylpiperidin-4-ol; |
| 159 | meso-(3-endo)-8-acetyl-N-{2-[4-([1,3]thiazolo[4,5-b]pyridin-2-yloxy)phenoxy]ethyl}-8-azabicyclo[3.2.1]octan-3-amine; |
| 160 | N-Methyl-2-(methyloxy)-N-[2-({4-[(7-methyl[1,3]thiazolo[4,5-b]pyridin-2-yl)oxy]phenyl}oxy)ethyl]ethanamine; |
| 162 | meso-2-{[4-({2-[8-Acetyl-3,8-diazabicyclo[3.2.1]oct-3-yl]ethyl}oxy)phenyl]oxy}[1,3]thiazolo[4,5-b]pyridine; |
| 163 | N-[1-(2-{[4-([1,3]Thiazolo[4,5-b]pyridin-2-yloxy)phenyl]oxy}ethyl)piperidin-4-yl]methanesulfonamide; |
| 165 | N-Methyl-1-[2-({4-[(7-methyl[1,3]thiazolo[4,5-b]pyridin-2-yl)oxy]phenyl}oxy)ethyl]piperidine-4-carboxamide; |
| 166 | meso-N-{(3-endo)-8-[2-({4-[(7-Methyl[1,3]thiazolo[4,5-b]pyridin-2-yl)oxy]phenyl}oxy)ethyl]-8-azabicyclo[3.2.1]oct-3-yl}glycinamide; |
| 171 | meso-3-{[4-([1,3]Thiazolo[4,5-b]pyridin-2-yloxy)phenyl]methyl}-3,8-diazabicyclo[3.2.1]octane-8-carboxamide; |
| 172 | N,N-Dimethyl-1-({4-[(6-methyl[1,3]thiazolo[4,5-b]pyridin-2-yl)oxy]phenyl}methyl)piperidine-4-carboxamide; |
| 178 | N-Ethyl-N-(2-{4-[(6-methyl[1,3]thiazolo[4,5-b]pyridin-2-yl)oxy]phenyl}ethyl)butan-1-amine; |
| 181 | meso-(3-exo)-8-Acetyl-N-({4-[(6-methyl[1,3]thiazolo[4,5-b]pyridin-2-yl)oxy]phenyl}methyl)-8-azabicyclo[3.2.1]octan-3-amine; |
| 182 | meso-N-[(3-endo)-8-{[4-([1,3]Thiazolo[4,5-b]pyridin-2-yloxy)phenyl]methyl}-8-azabicyclo[3.2.1]oct-3-yl]methanesulfonamide; |
| 183 | 2-({4-[(4-Cyclobutylpiperazin-1-yl)methyl]phenyl}oxy)-6-methyl[1,3]thiazolo[4,5-b]pyridine; |
| 185 | meso-2-[(4-{[8-Acetyl-3,8-diazabicyclo[3.2.1]oct-3-yl]methyl}phenyl)oxy][1,3]thiazolo[4,5-b]pyridine; |
| 187 | 6-Chloro-2-[(4-{[4-(2-thienylcarbonyl)piperazin-1-yl]methyl}phenyl)oxy][1,3]thiazolo[4,5-b]pyridine; |
| 188 | 6-Chloro-2-[(4-{[5-(methylsulfonyl)hexahydropyrrolo[3,4-c]pyrrol-2(1H)-yl]methyl}phenyl)oxy][1,3]thiazolo[4,5-b]pyridine; |
| 189 | 6-Chloro-2-{[4-(thiomorpholin-4-ylmethyl)phenyl]oxy}[1,3]thiazolo[4,5-b]pyridine; |
| 191 | (1R,4R)-5-({4-[(6-Chloro[1,3]thiazolo[4,5-b]pyridin-2-yl)oxy]phenyl}methyl)-2,5-diazabicyclo[2.2.1]heptane-2-carboxamide; |
| 193 | (1S,4S)-5-({4-[(6-Chloro[1,3]thiazolo[4,5-b]pyridin-2-yl)oxy]phenyl}methyl)-2,5-diazabicyclo[2.2.1]heptane-2-carboxamide; |
| 197 | 6-Chloro-2-[(4-{2-[4-(cyclopropylcarbonyl)piperazin-1-yl]ethyl}phenyl)oxy][1,3]thiazolo[4,5-b]pyridine; |
| 198 | 6-Methyl-2-[(4-{2-[4-(pyrrolidin-1-ylcarbonyl)piperidin-1-yl]ethyl}phenyl)oxy][1,3]thiazolo[4,5-b]pyridine; |
| 203 | meso-3-{4-[(7-Methyl [1,3]thiazolo[4,5-b]pyridin-2-yl)oxy]benzyl}-3,8-diazabicyclo[3.2.1]octane-8-carboxamide; |
| 205 | meso-7-Methyl-2-(4-{[3-(methylsulfonyl)-3,8-diazabicyclo[3.2.1]oct-8-yl]methyl}phenoxy)[1,3]thiazolo[4,5-b]pyridine; |
| 206 | N-(1-{4-[(7-Methyl[1,3]thiazolo[4,5-b]pyridin-2-yl)oxy]benzyl}piperidin-4-yl)pyridine-4-carboxamide; |
| 209 | meso-2-(4-{2-[8-Acetyl-3,8-diazabicyclo[3.2.1]oct-3-yl]ethyl}phenoxy)-7-methyl[1,3]thiazolo[4,5-b]pyridine; |
| 210 | meso-3-{2-[4-([1,3]Thiazolo[4,5-b]pyridin-2-yloxy)phenyl]ethyl}-3,8-diazabicyclo[3.2.1]octane-8-carboxamide; |
| 211 | meso-8-{2-[4-([1,3]Thiazolo[4,5-b]pyridin-2-yloxy)phenoxy]ethyl}-3,8-diazabicyclo[3.2.1]octane-3-carboxamide; |
| 212 | meso-2-(4-{2-[8-Acetyl-3,8-diazabicyclo[3.2.1]oct-3-yl]ethyl}phenoxy)[1,3]thiazolo[4,5-b]pyridine; |
| 213 | meso-2-(4-{2-[3-(Methylsulfonyl)-3,8-diazabicyclo[3.2.1]oct-8-yl]ethoxy}phenoxy)[1,3]thiazolo[4,5-b]pyridine; |
| 214 | meso-(3-exo)-8-Acetyl-N-{2-[4-([1,3]thiazolo[4,5-b]pyridin-2-yloxy)phenyl]ethyl}-8-azabicyclo[3.2.1]octan-3-amine; |
| 215 | meso-(3-exo)-8-Acetyl-N-{2-[4-([1,3]thiazolo[4,5-b]pyridin-2-yloxy)phenoxy]ethyl}-8-azabicyclo[3.2.1]octan-3-amine; |
| 216 | 2-Methoxy-N-(1-{4-[(6-methyl[1,3]thiazolo[4,5-b]pyridin-2-yl)oxy]benzyl}piperidin-4-yl)acetamide; |
| 218 | 2-{4-[(4-tert-Butylpiperidin-1-yl)methyl]phenoxy}-6-chloro[1,3]thiazolo[4,5-b]pyridine; |
| 220 | N-(1-{4-[(6-Methyl[1,3]thiazolo[4,5-b]pyridin-2-yl)oxy]benzyl}piperidin-4-yl)thiophene-2-carboxamide; |
| 223 | 1'-(2-{4-[(6-Chloro[1,3]thiazolo[4,5-b]pyridin-2-yl)oxy]phenyl}ethyl)-1,4'-bipiperidine; |

-continued

| Ex. | Chemical Name |
|---|---|
| 225 | 3-(4-{2-[4-([1,3]Thiazolo[4,5-b]pyridin-2-yloxy)phenyl]ethyl}piperazin-1-yl)propanoic acid; |
| 229 | 6-Methyl-2-(4-{[4-(piperazin-1-ylcarbonyl)piperidin-1-yl]methyl}phenoxy)[1,3]thiazolo[4,5-b]pyridine; |
| 230 | meso-3-(2-{4-[(6-Methyl[1,3]thiazolo[4,5-b]pyridin-2-yl)oxy]phenyl}ethyl)-3,8-diazabicyclo[3.2.1]octane-8-carboxamide; |
| 233 | meso-(3-exo)-8-Acetyl-N-(2-{4-[(6-methyl[1,3]thiazolo[4,5-b]pyridin-2-yl)oxy]phenyl}ethyl)-8-azabicyclo[3.2.1]octan-3-amine; |
| 234 | meso-(3-exo)-8-Acetyl-N-methyl-N-(2-{4-[(6-methyl[1,3]thiazolo[4,5-b]pyridin-2-yl)oxy]phenyl}ethyl)-8-azabicyclo[3.2.1]octan-3-amine; |
| 235 | $N^2$-(2-{4-[(6-Chloro[1,3]thiazolo[4,5-b]pyridin-2-yl)oxy]phenoxy}ethyl)-N2-methylglycinamide; |
| 238 | meso-8-[4-([1,3]Thiazolo[4,5-b]pyridin-2-yloxy)benzyl]-8-azabicyclo[3.2.1]octane-3-carboxylic acid; |
| 239 | 6-Chloro-2-(4-{2-[5-(1-methylethyl)hexahydropyrrolo[3,4-c]pyrrol-2(1H)-yl]ethoxy}phenoxy)[1,3]thiazolo[4,5-b]pyridine; |
| 241 | N-Methyl-N-(2-{4-[(6-methyl[1,3]thiazolo[4,5-b]pyridin-2-yl)oxy]phenoxy}ethyl)-beta-alanine; |
| 243 | N-(2-{4-[(6-Chloro[1,3]thiazolo[4,5-b]pyridin-2-yl)oxy]phenyl}ethyl)-N,1-dimethylpiperidin-4-amine; |
| 245 | 6-Methyl-2-{4-[2-(4-pyridin-2-ylpiperidin-1-yl)ethyl]phenoxy}[1,3]thiazolo[4,5-b]pyridine; |
| 247 | 1-(1-Acetylazetidin-3-yl)-N-{4-[(6-chloro[1,3]thiazolo[4,5-b]pyridin-2-yl)oxy]benzyl}-N-methylmethanamine; |
| 254 | meso-(3-exo)-3-{[4-([1,3]Thiazolo[4,5-b]pyridin-2-yloxy)benzyl]amino}-8-azabicyclo[3.2.1]octane-8-carboxamide; |
| 255 | 2-[4-(2-{4-[(4-Methylphenyl)sulfanyl]piperidin-1-yl}ethoxy)phenoxy][1,3]thiazolo[4,5-b]pyridine; |
| 256 | 1'-[4-([1,3]Thiazolo[4,5-b]pyridin-2-yloxy)benzyl]-1,4'-bipiperidine; |
| 257 | 2-{4-[(4-Morpholin-4-ylpiperidin-1-yl)methyl]phenoxy}[1,3]thiazolo[4,5-b]pyridine; |
| 258 | N,N-Dimethyl-2-{1-[4-([1,3]thiazolo[4,5-b]pyridin-2-yloxy)benzyl]piperidin-2-yl}ethanamine; |
| 259 | N,N-Dimethyl-1-[4-([1,3]thiazolo[4,5-b]pyridin-2-yloxy)benzyl]piperidin-4-amine; |
| 260 | 2-{4-[(4-Phenoxypiperidin-1-yl)methyl]phenoxy}[1,3]thiazolo[4,5-b]pyridine; |
| 261 | 2-(4-{[4-(Pyridin-2-yloxy)piperidin-1-yl]methyl}phenoxy)[1,3]thiazolo[4,5-b]pyridine; |
| 262 | 2-(4-{[4-(Pyridin-4-yloxy)piperidin-1-yl]methyl}phenoxy)[1,3]thiazolo[4,5-b]pyridine; |
| 263 | 2-(4-{[4-(Pyridin-2-ylsulfanyl)piperidin-1-yl]methyl}phenoxy)[1,3]thiazolo[4,5-b]pyridine; |
| 264 | 2-(4-{[4-(Phenylsulfanyl)piperidin-1-yl]methyl}phenoxy)[1,3]thiazolo[4,5-b]pyridine; |
| 265 | 2-(4-{[(1R,4R)-5-Acetyl-2,5-diazabicyclo[2.2.1]hept-2-yl]methyl}phenoxy)[1,3]thiazolo[4,5-b]pyridine; |
| 266 | (1R,4R)-5-[4-([1,3]Thiazolo[4,5-b]pyridin-2-yloxy)benzyl]-2,5-diazabicyclo[2.2.1]heptane-2-carboxamide; |
| 267 | 2-(4-{2-[(1R,4R)-5-Acetyl-2,5-diazabicyclo[2.2.1]hept-2-yl]ethoxy}phenoxy)[1,3]thiazolo[4,5-b]pyridine; |
| 268 | (1R,4R)-5-{2-[4-([1,3]Thiazolo[4,5-b]pyridin-2-yloxy)phenoxy]ethyl}-2,5-diazabicyclo[2.2.1]heptane-2-carboxamide; |
| 269 | (4R)-4-Hydroxy-1-{1-[4-([1,3]thiazolo[4,5-b]pyridin-2-yloxy)benzyl]piperidin-4-yl}pyrrolidin-2-one; |
| 270 | (4R)-4-Hydroxy-1-(1-{2-[4-([1,3]thiazolo[4,5-b]pyridin-2-yloxy)phenoxy]ethyl}piperidin-4-yl)pyrrolidin-2-one; |
| 271 | N-Methyl-2-piperidin-1-yl-N-[4-([1,3]thiazolo[4,5-b]pyridin-2-yloxy)benzyl]ethanamine; |
| 272 | N-(3-Methoxypropyl)-N-{2-[4-([1,3]thiazolo[4,5-b]pyridin-2-yloxy)phenoxy]ethyl}cyclopropanamine; |
| 273 | Ethyl N-benzyl-N-[4-([1,3]thiazolo[4,5-b]pyridin-2-yloxy)benzyl]glycinate; |
| 274 | N-Benzyl-N-[4-([1,3]thiazolo[4,5-b]pyridin-2-yloxy)benzyl]glycine; |
| 275 | N-[4-([1,3]Thiazolo[4,5-b]pyridin-2-yloxy)benzyl]-beta-alanine; |
| 276 | 2-{4-[(5-Acetylhexahydropyrrolo[3,4-c]pyrrol-2(1H)-yl)methyl]phenoxy}[1,3]thiazolo[4,5-b]pyridine; |
| 277 | 5-[4-([1,3]Thiazolo[4,5-b]pyridin-2-yloxy)benzyl]hexahydropyrrolo[3,4-c]pyrrole-2(1H)-carboxamide; |
| 278 | meso-1-{(3-endo)-8-[4-([1,3]Thiazolo[4,5-b]pyridin-2-yloxy)benzyl]-8-azabicyclo[3.2.1]oct-3-yl}urea; |
| 279 | 6-Chloro-2-(4-piperidin-1-ylmethyl-phenoxy)[1,3]thiazolo[4,5-b]pyridine; |
| 282 | 1-{4-[(7-Methyl[1,3]thiazolo[4,5-b]pyridin-2-yl)oxy]benzyl}piperidine-4-carboxamide; |
| 283 | 1-{4-[(6-Fluoro[1,3]thiazolo[4,5-b]pyridin-2-yl)oxy]benzyl}piperidine-4-carboxamide; |
| 284 | 1-{4-[(6-Chloro[1,3]thiazolo[4,5-b]pyridin-2-yl)oxy]benzyl}piperidine-4-carboxamide; |

| Ex. | Chemical Name |
|---|---|
| 287 | meso-endo-N-[8-{4-[(6-Chloro[1,3]thiazolo[4,5-b]pyridin-2-yl)oxy]benzyl}-8-azabicyclo[3.2.1]oct-3-yl]acetamide; |
| 288 | meso-endo-N-[8-{4-[(6-Fluoro[1,3]thiazolo[4,5-b]pyridin-2-yl)oxy]benzyl}-8-azabicyclo[3.2.1]oct-3-yl]acetamide; |
| 289 | meso-endo-N-[8-{4-[(7-Methyl[1,3]thiazolo[4,5-b]pyridin-2-yl)oxy]benzyl}-8-azabicyclo[3.2.1]oct-3-yl]acetamide; |
| 290 | 2-(4-{[(1S,4S)-5-Acetyl-2,5-diazabicyclo[2.2.2]oct-2-yl]methyl}phenoxy)[1,3]thiazolo[4,5-b]pyridine; |
| 291 | meso-N-{(3-endo)-8-[4-([1,3]Thiazolo[4,5-b]pyridin-2-ylmethyl)benzyl]-8-azabicyclo[3.2.1]oct-3-yl}acetamide; |
| 292 | 2-(4-{[(1S,4S)-5-Acetyl-2,5-diazabicyclo[2.2.1]hept-2-yl]methyl}benzyl)[1,3]thiazolo[4,5-b]pyridine; |
| 293 | meso-N-[(3-endo)-8-{2-[4-([1,3]Thiazolo[4,5-b]pyridin-2-ylmethyl)phenoxy]ethyl}-8-azabicyclo[3.2.1]oct-3-yl]acetamide; |
| 294 | 2-(4-{2-[(1S,4S)-5-Acetyl-2,5-diazabicyclo[2.2.1]hept-2-yl]ethoxy}benzyl)[1,3]thiazolo[4,5-b]pyridine; | and pharmaceutically acceptable salts, prodrugs, solvates, and active metabolites thereof.

In other embodiments, chemical entities of the present invention are selected from the group consisting of:

| Ex. | Chemical Name |
|---|---|
| 133 | 2-[4-(Piperidin-1-ylmethyl)phenoxy][1,3]thiazolo[4,5-c]pyridine; |
| 134 | meso-N-{(3-endo)-8-[4-([1,3]Thiazolo[4,5-c]pyridin-2-yloxy)benzyl]-8-azabicyclo[3.2.1]oct-3-yl}acetamide; |
| 161 | N-(2-Hydroxy-1,1-dimethylethyl)-1-(2-{[4-([1,3]thiazolo[4,5-c]pyridin-2-yloxy)phenyl]oxy}ethyl)piperidine-4-carboxamide; |
| 164 | 2-{[4-({2-[4-(Trifluoromethyl)piperidin-1-yl]ethyl}oxy)phenyl]oxy}[1,3]thiazolo[4,5-c]pyridine; |
| 186 | N-(Cyclopropylmethyl)-N-{[4-([1,3]thiazolo[4,5-c]pyridin-2-yloxy)phenyl]methyl}propan-1-amine; |
| 190 | 2-({4-[(4-Pyridin-4-ylpiperidin-1-yl)methyl]phenyl}oxy)[1,3]thiazolo[4,5-c]pyridine; |
| 192 | N-(1-{2-[4-([1,3]Thiazolo[5,4-c]pyridin-2-yloxy)phenyl]ethyl}piperidin-4-yl)cyclopropanecarboxamide; |
| 195 | (4-Chlorophenyl)(1-{2-[4-([1,3]thiazolo[4,5-c]pyridin-2-yloxy)phenyl]ethyl}piperidin-4-yl)methanone; |
| 196 | N-Propyl-N-{2-[4-([1,3]thiazolo[4,5-c]pyridin-2-yloxy)phenyl]ethyl}propan-1-amine; |
| 202 | meso-3-[4-([1,3]Thiazolo[4,5-c]pyridin-2-yloxy)benzyl]-3,8-diazabicyclo[3.2.1]octane-8-carboxamide; |
| 221 | 2-[4-(2-Pyrrolidin-1-ylethyl)phenoxy][1,3]thiazolo[4,5-c]pyridine; |
| 224 | 1-Methyl-4-[4-([1,3]thiazolo[4,5-c]pyridin-2-yloxy)benzyl]piperazin-2-one; |
| 231 | meso-(3-exo)-8-Acetyl-N-[4-([1,3]thiazolo[4,5-c]pyridin-2-yloxy)benzyl]-8-azabicyclo[3.2.1]octan-3-amine; |
| 232 | meso-8-{2-[4-([1,3]Thiazolo[4,5-c]pyridin-2-yloxy)phenoxy]ethyl}-3,8-diazabicyclo[3.2.1]octane-3-carboxamide; |
| 240 | N-(Cyclopropylmethyl)-N-{2-[4-([1,3]thiazolo[4,5-c]pyridin-2-yloxy)phenoxy]ethyl}-beta-alanine; |
| 244 | meso-2-(4-{2-[3-Acetyl-3,8-diazabicyclo[3.2.1]oct-8-yl]ethoxy}phenoxy)[1,3]thiazolo[4,5-c]pyridine; |
| 253 | N-Ethyl-N-[4-([1,3]thiazolo[4,5-c]pyridin-2-yloxy)benzyl]cyclohexanamine; | and pharmaceutically acceptable salts, prodrugs, solvates, and active metabolites thereof.

In some embodiments, chemical entities of the present invention are selected from the group consisting of:

| Ex. | Chemical Name |
|---|---|
| 114 | 2-[4-(Piperidin-1-ylmethyl)phenoxy][1,3]thiazolo[5,4-c]pyridine; |
| 115 | meso-N-{(3-endo)-8-[4-([1,3]Thiazolo[5,4-c]pyridin-2-yloxy)benzyl]-8-azabicyclo[3.2.1]oct-3-yl}acetamide; |
| 144 | 1-(1-{2-[4-([1,3]Thiazolo[5,4-c]pyridin-2-yloxy)phenoxy]ethyl}piperidin-4-yl)pyrrolidin-2-one; |
| 151 | 2-(4-{2-[(1R,4R)-5-(Methylsulfonyl)-2,5-diazabicyclo[2.2.1]hept-2-yl]ethoxy}phenoxy)[1,3]thiazolo[5,4-c]pyridine; |

| Ex. | Chemical Name |
|---|---|
| 156 | 3-[(Cyclopropylmethyl){2-[4-([1,3]thiazolo[5,4-c]pyridin-2-yloxy)phenoxy]ethyl}amino]propan-1-ol; |
| 175 | N-Methyl-N-[4-([1,3]thiazolo[5,4-c]pyridin-2-yloxy)benzyl]cyclohexanamine; |
| 176 | 2-{4-[2-(4-Acetylpiperazin-1-yl)ethyl]phenoxy}[1,3]thiazolo[5,4-c]pyridine; |
| 200 | meso-1-{(3-exo)-8-[4-([1,3]Thiazolo[5,4-c]pyridin-2-yloxy)benzyl]-8-azabicyclo[3.2.1]oct-3-yl}urea; |
| 204 | N-(Cyclopropylmethyl)-N-[4-([1,3]thiazolo[5,4-c]pyridin-2-yloxy)benzyl]propane-1,3-diamine; |
| 208 | 3-(Cyclopropyl{2-[4-([1,3]thiazolo[5,4-c]pyridin-2-yloxy)phenoxy]ethyl}amino)propan-1-ol; |
| 217 | 2-(4-{[4-(Pyridin-2-ylcarbonyl)piperazin-1-yl]methyl}phenoxy)[1,3]thiazolo[5,4-c]pyridine; |
| 226 | 2-{4-[(4-Acetyl-1,4-diazepan-1-yl)methyl]phenoxy}[1,3]thiazolo[5,4-c]pyridine; |
| 227 | 2-[4-({4-[(4-Methylpiperazin-1-yl)carbonyl]piperidin-1-yl}methyl)phenoxy][1,3]thiazolo[5,4-c]pyridine; |
| 236 | 2-[4-(2-Azetidin-1-ylethoxy)phenoxy][1,3]thiazolo[5,4-c]pyridine; |
| 246 | 5-{2-[4-([1,3]Thiazolo[5,4-c]pyridin-2-yloxy)phenyl]ethyl}hexahydropyrrolo[3,4-c]pyrrole-2(1H)-carboxamide; |
| 248 | 2-(4-{[4-(Pyridin-3-yloxy)piperidin-1-yl]methyl}phenoxy)[1,3]thiazolo[5,4-c]pyridine; |
| 249 | meso-N-{(3-exo)-8-[4-([1,3]Thiazolo[5,4-c]pyridin-2-yloxy)benzyl]-8-azabicyclo[3.2.1]oct-3-yl}methanesulfonamide; |
| 250 | N-[(1-{2-[4-([1,3]Thiazolo[5,4-c]pyridin-2-yloxy)phenoxy]ethyl}piperidin-4-yl)methyl]acetamide; | and pharmaceutically acceptable salts, prodrugs, solvates, and active metabolites thereof.

In other embodiments, chemical entities of the present invention are selected from the group consisting of:

| Ex. | Chemical Name |
|---|---|
| 20 | 2-(4-{2-[(1S,4S)-5-Acetyl-2,5-diazabicyclo[2.2.1]hept-2-yl]ethoxy}phenoxy)[1,3]thiazolo[5,4-b]pyridine; |
| 21 | (1S,4S)-5-{2-[4-([1,3]Thiazolo[5,4-b]pyridin-2-yloxy)phenoxy]ethyl}-2,5-diazabicyclo[2.2.1]heptane-2-carboxamide; |
| 35 | 1-{2-[4-([1,3]Thiazolo[5,4-b]pyridin-2-yloxy)phenoxy]ethyl}piperidine-4-carboxamide; |
| 37 | 1-{2-[4-([1,3]Thiazolo[5,4-b]pyridin-2-yloxy)phenoxy]ethyl}-4-[3-(trifluoromethyl)phenyl]piperidin-4-ol; |
| 38 | 2-{4-[2-(4-Pyridin-2-ylpiperidin-1-yl)ethoxy]phenoxy}[1,3]thiazolo[5,4-b]pyridine; |
| 39 | 4-(4-Chlorophenyl)-1-{2-[4-([1,3]thiazolo[5,4-b]pyridin-2-yloxy)phenoxy]ethyl}piperidin-4-ol; |
| 40 | 4-Phenyl-1-{2-[4-([1,3]thiazolo[5,4-b]pyridin-2-yloxy)phenoxy]ethyl}piperidin-4-ol; |
| 41 | 2-(4-{2-[4-(2-Methoxyphenyl)piperidin-1-yl]ethoxy}phenoxy)[1,3]thiazolo[5,4-b]pyridine; |
| 42 | 2-{4-[2-(4-Pyridin-4-ylpiperidin-1-yl)ethoxy]phenoxy}[1,3]thiazolo[5,4-b]pyridine; |
| 43 | 1-(1-{2-[4-([1,3]Thiazolo[5,4-b]pyridin-2-yloxy)phenoxy]ethyl}piperidin-4-yl)pyrrolidin-2-one; |
| 44 | 1-{2-[4-([1,3]Thiazolo[5,4-b]pyridin-2-yloxy)phenoxy]ethyl}piperidine-4-carboxylic acid; |
| 51 | 2-(4-{2-[(1S,4S)-5-Acetyl-2,5-diazabicyclo[2.2.1]hept-2-yl]ethyl}phenoxy)[1,3]thiazolo[5,4-b]pyridine; |
| 52 | meso-N-[(3-endo)-8-{2-[4-([1,3]Thiazolo[5,4-b]pyridin-2-yloxy)phenyl]ethyl}-8-azabicyclo[3.2.1]oct-3-yl]acetamide; |
| 53 | meso-2-(4-{2-[3-Acetyl-3,8-diazabicyclo[3.2.1]oct-8-yl]ethyl}phenoxy)[1,3]thiazolo[5,4-b]pyridine; |
| 67 | 1-{2-[4-([1,3]Thiazolo[5,4-b]pyridin-2-yloxy)phenyl]ethyl}piperidine-4-carboxamide; |
| 68 | 1-(1-{2-[4-([1,3]Thiazolo[5,4-b]pyridin-2-yloxy)phenyl]ethyl}piperidin-4-yl)pyrrolidin-2-one; |
| 69 | 2-{4-[2-(5-Acetylhexahydropyrrolo[3,4-c]pyrrol-2(1H)-yl)ethyl]phenoxy}[1,3]thiazolo[5,4-b]pyridine; |
| 70 | 5-{2-[4-([1,3]Thiazolo[5,4-b]pyridin-2-yloxy)phenyl]ethyl}hexahydropyrrolo[3,4-c]pyrrole-2(1H)-carboxamide; |
| 71 | meso-8-{2-[4-([1,3]Thiazolo[5,4-b]pyridin-2-yloxy)phenyl]ethyl}-3,8-diazabicyclo[3.2.1]octane-3-carboxamide; |
| 72 | meso-1-[(3-endo)-8-{2-[4-([1,3]Thiazolo[5,4-b]pyridin-2-yloxy)phenyl]ethyl}-8-azabicyclo[3.2.1]oct-3-yl]urea; |

| Ex. | Chemical Name |
|---|---|
| 78 | (1S,4S)-5-{2-[4-([1,3]Thiazolo[5,4-b]pyridin-2-yloxy)phenyl]ethyl}-2,5-diazabicyclo[2.2.1]heptane-2-carboxamide; |
| 112 | 1-{1-[4-([1,3]Thiazolo[5,4-b]pyridin-2-yloxy)benzyl]piperidin-4-yl}pyrrolidin-2-one; |
| 113 | 1-[4-([1,3]Thiazolo[5,4-b]pyridin-2-yloxy)benzyl]piperidine-4-carboxamide; |
| 118 | 2-(4-{[(1S,4S)-5-Acetyl-2,5-diazabicyclo[2.2.1]hept-2-yl]methyl}phenoxy)-5-methyl[1,3]thiazolo[5,4-b]pyridine; |
| 119 | meso-N-{(3-endo)-8-[4-([1,3]Thiazolo[5,4-b]pyridin-2-yloxy)benzyl]-8-azabicyclo[3.2.1]oct-3-yl}acetamide; |
| 123 | 2-(4-{[(1S,4S)-5-Acetyl-2,5-diazabicyclo[2.2.1]hept-2-yl]methyl}phenoxy)-6-fluoro[1,3]thiazolo[5,4-b]pyridine; |
| 124 | 2-(4-{[(1S,4S)-5-Acetyl-2,5-diazabicyclo[2.2.1]hept-2-yl]methyl}phenoxy)[1,3]thiazolo[5,4-b]pyridine; |
| 132 | 1-[4-([1,3]Thiazolo[5,4-b]pyridin-2-yloxy)benzyl]piperidine-4-carboxylic acid; |
| 152 | 2-{4-[2-(4-Methyl-1,4-diazepan-1-yl)ethoxy]phenoxy}[1,3]thiazolo[5,4-b]pyridine; |
| 153 | meso-N-[(3-exo)-8-{2-[4-([1,3]Thiazolo[5,4-b]pyridin-2-yloxy)phenoxy]ethyl}-8-azabicyclo[3.2.1]oct-3-yl]acetamide; |
| 157 | 2-[(Cyclopropylmethyl){2-[4-([1,3]thiazolo[5,4-b]pyridin-2-yloxy)phenoxy]ethyl}amino]ethanol; |
| 168 | 7-Methyl-2-({4-[(4-pyridin-4-ylpiperazin-1-yl)methyl]phenyl}oxy)[1,3]thiazolo[4,5-b]pyridine; |
| 169 | meso-(3-endo)-8-Acetyl-N-{[4-([1,3]thiazolo[4,5-b]pyridin-2-yloxy)phenyl]methyl}-8-azabicyclo[3.2.1]octan-3-amine; |
| 170 | meso-(3-exo)-8-Acetyl-N-{[4-([1,3]thiazolo[4,5-b]pyridin-2-yloxy)phenyl]methyl}-8-azabicyclo[3.2.1]octan-3-amine; |
| 174 | N-Ethyl-N-{2-[4-([1,3]thiazolo[5,4-b]pyridin-2-yloxy)phenyl]ethyl}cyclopropanamine; |
| 194 | meso-N-[(3-exo)-8-{2-[4-([1,3]Thiazolo[5,4-b]pyridin-2-yloxy)phenyl]ethyl}-8-azabicyclo[3.2.1]oct-3-yl]methanesulfonamide; |
| 201 | meso-(3-exo)-3-{[4-([1,3]Thiazolo[5,4-b]pyridin-2-yloxy)benzyl]amino}-8-azabicyclo[3.2.1]octane-8-carboxamide; |
| 207 | 4-Methyl-1-[4-([1,3]thiazolo[5,4-b]pyridin-2-yloxy)benzyl]-1,4-diazepan-5-one; |
| 219 | N-{1-[4-([1,3]Thiazolo[5,4-b]pyridin-2-yloxy)benzyl]piperidin-4-yl}propanamide; |
| 222 | 2-(4-{2-[4-(Cyclopropylcarbonyl)-1,4-diazepan-1-yl]ethyl}phenoxy)[1,3]thiazolo[5,4-b]pyridine; |
| 228 | meso-N-Methyl-N-{(3-exo)-8-[4-([1,3]thiazolo[5,4-b]pyridin-2-yloxy)benzyl]-8-azabicyclo[3.2.1]oct-3-yl}acetamide; |
| 242 | 2-(Cyclopropyl{2-[4-([1,3]thiazolo[5,4-b]pyridin-2-yloxy)phenoxy]ethyl}amino)ethanol; |
| 251 | 2-{4-[(4-Pyridin-2-ylpiperazin-1-yl)methyl]phenoxy}[1,3]thiazolo[5,4-b]pyridine; |
| 252 | 2-(4-{2-[(1R,4R)-5-Acetyl-2,5-diazabicyclo[2.2.1]hept-2-yl]ethyl}phenoxy)[1,3]thiazolo[5,4-b]pyridine; |
| 280 | 7-Methyl-2-[4-(piperidin-1-ylmethyl)phenoxy][1,3]thiazolo[5,4-b]pyridine; |
| 281 | 2-(4-{[(1S,4S)-5-Acetyl-2,5-diazabicyclo[2.2.1]hept-2-yl]methyl}phenoxy)-7-methyl[1,3]thiazolo[5,4-b]pyridine; |
| 286 | 1-{4-[(7-Methyl[1,3]thiazolo[5,4-b]pyridin-2-yl)oxy]benzyl}piperidine-4-carboxamide; | and pharmaceutically acceptable salts, prodrugs, solvates, and active metabolites thereof.

In other embodiments, chemical entities of the present invention are selected from the group consisting of:

| Ex. | Chemical Name |
|---|---|
| 22 | 4-Phenyl-1-{2-[4-([1,3]thiazolo[4,5-b]pyrazin-2-yloxy)phenoxy]ethyl}piperidin-4-ol; |
| 23 | 2-{4-[2-(4-Benzylpiperidin-1-yl)ethoxy]phenoxy}[1,3]thiazolo[4,5-b]pyrazine; |
| 24 | 1-{2-[4-([1,3]Thiazolo[4,5-b]pyrazin-2-yloxy)phenoxy]ethyl}-4-[3-(trifluoromethyl)phenyl]piperidin-4-ol; |
| 25 | 4-(4-Chlorophenyl)-1-{2-[4-([1,3]thiazolo[4,5-b]pyrazin-2-yloxy)phenoxy]ethyl}piperidin-4-ol; |
| 26 | 1-{2-[4-([1,3]Thiazolo[4,5-b]pyrazin-2-yloxy)phenoxy]ethyl}piperidine-4-carboxamide; |
| 120 | 2-(4-{[(1S,4S)-5-Acetyl-2,5-diazabicyclo[2.2.1]hept-2-yl]methyl}phenoxy)[1,3]thiazolo[4,5-b]pyrazine; |

-continued

| Ex. | Chemical Name |
|---|---|
| 148 | meso-N-[(3-endo)-8-{2-[4-([1,3]Thiazolo[4,5-b]pyrazin-2-yloxy)phenoxy]ethyl}-8-azabicyclo[3.2.1]oct-3-yl]acetamide; |
| 150 | 2-[4-(2-Morpholin-4-ylethoxy)phenoxy][1,3]thiazolo[4,5-b]pyrazine; |
| 167 | 2-({4-[(4-Pyrimidin-2-ylpiperazin-1-yl)methyl]phenyl}oxy)[1,3]thiazolo[4,5-b]pyrazine; |
| 173 | 2-[(4-{[4-(2-Thienylacetyl)piperazin-1-yl]methyl}phenyl)oxy][1,3]thiazolo[4,5-b]pyrazine; |
| 177 | 1-{2-[4-([1,3]Thiazolo[4,5-b]pyrazin-2-yloxy)phenyl]ethyl}-1,4-diazepan-5-one; |
| 179 | 2-{[4-(2-Azepan-1-ylethyl)phenyl]oxy}[1,3]thiazolo[4,5-b]pyrazine; |
| 180 | 2-({4-[2-(4-Fluoropiperidin-1-yl)ethyl]phenyl}oxy)[1,3]thiazolo[4,5-b]pyrazine; |
| 184 | 2-[(4-{[4-(Pyrimidin-2-yloxy)piperidin-1-yl]methyl}phenyl)oxy][1,3]thiazolo[4,5-b]pyrazine; |
| 199 | meso-1-{(3-exo)-8-[4-([1,3]Thiazolo[4,5-b]pyrazin-2-yloxy)benzyl]-8-azabicyclo[3.2.1]oct-3-yl}urea; |
| 237 | 2-(4-{2-[4-(Pyridin-2-yloxy)piperidin-1-yl]ethyl}phenoxy)[1,3]thiazolo[4,5-b]pyrazine; |
| 285 | 1-[4-([1,3]Thiazolo[4,5-b]pyrazin-2-yloxy)benzyl]piperidine-4-carboxamide; | and pharmaceutically acceptable salts, prodrugs, solvates, and active metabolites thereof.

The invention includes also pharmaceutically acceptable salts of the compounds represented by Formula (I), preferably of those described above and of the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology. Embodiments of salts of this invention are prepared by adding the corresponding acid to the base form of compounds of this invention. Illustrative examples of salts prepared with embodiments of this invention include acetates, formates, fumarates, citrates, hydrochlorides, tartrates, sulfates, phosphates, malates, malonates, bezoates and succinates. Embodiments of salts of this invention were prepared by adding the corresponding acid to the base form of compounds of this invention. Some embodiments of salts according to this invention were characterized as being 1:1 as to the base/acid molar ratio.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

In some embodiments, pharmaceutically acceptable salts of compounds of Formula (I) were hydrochloride, phosphate, sulfate, acetate, citrate, L-tartrate, or succinate salts. In further embodiments, compounds of Formula (I) were obtained as hydrochloride, phosphate, succinate or sulfate salts. In further embodiments, hydrochloride, or succinate salts of compounds of Formula (I) were obtained in crystalline form.

The invention also relates to pharmaceutically acceptable prodrugs of the compounds of Formula (I), and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "active agents") of the present invention are useful as LTA4H modulators in the methods of the invention. Such methods for modulating LTA4H activity comprise exposing LTA4H to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit LTA4H activity.

In some embodiments, the LTA4H is in a subject with a disease, disorder, or medical condition mediated by LTA4H activity, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through LTA4H activity, such as inflammation. Active agents according to the invention may therefore be used as an anti-inflammatory agents.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with an LTA4H modulating agent include inflammation due to any one of a plurality of conditions such as allergy, abdominal aortic aneurysm, asthma, nasal polyps, allergic rhinitis, nasal itch, ocular inflammation (e.g., post-surgical ocular inflammation), conjunctivitis, uveitis, dry eye, psoriasis, pruritis, itch, itchy skin, atopic dermatitis, urticaria (hives), contact dermatitis, scleroderma, skin burns, acne, inflammatory bowel diseases (including colitis, Crohn's disease and ulcerative colitis), chronic obstructed pulmonary disease (COPD), atherosclerosis, arthritis (including rheumatoid arthritis), multiple sclerosis, myocardial infarction, stroke, pain, gingivitis, bronchitis, cystic fibrosis, upper gastrointestinal cancer, sepsis, autoimmune thyroid diseases, and immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, Sjogren syndrome, and Sjogren-Larsson syndrome.

Pruritis treatable with an LTA4H-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, aortic aneurysm, asthma, autoimmune diseases, pruritis, inflammatory bowel disease, ulcerative colitis, or cardiovascular disease, including atherosclerosis and prevention of myocardial infarction. In further embodiments, an active agent of the present invention, alone or in combination with some other agent, is administered to treat aortic aneurysms, delaying the time to or avoiding the surgical intervention to repair aortic aneurysms, slowing the progression of aortic aneurysms, or avoiding or slowing down the progression towards or the incidence of aortic rupture. In certain embodiments, an active agent, alone or in combination with some other agent, is administered for any of such treatments when the aortic aneurysm is an abdominal aortic aneurysm. Examples of embodiments of such other agent are given by CysLT receptor antagonists and LTC4 synthase inhibitors.

Thus, the active agents may be used to treat subjects diagnosed with or suffering from a disease, disorder, or condition mediated through LTA4H activity. The term "treat" or "treating" as used herein is intended to refer to administration of an active agent or composition of the invention to a subject for the purpose of effecting a therapeutic or prophylactic benefit through modulation of LTA4H activity. Treating includes reversing, ameliorating, alleviating, inhibiting the progress of, lessening the severity of, or preventing a disease, disorder, or condition, or one or more symptoms of such disease, disorder or condition mediated through modulation of LTA4H activity. The term "subject" refers to a mammalian patient in need of such treatment, such as a human. "Modulators" include both inhibitors and activators, where "inhibitors" refer to compounds that decrease, prevent, inactivate, desensitize or down-regulate LTA4H expression or activity, and "activators" are compounds that increase, activate, facilitate, sensitize, or up-regulate LTA4H expression or activity. Embodiments of chemical entities according to this invention are LTA4H-modulating chemical entities.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. When referring to modulating the target receptor, an "effective amount" means an amount sufficient to at least affect the activity of such receptor. Measuring the activity of the target receptor may be performed by routine analytical methods. Target receptor modulation is useful in a variety of settings, including assays and treating conditions modulated through LTA4H activity.

In addition, effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably from about 0.05 to about 100 mg/kg/day, or from about 0.5 to about 35 mg/kg/day, or from about 0.5 to about 20 mg/kg/day, or from about 0.1 to about 10 mg/kg daily in single or divided dosage units (e.g., BID, TID, QID). For a 70-kg human, an illustrative range for a suitable dosage amount is from about 0.02 to about 7 g/day, or from about 0.2 to about 2.5 g/day. Dosages from about 20 mg/day to about 60 mg/day are contemplated. In some embodiments, such dosages would be administered once daily. Examples of embodiments of this invention are given by tablets containing from about 0.005 mol free base per tablet to about 0.5 mol free base per tablet. Other embodiments are given by tablets containing from about 0.005 mol free base per tablet to about 0.01 mol free base per tablet. Additional embodiments are given by tablets containing from about 0.03 mol free base per tablet to about 0.06 mol free base per tablet. Further embodiments are given by tablets containing from about 0.3 mol free base per tablet to about 0.6 mol free base per tablet. Some embodiments of this invention were prepared with about 0.0095 mol free base per tablet. Other embodiments of this invention were prepared with about 0.047 mol free base per tablet. Still other embodiments of this invention were prepared with about 0.47 mol free base per tablet.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions or with other active ingredients. Montelukast salts are examples of such additional active ingredients, such as montelukast sodium. Conditions that are mediated by LTA4H activity, such as asthma for example, could be treated by embodiments of this invention such as active agents of this invention alone or in combination with others, such as montelukast salts. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by LTA4H activity, such as another LTA4H modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

Other embodiments of this invention further comprise the administration of at least one CysLT receptor antagonist (for example, Montelukast/Singulair®) and/or at least one LTC4 synthase inhibitor. In some embodiments of this invention, such LTA4H modulator and CysLT receptor antagonist and/or LTC4 synthase inhibitor are coadministered. Examples of CysLT receptor antagonists are CysLT1 and CysLT2 antagonists.

The active agents of the invention are used, alone or in combination with one or more additional active ingredients, to formulate pharmaceutical compositions of the invention. A pharmaceutical composition of the invention comprises an effective amount of at least one active agent in accordance with the invention. Such compositions may further comprise a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols. Suitable excipients may also include antioxidants. Such antioxidants may be used in a pharmaceutical composition or in a storage medium to prolong the shelf-life of the drug product.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration. In further preferred embodiments, compounds of the present invention are orally active inhibitors of LTA4H. Some embodiments of this invention were prepared with a round tablet image, other embodiments were prepared with a capsule-shaped tablet image, and still other embodiments were prepared with an oval tablet image. Further embodiments of tablet images were prepared with masses of about 100 mg, 500 mg and 1000 mg.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily, or from about 0.2 to about 1 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating. Lactose Fast Flo #316 is one example of a filler that was used in the preparation of embodiments of this invention. Avicel PH102 is another example of a filler that was used in the preparation of embodiments of this invention. Polyplasdone XL-10 is an example of a disintegrant that was used in the preparation of embodiments of this invention. Magnesium stearate is an example of a lubricant that was used in the preparation of embodiments of this invention. Yellow ferroxide is an example of a pigment that was used in the preparation of embodiments of this invention. Intragranular excipients that were used in the preparation of embodiments of this invention are illustratively given by fillers, disintegrants, lubricants and pigments, such as lactose fast flow # 316, avicel PH102, polyplasdone XL-10, yellow ferroxide and magnesium stearate. Extragranular excipients that were used in the preparation of embodiments of this invention are illustratively given by lubricants and disintegrants, such as magnesium stearate and polyplasdone XL-10.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Embodiments of this invention are provided by tablet forms with an amount of active compound corresponding to from about 1% to about 30% of free base. Other embodiments contain active compound corresponding to from about 5% to about 25% of free base. Still other embodiments contain active compound corresponding to from about 1% to about 10% of free base. Further embodiments contain active compound corresponding to from about 20% to about 30% of free base. Additional embodiments contain active compound corresponding to from about 10% to about 20% of free base. Embodiments of this invention in the form of tablet doses of about 5 mg per tablet and about 25 mg per tablet were prepared in the form of compositions with active compound corresponding to about 5% free base. Embodiments of this invention in the form of tablet doses of about 250 mg per tablet were prepared in the form of compositions with active compound corresponding to about 25% free base. Actual amounts depended on the salt of choice. In some embodiments, lactose can be used as the adjustable excipient for suitable batch correction depending on the specific salt form being used. In other embodiments, avicel can be used as the adjustable excipient for suitable batch correction depending on the specific salt form being used. Embodiments of this invention in the form of tablets comprise from about 70% to about 95% of non-active intragranular excipients and from about 0.2% to about 4% of non-active extragranular excipients. Embodiments of this invention in the form of tablets comprise from about 90% to about 95% of non-active intragranular excipients and from about 0.2% to about 0.3% of non-active extragranular excipients. Embodiments of this invention in the form of tablets comprise from about 70% to about 75% of non-active intragranular excipients and from about 3% to about 4% of non-active extragranular excipients. Embodiments of this invention in the form of tablets comprise from about 65% to about 95% of intragranular filler. Embodiments of this invention in the form of tablets comprise from about 90% to about 95% of intragranular filler. Embodiments of this invention in the form of tablets comprise from about 65% to about 70% of intragranular filler. Embodiments of this invention in the form of tablets comprise from about 2.5% to about 3.5% of intragranular disintegrant. Embodiments of this invention in the form of tablets comprise from about 0.2% to about 0.4% of intragranular pigment. Embodiments of this invention in the form of tablets comprise from about 0.1% to about 1.0% of intragranular lubricant. Embodiments of this invention in the form of tablets comprise from about 0.1% to about 1.0% of extragranular lubricant. Embodiments of this invention in the form of tablets comprise from about 2.5% to about 3.5% of extragranular disintegrant. Embodiments of this invention in the form of tablets comprised about 91.2% intragranular filler, about 3.0% intragranular disintegrant, about 0.30% intragranular pigment, and about 0.25% intragranular lubricant. Embodiments of this invention in the form of tablets comprised about 0.25% extragranular lubricant. Embodiments of this invention in the form of tablets comprised about 67.7% intragranular filler, about 3.0% intragranular disintegrant, about 0.30% intragranular pigment, and about 0.75% intragranular lubricant. Embodiments of this invention in the form of tablets comprised about 0.25% extragranular lubricant and about 3.0% extragranular disintegrant.

Tabletting equipment used in the preparation of some embodiments of this invention comprised standard technology used to this effect, including 60 mesh sieve and balance for weighing, TFC labo roller compactor for compaction, TFC Labo granulator for granulating, Bohle bin blender for blending, and Piccola press for tabletting with various punch sets depending on the choice of tablet image.

Tabletting process used in embodiments of this invention comprised low shear blending of excipients, low shear blending with lubricant, milling and tablet formation. Some process embodiments included geometric blending.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Additionally, those skilled in the art will recognize the synthetic steps shown may be performed in a different order than that depicted in the Schemes below. Unless otherwise specified, the variables are as defined above in reference to Formula (I).

SCHEME A

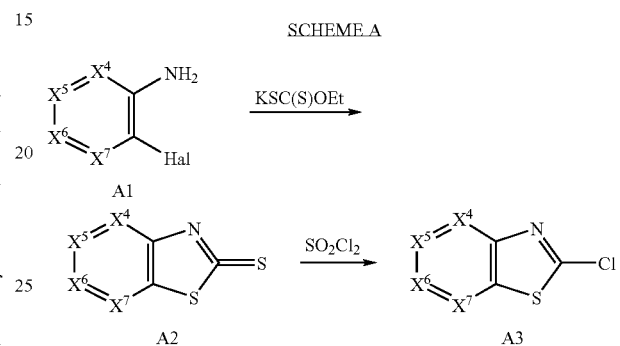

Intermediates of formula A3 are commercially available or are prepared according to Scheme A (See: Intl. Pat. Appl. Publ. WO2007/146066; Intl. Pat. Appl. No. WO 2006/04475; and L. Zhu, et al. *J. Heterocyclic Chem.* 2005, 42, 727-730). Compounds A1, where Hal is bromo or chloro, are reacted with a potassium alkyl xanthate, preferably potassium ethyl xanthate, in a polar solvent such as N,N-dimethylformamide (DMF) or N-methylpyrrolidinone (NMP) at a temperature from about 100° C. to about 150° C., to provide compounds A2. Treatment with sulfuryl chloride in dichloromethane or oxalyl chloride in DMF provides compounds A3. Compounds A3 may be optionally converted to their corresponding hydrochloride salts for storage.

SCHEME B

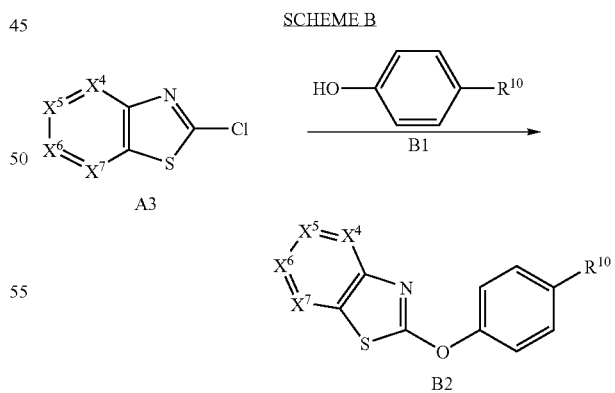

Intermediates of formula B2 are prepared according to Scheme B. Chlorothiazole analogs A3 are reacted with phenols B1, where $R^{10}$ is —CHO (optionally protected as a bisulfite complex), —$CH_2$CHO, -A-OH, -A-$NR^1R^2$, or -A-LG (where LG is a suitable leaving group, such as chloro, bromo, iodo, p-toluenesulfonyl, or methanesulfonyl), in the presence of a suitable base, such as $K_2CO_3$, $Cs_2CO_3$, Na$_2$CO$_3$, NaHCO$_3$, or K$_3$PO$_4$, in a polar solvent such as DMF, acetonitrile, methanol (MeOH), ethanol (EtOH), isopropanol, or tert-butanol, to form compounds B2. In other methods, compounds B1 are converted to their corresponding sodium or potassium salts before reaction with compounds A3 in a solvent such as DMF, tetrahydrofuran (THF) or diethyl ether. Where R$^{10}$ is -A-NR$^1$R$^2$, compounds B2 are compounds of Formula (I). Compounds B2 where R$^{10}$ is -A-OH are then converted into compounds B2 where R$^{10}$ is —CHO by oxidation methods known in the art. Alternatively, compounds B2 where R$^{10}$ is an ester may be reduced to the corresponding aldehydes where R$^{10}$ is —CHO or —CH$_2$CHO. Such aldehydes are optionally converted to the corresponding bisulfite adducts for purification and/or storage. Alternatively, compounds B2 where R$^{10}$ is -A-OH are converted into compounds B2 where R$^{10}$ is -A-LG by standard halogenation or sulfonylation methods known in the art. In preferred methods, such alcohols are reacted with methanesulfonic anhydride and a tertiary amine base in a solvent such as dichloromethane or dichloroethane, or with thionyl chloride, oxalyl chloride, or POCl$_3$, neat or in a solvent such as dichloromethane, 1,2-dichloroethane (DCE), toluene, or acetonitrile.

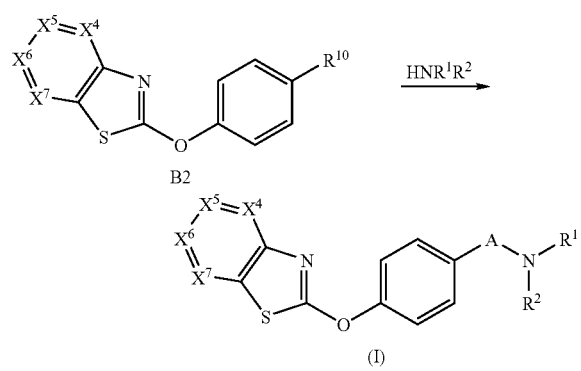

SCHEME C

Compounds of Formula (I) are alternatively prepared according to Scheme C. Compounds B2, where R$^{10}$ is -A-LG and LG is a suitable leaving group such as chloro, bromo, iodo, p-toluenesulfonyl, or methanesulfonyl), are reacted with amines HNR$^1$R$^2$, which are commercially available or prepared according to methods described in: Eur. Pat. EP 0266576; U.S. Provisional Pat. Appl. No. 60/984,126; U.S. Pat. No. 4,432,983; Intl. Pat. Appl. No. WO 2007/077508; Eur. J. Med. Chem. 1984, 19(2), 105-110, and Mapes et al., Org. Process Res Dev., 2007, 11, 482-486. In some embodiments, amines HNR$^1$R$^2$ are used in free base form, and in some embodiments, amines HNR$^1$R$^2$ are used in the corresponding salt form (such as a hydrochloride salt form). One skilled in the art will recognize amines HNR$^1$R$^2$ containing an additional amine functionality may have such functionality optionally protected with a suitable nitrogen protecting group. Reactions are preferably performed in the presence of a suitable base (such as Et$_3$N, iPr$_2$NEt, pyridine, K$_2$CO$_3$, Cs$_2$CO$_3$, Na$_2$CO$_3$, NaHCO$_3$, or K$_3$PO$_4$), in a polar solvent (such as acetonitrile, DMF, MeOH, EtOH, isopropanol, tert-butanol, or tert-amyl alcohol) to give compounds of Formula (I).

Alternatively, compounds of Formula (I) are prepared from compounds B2, where R$^{10}$ is —CHO or —CH$_2$CHO. Aldehydes B2 may optionally be used or purified in a protected form, such as a bisulfite complex. Reaction of aldehydes B2 with amines HNR$^1$R$^2$ (used as free amines or corresponding salts) in the presence of a suitable reducing agent (such as NaCNBH$_3$ or NaB(OAc)$_3$H) in a solvent such as DCE, CH$_2$Cl$_2$, MeOH, or EtOH, and optionally employing an acid catalyst (such as acetic acid or ZnCl$_2$), provides compounds of Formula (I). In some embodiments, the reaction with the corresponding HNR$^1$R$^2$ salts may optionally employ a base, such as Et$_3$N, to produce the free amine in situ.

SCHEME D

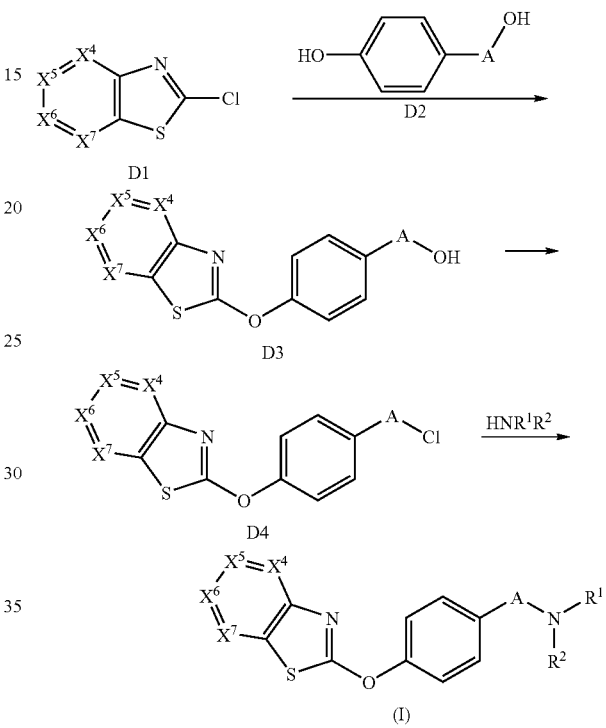

In preferred embodiments, compounds of Formula (I) are prepared as shown in Scheme D. Compounds D1 are reacted with phenols D2 to give compounds D3. In some embodiments, reactions are performed in the presence of a suitable base, such as K$_2$CO$_3$, Cs$_2$CO$_3$, Na$_2$CO$_3$, NaHCO$_3$, or K$_3$PO$_4$, in a polar solvent such as DMF, acetonitrile, MeOH, EtOH, isopropanol, or tert-butanol. In other embodiments, reactions are performed using K$_2$CO$_3$ or Cs$_2$CO$_3$, in DMF or acetonitrile. Next, compounds D3 are converted to chlorides D4 by chlorination methods. In preferred embodiments, reactions are accomplished by treatment with thionyl chloride, oxalyl chloride, or POCl$_3$, neat or in a solvent such as dichloromethane, dichloroethane, toluene, or acetonitrile. In some embodiments, reactions are accomplished by reaction with thionyl chloride in dichloromethane. Compounds D4 are then reacted with amines HNR$^1$R$^2$ to give compounds of Formula (I). In some embodiments, reactions are performed in the presence of a suitable base, such as Et$_3$N, pyridine, K$_2$CO$_3$, Cs$_2$CO$_3$, Na$_2$CO$_3$, NaHCO$_3$, or K$_3$PO$_4$, in a polar solvent, such as acetonitrile, DMF, MeOH, EtOH, isopropanol, or tert-butanol. In other embodiments, reactions are performed using K$_2$CO$_3$ or Cs$_2$CO$_3$ in acetonitrile.

Scheme F

Embodiments of some compounds of Formula (I) are alternatively prepared according to Scheme F.

Compound BX is reacted in the presence of a suitable reducing agent, such as NaB(OAc)$_3$H, NaCNBH$_3$, and chemically compatible mixtures thereof, in a solvent, such as MeOH, EtOH, 2-propanol, acetonitrile, DCE, CH$_2$Cl$_2$, and chemically compatible mixtures thereof, optionally in the presence of an acid catalyst, such as acetic acid, with compound HNR$^1$R$^2$ to make F1, where HNR$^1$R$^2$ is used in the free amine form, in a salt form or in the form of mixtures thereof.

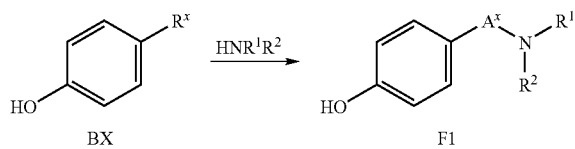

R$^x$ is one of —CHO and —CH$_2$CHO, and A$^x$ is one of —CH$_2$— and —CH$_2$CH$_2$—. Compound F1 is reacted with A3 in the presence of a suitable base, such as K$_2$CO$_3$, Cs$_2$CO$_3$, Na$_2$CO$_3$, NaHCO$_3$, K$_3$PO$_4$, and chemically compatible mixtures thereof, in a polar solvent such as DMF, acetonitrile, methanol (MeOH), ethanol (EtOH), isopropanol, tert-butanol, and chemically compatible mixtures thereof, to form compound (I$^x$),

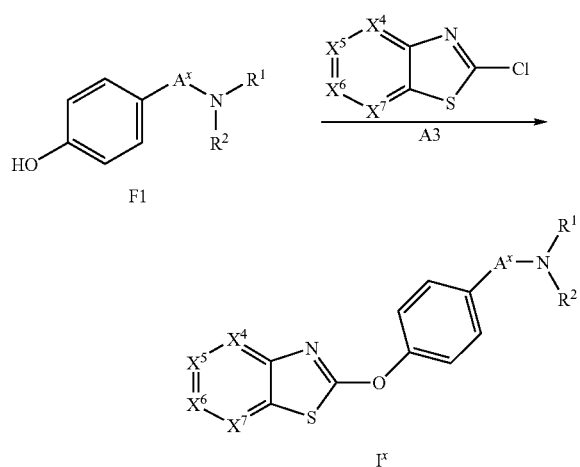

Synthesis according to Scheme F avoids the use of halogenated solvents and thionyl chloride, avoids the formation of halo-substituted intermediates, is shorter than other synthetic processes, and reduces the risk of side-reactions and byproducts.

Bicyclic substituted 8-aza-bicyclo[3.2.1]oct-3-ylamine endo a and exo b

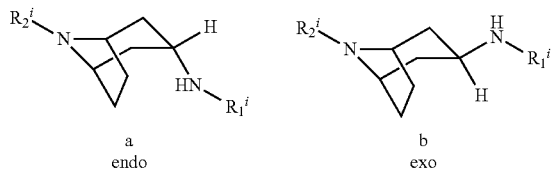

are integral intermediates utilized in a variety of drugs. See, for example, WO 2005/101989, U.S. Pat. No. 4,432,983, and M. G. Hael, et al., Organic Process Research & Development, 1997, 1, 198-210. Several methods have been developed to synthesize endo and/or exo substituted 8-aza-bicyclo[3.2.1] oct-3-ylamines a and b, but a highly selective synthesis of the endo form is desirable. Such highly selective synthesis of the endo form has been developed in the context of this invention. Embodiments of this synthesis were performed in one synthetic step from the corresponding oxime:

This endo synthesis is expected to be applicable to the syntheses of similar substituted endo a where R$_2{}^i$ are non-acid sensitive protecting groups and R$_1{}^i$ are acylated functional groups derived via reacting with substituted acid anhydrides. For example, embodiments of this synthesis are provided by the synthesis process described herein when R$_1{}^i$ is one of H, C$_{1-6}$alkylC(O)—, arylC(O)—, and EstOC(O)—, wherein the moiety "Est" signifies that the carboxy group is in some embodiments in an ester form. In some embodiments, the moieties C$_{1-6}$alkyl (linear or branched) and aryl in R$_1{}^i$ are optionally substituted with at least one substituent such as halo and linear or branched C$_{1-6}$alkyl. As further examples, embodiments of this synthesis are provided by the synthesis process described herein when R$_2{}^i$ is one of H, C$_{1-10}$alkyl (linear or branched), —CH$_2$aryl, —S(O)$_2$aryl, and —S(O)$_2$C$_{1-6}$alkyl. In some embodiments, the moieties linear or branched C$_{1-10}$alkyl and aryl in R$_2{}^i$ are optionally substituted with at least one substituent such as halo and C$_{1-6}$alkyl.

In conventional synthetic methodologies, the synthesis is a two-step process involving the reduction of substituted bicyclic oximes to primary amines via hydrogenation, transfer hydrogenation, aluminium-nickel alloy or Na metal then acetylation to form the bicyclic acetamide. It is known that in acidic or basic hydrogenation conditions, certain bicyclic endo stereochemistry can be favored over exo but frequently as mixtures of both. It was found in the context of this invention that the implementation of conventional synthetic conditions leads to poor endo selectivity and/or mixtures of the endo form with other species such as the following ketones and/or dimers:

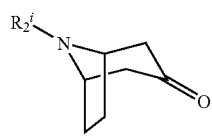

ketone

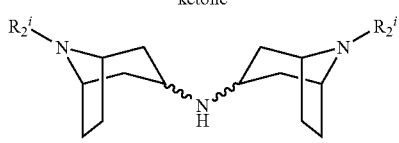

dimer
SCHEME E1

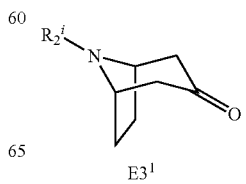

E3$^1$

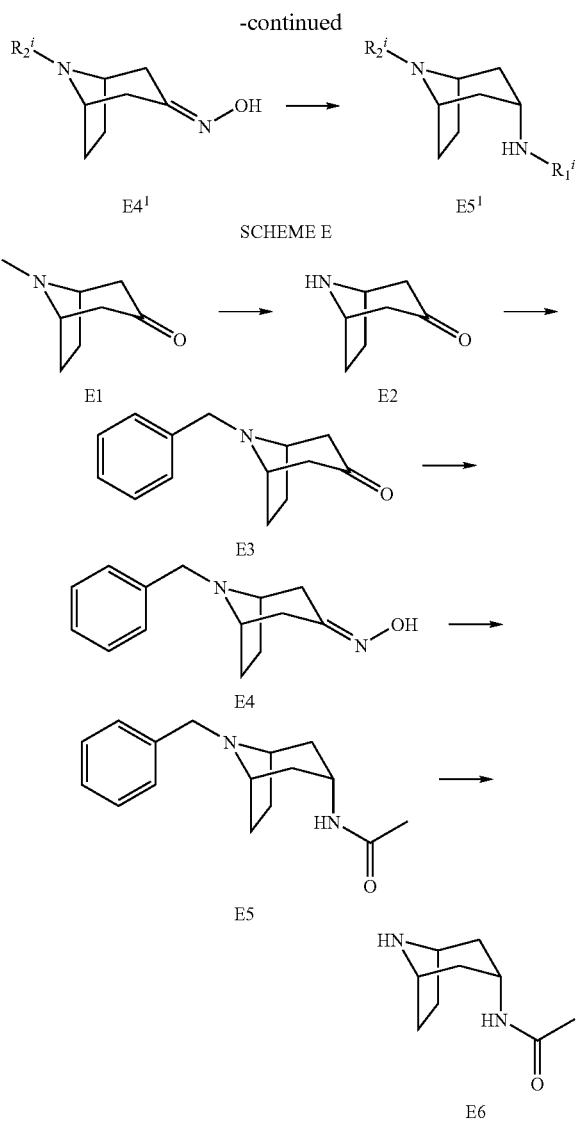

SCHEME E

In some methods of the invention, compounds E5¹ are prepared according to Scheme E1 by acetylation and reduction of oxime E4¹. When E5¹ is desired in a final form as a secondary amine ($R_2^i$ then being H), suitable protection of this group can then be implemented, such as by choosing another acceptable form of substituent $R_2^i$ as described herein. For example, by protecting the $R_2^i$-substituted N-member with $R_2^{i'}$, wherein $R_2^{i'}$ is one of the $R_2^i$ substituents except for H. Therefore, some embodiments of Formula (I) are available according to Schemes A-D using compound E5¹ as the amine HNR¹R². Compounds E5¹ are obtained from the reduction of oxime E4¹, which is commercially available or can be conventionally obtained from tropinone. Embodiments of synthetic methodologies according to this invention generate compounds E5¹ from compounds E4¹ in a single reaction step, with high selectivity, and with simplified isolation procedures. In some embodiments, compounds E4¹ are reacted with carboxylic acid anhydrides and hydrogen in the presence of a suitable hydrogenation catalyst in a chemically compatible solvent.

In some embodiments, the intermediate HNR¹R² is compound N-[(3-endo)-8-azabicyclo[3.2.1]oct-3-yl]acetamide (E6). In some methods of the invention, compound E6 is prepared according to Scheme E. Therefore, some embodiments of Formula (I) are available according to Schemes A-D using compound E6 as the amine HNR¹R². Compound E6 is prepared by debenzylation of compound E5. Compound E5 is available by reduction of oxime compound E4, which is commercially available (See also, U.S. Pat. No. 4,432,983), and generally prepared from tropinone (E1) as described in the art. Compounds E5 and E6 are known (See, Eur. J. Med. Chem. 1984, 19(2), 105-110; Eur. Pat. EP 0159174). However, methods of the invention generate compound E5 from compound E4 in a single reaction step, with high selectivity, and with simplified isolation procedures. While selective endo reduction of oxime E4 and related analogs is known (See, Bagley et al. J. Het. Chem. 1982, 19(3), 485-488; Wilstatter, Chem. Ber. 1896, 29, 393-403; Blackburn et al., Bioorg. Med. Chem. Lett. 2006, 16(10), 2621-2627; Suzuki et al., Chem. Pharm. Bull. 2001, 49(1), 29-39; Lewin et al., J. Med. Chem. 1998, 988-995; Eur. Pat. EP 0159174), reported procedures generate the corresponding free amines rather than functionalized products, such as the acetamide in E6. The free amine compounds are difficult to isolate, generally requiring formation of the corresponding salt. In the present invention, the desired functionalized amine is prepared in a single step with high endo selectivity over the corresponding enamine:

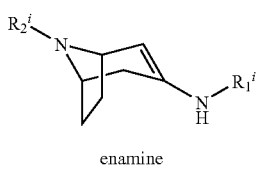

enamine

In some embodiments, the compound E4 is reacted with hydrogen in the presence of acetic anhydride to form compound E5 in a single step. In further embodiments, reactions are performed by reacting a compound E4 with carboxylic acid anhydrides (such as acetic, propionic, ethylbutyric, butyric, isobutyric, valeric, isovaleric, trimethyl acetic, and trifluoroacetic anhydrides) and hydrogen in the presence of a suitable catalyst (such as Pt/C, Raney Ni, Rh/C, or a mixture thereof), in a solvent such as ethyl acetate, acetic acid, MeOH, EtOH, isopropanol, or a mixture thereof. In some embodiments, the reaction of a compound E4 with acetic anhydride and hydrogen is performed in ethyl acetate, with Pt/C as the catalyst, and with added acetic acid. In other embodiments, a continuous flow hydrogenation H-Cube Midi™ instrument was used with Pt/C catalyst to react compound E4 with ethyl acetate, acetic anhydride and acetic acid, a reaction that provided endo E5. In some embodiments, the ethyl acetate, acetic anhydride and acetic acid mixture concentration to obtain an endo/enamine selectivity of about 95/5 was approximately 0.1M. Methods of the invention further comprise reacting a compound E5 to form N-[(3-endo)-8-azabicyclo[3.2.1]oct-3-yl]acetamide (compound E6) as described herein.

Embodiments of this invention included reactions performed with 10% Pt/C catalyst amounts ranging from about 0.015 g to about 0.15 g, with about 10 eq acetic anhydride in EtOAc-based solvents in the presence of various amounts of AcOH. Other embodiments included reactions performed with 5% Pt/C catalyst amounts ranging from about 0.025 g to about 0.25 g, with about 10 eq to about 40 eq acetic anhydride in EtOAc-based solvents in the presence of various amounts of AcOH. Still other embodiments included reactions performed with Raney Ni catalyst, with about 2 eq to about 10 eq acetic anhydride in solvents such as EtOAc, acetic acid, and EtOAc-based solvents in the presence of various amounts of AcOH. Embodiments of this invention that included the use of a continuous flow hydrogenation had a variety of reaction conditions, such as ethyl acetate, acetic anhydride and acetic acid mixture concentrations ranging from about 0.01M to about 0.6M, use of 10% Pt/C calyst, solution flow rates of about 3 ml/min, hydrogen flow rates of about 45 ml/min, at pressures of about 80 bar and temperatures of about 60° C.

Synthetic methodologies provided herein permit the synthesis of embodiments of compounds according to this invention, whether desired in meso, endo or exo form. Whether specific embodiments are only shown in one of such forms or in a plurality of them, the various meso, endo and exo forms are considered within the scope of this invention. Where the above Schemes produce compounds of Formula (I) in a protected form, such as where an amine is protected with a suitable protecting group (such as tert-butylcarbamoyl group), such intermediates are converted to compounds of Formula (I) using generally known methods. For example, where the protecting group is a Boc group, deprotection is accomplished using an acid such as HCl or trifluoroacetic acid (TFA), in a solvent such as diethyl ether, dioxane, or $CH_2Cl_2$. Additional substituents on the —$NR^1R^2$ group are then installed by acylation or carbamoylation protocols using methods known in the art.

Additional synthetic methods are described in U.S. Patent Appl. Publ. Nos. US2005/0043378 and US2005/0043379.

Compounds of Formula (I) may be converted to their corresponding salts using methods described in the art. For example, an amine of Formula (I) is treated with TFA, HCl, or citric acid in a solvent such as diethyl ether, $CH_2Cl_2$, THF, MeOH, or isopropanol to provide the corresponding salt form.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

Examples

Chemistry Methods

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Column chromatography was typically conducted on disposable silica gel columns for flash chromatography (Teledyne Isco, Inc.). Microwave reactions were performed on a CEM Discover microwave reactor.

Analytical reversed-phase high performance liquid chromatography (HPLC) was performed on an Agilent 1100 Series instrument using one of the following gradients: 1 to 99% acetonitrile/water (0.05% trifluoroacetic acid) over 5.0 min or 7.0 min with a flow rate of 1 mL/min (Waters XTerra MS C18 (5 µm, 4.6×100 mm) column or Phenomenex Synergi max-RP (4 µm, 4.6×150 mm) column) or 1 to 99% acetonitrile/water (20 mM $NH_4OH$) over 5.0 min or 7.0 min with a flow rate of 1.5 mL/min (Phenomenex Gemini C18 (5 µm, 3.0×150 mm) column). Analytical reversed phase LC/MS was performed either on an Agilent 1100 Series instrument using 5 to 99% acetonitrile/water (0.05% trifluoroacetic acid) over 5.0 min or 7.0 min with a flow rate of 0.6 mL/min (Waters XTerra RP18 (5 µm, 3.0×100 mm) column) or on a Waters 2790 instrument using 5 to 99% acetonitrile/water (0.1% formic acid) over 5.0 min with a flow rate of 0.6 mL/min (Waters XTerra RP18 (5 µm, 3.0×100 mm) column).

Preparative reversed phase HPLC was performed on a Dionex APS2000 LC/MS or HPLC with a Phenomenex Gemini C18 (5 µm, 30×100 mm) column or a Waters XBridge C18 (5 µm, 30×100 mm) column and variable gradients of acetonitrile/water (20 mM $NH_4OH$) at a flow rate of 30 mL/min. Alternatively, the purification was performed with a Phenomenex Gemini C18 (5 µm, 50×100 mm) column or a Waters XBridge C18 (5 µm, 50×100 mm) column and variable gradients of acetonitrile/water (20 mM $NH_4OH$) at a flow rate of 80 mL/min. Formate salts of desired compounds were obtained when purifications were performed using an Inertsil ODS-3 C18 (3 µm, 30×100 mm) column at 46° C. with variable gradients of acetonitrile/water (0.1% formic acid) at a flow rate of 90 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration). NMR interpretation was performed using MestReC or MestReNova software to assign chemical shift and multiplicity. In cases where two adjacent peaks of equal or unequal height were observed, these two peaks may be labeled either as a multiplet or as a doublet. In the case of a doublet a coupling constant using this software may be assigned. In any given example, one or more protons may not be reported due to obscurity by water and/or solvent peaks.

Chemical names were typically generated using ACD/Name Version 9 (Advanced Chemistry Development, Toronto, Ontario, Canada).

Intermediate 1:
[1,3]Thiazolo[4,5-b]pyrazine-2(3H)-thione

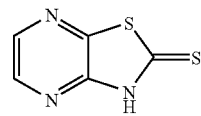

To a mixture of 2-amino-3-chloropyrazine (5.0 g, 38.6 mmol) and potassium ethyl xanthate (9.28 g, 57.9 mmol) was added 1-methyl-2-pyrrolidinone (68 mL). The solution was stirred and heated at 150° C. for 16 h. After cooling to rt, glacial acetic acid (10 mL) and water (1500 mL) were added to the solution. The solid precipitate was filtered. The solid was suspended in 1:1 EtOH/water (500 mL) and sonicated. The solid was once again filtered, washed with water, and dried with CaSO$_4$ in vacuo for 16 h to yield the product (4.36 g, 67%). $^1$H NMR (500 MHz, DMSO-d$_6$): 14.69 (br s, 1H), 8.42 (d, J=2.8, 1H), 8.39 (d, J=2.8, 1H). MS (ESI): mass calcd. for C$_5$H$_3$N$_3$S$_2$, 168.98; m/z found, 170.00 [M+H]$^+$.

Intermediate 2: 2-Chloro[1,3]thiazolo[4,5-b]pyrazine

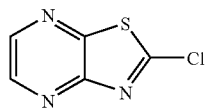

A mixture of [1,3]thiazolo[4,5-b]pyrazine-2(3H)-thione (4.36 g, 25.8 mmol) in CH$_2$Cl$_2$ (60 mL) was sonicated for 5 min. While stirring, sulfuryl chloride (60 mL) was added, and the solution was heated to 40° C. for 16 h. After cooling to rt, the solution was placed in an ice bath. Water (250 mL) was added slowly, followed by slow addition of 4 N NaOH (550 mL). The aqueous mixture was extracted with ethyl acetate (EtOAc, 2×1800 mL), dried, and concentrated to yield the product (2.63 g, 53%). $^1$H NMR (500 MHz, DMSO-d$_6$): 8.84 (d, J=2.5, 1H), 8.75 (d, J=2.5, 1H). MS (ESI): mass calcd. for C$_5$H$_2$ClN$_3$S, 170.97; m/z found, 172.10 [M+H]$^+$.

Intermediates 3 to 9 were prepared using methods analogous to those described for Intermediate 2.

Intermediate 3:
2-Chloro-6-methyl[1,3]thiazolo[4,5-b]pyridine

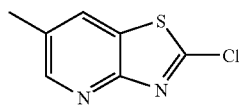

$^1$H NMR (500 MHz, DMSO-d$_6$): 8.55 (s, 1H), 8.40 (s, 1H), 2.44 (s, 3H). MS (ESI): mass calcd. for C$_7$H$_5$ClN$_2$S, 183.99; m/z found, 185.00 [M+H]$^+$.

Intermediate 4:
2-Chloro-6-chloro[1,3]thiazolo[4,5-b]pyridine

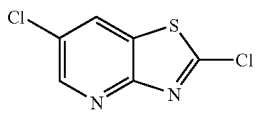

$^1$H NMR (500 MHz, DMSO-d$_6$): 8.78 (s, 1H), 8.75 (s, 1H). MS (ESI): mass calcd. for C$_6$H$_2$Cl$_2$N$_2$S, 203.93; m/z found, 204.90 [M+H]$^+$.

Intermediate 5:
2-Chloro-6-fluoro[1,3]thiazolo[5,4-b]pyridine

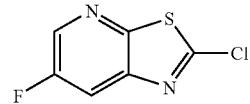

$^1$H NMR (500 MHz, DMSO-d$_6$): 8.77 (s, 1H), 8.55-8.46 (m, 1H). MS (ESI): mass calcd. for C$_6$H$_2$ClFN$_2$S, 187.96; m/z found, 189.00 [M+H]$^+$.

Intermediate 6:
2-Chloro-5-methyl[1,3]thiazolo[5,4-b]pyridine

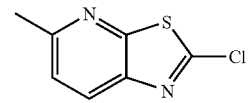

$^1$H NMR (400 MHz, DMSO-d$_6$): 8.32 (d, J=8.4, 1H), 7.56 (d, J=8.5, 1H), 2.67 (s, 3H). MS (ESI): mass calcd. for C$_7$H$_5$ClN$_2$S, 183.99; m/z found, 185.00 [M+H]$^+$.

Intermediate 7:
2-Chloro-6-fluoro[1,3]thiazolo[4,5-b]pyridine

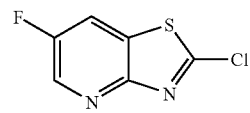

$^1$H NMR (600 MHz, DMSO-d$_6$): 8.75 (dd, J=2.8, 0.9, 1H), 8.58 (dd, J=8.2, 2.9, 1H). MS (ESI): mass calcd. for C$_6$H$_2$ClFN$_2$S, 187.96; m/z found, 189.00 [M+H]$^+$.

Intermediate 8:
2-Chloro-7-methyl[1,3]thiazolo[4,5-b]pyridine

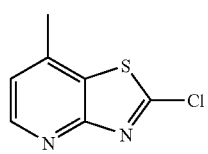

¹H NMR (600 MHz, DMSO-d₆): 8.61 (d, J=4.9, 1H), 7.41 (dd, J=4.8, 0.6, 1H), 2.58 (s, 3H). MS (ESI): mass calcd. for $C_7H_5ClN_2S$, 183.99; m/z found, 185.00 [M+H]⁺.

Intermediate 9:
2-Chloro-5-methyl[1,3]thiazolo[4,5-b]pyridine

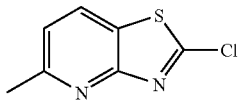

¹H NMR (500 MHz, DMSO-d₆): 8.46 (d, J=8.3, 1H), 7.42 (d, J=8.3, 1H), 2.61 (s, 3H). MS (ESI): mass calcd. for $C_7H_5ClN_2S$, 183.99; m/z found, 185.00 [M+H]⁺.

Intermediate 10:
2-Chloro[1,3]thiazolo[5,4-c]pyridine

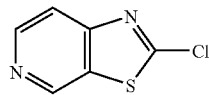

To an ice-cold mixture of dimethylformamide (DMF, 1.1 mL) and DCE (8 mL) was added dropwise a solution of oxalyl chloride (1.73 mL) in DCE (4 mL). A white precipitate formed, and the reaction mixture was stirred at rt for 5 min. [1,3]Thiazolo[5,4-c]pyridine-2(1H)-thione (1 g, 6 mmol) was added in portions, and the reaction mixture was stirred at reflux for 3 h. After cooling to rt, the reaction mixture was treated with water (20 mL) and saturated (satd.) aqueous (aq.) NaHCO₃ (100 mL) and then extracted with ethyl acetate (EtOAc) (2×100 mL). The combined organic layers were dried, filtered and concentrated to provide the desired product as a brown solid (1 g, 87%). ¹H NMR (400 MHz, CDCl₃): 9.11 (d, J=0.8, 1H), 8.68 (d, J=5.6, 1H), 7.85 (dd, J=5.6, 0.8, 1H). MS (ESI): mass calcd. for $C_6H_3ClN_2S$, 169.97; m/z found, 171.0 [M+H]⁺.

Intermediate 11: 2-[4-(2-Bromoethoxy)phenoxy][1,3]thiazolo[4,5-b]pyridine

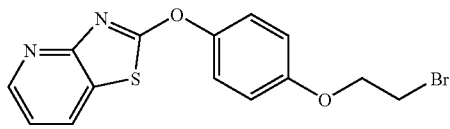

A mixture of 2-chloro[1,3]thiazolo[4,5-b]pyridine hydrochloride (863 mg, 4.17 mmol), 4-(2-bromo-ethoxy)-phenol (905 mg, 4.17 mmol), and Cs₂CO₃ (5.88 g, 16.67 mmol) was stirred in CH₃CN (42 mL) for 16 h. After filtration through diatomaceous earth, the organic filtrate was partitioned with 1 M NaOH (3×10 mL) and satd. aq. NaCl (1×10 mL). The organic layer was dried and concentrated to yield a red oil. Additional desiccation under high vacuum yielded a brown solid in red oil. Diethyl ether was added, and the mixture was sonicated for 20 min to give a homogenous suspension. The pink solid was filtered and discarded, and the ether solution was concentrated to yield the title compound as a yellow solid (1.28 g, 87%). ¹H NMR (500 MHz, CDCl₃): 8.58 (dd, J=4.8, 1.7, 1H), 8.02 (dd, J=7.9, 1.67 1H), 7.38-7.34 (m, 2H), 7.21 (dd, J=7.9, 4.8, 1H), 7.01-6.97 (m, 2H), 4.33 (t, J=6.2, 2H), 3.68 (t, J=6.2, 2H). MS (ESI): mass calcd. for $C_{14}H_{11}BrN_2O_2S$, 349.97; m/z found, 351.0 [M+H]⁺.

Intermediates 12-13 were prepared using methods analogous to those described for Intermediate 11.

Intermediate 12: 2-[4-(2-Bromoethoxy)phenoxyl][1,3]thiazolo[5,4-b]pyridine

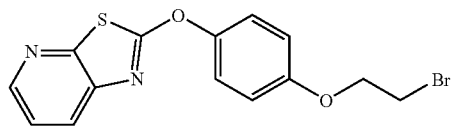

¹H NMR (500 MHz, CDCl₃): 8.42 (dd, J=4.6, 1.3, 1H), 7.95 (td, J=8.0, 2.2, 1H), 7.35 (dd, J=8.2, 4.8, 1H), 7.32-7.29 (m, 2H), 7.08-6.99 (m, 2H), 4.34 (t, J=6.2, 2H), 3.68 (t, J=6.2, 2H). MS (ESI): mass calcd. for $C_{14}H_{11}BrN_2O_2S$, 349.97; m/z found, 351.00 [M+H]⁺.

Intermediate 13: 2-[4-(2-Bromoethoxy)phenoxyl][1,3]thiazolo[4,5-b]pyrazine

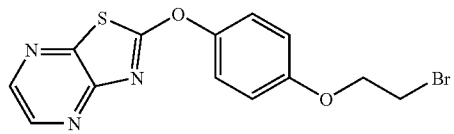

¹H NMR (400 MHz, CDCl₃): 8.52 (d, J=2.7, 1H), 8.34 (d, J=2.6, 1H), 7.36-7.30 (m, 2H), 7.05-6.95 (m, 2H), 4.33 (t, J=6.2, 2H), 3.67 (t, J=6.2, 2H). MS (ESI): mass calcd. for $C_{13}H_{10}BrN_3O_2S$, 351.0; m/z found, 351.9 [M+H]⁺.

Intermediate 14: 2-[4-([1,3]Thiazolo[4,5-b]pyridin-2-yloxy)phenyl]ethanol

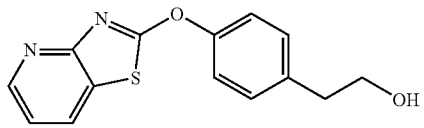

To a solution of 4-hydroxyphenethyl alcohol (1.16 g, 8.4 mmol, 1.2 equiv.) and K₂CO₃ (1.94 g, 14.06 mmol, 2 equiv.) in CH₃CN (12 mL) was added 2-chloro[1,3]thiazolo[4,5-b]pyridine (1.2 g, 7.03 mmol, 1 equiv.). The reaction mixture was heated to 80° C. and stirred for 16 h. Satd. aq. Na₂CO₃ (25 mL) was added to the reaction mixture, which was then extracted with isopropyl acetate (2×30 mL). The combined organic layers were dried, filtered, and concentrated. The crude material was purified by column chromatography (50% EtOAc/hexanes-100% EtOAc), which afforded the title compound as a light orange oil (74%). MS (ESI): mass calcd. for $C_{14}H_{12}N_2O_2S$, 272.32; m/z found, 273.0 [M+H]⁺. ¹H NMR (500 MHz, CDCl₃): 8.56 (dd, J=4.8, 1.6, 1H), 8.03 (dd, J=7.9, 1.7, 1H), 7.37-7.29 (m, 4H), 7.22 (dd, J=7.9, 4.8, 1H), 3.88 (dd, J=12.5, 6.5, 2H), 2.91 (t, J=6.6, 2H), 2.03 (t, J=5.9, 1H).

Intermediate 15: 2-[4-([1,3]Thiazolo[4,5-b]pyridin-2-yloxy)phenyl]ethyl methanesulfonate

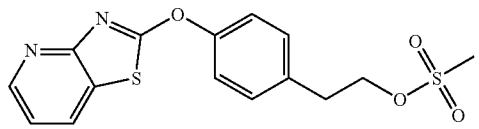

To a solution of 2-[4-([1,3]thiazolo[4,5-b]pyridin-2-yloxy) phenyl]ethanol (1.21 g, 4.46 mmol, 1 equiv.) and 4-dimethylaminopyridine (54 mg, 0.44 mmol, 0.1 equiv.) in CH$_2$Cl$_2$ (15 mL) was added N,N-diisopropylethylamine (0.93 mL, 5.36 mmol, 1.2 equiv.). Methanesulfonic anhydride (934 mg, 5.36 mmol, 1.2 equiv.) was added while the solution stirred in a cold water bath. The reaction mixture was stirred at rt for 15 min. The reaction mixture was washed with satd. aq. NH$_4$Cl (2×20 mL), followed by satd. aq. Na$_2$CO$_3$ (3×20 mL). The organic layer was dried, filtered, and concentrated to produce a yellow/orange solid (91%). MS (ESI): mass calcd. for C$_{15}$H$_{14}$N$_2$O$_4$S$_2$, 350.41; m/z found, 351.0 [M+H]$^+$. $^1$H NMR (500 MHz, CDCl$_3$): 8.58 (dd, J=4.8, 1.6, 1H), 8.05 (dd, J=7.9, 1.7, 1H), 7.44-7.31 (m, 4H), 7.23 (dd, J=7.9, 4.8, 1H), 4.46 (t, J=6.8, 2H), 3.12 (t, J=6.8, 2H), 2.94 (s, 3H).

Intermediate 16: 2-[4-([1,3]Thiazolo[5,4-b]pyridin-2-yloxy)phenyl]ethanol

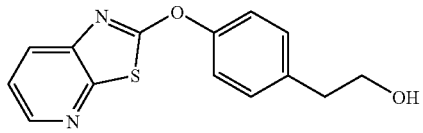

The title compound was prepared using methods analogous to those described for Intermediate 14. $^1$H NMR (500 MHz, CDCl$_3$): 8.38 (dd, J=4.8, 1.5, 1H), 7.91 (dd, J=8.1, 1.6, 1H), 7.35-7.26 (m, 5H), 3.88 (dd, J=12.3, 6.5, 2H), 2.90 (t, J=6.6, 2H), 2.13 (t, J=5.7, 1H). MS (ESI): mass calcd. for C$_{14}$H$_{12}$N$_2$O$_2$S, 272.06; m/z found, 273.1 [M+H]$^+$.

Intermediate 17: 2-[4-([1,3]Thiazolo[5,4-b]pyridin-2-yloxy)phenyl]ethyl methanesulfonate

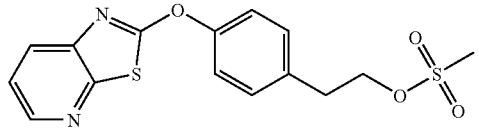

The title compound was prepared using methods analogous to those described for Intermediate 15. $^1$H NMR (500 MHz, CDCl$_3$): 8.40 (dd, J=4.8, 1.5, 1H), 7.92 (dd, J=8.1, 1.5, 1H), 7.36-7.31 (m, 5H), 4.45 (t, J=6.8, 2H), 3.11 (t, J=6.8, 2H), 2.92 (s, 3H). MS (ESI): mass calcd. for C$_{15}$H$_{14}$N$_2$O$_4$S$_2$, 350.04; m/z found, 351.0 [M+H]$^+$.

Intermediate 18: 4-([1,3]Thiazolo[4,5-b]pyridin-2-yloxy)benzaldehyde

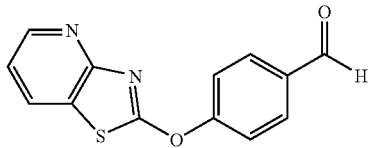

To a solution of 2-chloro[1,3]thiazolo[4,5-b]pyridine (25 g, 147 mmol) in CH$_3$CN (500 mL) was added 4-hydroxybenzaldehyde (19.8 g, 147 mmol, 1 equiv.) and K$_2$CO$_3$ (22.3 g, 147 mmol, 1 equiv.). The heterogeneous mixture was heated at reflux for 72 h and then cooled to rt. Purification was conducted using one of the following methods.

Method A. Water was added to the reaction mixture, and the product was extracted with CH$_2$Cl$_2$ and washed with 1 M NaOH. Charcoal was added to the organic layer, and the mixture stirred for 2 h. After drying and filtration through diatomaceous earth, the solution was concentrated to afford the desired product.

Method B. The solids were removed by filtration and washed with CH$_3$CN (100 mL). To the filtrate was added an aqueous solution of NaHSO$_3$ (22 g, 147 mmol, 54 mL water). After stirring for 3.5 h, the mixture was filtered and the wet cake was dried under vacuum overnight to afford the bisulfite complex as a white powder (57.2 g). To a solution of this bisulfite complex (57.2 g) in CH$_2$Cl$_2$ (520 mL) was added an aqueous solution of NaOH (8 g in 540 mL water, 1.25 equiv.). The resulting mixture was vigorously stirred at rt for 2 h. The product was extracted with CH$_2$Cl$_2$ (200 mL), washed with satd. aq. NaCl (200 mL) and dried. After filtration and concentration, the desired aldehyde was obtained as a white solid (24.6 g, 65% for two steps). $^1$H NMR (500 MHz, CDCl$_3$): 10.02 (s, 1H), 8.59 (dd, J=4.8, 1.6, 1H), 8.10 (dd, J=7.9, 1.6, 1H), 7.97 (d, J=8.7, 2H), 7.66 (d, J=8.7, 2H), 7.28-7.25 (m, 1H). MS (ESI): mass calcd. for C$_{13}$H$_8$N$_2$O$_2$S, 256.04; m/z found, 257.2 [M+H]$^+$.

Intermediate 19: [4-([1,3]Thiazolo[4,5-b]pyridin-2-yloxy)phenyl]methanol

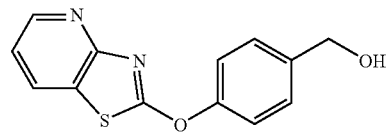

To a suspension of 2-chloro[1,3]thiazolo[4,5-b]pyridine hydrochloride (1.0 equiv.) in CH$_3$CN (0.25 M), was added K$_2$CO$_3$ (powder, 325 mesh; 2.1 equiv.). The mixture was stirred at 50° C. under N$_2$ for 3 h prior to the addition of 4-hydroxymethyl-phenol (1.0 equiv.). The reaction mixture was heated at reflux for 3 h and cooled to rt. Some product precipitated out from the reaction solution and was dissolved by adding CH$_2$Cl$_2$. The insoluble inorganic salt was then filtered off and washed with CH$_2$Cl$_2$. The filtrate solution was concentrated to give the title compound (99%), which was used without further purification. MS (ESI): mass calcd. for C$_{13}$H$_{10}$N$_2$O$_2$S, 258.1; m/z found, 258.9 [M+H]$^+$. $^1$H NMR (400 MHz, CDCl$_3$): 8.56 (ddd, J=4.9, 1.7, 0.4, 1H), 8.02 (ddd, J=7.9, 1.7, 0.4, 1H), 7.48-7.38 (m, 4H), 7.21 (ddd, J=7.9, 4.8, 0.4, 1H), 4.74 (s, 2H).

Intermediate 20: 2-[4-(Chloromethyl)phenoxyl][1,3]thiazolo[4,5-b]pyridine

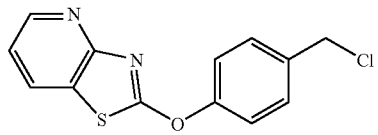

To a solution of [4-([1,3]thiazolo[4,5-b]pyridin-2-yloxy)phenyl]methanol (1.0 equiv.) in CH$_2$Cl$_2$ (0.3 M), SOCl$_2$ (1.2 equiv.) was slowly added over 1 h at rt. In some embodiments, an excess of thionyl chloride was used, which was distilled off prior to the subsequent reaction step. After stirring at rt for another 30 min, the precipitated solid was collected by filtration and washed with CH$_2$Cl$_2$ to afford the title compound (100%), which was used without further purification. MS (ESI): mass calcd. for C$_{13}$H$_9$ClN$_2$OS, 276.0; m/z found, 277.0 [M+H]$^+$. $^1$H NMR (400 MHz, DMSO-d$_6$): 8.55 (dd, J=4.9, 1.7, 1H), 8.47 (dd, J=8.0, 1.7, 1H), 7.62 (dt, J=8.7, 2.1, 2H), 7.52 (dt, J=8.7, 2.1, 2H), 7.39 (dd, J=8.0, 4.9, 1H), 6.42 (br s, 1H), 4.84 (s, 2H).

Intermediate 21: [4-([1,3]Thiazolo[5,4-b]pyridin-2-yloxy)phenyl]methanol

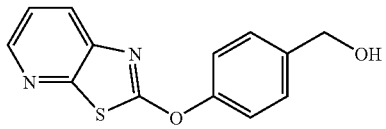

To a solution of 2-chloro[1,3]thiazolo[5,4-b]pyridine (103 mg, 0.604 mmol) in DMF (2.0 mL) was added 4-hydroxymethyl-phenol (75 mg, 0.604 mmol, 1.0 equiv.) and Cs$_2$CO$_3$ (221 mg, 0.628 mmol, 1.04 equiv.). The reaction mixture was then allowed to stir at rt for 14 h. The reaction mixture was then filtered through diatomaceous earth, diluted with EtOAc (15 mL), washed with water (4×50 mL) and dried. After filtration and concentration, the desired product was obtained as a cream-colored solid (140 mg, 90%). MS (ESI): mass calcd. for C$_{13}$H$_{10}$N$_2$O$_2$S, 258.1; m/z found, 259.0 [M+H]$^+$. $^1$H NMR (600 MHz, DMSO-d$_6$): 8.46-8.44 (m, 1H), 8.11-8.08 (m, 1H), 7.51 (dd, J=8.2, 4.7, 1H), 7.48-7.42 (m, 4H), 5.32 (t, J=5.8, 1H), 4.55 (d, J=5.8, 2H).

Intermediate 22: 2-[4-(Chloromethyl)phenoxy][1,3]thiazolo[5,4-b]pyridine

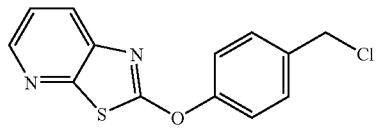

To a solution of [4-([1,3]thiazolo[5,4-b]pyridin-2-yloxy)phenyl]methanol (140 mg, 0.542 mmol) in CH$_2$Cl$_2$ (3.6 mL) was added SOCl$_2$ (43 µL, 0.596 mmol, 1.1 equiv.). The solution was allowed to stir under N$_2$ at rt for 4 h. The reaction mixture was then concentrated to afford the desired product as a cream-colored solid (157 mg, 92%). MS (ESI): mass calcd. for C$_{13}$H$_9$ClN$_2$OS, 276.0; m/z found, 277.0 [M+H]$^+$. $^1$H NMR (600 MHz, DMSO-d$_6$): 8.47 (dd, J=4.4, 1.5, 1H), 8.11 (dd, J=8.2, 1.5, 1H), 7.65-7.57 (m, 2H), 7.56-7.47 (m, 3H), 4.85 (s, 2H).

Intermediate 23: [4-([1,3]Thiazolo[5,4-c]pyridin-2-yloxy)phenyl]methanol

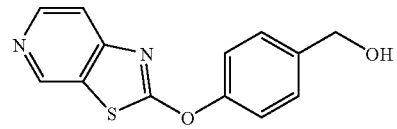

The title compound was prepared using methods analogous to those described for Intermediate 21. $^1$H NMR (400 MHz, CDCl$_3$): 8.82 (d, J=1.2, 1H), 8.53 (d, J=5.6, 1H), 7.61 (dd, J=5.6, 0.8, 1H), 7.51-7.49 (m, 2H), 7.37-7.33 (m, 2H), 4.76 (s, 2H). MS (ESI): mass calcd. for C$_{13}$H$_{10}$N$_2$O$_2$S, 258.05; m/z found, 259.00 [M+H]$^+$.

Intermediate 24: 2-[4-(Chloromethyl)phenoxyl][1,3]thiazolo[5,4-c]pyridine hydrochloride

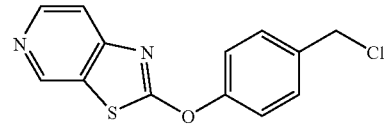

The title compound was prepared using methods analogous to those described for Intermediate 22. This material was used directly in the next step. MS (ESI): mass calcd. for C$_{13}$H$_9$ClN$_2$OS, 276.01; m/z found, 277.00 [M+H]$^+$.

Intermediate 25: (1S,4S)-2,5-Diazabicyclo[2.2.1]heptane-2-carboxamide hydrochloride

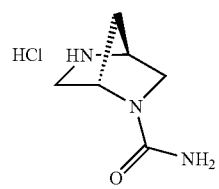

To a solution of tert-butyl-(S,S)-2,5-diazabicyclo[2.2.1]heptane-2-carboxylate (35.6 g, 179 mmol) in CH$_2$Cl$_2$ (600 mL) was added trimethylsilylisocyanate (82.5 g, 716 mmol, 4 equiv.). The reaction was stirred at rt for 2 h. After concentration, the resulting white solid was dissolved in CH$_2$Cl$_2$ (500 mL) and treated with a solution of HCl (4 M in dioxane, 135 mL, 3 equiv.). The solution quickly became heterogeneous. The suspension was then stirred at rt overnight. Upon concentration, the desired product was isolated as a white solid (33 g, 104%), which was used directly in the next step. [Note: the mass balance was found to be 104%, which arises from additional HCl that could not be removed by standard evaporation under vacuum]. $^1$H NMR (500 MHz, CD$_3$OD): 4.77 (s, 1H), 4.55 (s, 1H), 3.69 and 3.64 (AB, J$_{AB}$=12.1, 2H), 3.47 and 3.40 (AB, J$_{AB}$=11.3, 2H), 2.22 and 2.15 (AB, J$_{AB}$=11.5, 2H).

Intermediates 26-29 were prepared using methods analogous to those described for Intermediate 25.

Intermediate 26:
meso-1-[(3-endo)-8-Azabicyclo[3.2.1]oct-3-yl]urea hydrochloride

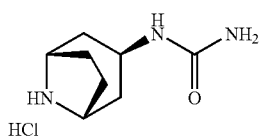

$^1$H NMR (400 MHz, CD$_3$OD): 4.16-4.07 (m, 1H), 4.06-3.99 (m, 1H), 3.95-3.88 (m, 0.5H), 3.75-3.60 (m, 0.5H), 2.60 (ddd, J=16.4, 7.3, 4.7, 1H), 2.40-2.23 (m, 3H), 2.23-2.12 (m, 2H), 2.12-1.98 (m, 2H).

Intermediate 27:
meso-3,8-Diazabicyclo[3.2.1]octane-3-carboxamide hydrochloride

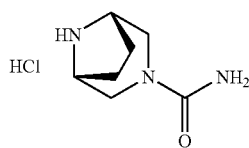

$^1$H NMR (400 MHz, CD$_3$OD): 4.41-4.24 (m, 1H), 4.17-4.07 (m, 2H), 4.02-3.87 (m, 2H), 3.71-3.60 (m, 1H), 3.56-3.49 (m, 1H), 3.41-3.33 (m, 3H). MS (ESI): mass calcd. for C$_7$H$_{13}$N$_3$O, 155.11; m/z found, 156.1 [M+H]$^+$.

Intermediate 28:
meso-1-[(3-exo)-8-Azabicyclo[3.2.1]oct-3-yl]urea hydrochloride

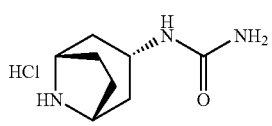

$^1$H NMR (500 MHz, CD$_3$OD): 4.09 (s, 2H), 4.07-3.99 (m, 1H), 2.20-2.06 (m, 6H), 1.81 (t, J=12.3, 2H). MS (ESI): mass calcd. for C$_8$H$_{15}$N$_3$O, 169.12; m/z found, 170.10 [M+H]$^+$.

Intermediate 29:
Hexahydropyrrolo[3,4-c]pyrrole-2(1H)-carboxamide hydrochloride

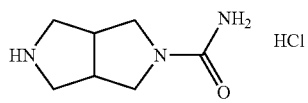

$^1$H NMR (400 MHz, DMSO-d$_6$): 9.84 (s, 1H), 3.75 (s, 6H), 3.48-3.17 (m, 4H), 3.04-2.89 (m, 2H).

Intermediate 30: meso-N-[(3-endo)-8-Azabicyclo[3.2.1]oct-3-yl]acetamide hydrochloride

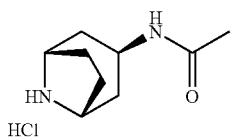

To a solution of tert-butyl (3-endo)-3-amino-8-azabicyclo[3.2.1]octane-8-carboxylate (3.4 g, 15 mmol) in CH$_2$Cl$_2$ (50 mL) was added acetic anhydride (1.2 mL, 16.5 mmol, 1.1 equiv.). The reaction was stirred at rt for 2 h. After concentration, the resulting white solid was dissolved in CH$_2$Cl$_2$ (50 mL) and treated with HCl (4 M in dioxane, 15 mL, 4 equiv.). The solution quickly became heterogeneous. The suspension was then stirred at rt overnight. Upon concentration, the desired product was isolated as a white solid (3.35 g, 109%). [Note: the mass balance was found to be 109% is attributed to additional HCl that could not be removed by standard evaporation under reduced pressure]. $^1$H NMR (400 MHz, CD$_3$OD): 4.05-3.99 (m, 2H), 3.99-3.94 (m, 1H), 2.40-2.24 (m, 4H), 2.21-2.07 (m, 4H), 2.04 (s, 3H).

Alternative Synthesis of Intermediate 30:

Step 1: meso-8-Azabicyclo[3.2.1]octan-3-one hydrochloride. A solution of tropinone (1.0 equiv.) in toluene (1.2 M) was treated with 1-chloroethyl chloroformate (1.5 equiv.). The reaction mixture was heated at reflux overnight (18 h) then cooled to rt and concentrated to a brown oil. To this brown oil was slowly added MeOH (1.2 M relative to starting material) over a period of 10 min with vigorous stirring. After heating at reflux for 3 h, the reaction was cooled to rt and then concentrated to a dark colored oil. With vigorous stirring, CH$_3$CN (4.8 M relative to starting material) was added to form a precipitate. To this mixture was added EtOAc (1.2 M relative to starting material). The resultant slurry was stirred overnight and filtered to recover the title compound as a brown solid. The filtrate was concentrated down before the addition of CH$_3$CN/EtOAc (1:4). The solids were filtered to recover another portion of product for an overall yield of 78%. $^1$H NMR (500 MHz, CD$_3$OD): 1.96-2.00 (q, J=7.0, 15.5, 2H), 2.24-2.27 (m, 2H), 2.55 (d, J=17.3, 2H), 2.95 (dd, J=4.8, 17.7, 2H), 4.33-4.35 (m, 2H). MS (ESI): mass calcd. for C$_7$H$_{11}$NO, 125.08; m/z found, 126.1 [M+H]$^+$.

Step 2: meso-8-Benzyl-8-azabicyclo[3.2.1]octan-3-one. A mixture of meso-8-azabicyclo[3.2.1]octan-3-one hydrochloride (1.0 equiv.), benzyl bromide (1.0 equiv.), and Na$_2$CO$_3$ (2.5 equiv.) in CH$_3$CN (0.8 M) was heated at reflux for 2 h and then concentrated to half the original volume. The mixture was quenched with water (1.2 M relative to starting material) and tert-butyl methyl ether (1.2 M relative to starting material) and then, with vigorous stirring, slowly acidified to pH 1-2 with concentrated HCl. The separated aqueous layer was basified with NaOH pellets until pH 13-14 was obtained and extracted with tert-butyl methyl ether. The combined organic layers were dried, filtered and concentrated to afford the title compound (75%). $^1$H NMR (500 MHz, CDCl$_3$): 1.62-1.64 (d, J=7.9, 2H), 2.11-2.13 (m, 2H), 2.21 (dd, J=1.5, 17.1, 2H), 2.69 (dd, J=4.4, 16.1, 2H), 3.49-3.5 (m, 2H), 3.75 (s, 2H), 7.28 (d, J=7.3, 1H), 7.35 (t, J=7.5, 2H), 7.42 (d, J=7.5, 2H). MS (ESI): mass calcd. for C$_{14}$H$_{17}$NO, 215.13; m/z found, 216.1 [M+H]$^+$.

Step 3: meso-8-Benzyl-8-azabicyclo[3.2.1]octan-3-one oxime. A solution of meso-8-benzyl-8-azabicyclo[3.2.1]octan-3-one (1.0 equiv.) in EtOH (0.78 M) and water (0.78 M). Hydroxylamine hydrochloride (2.0 equiv.) was added causing mild exotherm. With vigorous stirring, slowly NaHCO$_3$ was added in six portions over a period of 15 min to minimize gas evolution. The reaction mixture was heated to 50° C. for 1 h, becoming cloudy in appearance before precipitation occurred. After stirring for 48 h at rt, the white slurry was filtered and washed with 9:1 water/EtOH (0.25 M relative to starting material). The white solids were dried to recover the title compound (93%). $^1$H NMR (500 MHz, CDCl$_3$): 1.47-1.68 (m, 2H), 1.97-2.09 (m, 2H), 2.13 (d, J=14.7, 1H), 2.23 (dd, J=3.9, 15.5, 1H), 2.59 (dd, J=3.5, 14.7, 1H), 2.96-3.0 (d, J=15.5, 1H), 3.33-3.36 (m, 2H), 3.65 (s, 2H), 7.24-7.27 (m, 1H), 7.31-7.35 (m, 2H), 7.39-7.41 (m, 2H), 8.22 (s, 1H). MS (ESI): mass calcd. for C$_{14}$H$_{18}$N$_2$O, 230.14; m/z found, 231.1 [M+H]$^+$.

Step 4: meso-N-[(3-endo)-8-Benzyl-8-azabicyclo[3.2.1]oct-3-yl]acetamide. To a solution of meso-8-benzyl-8-azabicyclo[3.2.1]octan-3-one oxime (1.0 equiv.) in EtOAc (1.6 M) was added acetic anhydride (1.05 M), acetic acid (15% wt) and 10% Pt/C (41% wt). The mixture was agitated under 55 psi H$_2$ (g) overnight at rt. After the reaction was complete, the catalyst was filtered and washed with EtOAc. The filtrate was quenched with water then carefully basified to pH 10-11 using excess NaOH pellets under a cold bath. Caution was exercised as a high exotherm could cause partial deacylation and hydrolysis of the amine to give meso-8-benzyl-8-azabicyclo[3.2.1]octan-3-one. The aqueous layer was extracted with EtOAc (6×). The combined organic layers were dried, filtered and concentrated to a crude solid. The crude product was slurried overnight in 1:1 tert-butyl methyl ether/hexanes (0.6 M relative to starting material) and filtered to recover the title compound with a yield of about 75%, of which at least 95% was in endo form. $^1$H NMR (500 MHz, CDCl$_3$): 1.58 (d, J=14.8, 2H), 1.73-1.77 (m, 2H), 1.96 (s, 3H), 2.13-2.17 (m, 2H), 2.19-2.24 (m, 2H), 3.19 (s, 2H), 3.52 (s, 2H), 4.11 (q, J=7.1, 14.3, 1H), 5.82 (s, 1H), 7.24 (t, J=7.2, 1H), 7.31 (t, J=7.7, 2H) 7.36 (d, J=6.9, 2H). MS (ESI): mass calcd. for C$_{16}$H$_{22}$N$_2$O, 258.17; m/z found, 259.1 [M+H]$^+$.

In other embodiments, to a solution of meso-8-benzyl-8-azabicyclo[3.2.1]octan-3-one oxime (1.0 equiv.) in EtOAc (0.1 M) was added AcOH (0.5 equiv.) and acetic anhydride (10 equiv.) forming an ethyl acetate, acetic anhydride and acetic acid solution approximately 0.1 M. An H-Cube Midi™ continuous flow hydrogenation instrument with 10% Pt/C was utilized to hydrogenate the mixture at flow rate of 3 ml/min, 80 bar and 60° C. After completion, GC/MS analysis showed a 95/5 endo/enamine isomer ratio. The reaction mixture from the continuous flow hydrogenation instrument was concentrated to oil, then washed with 1 N NaOH solution and EtOAc. The organic layer was extracted, dried with Na$_2$SO$_4$, filtered and concentrated to recover title compound (80%).

Step 5: meso-N-[(3-endo)-8-Azabicyclo[3.2.1]oct-3-yl]acetamide. To a solution of meso-N-[(3-endo)-8-benzyl-8-azabicyclo[3.2.1]oct-3-yl]acetamide (1.0 equiv.) in EtOH (0.5 M) was added 20% Pd(OH)$_2$ (16% wt). The mixture was agitated under 55 psi H$_{2(g)}$ overnight at rt. After the reaction was complete, the catalyst was filtered and washed with EtOH (1.2 M relative to starting material). The filtrate was concentrated to a white solid then dried overnight to afford the title compound (100%). $^1$H NMR (500 MHz, CDCl$_3$): 1.68 (dd, J=1.4, 14.8, 2H), 1.84-1.94 (m, 4H), 1.97 (s, 3H), 2.07-2.12 (m, 2H), 3.54 (s, 2H), 4.11 (q, J=6.9, 14.0, 1H), 5.84 (s, 1H). $^{13}$C NMR (500 MHz, CDCl$_3$): 169.01, 53.31, 41.97, 37.34, 29.08, 23.55. MS (ESI): mass calcd. for C$_9$H$_{16}$N$_2$O, 168.13; m/z found, 169.1 [M+H]$^+$.

Intermediates 31-34 were prepared using methods analogous to those described for Intermediate 30.

Intermediate 31:
meso-3-Acetyl-3,8-diazabicyclo[3.2.1]octane hydrochloride

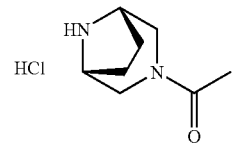

$^1$H NMR (400 MHz, CD$_3$OD): 4.45-4.36 (m, 1H), 4.35-4.29 (m, 2H), 4.15-4.08 (m, 2H), 3.97-3.86 (m, 1H), 3.71-3.58 (m, 2H), 3.57-3.47 (m, 2H), 2.15 (s, 3H). MS (ESI): mass calcd. for C$_8$H$_{14}$N$_2$O, 154.14; m/z found, 155.1 [M+H]$^+$.

Intermediate 32: meso-N-[(3-exo)-8-Azabicyclo[3.2.1]oct-3-yl]acetamide hydrochloride

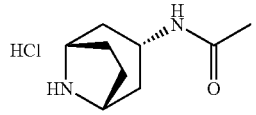

$^1$H NMR (500 MHz, CD$_3$OD): 4.20 (tt, J=11.6, 5.6, 1H), 4.09 (s, 2H), 2.19-2.03 (m, 6H), 1.96 (d, J=3.0, 3H), 1.85-1.76 (m, 2H). MS (ESI): mass calcd. for C$_9$H$_{16}$N$_2$O, 168.13; m/z found, 169.20 [M+H]$^+$.

Intermediate 33:
(1S,4S)-2-Acetyl-2,5-diazabicyclo[2.2.1]heptane hydrochloride

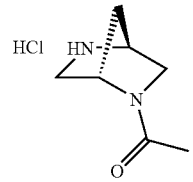

$^1$H NMR (500 MHz, CD$_3$OD): 4.98-4.78 (m, 1H), 4.52 (d, J=17.2, 1H), 3.79-3.66 (m, 1H), 3.63-3.52 (m, 1H), 3.43 (q, J=11.6, 1H), 3.36 (s, 1H), 2.23 (d, J=11.5, 0.6H), 2.20-2.13

(m, 2H), 2.12-2.03 (m, 2H), 2.01 (d, J=11.5, 0.4H). MS (ESI): mass calcd. for $C_7H_{12}N_2O$, 140.09; m/z found, 141.10 [M+H]+.

Intermediate 34: 2-Acetyloctahydropyrrolo[3,4-c]pyrrole Hydrochloride

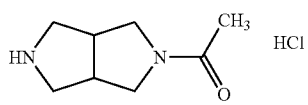

$^1$H NMR (500 MHz, DMSO-$d_6$): 9.59 (s, 1H), 3.86 (s, 8H), 3.50-3.42 (m, 1H), 3.38-3.29 (m, 2H), 3.09-2.90 (m, 2H).

Intermediate 35: tert-Butyl (1S,4S)-5-(4-hydroxybenzyl)-2,5-diazabicyclo[2.2.1]heptane-2-carboxylate

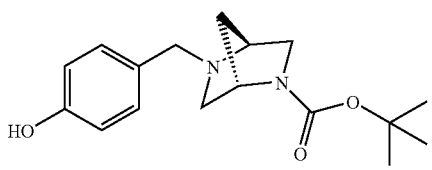

To a solution of 4-hydroxybenzaldehyde (20 g, 0.163 mol, 1 equiv.) in $CH_2Cl_2$ (340 mL) was added tert-butyl (1S,4S)-2,5-diazabicyclo[2.2.1]heptane-2-carboxylate (35.7 g, 0.18 mol, 1.1 equiv.), acetic acid (2.8 mL, 0.05 mol, 0.3 equiv.) and sodium triacetoxyborohydride (41.4 g, 0.195 mol, 1.2 equiv.). The reaction was stirred at rt for 16 h. The reaction was quenched with satd. aq. $NaHCO_3$ (3×150 mL) and 1 M NaOH (1×100 mL). The combined aqueous layers were reacidified with 1 M HCl and extracted with $CH_2Cl_2$ (2×300 mL). The organic layers were dried, filtered, and concentrated. Purification by column chromatography (5% MeOH/$CH_2Cl_2$) yielded product as a white powdery solid (24.4 g, 50%). $^1$H NMR (500 MHz, CDCl$_3$): 7.16 (d, J=8.5, 2H), 6.74 (d, J=8.5, 2H), 4.37 (s, 0.5H), 4.25 (s, 0.5H), 3.65 (s, 2.5H), 3.52 (s, 0.5H), 3.47 (s, 1H), 3.16 (d, J=10.3, 1H), 2.92 (s, 0.5H), 2.82 (s, 0.5H), 2.72 (s, 0.5H), 2.57 (d, J=9.6, 0.5H), 1.85 (s, 1H), 1.74-1.62 (m, 1H), 1.47 (s, 9H). MS (ESI): mass calcd. for $C_{17}H_{24}N_2O_3$, 304.38; m/z found, 305.2 [M+H]+.

Intermediate 36: 4-[(1S,4S)-2,5-Diazabicyclo[2.2.1]hept-2-ylmethyl]phenol Dihydrochloride

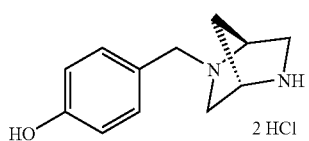

To a solution of tert-butyl (1S,4S)-5-(4-hydroxybenzyl)-2,5-diazabicyclo[2.2.1]heptane-2-carboxylate (3.47 g, 0.0114 mol, 1 equiv.) in $CH_2Cl_2$ (42 mL) was added HCl (4 M in dioxane, 22.5 mL, 0.114 mol, 10 equiv.). The solution was stirred at rt for 12 h. The mixture was then concentrated, affording a white solid (100%). $^1$H NMR (500 MHz, DMSO-$d_6$): 11.60-11.28 (m, 1H), 10.38-9.95 (m, 1H), 9.93-9.56 (m, 2H), 7.49 (s, 2H), 6.81 (s, 2H), 4.39 (m, 4H), 3.88 (s, 1H), 3.67 (s, 1H), 2.72-2.52 (m, 0.5H), 2.45-2.30 (m, 0.5H), 2.08 (s, 1H). MS (ESI): mass calcd. for $C_{12}H_{16}N_2O$, 204.27; m/z found, 205.1 [M+H]+.

Intermediate 37: 4-{[(1S,4S)-5-Acetyl-2,5-diazabicyclo[2.2.1]hept-2-yl]methyl}phenyl Acetate

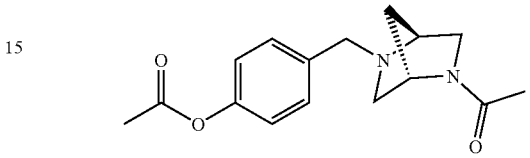

To a solution of 4-{[(1S,4S)-5-acetyl-2,5-diazabicyclo[2.2.1]hept-2-yl]methyl}phenyl acetate (3.3 g, 13.73 mmol, 1 equiv.) and Et$_3$N (8.42 mL, 60.4 mmol, 4.4 equiv.) in $CH_2Cl_2$ (44 mL) was added acetic anhydride (2.85 mL, 30.21 mmol, 2.2 equiv.). The solution was stirred at rt for 4 h. The reaction mixture was washed with water (1×75 mL) and satd. aq. $NaHCO_3$ (1×75 mL). The organic layer was dried, filtered and concentrated. Purification by column chromatography (5% MeOH/$CH_2Cl_2$) yielded the title compound as a clear yellow oil (2.33 g, 59%). $^1$H NMR (500 MHz, CDCl$_3$): 7.34 (m, 2H), 7.03 (m, 2H), 4.75 (s, 0.5H), 4.22 (s, 0.5H), 3.73 (s, 1H), 3.70 (s, 1H), 3.57-3.53 (m, 2H), 3.29 (dd, J=9.8, 2.6, 0.5H), 3.24 (dd, J=11.4, 2.1, 0.5H), 2.98 (dd, J=9.9, 2.2, 0.5H), 2.82 (dd, J=9.8, 2.2, 0.5H), 2.75 (d, J=10.5, 0.5H), 2.55 (d, J=9.8, 0.5H), 2.27 (s, 3H), 2.06 (s, 1H), 1.98 (s, 2H), 1.96 (d, J=9.9, 0.5H), 1.88 (d, J=9.9, 0.5H), 1.77 (d, J=9.9, 0.5H), 1.64 (d, J=10.5, 0.5H). MS (ESI): mass calcd. for $C_{16}H_{20}N_2O_3$, 288.34; m/z found, 289.2 [M+H]+.

Intermediate 38: Sodium 4-{[(1S,4S)-5-acetyl-2,5-diazabicyclo[2.2.1]hept-2-yl]methyl}phenolate

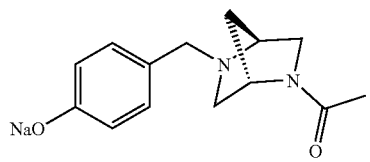

To a solution of 4-{[(1S,4S)-5-acetyl-2,5-diazabicyclo[2.2.1]hept-2-yl]methyl}phenyl acetate (2.33 g, 8.08 mmol, 1 equiv.) in $CH_2Cl_2$ (12.1 mL) and MeOH (8.1 mL) was added a solution of NaOH (0.323 g, 8.08 mmol, 1 equiv.) in water (4.1 mL). The solution was stirred at rt for 3 h. The reaction mixture was concentrated to afford product as an off-white solid (100%). $^1$H NMR (500 MHz, CD$_3$OD): 7.01 (dd, J=8.8, 2.7, 2H), 6.61 (d, J=8.2, 2H), 4.63 (s, 0.5H), 4.41 (s, 0.5H), 3.63-3.53 (m, 4H), 3.35 (s, 3H), 3.28 (m, 0.5H), 3.19 (d, J=11.5, 0.5H), 2.91 (dd, J=10.3, 2.1, 0.5H), 2.82 (dd, J=10.2, 2.2, 0.5H), 2.67 (m, 1H), 1.94 (m, 1H), 1.76 (d, J=9.9, 0.5H), 1.66 (d, J=9.9, 0.5H).

Intermediate 39: 4-(Piperidin-1-ylmethyl)phenol

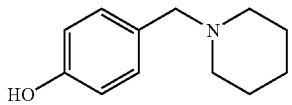

The title compound was prepared using methods analogous to those described for Intermediate 35, substituting DCE for CH$_2$Cl$_2$. $^1$H NMR (500 MHz, CDCl$_3$): 7.14-7.03 (m, 2H), 6.75 (br s, 1H), 6.62-6.53 (m, 2H), 3.41 (s, 2H), 2.49 (s, 4H), 1.66-1.59 (m, 4H), 1.50-1.42 (m, 2H). MS (ESI): mass calcd. for C$_{12}$H$_{17}$NO, 191.13; m/z found, 192.20 [M+H]$^+$.

Intermediate 40: Ethyl 1-(4-hydroxybenzyl)piperidine-4-carboxylate

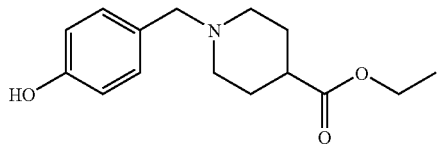

The title compound was prepared using methods analogous to those described for Intermediate 35. $^1$H NMR (400 MHz, CD$_3$OD): 7.23-7.13 (m, 2H), 6.82-6.73 (m, 2H), 4.13 (q, J=7.1, 2H), 3.76 (s, 2H), 3.13-3.01 (m, 2H), 2.58-2.37 (m, 3H), 2.04-1.97 (m, 2H), 1.88-1.71 (m, 2H), 1.24 (t, J=7.1, 3H). MS (ESI): mass calcd. for C$_{15}$H$_{21}$NO$_3$, 263.15; m/z found, 264.2 [M+H]$^+$.

Intermediate 41: Ethyl 1-[2-(4-hydroxyphenoxy)ethyl]piperidine-4-carboxylate

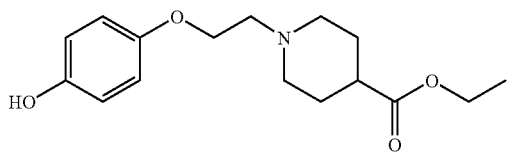

To a stirred suspension of 4-(2-bromo-ethoxy)-phenol (600 mg, 2.77 mmol) and ethyl isonipecotate (470 μL, 3.06 mmol) in CH$_3$CN (12 mL) was added Et$_3$N (768 μL, 5.54 mmol). The resultant mixture was stirred at rt overnight and then concentrated to afford the title compound, which was used immediately in the next step. MS (ESI): mass calcd. for C$_{16}$H$_{23}$NO$_4$, 293.16; m/z found, 294.1 [M+H]$^+$.

Intermediate 42: 2-Chloro[1,3]thiazolo[4,5-c]pyridine

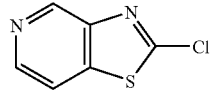

The title compound was prepared using methods analogous to those described for Intermediate 10. $^1$H NMR (500 MHz, CDCl$_3$): 9.26 (s, 1H), 8.59 (d, J=6.1, 1H), 7.77 (dd, J=5.5, 0.9, 1H). MS (ESI): mass calcd. for C$_6$H$_3$ClN$_2$S, 169.97; m/z found, 171.0 [M+H]$^+$.

Intermediate 43: [4-([1,3]Thiazolo[4,5-c]pyridin-2-yloxy)phenyl]methanol

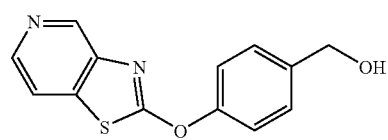

The title compound was prepared using methods analogous to those described for Intermediate 21. $^1$H NMR (500 MHz, CDCl$_3$): 8.99 (s, 1H), 8.45 (d, J=5.3, 1H), 7.67 (dd, J=5.3, 0.8, 1H), 7.39-7.38 (m, 2H), 7.28-7.25 (m, 2H), 4.78 (s, 2H). MS (ESI): mass calcd. for C$_{13}$H$_{10}$N$_2$O$_2$S, 258.05; m/z found, 259.00 [M+H]$^+$.

Intermediate 44: 2-[4-(Chloromethyl)phenoxyl][1,3]thiazolo[4,5-c]pyridine

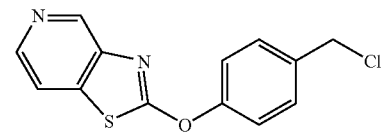

The title compound was prepared using methods analogous to those described for Intermediate 22. $^1$H NMR (500 MHz, CDCl$_3$): 9.02 (s, 1H), 8.65 (d, J=5.0, 1H), 8.32 (d, J=5.0, 1H), 7.54-7.52 (m, 2H), 7.38-7.36 (m, 2H), 4.62 (s, 2H). MS (ESI): mass calcd. for C$_{13}$H$_9$ClN$_2$OS, 276.01; m/z found, 277.00 [M+H]$^+$.

Intermediate 45: meso-1-(3,7-Diazabicyclo[3.3.1]non-3-yl)ethanone

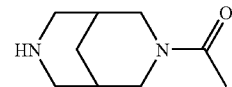

To meso-3-benzyl-3,7-diazabicyclo[3.3.1]nonane (1.1 g, 5.08 mmol) in CH$_2$Cl$_2$ (51 mL) was added acetic anhydride (0.55 mL, 5.83 mmol) and Et$_3$N (2.13 mL, 15.3 mmol). The mixture was stirred for 16 h, diluted with CH$_2$Cl$_2$ (100 mL) and washed with water (3×50 mL) and brine (1×50 mL). The organic layer was dried and concentrated to yield 1-(7-benzyl-3,7-diaza-bicyclo[3.3.1]non-3-yl)-ethanone (1.32 g, 100%). This intermediate (1.22 g, 4.72 mmol) was dissolved in ethanol (12 mL) and added onto a mixture of 20% palladium hydroxide (150 mg) and ethanol (10 mL). The mixture was stirred under a hydrogen balloon for 48 h, filtered through Celite, and concentrated to yield the product (794 mg, 100%). $^1$H NMR (500 MHz, CDCl$_3$): 4.58 (d, J=13.8, 1H), 3.87 (d, J=12.5, 1H), 3.48-3.39 (m, 1H), 3.15-3.01 (m, 3H), 2.97 (dd, J=13.3, 2.9, 2H), 2.13 (s, 3H), 1.96-1.90 (m, 1H), 1.86-1.80 (m, 1H), 1.79-1.69 (m, 3H). MS (ESI): mass calculated for C$_9$H$_{16}$N$_2$O, 168.13; m/z found, 169.20 [M+H]$^+$.

Intermediate 46: (1S,4S)-2,5-Diazabicyclo[2.2.2]octane-2-carboxamide Hydrochloride

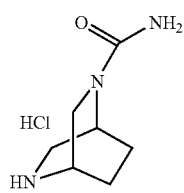

This intermediate was prepared using methods analogous to those described for Intermediate 25. $^1$H NMR (500 MHz, CD$_3$OD): 4.36 (s, 1H), 3.89-3.78 (m, 2H), 3.66 (s, 2H), 3.65-3.59 (m, 1H), 3.53-3.39 (m, 2H), 2.24-2.04 (m, 2H), 2.03-1.88 (m, 2H). MS (ESI): mass calculated for C$_7$H$_{13}$N$_3$O, 155.11; m/z found, 156.15 [M+H]$^+$.

Intermediates 47-48 were prepared using methods analogous to those described for Intermediate 30.

Intermediate 47: 1-(3,9-Diazaspiro[5.5]undec-3-yl)ethanone Hydrochloride

$^1$H NMR (400 MHz, CD$_3$OD): 3.63-3.51 (m, 4H), 3.23-3.16 (m, 4H), 2.13 (s, 3H), 1.81-1.73 (m, 4H), 1.68-1.52 (m, 4H). MS (ESI): mass calculated for C$_{11}$H$_{20}$N$_2$O, 196.16; m/z found, 197.10 [M+H]$^+$.

Intermediate 48: 1-[(1S,4S)-2,5-Diazabicyclo[2.2.2]oct-2-yl]ethanone Hydrochloride

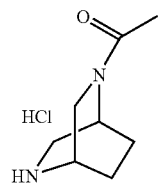

$^1$H NMR (400 MHz, CD$_3$OD): 4.72-4.67 (m, 0.5H), 4.26-4.20 (m, 0.5H), 3.92 (dt, J=12.0, 2.6, 0.5H), 3.87-3.80 (m, 1H), 3.80-3.56 (m, 1.5H), 3.55-3.39 (m, 2H), 2.76 (br s, 1H), 2.22-1.87 (m, 6H). MS (ESI): mass calculated for C$_8$H$_{14}$N$_2$O, 154.11; m/z found, 155.20 [M+H]$^+$.

Intermediate 49: meso-N-[(3-endo)-8-(4-Hydroxybenzyl)-8-aza-bicyclo[3.2.1]oct-3-yl]acetamide Hydrochloride

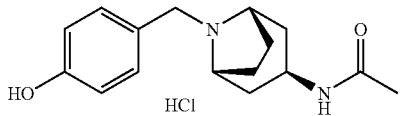

meso-N-[(3-endo-(8-Aza-bicyclo[3.2.1]oct-3-yl)acetamide]hydrochloride (1.552 kg, 7.58 mol) was added to a suspension of potassium carbonate (2.068 kg, 15.0 mol) in acetonitrile (19.40 kg) at room temperature. The mixture was heated to 60° C. for 2 hours, then the salts were removed by filtration. The filter cake was washed with acetonitrile (9.312 kg) at 60° C. for 30 min, before the salts were filtered off again. The acetonitrile solutions were united and about 50% of the solvent was removed by distillation. 4-Hydroxybenzaldehyde (1.107 kg, 9.06 mol) was added to the residue at room temperature, followed by acetic acid (0.449 kg, 7.48 mol). When sodium triacetoxyborohydride (1.836 kg, 8.66 mol) was added to the resulting brown solution a temperature rise of 5° C. was observed. The reaction mixture was heated to 70° C. until the reaction was complete (about 5 h, monitoring by HPLC). The reaction mixture was then cooled to 20° C. and isopropanol (12.882 kg) was added within 40 min. The mixture was stirred at room temperature overnight, then 13.90 kg of the solvent were distilled off. Isopropanol (12.882 kg) was added and another 10.26 kg solvent were distilled off. The resulting thick suspension was filtered and the filter cake washed with isopropanol (5.0 kg). The reddish-orange filtrate was heated to 45° C. and hydrochloric acid (HCl 37% aq.) (0.817 kg, 8.28 mol) was added dropwise within 20 min (until pH 2-3), resulting in the crystallization of the product. The mixture was kept at 40-45° C. for 1 h, before acetone (6.0 kg) was added. After cooling to 0° C., the product was isolated by filtration, washed with a mixture of acetone (1.5 kg) and isopropanol (1.5 kg) and dried in vacuo at 70° C. Yield: 2.35 kg yellowish solid (96%).

Intermediates 50-51 were prepared using methods analogous to those described for Intermediate 35, substituting 4-acetoxybenzaldehyde for 4-hydroxybenzaldehyde.

Intermediate 50: meso-4-{[(3-endo)-3-(Acetylamino)-8-azabicyclo[3.2.1]oct-8-yl]methyl}phenyl Acetate

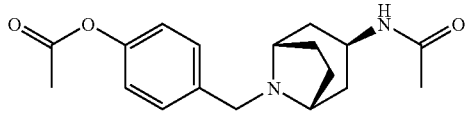

$^1$H NMR (400 MHz, CDCl$_3$): 7.37 (d, J=8.6, 2H), 7.05-6.99 (m, 2H), 5.83-5.72 (m, 1H), 4.11 (q, J=7.1, 1H), 3.48 (s, 2H), 3.24-3.15 (m, 2H), 2.29 (s, 3H), 2.25-2.07 (m, 5H), 1.95 (s, 3H), 1.80-1.69 (m, 2H), 1.59 (s, 1H). MS (ESI): mass calculated for C$_{18}$H$_{24}$N$_2$O$_3$, 316.18; m/z found, 317.20 [M+H]$^+$.

Intermediate 51: 4-[(4-Carbamoylpiperidin-1-yl)methyl]phenyl Acetate

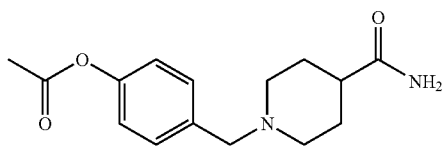

$^1$H NMR (500 MHz, CDCl$_3$): 7.33 (d, J=8.5, 2H), 7.06-7.02 (m, 2H), 5.58-5.20 (m, 2H), 3.50 (d, J=7.9, 2H), 2.98-2.90 (m, 2H), 2.31 (s, 3H), 2.22-2.10 (m, 1H), 2.01 (td, J=11.6, 2.4, 2H), 1.88 (d, J=12.8, 2H), 1.76 (ddd, J=15.5, 12.3, 3.6, 2H). MS (ESI): mass calculated for C$_{15}$H$_{20}$N$_2$O$_3$, 276.15; m/z found, 277.10 [M+H]$^+$.

Intermediates 52-53 were prepared using methods analogous to those described for Intermediate 38.

Intermediate 52: Sodium meso-4-{[(3-endo)-3-(acetylamino)-8-azabicyclo[3.2.1]oct-8-yl]methyl}phenolate

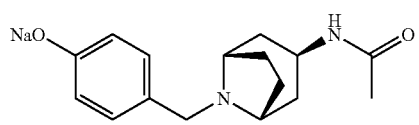

$^1$H NMR (600 MHz, CD$_3$OD): 7.10-7.06 (m, 2H), 6.68-6.63 (m, 2H), 3.85 (t, J=7.1, 1H), 3.39 (s, 2H), 3.19-3.14 (m, 2H), 2.16-2.05 (m, 5H), 1.94-1.87 (m, 4H), 1.66 (d, J=13.8, 2H). MS (ESI): mass calculated for C$_{16}$H$_{22}$N$_2$O$_2$ (phenol), 274.17; m/z found, 275.10 [M+H]$^+$.

Intermediate 53: Sodium 4-[(4-carbamoylpiperidin-1-yl)methyl]phenolate

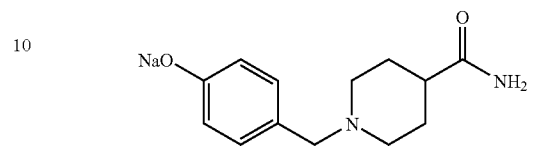

$^1$H NMR (500 MHz, CD$_3$OD): 7.05-7.01 (m, 2H), 6.68-6.63 (m, 2H), 3.40 (s, 2H), 2.98-2.91 (m, 2H), 2.24-2.15 (m, 1H), 2.02 (td, J=11.8, 2.7, 2H), 1.83-1.67 (m, 4H). MS (ESI): mass calculated for C$_{13}$H$_{18}$N$_2$O$_2$ (phenol), 234.14; m/z found, 235.10 [M+H]$^+$.

Example 1

2-(4-{2-[4-(Pyrimidin-2-yloxy)piperidin-1-yl]ethoxy}phenoxy)[1,3]thiazolo[4,5-b]pyridine

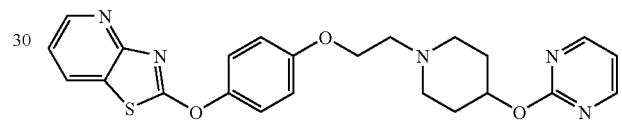

To a solution of 2-[4-(2-bromoethoxy)phenoxy][1,3]thiazolo[4,5-b]pyridine (131 mg, 0.37 mmol) and 2-(piperidin-4-yloxy)-pyrimidine (80 mg, 0.45 mmol, 1.2 equiv.) in CH$_3$CN (1.9 mL) was added N,N-diisopropylethylamine (97 µL, 0.56 mmol, 1.5 equiv.). The resulting solution was allowed to stir at 70° C. for 18 h. The solution was then cooled to rt, filtered and purified using preparative reverse phase HPLC to afford the desired product as a yellow-brown solid (64 mg, 38%). $^1$H NMR (600 MHz, CDCl$_3$): 8.58-8.54 (m, 1H), 8.52-8.48 (m, 2H), 8.01-7.96 (m, 1H), 7.34-7.30 (m, 2H), 7.18 (dd, J=6.7, 4.8, 1H), 6.96 (d, J=8.1, 2H), 6.92-6.87 (m, 1H), 5.14-5.04 (m, 1H), 4.14 (t, J=5.6, 2H), 2.96-2.88 (m, 2H), 2.86 (t, J=5.5, 2H), 2.56-2.46 (m, 2H), 2.16-2.04 (m, 2H), 2.01-1.90 (m, 2H). MS (ESI): mass calcd. for C$_{23}$H$_{23}$N$_5$O$_3$S, 449.15; m/z found, 450.1 [M+H]$^+$.

Examples 2-13 were prepared using methods analogous to those described for Example 1.

Example 2

2-{4-[2-(1,3-Dihydro-2H-isoindol-2-yl)ethoxy]phenoxy}[1,3]thiazolo[4,5-b]pyridine

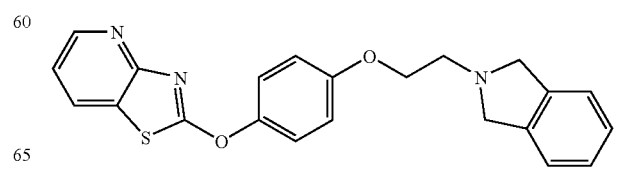

¹H NMR (600 MHz, CDCl₃): 8.56 (dd, J=4.8, 1.6, 1H), 7.99 (dd, J=7.9, 1.6, 1H), 7.36-7.30 (m, 2H), 7.24-7.16 (m, 5H), 7.02-6.98 (m, 2H), 4.21 (t, J=5.7, 2H), 4.08 (s, 4H), 3.20 (t, J=5.7, 2H). MS (ESI): mass calcd. for C₂₂H₁₉N₃O₂S, 389.12; m/z found, 390.1 [M+H]⁺.

Example 3

2-(4-{2-[4-(Phenylsulfanyl)piperidin-1-yl]ethoxy}phenoxy)[1,3]thiazolo[4,5-b]pyridine

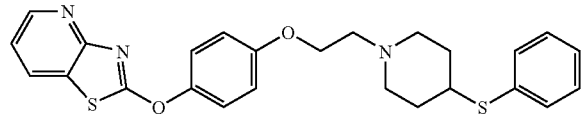

¹H NMR (500 MHz, CDCl₃): 8.58 (dd, J=4.8, 1.7, 1H), 8.01 (dd, J=7.9, 1.7, 1H), 7.47-7.41 (m, 2H), 7.34-7.29 (m, 4H), 7.27-7.24 (m, 1H), 7.21 (dd, J=7.9, 4.8, 1H), 6.98-6.93 (m, 2H), 4.12 (t, J=5.6, 2H), 3.18-3.08 (m, 1H), 3.03-2.94 (m, 2H), 2.83 (t, J=5.9, 2H), 2.32-2.22 (m, 2H), 2.06-1.96 (m, 2H), 1.79-1.67 (m, 2H). MS (ESI): mass calcd. for C₂₅H₂₅N₃O₂S₂, 463.14; m/z found, 464.1 [M+H]⁺.

Example 4

2-(4-{2-[4-(Pyridin-3-yloxy)piperidin-1-yl]ethoxy}phenoxy)[1,3]thiazolo[4,5-b]pyridine

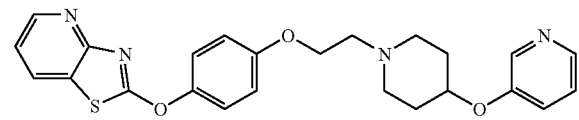

¹H NMR (600 MHz, CDCl₃): 8.56 (dd, J=4.8, 1.6, 1H), 8.34-8.30 (m, 1H), 8.23-8.18 (m, 1H), 7.99 (dd, J=7.9, 1.6, 1H), 7.35-7.29 (m, 2H), 7.22-7.16 (m, 3H), 6.99-6.93 (m, 2H), 4.43-4.33 (m, 1H), 4.14 (t, J=5.8, 2H), 2.91-2.82 (m, 4H), 2.54-2.44 (m, 2H), 2.09-1.98 (m, 2H), 1.93-1.83 (m, 2H). MS (ESI): mass calcd. for C₂₄H₂₄N₄O₃S, 448.16; m/z found, 449.1 [M+H]⁺.

Example 5

4-Pyridin-2-yl-1-{2-[4-([1,3]thiazolo[4,5-b]pyridin-2-yloxy)phenoxy]ethyl}piperidin-4-ol

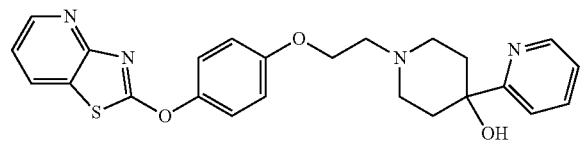

¹H NMR (600 MHz, CDCl₃): 8.56 (dd, J=4.8, 1.6, 1H), 8.54-8.52 (m, 1H), 7.99 (dd, J=7.9, 1.6, 1H), 7.76-7.68 (m, 1H), 7.41 (d, J=8.0, 1H), 7.35-7.30 (m, 2H), 7.24-7.16 (m, 2H), 7.02-6.96 (m, 2H), 5.26 (s, 1H), 4.19 (t, J=5.9, 2H), 3.02-2.89 (m, 4H), 2.77-2.68 (m, 2H), 2.19-2.09 (m, 2H), 1.72-1.62 (m, 2H). MS (ESI): mass calcd. for C₂₄H₂₄N₄O₃S, 448.16; m/z found, 449.1 [M+H]⁺.

Example 6

2-{2-[4-([1,3]Thiazolo[4,5-b]pyridin-2-yloxy)phenoxy]ethyl}-1,2,3,4-tetrahydroisoquinoline

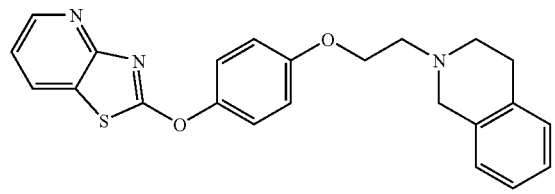

¹H NMR (600 MHz, CDCl₃): 8.56 (dd, J=4.8, 1.7, 1H), 7.99 (dd, J=7.9, 1.7, 1H), 7.34-7.31 (m, 2H), 7.18 (dd, J=7.9, 4.8, 1H), 7.14-7.09 (m, 3H), 7.05-7.02 (m, 1H), 7.00-6.96 (m, 2H), 4.22 (t, J=5.9, 2H), 3.79 (s, 2H), 3.00 (t, J=5.9, 2H), 2.96-2.92 (m, 2H), 2.92-2.88 (m, 2H). MS (ESI): mass calcd. for C₂₃H₂₁N₃O₂S, 403.14; m/z found, 404.1 [M+H]⁺.

Example 7

1-{2-[4-([1,3]Thiazolo[4,5-b]pyridin-2-yloxy)phenoxy]ethyl}-1,2,3,4-tetrahydroquinoline

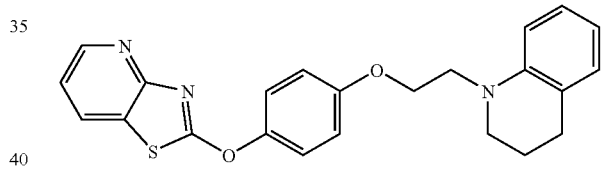

¹H NMR (600 MHz, CDCl₃): 8.56 (dd, J=4.8, 1.7, 1H), 7.99 (dd, J=7.9, 1.7, 1H), 7.32-7.29 (m, 2H), 7.18 (dd, J=7.9, 4.8, 1H), 7.08-7.04 (m, 1H), 6.97-6.91 (m, 3H), 6.64 (d, J=8.0, 1H), 6.59 (dd, J=7.7, 6.9, 1H), 4.17 (t, J=6.1, 2H), 3.71 (t, J=6.1, 2H), 3.45-3.42 (m, 2H), 2.77 (t, J=6.4, 2H), 2.01-1.92 (m, 2H). MS (ESI): mass calcd. for C₂₃H₂₁N₃O₂S, 403.14; m/z found, 404.1 [M+H]⁺.

Example 8

2-{4-[2-(4-Phenoxypiperidin-1-yl)ethoxy]phenoxy}[1,3]thiazolo[4,5-b]pyridine

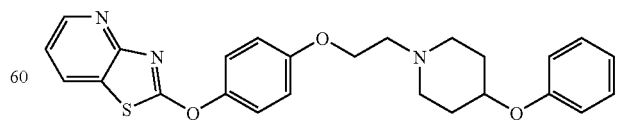

¹H NMR (600 MHz, CDCl₃): 8.56 (dd, J=4.8, 1.6, 1H), 7.99 (dd, J=7.9, 1.6, 1H), 7.34-7.29 (m, 2H), 7.30-7.27 (m, 2H), 7.18 (dd, J=7.9, 4.8, 1H), 6.98-6.95 (m, 2H), 6.95-6.90 (m, 3H), 4.38-4.29 (m, 1H), 4.13 (t, J=5.8, 2H), 2.91-2.80 (m,

4H), 2.52-2.41 (m, 2H), 2.07-1.97 (m, 2H), 1.91-1.81 (m, 2H). MS (ESI): mass calcd. for $C_{25}H_{25}N_3O_3S$, 447.16; m/z found, 448.1 [M+H]$^+$.

Example 9

2-[4-(2-Pyrrolidin-1-ylethoxy)phenoxy][1,3]thiazolo[4,5-b]pyridine

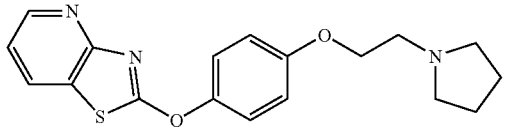

$^1$H NMR (600 MHz, CDCl$_3$): 8.56 (dd, J=4.8, 1.7, 1H), 7.99 (dd, J=7.9, 1.7, 1H), 7.33-7.28 (m, 2H), 7.18 (dd, J=7.9, 4.8, 1H), 6.99-6.93 (m, 2H), 4.16-4.09 (m, 2H), 2.96-2.87 (m, 2H), 2.68-2.59 (m, 4H), 1.84-1.78 (m, 4H) MS (ESI): mass calcd. for $C_{18}H_{19}N_3O_2S$, 341.12; m/z found, 342.1 [M+H]$^+$.

Example 10

2-[4-(2-Piperidin-1-ylethoxy)phenoxy][1,3]thiazolo[4,5-b]pyridine

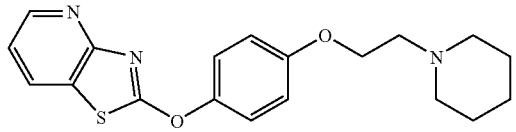

$^1$H NMR (600 MHz, CDCl$_3$): 8.56 (dd, J=4.8, 1.7, 1H), 7.99 (dd, J=7.9, 1.7, 1H), 7.33-7.28 (m, 2H), 7.18 (dd, J=7.9, 4.8, 1H), 6.98-6.92 (m, 2H), 4.16-4.07 (m, 2H), 2.84-2.74 (m, 2H), 2.58-2.49 (m, 4H), 1.65-1.58 (m, 4H), 1.50-1.40 (m, 2H). MS (ESI): mass calcd. for $C_{19}H_{21}N_3O_2S$, 355.14; m/z found, 356.1 [M+H]$^+$.

Example 11

2-[4-(2-Morpholin-4-ylethoxy)phenoxy][1,3]thiazolo[4,5-b]pyridine

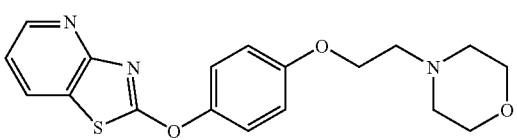

$^1$H NMR (600 MHz, CDCl$_3$): 8.55 (dd, J=4.8, 1.7, 1H), 7.99 (dd, J=7.9, 1.7, 1H), 7.34-7.29 (m, 2H), 7.18 (dd, J=7.9, 4.8, 1H), 6.98-6.92 (m, 2H), 4.16-4.10 (m, 2H), 3.77-3.71 (m, 4H), 2.85-2.77 (m, 2H), 2.64-2.55 (m, 4H). MS (ESI): mass calcd. for $C_{18}H_{19}N_3O_3S$, 357.12; m/z found, 358.1 [M+H]$^+$.

Example 12

2-(4-{2-[4-(Pyridin-2-yloxy)piperidin-1-yl]ethoxy}phenoxy)[1,3]thiazolo[4,5-b]pyridine

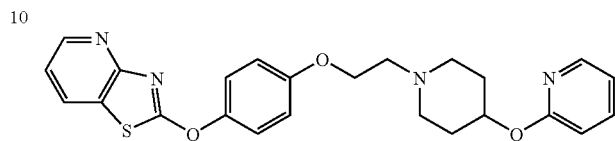

$^1$H NMR (600 MHz, CDCl$_3$): 8.58-8.53 (m, 1H), 8.15-8.10 (m, 1H), 8.01-7.96 (m, 1H), 7.57-7.52 (m, 1H), 7.35-7.29 (m, 2H), 7.18 (dd, J=7.9, 4.8, 1H), 6.99-6.93 (m, 2H), 6.85-6.80 (m, 1H), 6.71 (d, J=8.3, 1H), 5.15-5.05 (m, 1H), 4.18-4.10 (m, 2H), 2.93-2.81 (m, 4H), 2.54-2.45 (m, 2H), 2.13-2.02 (m, 2H), 1.92-1.80 (m, 2H). MS (ESI): mass calcd. for $C_{24}H_{24}N_4O_3S$, 448.16; m/z found, 449.1 [M+H]$^+$.

Example 13

2-(4-{2-[4-(Pyridin-4-yloxy)piperidin-1-yl]ethoxy}phenoxy)[1,3]thiazolo[4,5-b]pyridine

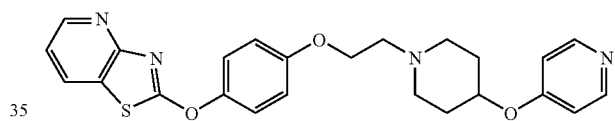

$^1$H NMR (600 MHz, CDCl$_3$): 8.56 (dd, J=4.8, 1.6, 1H), 8.43-8.39 (m, 2H), 7.99 (dd, J=7.9, 1.6, 1H), 7.34-7.30 (m, 2H), 7.19 (dd, J=7.9, 4.8, 1H), 6.99-6.94 (m, 2H), 6.82-6.77 (m, 2H), 4.49-4.40 (m, 1H), 4.17-4.10 (m, 2H), 2.90-2.82 (m, 4H), 2.55-2.46 (m, 2H), 2.09-1.99 (m, 2H), 1.93-1.83 (m, 2H). MS (ESI): mass calcd. for $C_{24}H_{24}N_4O_3S$, 448.16; m/z found, 449.1 [M+H]$^+$.

Examples 14-16 were prepared using methods analogous to those described for Example 1, substituting the reaction conditions of Cs$_2$CO$_3$ in CH$_3$CN at 75° C. for N,N-diisopropylethylamine in CH$_3$CN at 50-70° C.

Example 14

2-(4-{2-[(1S,4S)-5-Acetyl-2,5-diazabicyclo[2.2.1]hept-2-yl]ethoxy}phenoxy)[1,3]thiazolo[4,5-b]ipyridine

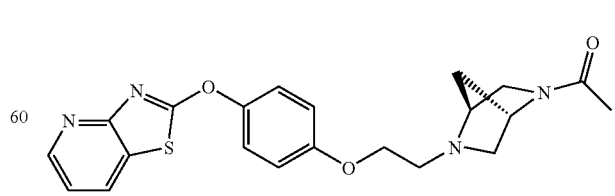

$^1$H NMR (500 MHz, CDCl$_3$): 8.58 (dd, J=4.8, 1.7, 1H), 8.02 (ddd, J=7.9, 1.6, 0.9, 1H), 7.36-7.31 (m, 2H), 7.21 (ddd, J=7.9, 4.8, 0.9, 1H), 6.98-6.94 (m, 2H), 4.79 (s, 0.5H), 4.25 (s, 0.5H), 4.12-4.05 (m, 2H), 3.76-3.68 (m, 1.5H), 3.63 (dd, J=9.5, 1.2, 0.5H), 3.37 (dd, J=9.5, 2.2, 0.5H), 3.31 (dd, J=11.5, 1.9, 0.5H), 3.22 (dd, J=9.6, 2.2, 0.5H), 3.07-2.95 (m, 2.5H), 2.82 (dd, J=9.7, 0.9, 0.5H), 2.67 (dd, J=9.6, 1.3, 0.5H), 2.11 (s, 1.5H), 2.03-1.98 (m, 2H), 1.92 (d, J=10.0, 0.5H), 1.83 (d, J=9.7, 0.5H), 1.72 (d, J=9.9, 0.5H). MS (ESI): mass calcd. for $C_{21}H_{22}N_4O_3S$, 410.14; m/z found, 411.1 $[M+H]^+$.

Example 15

(1S,4S)-5-{2-[4-([1,3]Thiazolo[4,5-b]pyridin-2-yloxy)phenoxy]ethyl}-2,5-diazabicyclo[2.2.1]heptane-2-carboxamide

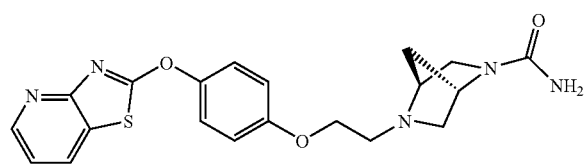

$^1$H NMR (400 MHz, CDCl$_3$): 8.55 (dd, J=4.8, 1.7, 1H), 8.00 (dd, J=8.0, 1.7, 1H), 7.34-7.28 (m, 2H), 7.19 (dd, J=8.0, 4.9, 1H), 6.97-6.91 (m, 2H), 4.50-4.24 (m, 3H), 4.08 (t, J=5.6, 2H), 3.68 (s, 1H), 3.52 (d, J=8.6, 1H), 3.24 (dd, J=8.9, 2.1, 1H), 3.11-2.93 (m, 3H), 2.80 (d, J=9.6, 1H), 1.91 (d, J=9.6, 1H), 1.77 (d, J=9.5, 1H). MS (ESI): mass calcd. for $C_{20}H_{21}N_5O_3S$, 411.14; m/z found, 412.1 $[M+H]^+$.

Example 16 meso-N-[(3-endo)-8-{2-[4-([1,3]Thiazolo[4,5-b]pyridin-2-yloxy)phenoxy]ethyl}-8-azabicyclo[3.2.1]oct-3-yl]acetamide

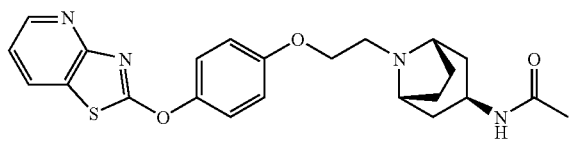

$^1$H NMR (400 MHz, CDCl$_3$): 8.56 (dd, J=4.8, 1.6, 1H), 8.00 (dd, J=7.9, 1.6, 1H), 7.35-7.28 (m, 2H), 7.19 (dd, J=7.9, 4.6, 1H), 6.98-6.92 (m, 2H), 5.81 (d, J=6.1, 1H), 4.15-4.05 (m, 3H), 3.33 (s, 2H), 2.78 (t, J=6.2, 2H), 2.30-2.19 (m, 2H), 2.16-2.07 (m, 2H), 1.97 (s, 3H), 1.82-1.73 (m, 2H), 1.71-1.62 (m, 2H). MS (ESI): mass calcd. for $C_{23}H_{26}N_4O_3S$, 438.17; m/z found, 439.2 $[M+H]^+$.

Examples 17-21 were prepared using methods analogous to those described for Example 1, substituting the reaction conditions of DMF at 50-80° C. for CH$_3$CN at 70° C.

Example 17 meso-N-[(3-exo)-8-{2-[4-([1,3]Thiazolo[4,5-b]pyridin-2-yloxy)phenoxy]ethyl}-8-azabicyclo[3.2.1]oct-3-yl]acetamide

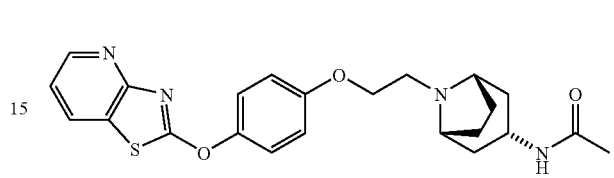

$^1$H NMR (500 MHz, CDCl$_3$): 8.58 (dd, J=4.8, 1.6, 1H), 8.02 (dd, J=7.9, 1.6, 1H), 7.36-7.31 (m, 2H), 7.21 (dd, J=7.9, 4.8, 1H), 6.99-6.94 (m, 2H), 5.23 (d, J=7.8, 1H), 4.22-4.08 (m, 3H), 3.39-3.35 (m, 2H), 2.82 (t, J=6.1, 2H), 2.08-1.98 (m, 2H), 1.95 (s, 3H), 1.88-1.82 (m, 2H), 1.79-1.73 (m, 2H), 1.53 (dt, J=12.5, 2.2, 2H). MS (ESI): mass calcd. for $C_{23}H_{26}N_4O_3S$, 438.17; m/z found, 439.2 $[M+H]^+$.

Example 18

2-{4-[2-(5-Acetylhexahydropyrrolo[3,4-c]pyrrol-2(1H)-yl)ethoxy]phenoxy}[1,3]thiazolo[4,5-b]pyridine

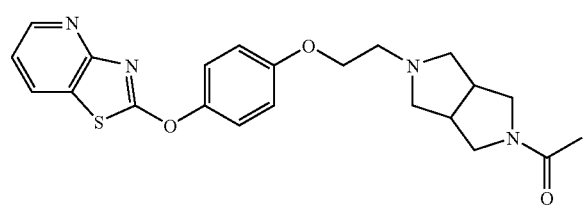

$^1$H NMR (400 MHz, CDCl$_3$): 8.56 (dd, J=4.8, 1.7, 1H), 8.01-7.98 (m, 1H), 7.34-7.29 (m, 2H), 7.19 (dd, J=7.9, 4.8, 1H), 6.97-6.92 (m, 2H), 4.10 (t, J=5.7, 2H), 3.73-3.62 (m, 2H), 3.49-3.43 (m, 1H), 3.37-3.31 (m, 1H), 2.96-2.78 (m, 6H), 2.58-2.51 (m, 2H), 2.05 (s, 3H). MS (ESI): mass calcd. for $C_{22}H_{24}N_4O_3S$, 424.16; m/z found, 425.2 $[M+H]^+$.

Example 19

5-{2-[4-([1,3]Thiazolo[4,5-b]pyridin-2-yloxy)phenoxy]ethyl}hexahydropyrrolo[3,4-c]pyrrole-2(1H)-carboxamide

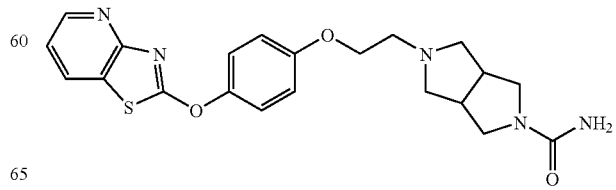

$^1$H NMR (400 MHz, CDCl$_3$): 8.55 (dd, J=4.8, 1.7, 1H), 8.01-7.98 (m, 1H), 7.34-7.29 (m, 2H), 7.19 (dd, J=7.9, 4.9, 1H), 6.98-6.92 (m, 2H), 4.39 (br s, 2H), 4.10 (t, J=5.7, 2H), 3.63-3.54 (m, 2H), 3.32-3.25 (m, 2H), 2.94-2.79 (m, 6H), 2.59-2.52 (m, 2H). MS (ESI): mass calcd. for C$_{21}$H$_{23}$N$_5$O$_3$S, 425.15; m/z found, 426.1 [M+H]$^+$.

Example 20

2-(4-{2-[(1S,4S)-5-Acetyl-2,5-diazabicyclo[2.2.1]hept-2-yl]ethoxy}phenoxy)[1,3]thiazolo[5,4-b]pyridine

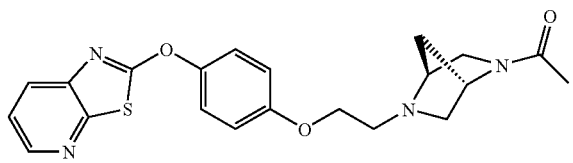

$^1$H NMR (400 MHz, CDCl$_3$): 8.39 (dd, J=4.7, 1.2, 1H), 7.93 (dd, J=8.2, 1.5, 1H), 7.34-7.23 (m, 3H), 7.02-6.92 (m, 2H), 4.77 (s, 0.5H), 4.23 (s, 0.5H), 4.14-3.96 (m, 2H), 3.75-3.64 (m, 1.5H), 3.60 (d, J=9.5, 0.5H), 3.34 (dd, J=9.5, 2.2, 0.5H), 3.29 (dd, J=11.6, 2.0, 0.5H), 3.20 (d, J=9.6, 2.1, 0.5H), 3.07-2.93 (m, 2.5H), 2.81 (d, J=9.7, 0.5H), 2.65 (d, J=9.5, 0.5H), 2.12-1.94 (m, 3.5H), 1.89 (d, J=10.0, 0.5H), 1.81 (d, J=8.6, 0.5H), 1.69 (d, J=10.0, 0.5H). MS (ESI): mass calcd. for C$_{21}$H$_{22}$N$_4$O$_3$S, 410.14; m/z found, 411.1 [M+H]$^+$.

Example 21

(1S,4S)-5-{2-[4-([1,3]Thiazolo[5,4-b]pyridin-2-yloxy)phenoxy}ethyl]-2,5-diazabicyclo[2.2.1]heptane-2-carboxamide

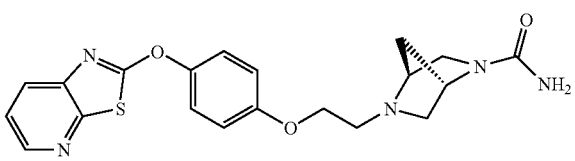

$^1$H NMR (400 MHz, CDCl$_3$): 8.39 (dd, J=4.8, 1.5, 1H), 7.93 (dd, J=8.1, 1.5, 1H), 7.32 (dd, J=8.2, 4.8, 1H), 7.29-7.24 (m, 2H), 6.99-6.93 (m, 2H), 4.50-4.22 (m, 3H), 4.12-4.03 (m, 2H), 3.69 (s, 1H), 3.54 (d, J=8.5, 1H), 3.25 (dd, J=8.9, 2.1, 1H), 3.11-2.94 (m, 3H), 2.81 (d, J=9.4, 1H), 1.92 (d, J=9.8, 1H), 1.77 (d, J=9.5, 1H). MS (ESI): mass calcd. for C$_{20}$H$_{21}$N$_5$O$_3$S, 411.14; m/z found, 412.1 [M+H]$^+$.

Examples 22-26 were prepared using methods analogous to those described for Example 1, substituting the reaction conditions of DMF at rt for CH$_3$CN at 70° C.

Example 22

4-Phenyl-1-{2-[4-([1,3]thiazolo[4,5-b]pyrazin-2-yloxy)phenoxy]ethyl}piperidin-4-ol

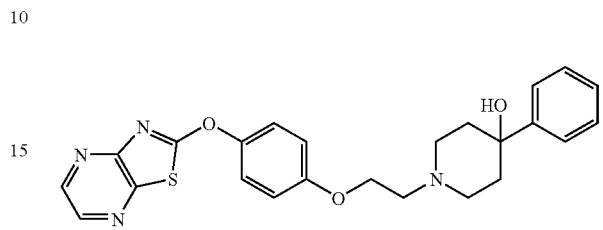

$^1$H NMR (400 MHz, CDCl$_3$): 8.51 (d, J=2.6, 1H), 8.33 (d, J=2.6, 1H), 7.53 (d, J=7.27, 2H), 7.41-7.27 (m, 5H), 7.00 (d, J=9.1, 2H), 4.21 (t, J=5.7, 2H), 3.03-2.93 (m, 4H), 2.72 (t, J=11.2, 2H), 2.33-2.19 (m, 3H), 1.81 (d, J=11.9, 1H), 1.63 (s, 1H). MS (ESI): mass calcd. for C$_{24}$H$_{24}$N$_4$O$_3$S, 448.16; m/z found, 449.1 [M+H]$^+$.

Example 23

2-{4-[2-(4-Benzylpiperidin-1-yl)ethoxy]phenoxy}[1,3]thiazolo[4,5-b]pyrazine

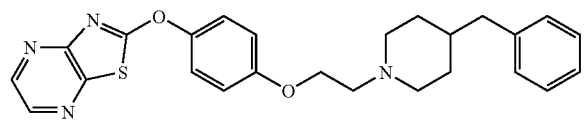

$^1$H NMR (600 MHz, CDCl$_3$): 8.51 (d, J=2.6, 1H), 8.33 (d, J=2.6, 1H), 7.30-7.27 (m, 2H), 7.19 (t, J=7.4, 1H), 7.14 (d, J=7.0, 2H), 6.95 (d, J=9.1, 2H), 6.80 (d, J=9.0, 1H), 6.77 (d, J=9.0, 1H), 4.23 (t, J=6.3, 1H), 4.15 (t, J=5.7, 2H), 3.61 (t, J=6.3, 1H), 3.11-3.02 (m, 2H), 2.87 (s, 2H), 2.55 (d, J=7.2, 2H), 2.18-2.09 (m, 2H), 1.68 (d, J=12.9, 2H), 1.57 (s, 1H). MS (ESI): mass calcd. for C$_{25}$H$_{26}$N$_4$O$_2$S, 446.18; m/z found, 447.2 [M+H]

Example 24

1-{2-[4-([1,3]Thiazolo[4,5-b]pyrazin-2-yloxy)phenoxy]ethyl}-4-[3-(trifluoromethyl)phenyl]piperidin-4-ol

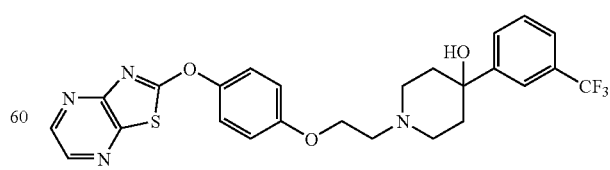

$^1$H NMR (600 MHz, CDCl$_3$): 8.51 (d, J=2.6, 1H), 8.34 (d, J=2.6, 1H), 7.82 (s, 1H), 7.70 (d, J=7.9, 1H), 7.53 (d, J=7.6, 1H), 7.48 (t, J=7.8, 1H), 7.31 (d, J=9.0, 2H), 7.00 (d, J=9.0, 2H), 4.21 (t, J=5.6, 2H), 3.04-2.97 (m, 4H), 2.73 (t, J=11.5,

2H), 2.33-2.20 (m, 2H), 1.80 (d, J=12.2, 2H), 1.63 (s, 1H). MS (ESI): mass calcd. for $C_{25}H_{23}F_3N_4O_3S$, 516.14; m/z found, 517.1 [M+H]$^+$.

Example 25

4-(4-Chlorophenyl)-1-{2-[4-([1,3]thiazolo[4,5-b]pyrazin-2-yloxy)phenoxy]ethyl}piperidin-4-ol

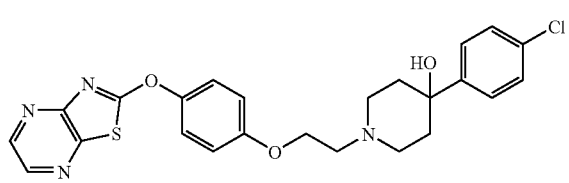

$^1$H NMR (600 MHz, CDCl$_3$): 8.51 (d, J=2.6, 1H), 8.34 (d, J=2.6, 1H), 7.46 (d, J=8.6, 2H), 7.35-7.29 (m, 4H), 6.99 (d, J=9.1, 2H), 4.23-4.16 (m, 2H), 3.02-2.92 (m, 4H), 2.69 (t, J=11.3, 2H), 2.26-2.16 (m, 2H), 1.77 (d, J=12.3, 2H), 1.63 (s, 1H). MS (ESI): mass calcd. for $C_{24}H_{23}ClN_4O_3S$, 482.12; m/z found, 483.1 [M+H]$^+$.

Example 26

1-{2-[4-([1,3]Thiazolo[4,5-b]pyrazin-2-yloxy)phenoxy]ethyl}piperidine-4-carboxamide

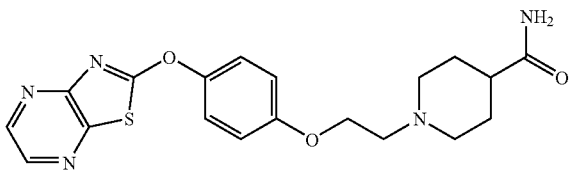

$^1$H NMR (600 MHz, CDCl$_3$): 8.47 (d, J=2.6, 1H), 8.29 (d, J=2.6, 1H), 7.30 (d, J=9.0, 2H), 6.96 (d, J=9.0, 2H), 5.28 (s, 2H), 4.17-4.09 (m, 2H), 3.08-3.00 (m, 2H), 2.86-2.79 (m, 2H), 2.31-2.14 (m, 3H), 1.94-1.75 (m, 4H). MS (ESI): mass calcd. for $C_{19}H_{21}N_5O_3S$, 399.14; m/z found, 400.1 [M+H]$^+$.

Examples 27-42 were prepared using methods analogous to those described for Example 1, substituting DMF for CH$_3$CN.

Example 27

4-Phenyl-1-{2-[4-([1,3]thiazolo[4,5-b]pyridin-2-yloxy)phenoxy]ethyl}piperidin-4-ol

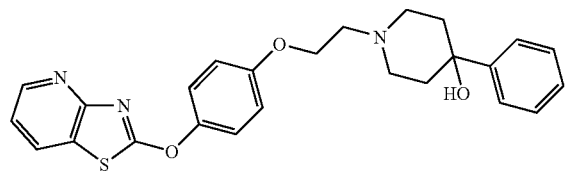

$^1$H NMR (400 MHz, CDCl$_3$): 8.56 (dd, J=4.6, 1.7, 1H), 8.00 (dd, J=7.9, 1.7, 1H), 7.53 (d, J=7.2, 2H), 7.40-7.28 (m, 5H), 7.19 (dd, J=7.9, 4.9, 1H), 6.98 (d, J=9.1, 2H), 4.17 (t,

J=5.9, 2H), 2.92 (t, J=5.9, 4H), 2.70-2.61 (m, 2H), 2.28-2.16 (m, 2H), 1.84-1.75 (m, 2H). MS (ESI): mass calcd. for $C_{25}H_{25}N_3O_3S$, 447.16; m/z found, 448.1 [M+H]$^+$.

Example 28

2-{4-[2-(4-Benzylpiperidin-1-yl)ethoxy]phenoxy}[1,3]thiazolo[4,5-b]pyridine

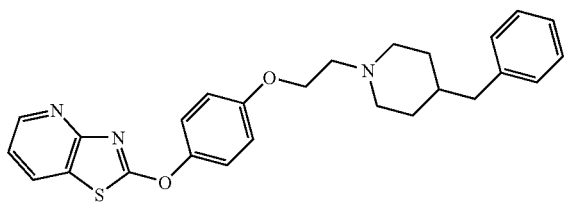

$^1$H NMR (400 MHz, CDCl$_3$): 8.56 (dd, J=4.8, 1.7, 1H), 7.99 (dd, J=7.9, 1.7, 1H), 7.32-7.28 (m, 4H), 7.22-7.12 (m, 4H), 6.94 (d, J=9.1, 2H), 4.11 (t, J=5.9, 2H), 3.04-2.93 (m, 2H), 2.85-2.74 (m, 2H), 2.55 (d, J=7.0, 2H), 2.14-2.01 (m, 2H), 1.71-1.62 (m, 2H), 1.47-1.22 (m, 3H). MS (ESI): mass calcd. for $C_{26}H_{27}N_3O_2S$, 445.18; m/z found, 446.2 [M+H]$^+$.

Example 29

2-{4-[2-(4-Pyridin-4-ylpiperidin-1-yl)ethoxy]phenoxy}[1,3]thiazolo[4,5-b]pyridine

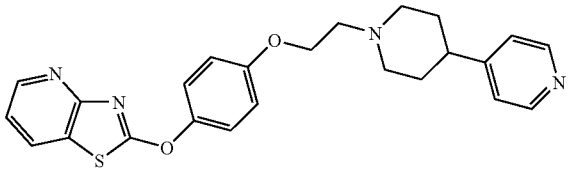

$^1$H NMR (400 MHz, CDCl$_3$): 8.56 (dd, J=4.8, 1.6, 1H), 8.52 (d, J=6.1, 2H), 8.00 (dd, J=7.9, 1.6, 1H), 7.33 (d, J=9.1, 2H), 7.20 (dd, J=7.9, 4.9, 1H), 7.16 (d, J=6.1, 2H), 6.97 (d, J=9.1, 2H), 4.16 (t, J=5.8, 2H), 3.21-3.11 (m, 2H), 2.94-2.84 (m, 2H), 2.59-2.48 (m, 1H), 2.34-2.20 (m, 2H), 1.92-1.82 (m, 4H). MS (ESI): mass calcd. for $C_{24}H_{24}N_4O_2S$, 432.16; m/z found, 433.1 [M+H]$^+$.

Example 30

4-(4-Chlorophenyl)-1-{2-[4-([1,3]thiazolo[4,5-b]pyridin-2-yloxy)phenoxy]ethyl}piperidin-4-ol

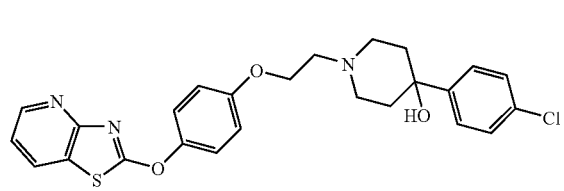

$^1$H NMR (400 MHz, CDCl$_3$): 8.56 (dd, J=4.8, 1.7, 1H), 8.00 (dd, J=7.9, 1.7, 1H), 7.46 (d, J=8.7, 2H), 7.32 (d, J=8.9, 4H), 7.19 (dd, J=7.9, 4.6, 1H), 6.98 (d, J=9.1, 2H), 4.17 (t,

J=5.8, 2H), 2.94-2.89 (m, 4H), 2.68-2.59 (m, 2H), 2.23-2.12 (m, 2H), 1.80-1.72 (m, 2H). MS (ESI): mass calcd. for $C_{25}H_{24}ClN_3O_3S$, 481.12; m/z found, 482.1 [M+H]⁺.

Example 31

1-{2-[4-([1,3]Thiazolo[4,5-b]pyridin-2-yloxy)phenoxy]ethyl}piperidine-4-carboxamide

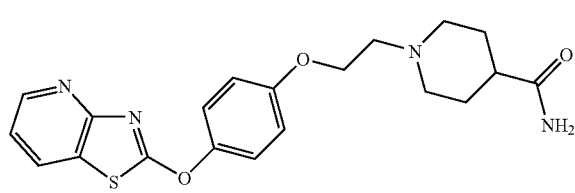

¹H NMR (400 MHz, CDCl₃): 8.56 (dd, J=4.8, 1.7, 1H), 8.00 (dd, J=7.9, 1.7, 1H), 7.31 (d, J=9.1, 2H), 7.19 (dd, J=7.9, 4.9, 1H), 6.96 (d, J=9.1, 2H), 5.50 (s, 1H), 5.32 (s, 1H), 4.12 (t, J=5.8, 2H), 3.11-3.01 (m, 2H), 2.82 (t, J=5.8, 2H), 2.24-2.13 (m, 3H), 1.97-1.88 (m, 2H), 1.85-1.72 (m, 2H). MS (ESI): mass calcd. for $C_{20}H_{22}N_4O_3S$, 398.14; m/z found, 399.2 [M+H]⁺.

Example 32

1-(1-{2-[4-([1,3]Thiazolo[4,5-b]pyridin-2-yloxy)phenoxy]ethyl}piperidin-4-yl)pyrrolidin-2-one

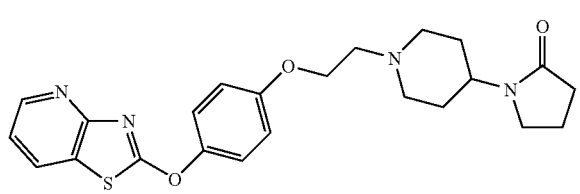

¹H NMR (400 MHz, CDCl₃): 8.56 (dd, J=4.9, 1.7, 1H), 8.00 (dd, J=7.9, 1.7, 1H), 7.32 (d, J=9.1, 2H), 7.19 (dd, J=7.9, 4.9, 1H), 6.95 (d, J=9.1, 2H), 4.11 (t, J=5.8, 2H), 3.37 (t, J=7.0, 2H), 3.11-3.03 (m, 2H), 2.83 (t, J=5.8, 2H), 2.40 (t, J=8.1, 2H), 2.30-2.21 (m, 2H), 2.04 (d, J=7.9, 1H), 2.00 (d, J=7.7, 1H), 1.83-1.73 (m, 2H), 1.72-1.63 (m, 2H), 1.30-1.22 (m, 1H). MS (ESI): mass calcd. for $C_{23}H_{26}N_4O_3S$, 438.17; m/z found, 439.2 [M+H]⁺.

Example 33

1-{2-[4-([1,3]Thiazolo[4,5-b]pyridin-2-yloxy)phenoxy]ethyl}-4-[3-(trifluoromethyl)phenyl]piperidin-4-ol

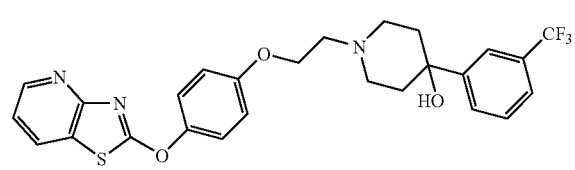

¹H NMR (600 MHz, CDCl₃): 8.54 (dd, J=4.8, 1.7, 1H), 7.96 (dd, J=7.9, 1.6, 1H), 7.81 (s, 1H), 7.69 (d, J=7.8, 1H), 7.51 (d, J=7.6, 1H), 7.44 (t, J=7.8, 1H), 7.32 (d, J=9.1, 2H), 7.15 (dd, J=7.9, 4.8, 1H), 6.96 (d, J=9.1, 2H), 4.16 (t, J=5.8, 2H), 2.93-2.86 (m, 4H), 2.70-2.62 (m, 2H), 2.24-2.16 (m, 2H), 1.79-1.74 (m, 2H), 1.61 (s, 1H). MS (ESI): mass calcd. for $C_{26}H_{24}F_3N_3O_3S$, 515.15; m/z found, 516.1 [M+H]⁺.

Example 34

2-{4-[2-(4-Pyridin-2-ylpiperidin-1-yl)ethoxy]phenoxy}[1,3]thiazolo[4,5-b]pyridine

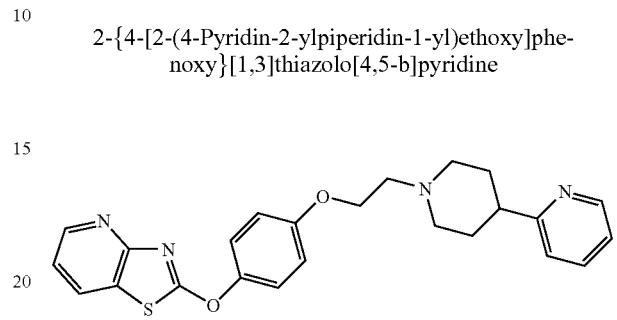

¹H NMR (600 MHz, CDCl₃): 8.56-8.50 (m, 2H), 7.95 (dd, J=7.9, 1.6, 1H), 7.59-7.54 (m, 1H), 7.31 (d, J=9.0, 2H), 7.17-7.13 (m, 2H), 7.08-7.04 (m, 1H), 6.96 (d, J=9.0, 2H), 4.15 (t, J=6.0, 2H), 3.15-3.06 (m, 2H), 2.85 (t, J=6.0, 2H), 2.76-2.69 (m, 1H), 2.35-2.27 (m, 2H), 1.99-1.85 (m, 4H). MS (ESI): mass calcd. for $C_{24}H_{24}N_4O_2S$, 432.16; m/z found, 433.2 [M+H]⁺.

Example 35

1-{2-[4-([1,3]Thiazolo[5,4-b]pyridin-2-yloxy)phenoxy]ethyl}pipiperidine-4-carboxamide

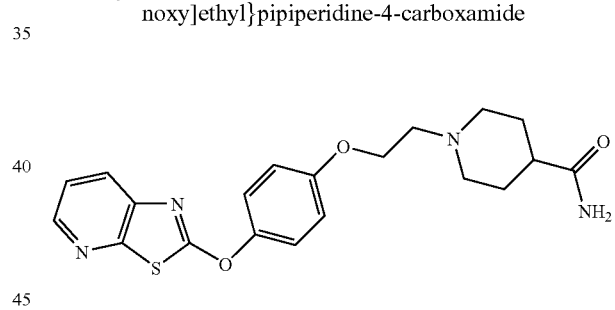

¹H NMR (600 MHz, CD₃OD): 8.39 (d, J=3.4, 1H), 7.99 (d, J=6.8, 1H), 7.47 (dd, J=8.1, 4.8, 1H), 7.33 (d, J=9.0, 2H), 7.07 (d, J=9.0, 2H), 4.22-4.16 (m, 2H), 3.15-3.07 (m, 2H), 2.88-2.81 (m, 2H), 2.31-2.17 (m, 3H), 1.87-1.75 (m, 4H). MS (ESI): mass calcd. for $C_{20}H_{22}N_4O_3S$, 398.14; m/z found, 399.1 [M+H]⁺.

Example 36

N-Benzyl-N-methyl-2-[4-([1,3]thiazolo[4,5-b]pyridin-2-yloxy)phenoxy]ethanamine

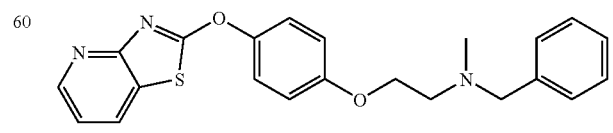

¹H NMR (400 MHz, CDCl₃): 8.56 (dd, J=4.8, 1.7, 1H), 7.98 (dd, J=7.9, 1.7, 1H), 7.37-7.23 (m, 7H), 7.18 (dd, J=7.9, 4.8, 1H), 6.95-6.90 (m, 2H), 4.10 (t, J=5.9, 2H), 3.63 (s, 2H), 2.85 (t, J=5.9, 2H), 2.36 (s, 3H). MS (ESI): mass calcd. for $C_{22}H_{21}N_3O_2S$, 391.14; m/z found, 392.1 [M+H]$^+$.

Example 37

1-{2-[4-([1,3]Thiazolo[5,4-b]pyridin-2-yloxy)phenoxy]ethyl}-4-[3-(trifluoromethyl)phenyl]piperidin-4-ol

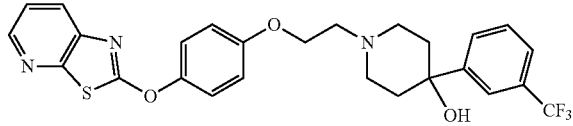

$^1$H NMR (600 MHz, CDCl$_3$): 8.38 (dd, J=4.7, 1.5, 1H), 7.92 (dd, J=8.1, 1.5, 1H), 7.82 (s, 1H), 7.70 (d, J=7.8, 1H), 7.52 (d, J=7.7, 1H), 7.47 (t, J=7.7, 1H), 7.32 (dd, J=8.1, 4.8, 1H), 7.29-7.24 (m, 2H), 7.05-6.95 (m, 2H), 4.17 (t, J=5.8, 2H), 3.01-2.86 (m, 4H), 2.65 (dt, J=12.2, 2.5, 2H), 2.21 (dt, J=13.4, 4.6, 2H), 1.83-1.71 (m, 3H). MS (ESI): mass calcd. for $C_{26}H_{24}F_3N_3O_3S$, 515.15; m/z found, 516.1 [M+H]$^+$.

Example 38

2-{4-[2-(4-Pyridin-2-ylpiperidin-1-yl)ethoxy]phenoxy}[1,3]thiazolo[5,4-b]pyridine

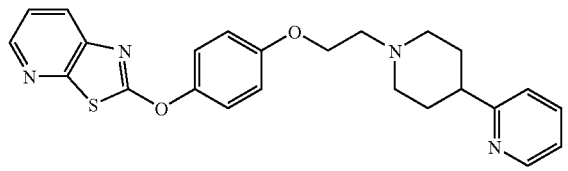

$^1$H NMR (600 MHz, CDCl$_3$): 8.59-8.49 (m, 1H), 8.38 (dd, J=4.8, 1.5, 1H), 7.92 (dd, J=8.1, 1.5, 1H), 7.61 (dt, J=7.7, 1.8, 1H), 7.31 (dd, J=8.1, 4.8, 1H), 7.29-7.23 (m, 2H), 7.22-7.16 (m, 1H), 7.11 (ddd, J=7.4, 4.8, 1.0, 1H), 7.02-6.96 (m, 2H), 4.16 (t, J=6.0, 2H), 3.19-3.08 (m, 2H), 2.87 (t, J=6.0, 2H), 2.74 (tt, J=12.1, 3.8, 1H), 2.29 (dt, J=11.8, 2.4, 2H), 2.05-1.94 (m, 2H), 1.89 (ddd, J=25.2, 12.5, 3.7, 2H). MS (ESI): mass calcd. for $C_{24}H_{24}N_4O_2S$, 432.16; m/z found, 433.2 [M+H]$^+$.

Example 39

4-(4-Chlorophenyl)-1-{2-[4-([1,3]thiazolo[5,4-b]pyridin-2-yloxy)phenoxy]ethyl}piperidin-4-ol

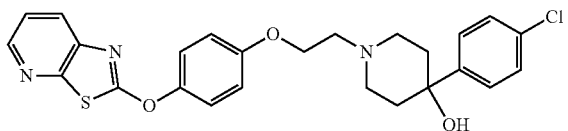

$^1$H NMR (600 MHz, CD$_3$OD): 8.38 (dd, J=4.8, 1.5, 1H), 7.98 (dd, J=8.1, 1.5 1H), 7.54-7.47 (m, 2H), 7.45 (dd, J=8.1, 4.8, 1H), 7.38-7.25 (m, 4H), 7.11-7.06 (m, 2H), 4.22 (t, J=5.5, 2H), 2.98-2.85 (m, 4H), 2.74-2.67 (m, 2H), 2.15 (dt, J=13.5, 4.4, 2H), 1.74 (d, J=14.1, 2H). MS (ESI): mass calcd. for $C_{25}H_{24}N_3O_3SCl$, 481.12; m/z found, 482.1 [M+H]$^+$.

Example 40

4-Phenyl-1-{2-[4-([1,3]thiazolo[5,4-b]pyridin-2-yloxy)phenoxy]ethyl}piperidin-4-ol

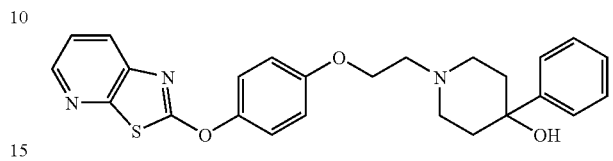

$^1$H NMR (600 MHz, CDCl$_3$): 8.38 (dd, J=4.8, 1.5, 1H), 7.92 (dd, J=8.1, 1.5, 1H), 7.56-7.48 (m, 2H), 7.39-7.34 (m, 2H), 7.31 (dd, J=8.1, 4.8, 1H), 7.29-7.25 (m, 3H), 7.03-6.98 (m, 2H), 4.18 (t, J=5.9, 2H), 2.95-2.86 (m, 4H), 2.66 (dt, J=12.1, 2.5, 2H), 2.21 (dt, J=13.4, 4.5, 2H), 1.83-1.74 (m, 2H). MS (ESI): mass calcd. for $C_{25}H_{25}N_3O_3S$, 447.16; m/z found, 448.1 [M+H]$^+$.

Example 41

2-(4-{2-[4-(2-Methoxyphenyl)piperidin-1-yl]ethoxy}phenoxy)[1,3]thiazolo[5,4-b]pyridine

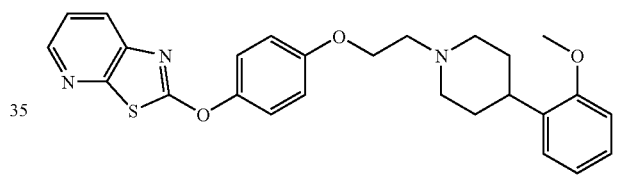

$^1$H NMR (600 MHz, CDCl$_3$): 8.39 (dd, J=4.8, 1.5, 1H), 7.93 (dd, J=8.1, 1.5, 1H), 7.31 (dd, J=8.1, 4.8, 1H), 7.29-7.24 (m, 2H), 7.22 (dd, J=7.6, 1.5, 1H), 7.19-7.15 (m, 1H), 7.02-6.97 (m, 2H), 6.95-6.91 (m, 1H), 6.87-6.84 (m, 1H), 4.17 (t, J=6.0, 2H), 3.83 (s, 3H), 3.12 (d, J=3.1, 2H), 3.04-2.93 (m, 1H), 2.87 (t, J=6.0, 2H), 2.30 (dt, J=11.4, 3.1, 2H), 1.90-1.70 (m, 4H). MS (ESI): mass calcd. for $C_{26}H_{27}N_3O_3S$, 461.18; m/z found, 462.2 [M+H]$^+$.

Example 42

2-{4-[2-(4-Pyridin-4-ylpiperidin-1-yl)ethoxy]phenoxy}[1,3]thiazolo[5,4-b]pyridine

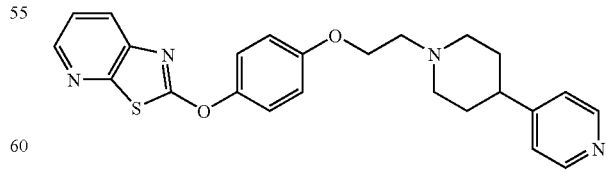

$^1$H NMR (600 MHz, CDCl$_3$): 8.51 (dd, J=4.5, 1.6, 2H), 8.39 (dd, J=4.5, 1.5, 1H), 7.92 (dd, J=8.1, 1.5, 1H), 7.31 (dd, J=8.1, 4.7, 1H), 7.29-7.25 (m, 2H), 7.15 (dd, J=4.6, 1.5, 2H), 7.01-6.96 (m, 2H), 4.16 (t, J=5.8, 2H), 3.22-3.05 (m, 2H), 2.87 (t, J=5.8, 2H), 2.52 (tt, J=11.7, 4.0, 1H), 2.27 (dt, J=11.6, 2.7, 2H), 1.91-1.74 (m, 4H). MS (ESI): mass calcd. for $C_{24}H_{24}N_4O_2S$, 432.16; m/z found, 433.1 [M+H]$^+$.

Example 43

1-(1-{2-[4-([1,3]Thiazolo[5,4-b]pyridin-2-yloxy)phenoxy]ethyl}piperidin-4-yl)pyrrolidin-2-one

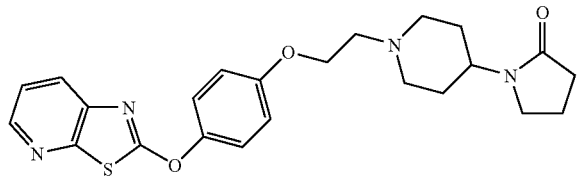

The title compound was prepared using methods analogous to those described for Example 1, with the addition of sodium iodide (1 equiv.) as well as an extra equivalent of N,N-diisopropylethylamine and the appropriate amine. $^1$H NMR (600 MHz, CDCl$_3$): 8.40 (dd, J=4.8, 1.6, 1H), 7.94 (dd, J=8.1, 1.6, 1H), 7.33 (dd, J=8.1, 4.8, 1H), 7.29-7.27 (m, 2H), 6.98 (d, J=9.1, 2H), 4.12 (t, J=5.7, 2H), 3.36 (t, J=7.0, 2H), 3.11-3.05 (m, 2H), 2.96 (s, 1H), 2.89 (s, 1H), 2.84 (t, J=5.7, 2H), 2.40 (t, J=8.1, 2H), 2.30-2.22 (m, 2H), 2.03-1.97 (m, 2H), 1.84-1.73 (m, 3H). MS (ESI): mass calcd. for $C_{23}H_{26}N_4O_3S$, 438.17; m/z found, 439.2 [M+H]$^+$.

Example 44

1-{2-[4-([1,3]Thiazolo[5,4-b]pyridin-2-yloxy)phenoxy]ethyl}piperidine-4-carboxylic Acid

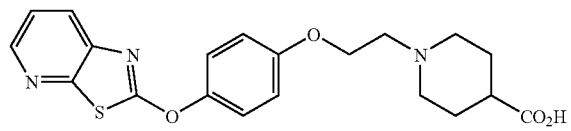

To a stirred solution of ethyl 1-[2-(4-hydroxyphenoxy)ethyl]piperidine-4-carboxylate (400 mg, 1.37 mmol) and 2-chloro[1,3]thiazolo[5,4-b]pyridine (231 mg, 1.37 mmol) in DMF (6 mL) was added Cs$_2$CO$_3$ (887 mg, 2.73 mmol). The resultant dark red-orange suspension was stirred at rt for 1 h. The reaction mixture was concentrated, and the residue redissolved in CH$_2$Cl$_2$ (10 mL) and filtered. To a solution of this crude material in isopropyl alcohol was added 1 N KOH (1 equiv.). The mixture was allowed to stir at rt for 2 h and then poured into water and basified to pH 9. The resultant solution was extracted with a 1:1 solution of CHCl$_3$/isopropyl alcohol. The combined organic extracts were dried, filtered, and concentrated to afford the title compound (39% over two steps). $^1$H NMR (400 MHz, DMSO-d$_6$): 8.43 (dd, J=4.8, 1.5, 1H), 8.07 (dd, J=8.2, 1.5, 1H), 7.50 (dd, J=8.2, 4.8, 1H), 7.44-7.34 (m, 2H), 7.10-7.04 (m, 2H), 4.11 (t, J=5.8, 2H), 2.94-2.82 (m, 2H), 2.70 (t, J=5.8, 2H), 2.27-2.15 (m, 1H), 2.15-2.04 (m, 2H), 1.85-1.71 (m, 2H), 1.64-1.47 (m, 2H). MS (ESI): mass calcd. for $C_{20}H_{21}N_3O_4S$, 399.13; m/z found, 400.1 [M+H]$^+$.

Example 45

(1S,4S)-5-{2-[4-([1,3]Thiazolo[4,5-b]pyridin-2-yloxy)phenyl]ethyl}-2,5-diazabicyclo[2.2.1]heptane-2-carboxamide

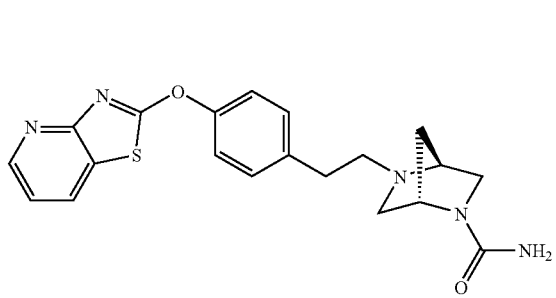

To a solution of 2-[4-([1,3]thiazolo[4,5-b]pyridin-2-yloxy)phenyl]ethyl methanesulfonate (100 mg, 0.29 mmol, 1.0 equiv.) and (1S,4S)-2-acetyl-2,5-diazabicyclo[2.2.1]heptane (48 mg, 0.34 mmol, 1.2 equiv.) in CH$_3$CN (3 mL) was added K$_2$CO$_3$ (39 mg, 0.29 mmol, 1.0 equiv.). The solution was stirred at 80° C. for 16 h and then cooled to rt. Purification by preparative reverse phase HPLC produced a white solid (16%). $^1$H NMR (500 MHz, CDCl$_3$): 8.57 (dd, J=4.8, 1.7, 1H), 8.03 (dd, J=7.9, 1.7, 1H), 7.36-7.28 (m, 4H), 7.22 (dd, J=7.9, 4.8, 1H), 4.32 (s, 2H), 3.61 (s, 1H), 3.23 (dd, J=8.8, 2.1, 1H), 3.02 (dd, J=9.5, 2.0, 1H), 3.53-3.46 (m, 1H), 2.90-2.77 (m, 4H), 2.73 (d, J=9.4, 1H), 1.92 (d, J=9.6, 1H), 1.77 (d, J=9.3, 1H), 1.62 (s, 1H). MS (ESI): mass calcd. for $C_{20}H_{21}N_5O_2S$, 395.14; m/z found, 396.1 [M+H]$^+$.

Examples 46-65 were prepared using methods analogous to those described for Example 45.

Example 46

1-(1-{2-[4-([1,3]Thiazolo[4,5-b]pyridin-2-yloxy)phenyl]ethyl}piperidin-4-yl)pyrrolidin-2-one

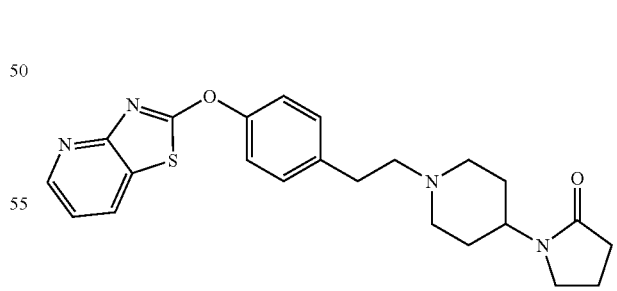

$^1$H NMR (400 MHz, CDCl$_3$): 8.56 (dd, J=4.8, 1.7, 1H), 8.01 (dd, J=7.9, 1.7, 1H), 7.35-7.30 (m, 2H), 7.30-7.26 (m, 2H), 7.20 (dd, J=7.9, 4.8, 1H), 4.10-3.97 (m, 1H), 3.38 (t, J=7.0, 2H), 3.11-3.03 (m, 2H), 2.88-2.79 (m, 2H), 2.67-2.57 (m, 2H), 2.41 (t, J=8.1, 2H), 2.22-2.10 (m, 2H), 2.07-1.96 (m,

2H), 1.82-1.65 (m, 4H). MS (ESI): mass calcd. for C$_{23}$H$_{26}$N$_4$O$_2$S, 422.18; m/z found, 423.2 [M+H]$^+$.

Example 47

4-(4-Chlorophenyl)-1-{2-[4-([1,3]thiazolo[4,5-b]pyridin-2-yloxy)phenyl]ethyl}piperidin-4-ol

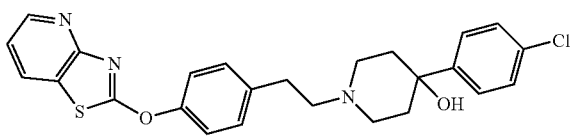

$^1$H NMR (400 MHz, CDCl$_3$): 8.56 (dd, J=4.6, 1.6, 1H), 8.01 (dd, J=7.9, 1.7, 1H), 7.50-7.44 (m, 2H), 7.37-7.28 (m, 6H), 7.20 (dd, J=7.93, 4.85, 1H), 2.98-2.83 (m, 4H), 2.74-2.66 (m, 2H), 2.60-2.47 (m, 2H), 2.24-2.09 (m, 2H), 1.84-1.71 (m, 2H). MS (ESI): mass calcd. for C$_{25}$H$_{24}$ClN$_3$O$_2$S, 465.13; m/z found, 466.1 [M+H]$^+$.

Example 48

2-{4-[2-(4-Pyridin-2-ylpiperidin-1-yl)ethyl]phenoxy}[1,3]thiazolo[4,5-b]pyridine

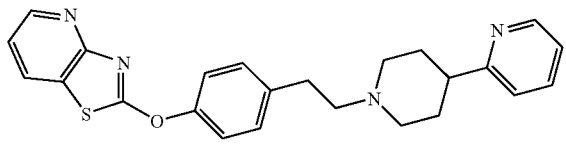

$^1$H NMR (500 MHz, CDCl$_3$): 8.60-8.53 (m, 2H), 8.03 (dd, J=7.9, 1.5, 1H), 7.68-7.62 (m, 1H), 7.37-7.30 (m, 4H), 7.25-7.19 (m, 2H), 7.16-7.12 (m, 1H), 3.23-3.14 (m, 2H), 2.95-2.86 (m, 2H), 2.82-2.72 (m, 1H), 2.71-2.64 (m, 2H), 2.26-2.16 (m, 2H), 2.07-1.99 (m, 2H), 1.95-1.84 (m, 2H). MS (ESI): mass calcd. for C$_{24}$H$_{24}$N$_4$OS, 416.17; m/z found, 417.1 [M+H]$^+$.

Example 49 meso-N-[(3-exo)-8-{2-[4-([1,3]Thiazolo[4,5-b]pyridin-2-yloxy)phenyl]ethyl}-8-azabicyclo[3.2.1]oct-3-yl]acetamide

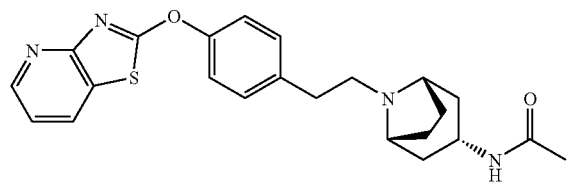

$^1$H NMR (400 MHz, CDCl$_3$): 8.56 (dd, J=4.8, 1.6, 1H), 8.01 (dd, J=7.9, 1.6, 1H), 7.34-7.27 (m, 4H), 7.20 (dd, J=7.9, 4.8, 1H), 5.19 (d, J=8.4, 1H), 4.23-4.07 (m, 1H), 3.31 (s, 2H), 2.80 (dd, J=9.3, 6.6, 2H), 2.61 (dd, J=9.1, 6.5, 2H), 2.03-1.89 (m, 5H), 1.88-1.78 (m, 2H), 1.72 (d, J=7.9, 2H), 1.47 (dd, J=12.7, 2.1, 2H). MS (ESI): mass calcd. for C$_{23}$H$_{26}$N$_4$O$_2$S, 422.18; m/z found, 423.1 [M+H]$^+$.

Example 50 meso-1-[(3-exo)-8-{2-[4-([1,3]Thiazolo[4,5-b]pyridin-2-yloxy)phenyl]ethyl}-8-azabicyclo[3.2.1]oct-3-yl]urea

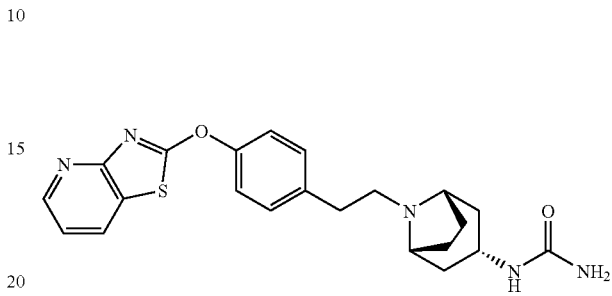

$^1$H NMR (500 MHz, CDCl$_3$): 8.56 (dd, J=4.9, 1.6, 1H), 8.06 (dd, J=7.9, 1.6, 1H), 7.37-7.28 (m, 4H), 7.24 (dd, J=7.9, 4.9, 1H), 5.16 (d, J=8.0, 1H), 4.39 (s, 2H), 3.94 (s, 1H), 3.34 (s, 2H), 2.82 (dd, J=9.0, 6.5, 2H), 2.68 (dd, J=9.0, 6.6, 2H), 2.01-1.96 (m, 2H), 1.87-1.77 (m, 2H), 1.72 (q, J=6.5, 2H), 1.53 (t, J=11.0, 2H). MS (ESI): mass calcd. for C$_{22}$H$_{25}$N$_5$O$_2$S, 423.17; m/z found, 424.2 [M+H]$^+$.

Example 51

2-(4-{2-[(1S,4S)-5-Acetyl-2,5-diazabicyclo[2.2.1]hept-2-yl]ethyl}phenoxy)[1,3]thiazolo[5,4-b]pyridine

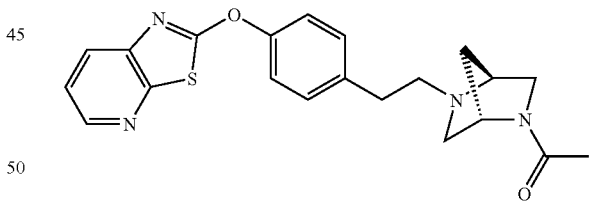

$^1$H NMR (500 MHz, CDCl$_3$): 8.40 (ddd, J=4.8, 1.5, 1.0, 1H), 7.93 (dd, J=8.1, 1.5, 1H), 7.33 (ddd, J=8.1, 4.8, 1.0, 1H), 7.30-7.27 (m, 4H), 4.77 (s, 0.5H), 4.22 (s, 0.5H), 3.68 (dd, J=11.4, 1.5, 0.5H), 3.59 (s, 1H), 3.58-3.53 (m, 0.5H), 3.49 (d, J=3.8, 0.5H), 3.31 (dd, J=9.4, 2.2, 0.5H), 3.26 (dd, J=11.4, 1.9, 0.5H), 3.11 (dd, J=9.5, 2.1, 0.5H), 2.95 (dd, J=9.6, 2.2, 0.5H), 2.89-2.75 (m, 4H), 2.73 (dd, J=9.6, 1.0, 0.5H), 2.55 (dd, J=9.4, 1.2, 0.5H), 2.08 (s, 1H), 1.98 (s, 2H), 1.95 (d, J=10.3, 0.5H), 1.88 (d, J=9.9, 0.5H), 1.79 (d, J=9.7, 0.5H). MS (ESI): mass calcd. for C$_{21}$H$_{22}$N$_4$O$_2$S, 394.15; m/z found, 395.1 [M+H]$^+$.

Example 52 meso-N-[(3-endo)-8-{2-[4-([1,3]Thiazolo[5,4-b]pyridin-2-yloxy)phenyl]ethyl}-8-azabicyclo[3.2.1]oct-3-yl]acetamide

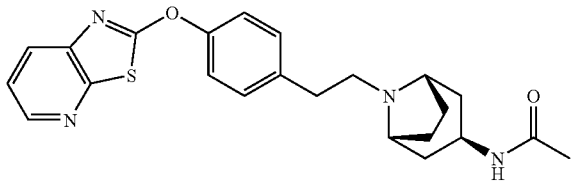

$^1$H NMR (500 MHz, CDCl$_3$): 8.42 (dd, J=4.7, 1.5, 1H), 7.95 (dd, J=8.1, 1.5, 1H), 7.36-7.32 (m, 1H), 7.32-7.28 (m, 4H), 5.81 (dd, J=5.8, 1.3, 1H), 4.12 (q, J=7.2, 1H), 3.31 (s, 2H), 2.83 (dd, J=9.4, 6.6, 2H), 2.62 (dd, J=9.3, 6.7, 2H), 2.24 (ddd, J=14.8, 6.8, 3.6, 2H), 2.13-2.07 (m, 2H), 1.99 (s, 3H), 1.81-1.73 (m, 2H), 1.63 (d, J=14.3, 2H). MS (ESI): mass calcd. for C$_{23}$H$_{26}$N$_4$O$_2$S, 422.18; m/z found, 423.2 [M+H]$^+$.

Example 53 meso-2-(4-{2-[3-Acetyl-3,8-diazabicyclo[3.2.1]oct-8-yl]ethyl}phenoxy)[1,3]thiazolo[5,4-b]pyridine

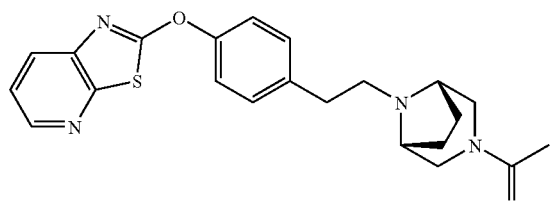

$^1$H NMR (400 MHz, CDCl$_3$): 8.40 (dd, J=4.8, 1.5, 1H), 7.93 (dd, J=8.1, 1.5, 1H), 7.35-7.27 (m, 5H), 4.17 (dd, J=12.7, 2.5, 1H), 3.27 (dd, J=18.7, 3.5, 2H), 3.43-3.35 (m, 2H), 2.92-2.81 (m, 3H), 2.64-2.59 (m, 2H), 2.06 (s, 3H), 1.99-1.85 (m, 2H), 1.60 (ddd, J=17.2, 9.4, 6.5, 2H). MS (ESI): mass calcd. for C$_{22}$H$_{24}$N$_4$O$_2$S, 408.16; m/z found, 409.2 [M+H]$^+$.

Example 54 meso-8-{2-[4-([1,3]Thiazolo[4,5-b]pyridin-2-yloxy)phenyl]ethyl}-3,8-diazabicyclo[3.2.1]octane-3-carboxamide

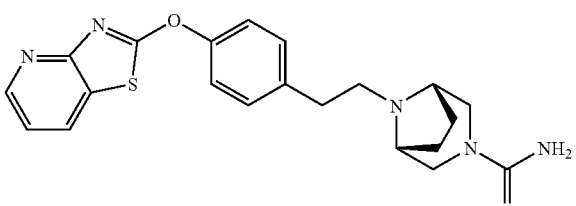

$^1$H NMR (500 MHz, CDCl$_3$): 8.57 (dd, J=4.8, 1.7, 1H), 8.03 (dd, J=7.9, 1.5, 1H), 7.39-7.28 (m, 4H), 7.22 (dd, J=7.9, 4.9, 1H), 4.42 (s, 2H), 3.53 (s, 1H), 3.26 (s, 2H), 3.18 (d, J=10.0, 2H), 2.87-2.80 (m, 2H), 2.66-2.59 (m, 2H), 1.95 (s, 2H), 1.75-1.66 (m, 3H). MS (ESI): mass calcd. for C$_{21}$H$_{23}$N$_5$O$_2$S, 409.16; m/z found, 410.1 [M+H]$^+$.

Example 55 meso-2-(4-{2-[3-Acetyl-3,8-diazabicyclo[3.2.1]oct-8-yl]ethyl}phenoxy)[1,3]thiazolo[4,5-b]pyridine

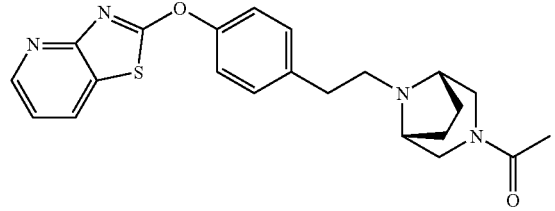

$^1$H NMR (500 MHz, CDCl$_3$): 8.58 (dd, J=4.8, 1.6, 1H), 8.03 (dd, J=7.9, 1.7, 1H), 7.37-7.29 (m, 4H), 7.22 (dd, J=7.9, 4.8, 1H), 4.19 (dd, J=12.8, 1.8, 1H), 3.41 (dd, J=6.6, 1.6, 2H), 3.29 (d, J=23.7, 2H), 2.91 (d, J=11.9, 1H), 2.88-2.80 (m, 2H), 2.66-2.58 (m, 2H), 2.08 (s, 3H), 2.04-1.84 (m, 2H), 1.72-1.53 (m, 2H). MS (ESI): mass calcd. for C$_{22}$H$_{24}$N$_4$O$_2$S, 408.16; m/z found, 409.2 [M+H]$^+$.

Example 56

2-(Ethyl{2-[4-([1,3]thiazolo[4,5-b]pyridin-2-yloxy)phenyl]ethyl}amino)ethanol

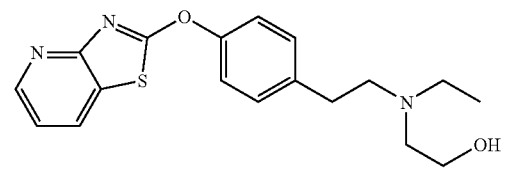

$^1$H NMR (400 MHz, CDCl$_3$): 8.56 (dd, J=4.8, 1.7, 1H), 8.00 (dd, J=7.9, 1.7, 1H), 7.36-7.32 (m, 2H), 7.28-7.23 (m, 2H), 7.19 (dd, J=7.9, 4.8, 1H), 3.55 (t, J=5.3, 2H), 2.91 (br s, 1H), 2.82-2.76 (m, 4H), 2.71-2.64 (m, 4H), 1.07 (t, J=7.1, 3H). MS (ESI): mass calcd. for C$_{18}$H$_{21}$N$_3$O$_2$S, 343.14; m/z found, 344.1 [M+H]$^+$.

Example 57

N-(Cyclopropylmethyl)-N-{2-[4-([1,3]thiazolo[4,5-b]pyridin-2-yloxy)phenyl]ethyl}propan-1-amine

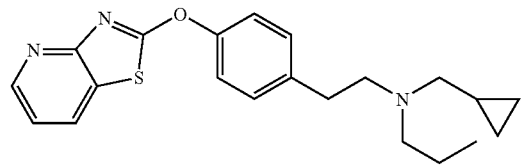

¹H NMR (500 MHz, CDCl₃): 8.56 (dd, J=4.8, 1.7, 1H), 8.00 (dd, J=7.9, 1.7, 1H), 7.34-7.26 (m, 4H), 7.20 (dd, J=7.9, 4.8, 1H), 2.83-2.77 (m, 4H), 2.59-2.54 (m, 2H), 2.44 (d, J=6.5, 2H), 1.55-1.46 (m, 2H), 0.91 (t, J=7.8, 4H), 0.55-0.49 (m, 2H), 0.16-0.11 (m, 2H). MS (ESI): mass calcd. for C₂₁H₂₅N₃OS, 367.17; m/z found, 368.1 [M+H]⁺.

Example 58

(1R)-N-Methyl-1-phenyl-N-{2-[4-([1,3]thiazolo[4,5-b]pyridin-2-yloxy)phenyl]ethyl}ethanamine

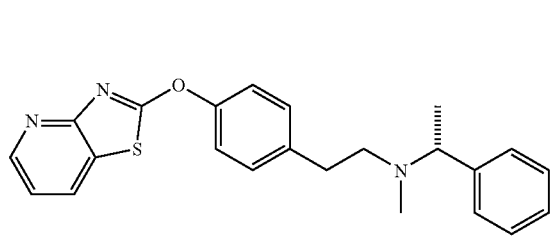

¹H NMR (500 MHz, CDCl₃): 8.58 (dd, J=4.8, 1.7, 1H), 8.02 (dd, J=7.9, 1.7, 1H), 7.35-7.17 (m, 10H), 3.65 (q, J=6.7, 1H), 2.86-2.75 (m, 2H), 2.75-2.66 (m, 1H), 2.62-2.55 (m, 1H), 2.33 (s, 3H), 1.39 (d, J=6.7, 3H). MS (ESI): mass calcd. for C₂₃H₂₃N₃OS, 389.16; m/z found, 390.1 [M+H]⁺.

Example 59

2-[4-(2-Morpholin-4-ylethyl)phenoxyl][1,3]thiazolo[4,5-b]pyridine

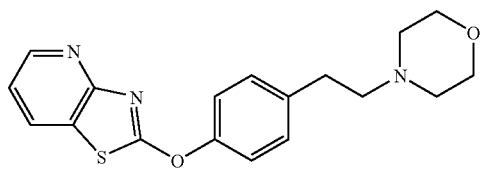

¹H NMR (600 MHz, CDCl₃): 8.56 (dd, J=4.8, 1.6, 1H), 8.00 (dd, J=7.9, 1.6, 1H), 7.35-7.31 (m, 2H), 7.30-7.26 (m, 2H), 7.19 (dd, J=7.9, 4.8, 1H), 3.77-3.73 (m, 4H), 2.87-2.80 (m, 2H), 2.65-2.59 (m, 2H), 2.56-2.50 (m, 4H). MS (ESI): mass calcd. for C₁₈H₁₉N₃O₂S, 341.12; m/z found, 342.1 [M+H]⁺.

Example 60

2-[4-(2-Piperidin-1-ylethyl)phenoxy][1,3]thiazolo[4,5-b]pyridine

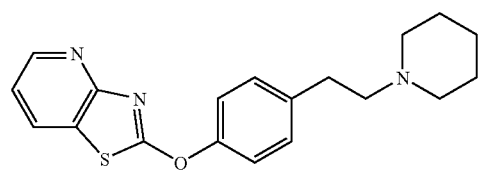

¹H NMR (600 MHz, CDCl₃): 8.56 (dd, J=4.8, 1.7, 1H), 8.00 (dd, J=7.9, 1.7, 1H), 7.34-7.30 (m, 2H), 7.29-7.26 (m, 2H), 7.19 (dd, J=7.9, 4.8, 1H), 2.87-2.81 (m, 2H), 2.60-2.54 (m, 2H), 2.52-2.43 (m, 4H), 1.66-1.59 (m, 4H), 1.50-1.43 (m, 2H). MS (ESI): mass calcd. for C₁₉H₂₁N₃OS, 339.14; m/z found, 340.1 [M+H]⁺.

Example 61

2-[4-(2-Pyrrolidin-1-ylethyl)phenoxyl][1,3]thiazolo[4,5-b]pyridine

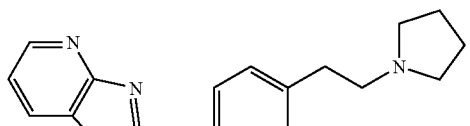

¹H NMR (600 MHz, CDCl₃): 8.58-8.53 (m, 1H), 8.02-7.98 (m, 1H), 7.35-7.31 (m, 2H), 7.31-7.27 (m, 2H), 7.19 (dd, J=7.9, 4.8, 1H), 2.96-2.86 (m, 2H), 2.83-2.75 (m, 2H), 2.69 (s, 4H), 1.85 (m, 4H). MS (ESI): mass calcd. for C₁₈H₁₉N₃OS, 325.13; m/z found, 326.1 [M+H]⁺.

Example 62

4-Phenyl-1-{2-[4-([1,3]thiazolo[4,5-b]pyridin-2-yloxy)phenyl]ethyl}piperidin-4-ol

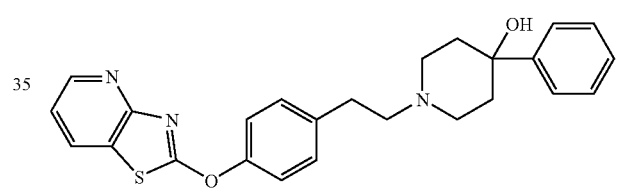

¹H NMR (500 MHz, CDCl₃): 8.58 (dd, J=4.8, 1.6, 1H), 8.03 (dd, J=7.9, 1.6, 1H), 7.59-7.54 (m, 2H), 7.42-7.29 (m, 7H), 7.22 (dd, J=7.9, 4.8, 1H), 2.97-2.87 (m, 4H), 2.73 (dd, J=9.8, 6.5, 2H), 2.58 (dt, J=11.8, 2.1, 2H), 2.23 (dt, J=13.1, 4.5, 2H), 1.92-1.72 (m, 2H). MS (ESI): mass calcd. for C₂₅H₂₅N₃O₂S, 431.17; m/z found, 432.2 [M+H]⁺.

Example 63

2-{4-[2-(4-Benzylpiperidin-1-yl)ethyl]phenoxy}[1,3]thiazolo[4,5-b]pyridine

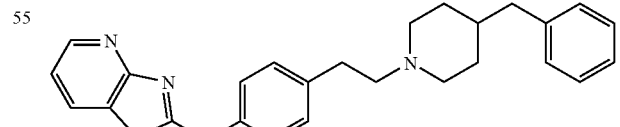

¹H NMR (500 MHz, CDCl₃): 8.58 (ddd, J=4.8, 1.6, 0.5, 1H), 8.02 (ddd, J=7.8, 1.6, 0.5, 1H), 7.35-7.26 (m, 6H), 7.24-7.15 (m, 4H), 3.05-2.93 (m, 2H), 2.88-2.79 (m, 2H), 2.64-2.52 (m, 4H), 1.98 (dt, J=11.7, 1.9, 2H), 1.74-1.67 (m, 2H), 1.63-1.52 (m, 1H), 1.36 (dq, J=12.4, 3.8, 2H). MS (ESI): mass calcd. for C₂₆H₂₇N₃OS, 429.19; m/z found, 430.2 [M+H]⁺.

Example 64

1-{2-[4-([1,3]Thiazolo[4,5-b]pyridin-2-yloxy)phenyl]ethyl}-4-[3-(trifluoromethyl)phenyl]piperidin-4-ol

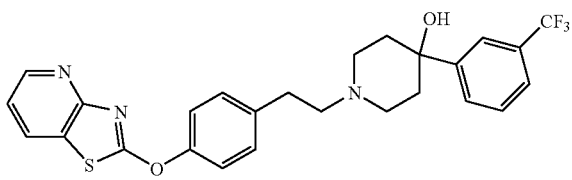

¹H NMR (500 MHz, CDCl₃): 8.58 (dd, J=4.8, 1.6, 1H), 8.03 (dd, J=7.9, 1.6, 1H), 7.86 (s, 1H), 7.73 (d, J=7.5, 1H), 7.55 (d, J=7.6, 1H), 7.50 (d, J=7.5, 1H), 7.38-7.30 (m, 4H), 7.22 (dd, J=7.9, 4.8, 1H), 3.01-2.86 (m, 4H), 2.74 (dd, J=9.6, 6.5, 2H), 2.57 (dt, J=12.3, 2.3, 2H), 2.23 (dt, J=13.4, 4.7, 2H), 1.81 (dd, J=13.9, 2.4, 2H). MS (ESI): mass calcd. for $C_{26}H_{24}F_3N_3O_2S$, 499.15; m/z found, 500.1 [M+H]⁺.

Example 65

2-{4-[2-(4-Pyridin-4-ylpiperidin-1-yl)ethyl]phenoxy}[1,3]thiazolo[4,5-b]pyridine

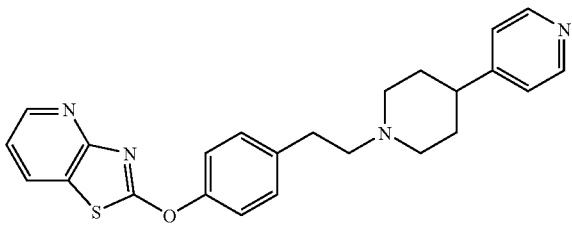

¹H NMR (500 MHz, CDCl₃): 8.58 (dd, J=4.8, 1.7, 1H), 8.55-8.52 (m, 2H), 8.03 (dd, J=7.9, 1.7, 1H), 7.37-7.34 (m, 2H), 7.33-7.29 (m, 2H), 7.22 (dd, J=7.9, 4.8, 1H), 7.19-7.17 (m, 2H), 3.21-3.14 (m, 2H), 2.94-2.86 (m, 2H), 2.71-2.64 (m, 2H), 2.59-2.50 (m, 1H), 2.23-2.13 (m, 2H), 1.95-1.77 (m, 4H). MS (ESI): mass calcd. for $C_{24}H_{24}N_4OS$, 416.17; m/z found, 417.1 [M+H]⁺.

Example 66

1-{2-[4-([1,3]Thiazolo[4,5-b]pyridin-2-yloxy)phenyl]ethyl}piperidine-4-carboxamide

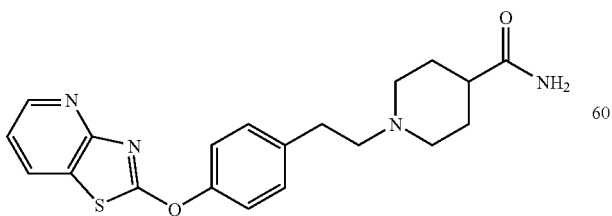

The title compound was prepared using methods analogous to those described for Example 45, substituting Cs₂CO₃ for K₂CO₃. ¹H NMR (600 MHz, DMSO-d₆): 8.52 (dd, J=4.8, 1.7, 1H), 8.39 (dd, J=8.0, 1.7, 1H), 7.39 (s, 4H), 7.33 (dd, J=8.0, 4.8, 1H), 7.17 (s, 1H), 6.66 (s, 1H), 2.99-2.91 (m, 2H), 2.84-2.75 (m, 2H), 2.55-2.51 (m, 2H), 2.10-2.01 (m, 1H), 1.98-1.89 (m, 2H), 1.71-1.64 (m, 2H), 1.59-1.50 (m, 2H). MS (ESI): mass calcd. for $C_{20}H_{22}N_4O_2S$, 382.15; m/z found, 383.1 [M+H]⁺.

Examples 67-78 were prepared using methods analogous to those described for Example 45, substituting tert-amyl alcohol for CH₃CN.

Example 67

1-{2-[4-([1,3]Thiazolo[5,4-b]pyridin-2-yloxy)phenyl]ethyl}piperidine-4-carboxamide

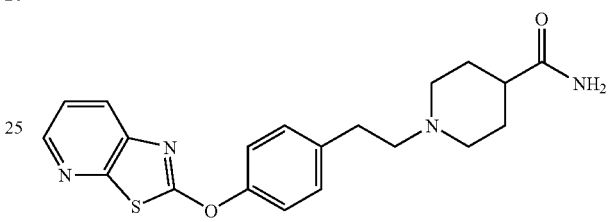

¹H NMR (400 MHz, CDCl₃): 8.40 (dd, J=4.8, 1.5, 1H), 7.94 (dd, J=8.1, 1.5, 1H), 7.36-7.27 (m, 5H), 5.47 (s, 1H), 5.26 (s, 1H), 3.10-3.02 (m, 2H), 2.89-2.80 (m, 2H), 2.66-2.59 (m, 2H), 2.25-2.15 (m, 1H), 2.15-2.03 (m, 2H), 1.98-1.89 (m, 2H), 1.84-1.73 (m, 2H). MS (ESI): mass calcd. for $C_{20}H_{22}N_4O_2S$, 382.15; m/z found, 383.1 [M+H]⁺.

Example 68

1-(1-{2-[4-([1,3]Thiazolo[5,4-b]pyridin-2-yloxy)phenyl]ethyl}piperidin-4-yl)pyrrolidin-2-one

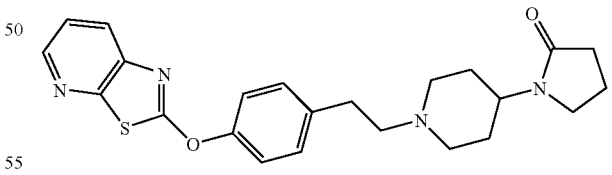

¹H NMR (600 MHz, DMSO-d₆): 8.44 (dd, J=4.7, 1.5, 1H), 8.08 (dd, J=8.2, 1.5, 1H), 7.50 (dd, J=8.2, 4.7, 1H), 7.37 (s, 4H), 3.77-3.68 (m, 1H), 3.33-3.30 (m, 1H), 3.03-2.98 (m, 2H), 2.82-2.76 (m, 2H), 2.59-2.54 (m, 2H), 2.21 (t, J=8.1, 2H), 2.07-2.00 (m, 2H), 1.93-1.86 (m, 2H), 1.70-1.60 (m, 2H), 1.55-1.47 (m, 2H), 1.21-1.13 (m, 1H). MS (ESI): mass calcd. for $C_{23}H_{26}N_4O_2S$, 422.18; m/z found, 423.2 [M+H]⁺.

Example 69

2-{4-[2-(5-Acetylhexahydropyrrolo[3,4-c]pyrrol-2(1H)-yl)ethyl]phenoxy}[1,3]thiazolo[5,4-b]pyridine

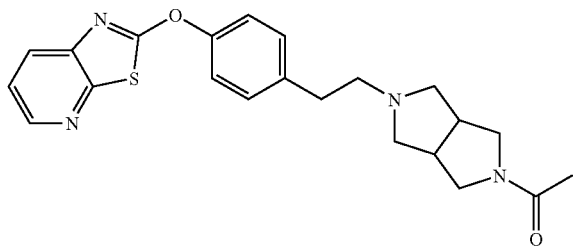

$^1$H NMR (500 MHz, CDCl$_3$): 8.41 (dd, J=4.8, 1.5, 1H), 7.95 (dd, J=8.1, 1.5, 1H), 7.36-7.26 (m, 5H), 3.76-3.64 (m, 2H), 3.51-3.45 (m, 1H), 3.34 (dd, J=10.8, 4.5, 1H), 3.00-2.80 (m, 4H), 2.78-2.67 (m, 4H), 2.53 (ddd, J=13.6, 9.3, 4.0, 2H), 2.06 (s, 3H). MS (ESI): mass calcd. for C$_{22}$H$_{24}$N$_4$O$_2$S, 408.16; m/z found, 409.2 [M+H]$^+$.

Example 70

5-{2-[4-([1,3]Thiazolo[5,4-b]pyridin-2-yloxy)phenyl]ethyl}hexahydropyrrolo[3,4-c]pyrrole-2(1H)-carboxamide

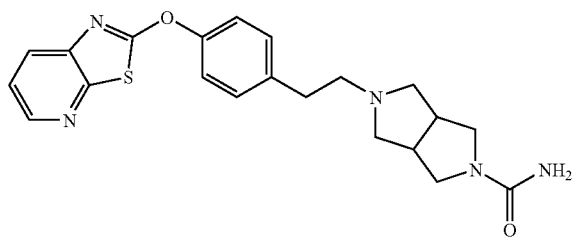

$^1$H NMR (500 MHz, CDCl$_3$): 8.42 (dd, J=4.8, 1.6, 1H), 7.95 (dd, J=8.1, 1.5, 1H), 7.37-7.26 (m, 5H), 4.33 (s, 2H), 3.61 (dd, J=10.3, 8.3, 2H), 3.30 (d, J=9.3, 2H), 2.96-2.70 (m, 8H), 2.55 (dd, J=9.2, 3.3, 2H). MS (ESI): mass calcd. for C$_{21}$H$_{23}$N$_5$O$_2$S, 409.16; m/z found, 410.2 [M+H]$^+$.

Example 71 meso-8-{2-[4-([1,3]thiazolo[5,4-b]pyridin-2-yloxy)phenyl]ethyl}-3,8-diazabicyclo[3.2.1]octane-3-carboxamide

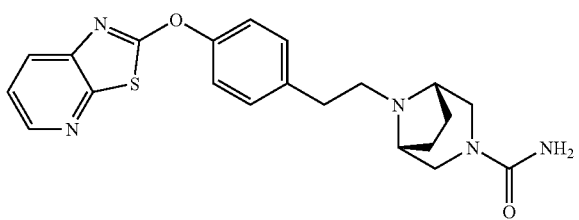

$^1$H NMR (500 MHz, CDCl$_3$): 8.42 (dd, J=4.8, 1.5, 1H), 7.95 (dd, J=8.1, 1.5, 1H), 7.38-7.25 (m, 5H), 4.37 (s, 2H), 3.30 (br s, 2H), 3.19 (d, J=11.4, 2H), 2.91-2.81 (m, 2H), 2.69-2.59 (m, 2H), 2.01-1.90 (m, 2H), 1.72 (d, J=7.8, 2H). MS (ESI): mass calcd. for C$_{21}$H$_{23}$N$_5$O$_2$S, 409.16; m/z found, 410.2 [M+H]$^+$.

Example 72 meso-1-[(3-endo)-8-{2-[4-([1,3]Thiazolo[5,4-b]pyridin-2-yloxy)phenyl]ethyl}-8-azabicyclo[3.2.1]oct-3-yl]urea

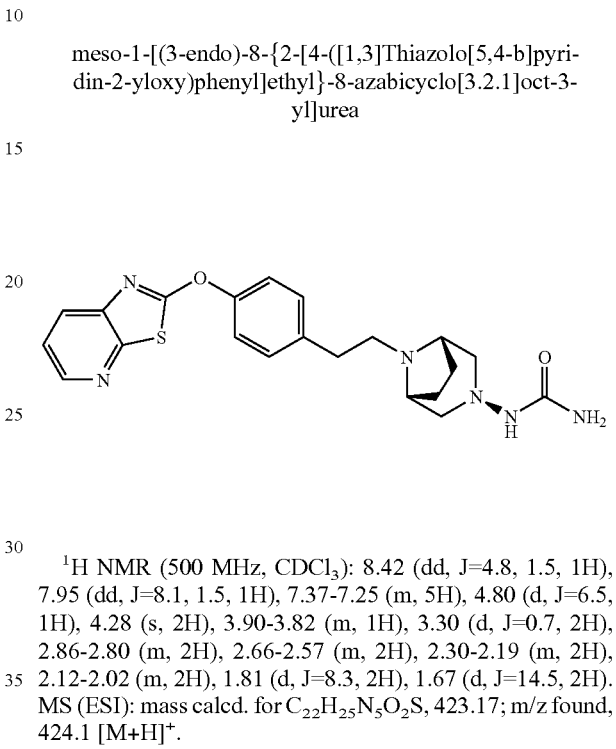

$^1$H NMR (500 MHz, CDCl$_3$): 8.42 (dd, J=4.8, 1.5, 1H), 7.95 (dd, J=8.1, 1.5, 1H), 7.37-7.25 (m, 5H), 4.80 (d, J=6.5, 1H), 4.28 (s, 2H), 3.90-3.82 (m, 1H), 3.30 (d, J=0.7, 2H), 2.86-2.80 (m, 2H), 2.66-2.57 (m, 2H), 2.30-2.19 (m, 2H), 2.12-2.02 (m, 2H), 1.81 (d, J=8.3, 2H), 1.67 (d, J=14.5, 2H). MS (ESI): mass calcd. for C$_{22}$H$_{25}$N$_5$O$_2$S, 423.17; m/z found, 424.1 [M+H]$^+$.

Example 73

2-{4-[2-(5-Acetylhexahydropyrrolo[3,4-c]pyrrol-2(1H)-yl)ethyl]phenoxy}[1,3]thiazolo[4,5-b]pyridine

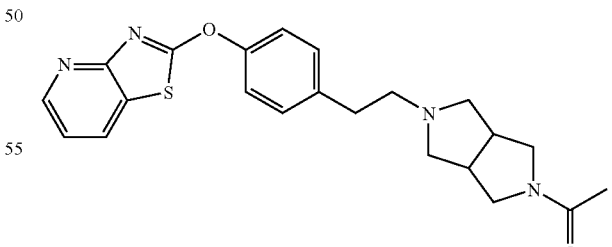

$^1$H NMR (500 MHz, CDCl$_3$): 8.58 (dd, J=4.8, 1.7, 1H), 8.04 (dd, J=7.9, 1.7, 1H), 7.36-7.28 (m, 4H), 7.22 (dd, J=7.9, 4.8, 1H), 3.75-3.65 (m, 2H), 3.46 (dd, J=12.4, 4.2, 1H), 3.34 (dd, J=10.8, 4.6, 1H), 3.00-2.79 (m, 4H), 2.76-2.65 (m, 4H),

Example 74

5-{2-[4-([1,3]Thiazolo[4,5-b]pyridin-2-yloxy)phenyl]ethyl}hexahydropyrrolo[3,4-c]pyrrole-2(1H)-carboxamide

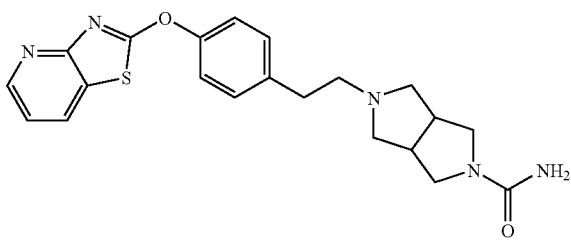

$^1$H NMR (500 MHz, CDCl$_3$): 8.57 (dd, J=4.8, 1.6, 1H), 8.04 (dd, J=7.9, 1.6, 1H), 7.35-7.29 (m, 4H), 7.22 (dd, J=7.9, 4.8, 1H), 4.40 (s, 2H), 3.61 (dd, J=10.2, 8.3, 2H), 3.29 (dd, J=10.2, 2.2, 2H), 2.96-2.79 (m, 4H), 2.75-2.69 (m, 4H), 2.55 (dd, J=9.3, 3.2, 2H). MS (ESI): mass calcd. for C$_{21}$H$_{23}$N$_5$O$_2$S, 409.16; m/z found, 410.1 [M+H]$^+$.

Example 75

2-(4-{2-[(1S,4S)-5-Acetyl-2,5-diazabicyclo[2.2.1]hept-2-yl]ethyl}phenoxy)[1,3]thiazolo[4,5-b]pyridine

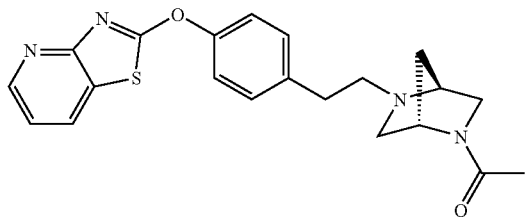

$^1$H NMR (500 MHz, CDCl$_3$): 8.58-8.56 (m, 1H), 8.05-8.01 (m, 1H), 7.37-7.31 (m, 4H), 7.22 (ddd, J=7.9, 4.8, 1.3, 1H), 4.78 (s, 0.5H), 4.24 (s, 0.5H), 3.69 (dd, J=11.5, 1.5, 0.5H), 3.61 (s, 1H), 3.58 (dd, J=9.5, 1.1, 0.5H), 3.33 (dd, J=9.5, 2.2, 0.5H), 3.27 (dd, J=11.5, 1.9, 0.5H), 3.11 (dd, J=9.5, 2.2, 0.5H), 2.96 (dd, J=9.6, 2.2, 0.5H), 2.89-2.75 (m, 4H), 2.73 (dd, J=9.7, 0.80, 0.5H), 2.56 (dd, J=9.5, 1.2, 0.5H), 2.10 (s, 1H), 2.00 (s, 2H), 1.96 (d, J=9.5, 0.5H), 1.90 (d, J=9.9, 0.5H), 1.81 (d, J=9.8, 0.5H), 1.69 (d, J=9.9, 0.5H). MS (ESI): mass calcd. for C$_{21}$H$_{22}$N$_4$O$_2$S, 394.15; m/z found, 395.1 [M+H]$^+$.

Example 76 meso-N-[(3-endo)-8-{2-[4-([1,3]Thiazolo[4,5-b]pyridin-2-yloxy)phenyl]ethyl}-8-azabicyclo[3.2.1]oct-3-yl]acetamide

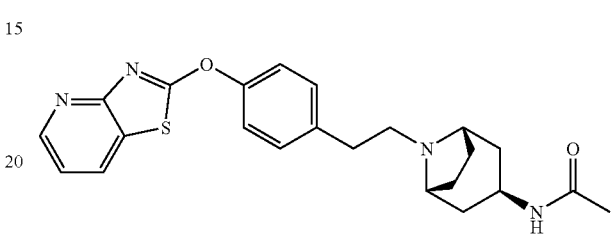

$^1$H NMR (500 MHz, CDCl$_3$): 8.58 (dd, J=4.8, 1.7, 1H), 8.03 (dd, J=7.9, 1.7, 1H), 7.36-7.29 (m, 4H), 7.22 (dd, J=7.9, 4.8, 1H), 5.82 (d, J=6.0, 1H), 4.12 (q, J=7.1, 1H), 3.31 (s, 2H), 2.82 (dd, J=9.4, 6.7, 2H), 2.60 (dd, J=9.4, 6.8, 2H), 2.24 (ddd, J=14.7, 6.9, 3.7, 2H), 2.15-2.05 (m, 2H), 1.99 (s, 3H), 1.77 (q, J=6.8, 2H), 1.71-1.57 (m, 2H). MS (ESI): mass calcd. for C$_{23}$H$_{26}$N$_4$O$_2$S, 422.18; m/z found, 423.2 [M+H]$^+$.

Example 77 meso-1-[(3-endo)-8-{2-[4-([1,3]Thiazolo[4,5-b]pyridin-2-yloxy)phenyl]ethyl}-8-azabicyclo[3.2.1]oct-3-yl]urea

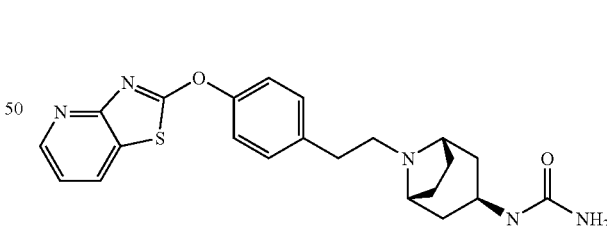

$^1$H NMR (500 MHz, CDCl$_3$): 8.57 (dd, J=4.9, 1.6, 1H), 8.03 (dd, J=7.9, 1.6, 1H), 7.39-7.27 (m, 4H), 7.22 (dd, J=7.9, 4.9, 1H), 4.91 (s, 1H), 4.36 (s, 2H), 3.94-3.80 (m, 1H), 3.31 (s, 2H), 2.83 (dd, J=9.2, 6.8, 2H), 2.61 (dd, J=9.3, 6.7, 2H), 2.30-2.20 (m, 2H), 2.10-2.00 (m, 2H), 1.82 (d, J=8.3, 2H), 1.67 (s, 2H). MS (ESI): mass calcd. for C$_{22}$H$_{25}$N$_5$O$_2$S, 423.13; m/z found, 424.1 [M+H]$^+$.

Example 78

(1S,4S)-5-{2-[4-([1,3]Thiazolo[5,4-b]pyridin-2-yloxy)phenyl]ethyl}-2,5-diazabicyclo[2.2.1]heptane-2-carboxamide

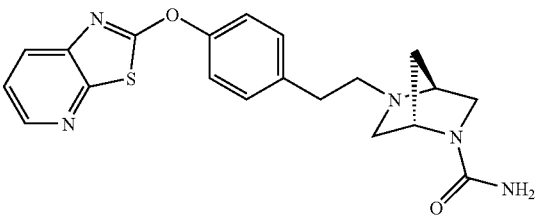

$^1$H NMR (500 MHz, CDCl$_3$): 8.42 (dd, J=4.8, 1.5, 1H), 7.95 (dd, J=8.1, 1.5, 1H), 7.35 (dd, J=8.1, 4.8, 1H), 7.33-7.28 (m, 4H), 4.44 (s, 1H), 4.33 (s, 2H), 3.62 (s, 1H), 3.51 (s, 1H), 3.24 (dd, J=8.8, 2.1, 1H), 3.03 (dd, J=9.5, 1.8, 1H), 2.92-2.77 (m, 4H), 2.73 (d, J=8.9, 1H), 1.92 (d, J=9.3, 1H), 1.78 (d, J=9.4, 1H). MS (ESI): mass calcd. for C$_{20}$H$_{21}$N$_5$O$_2$S, 395.14; m/z found, 396.1 [M+H]$^+$.

Example 79

2-(4-{2-[(1R,4R)-5-Acetyl-2,5-diazabicyclo[2.2.1]hept-2-yl]ethyl}phenoxy)[1,3]thiazolo[4,5-b]pyridine

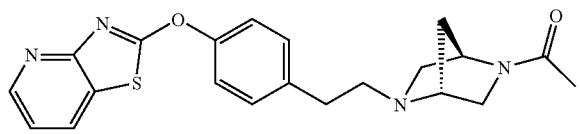

To a solution of 2-[4-([1,3]thiazolo[4,5-b]pyridin-2-yloxy)phenyl]ethyl methanesulfonate (500 mg, 1.42 mmol, 1 equiv.) and K$_2$CO$_3$ (196 mg, 1.42 mmol, 1 equiv.) in CH$_3$CN (14 mL) was added (1R,4R)-2,5-diaza-bicyclo[2.2.1]heptane-2-carboxylic acid tert-butyl ester (340 mg, 1.7 mmol, 1.2 equiv.). The mixture was stirred at 80° C. for 16 h, concentrated, diluted in CH$_2$Cl$_2$ (25 mL), and washed with satd. aq. NaHCO$_3$ (2×25 mL). The organic layer was dried, filtered, and concentrated. Purification using column chromatography (10% MeOH/CH$_2$Cl$_2$) afforded an oil (202 mg, 31%), which was re-dissolved in CH$_2$Cl$_2$. To this solution was added HCl (4 M in dioxane, 1.3 mL, 10 equiv.). The reaction mixture was stirred at rt for 16 h and concentrated to afford the amine hydrochloride salt as a pink solid (100%). To a solution of this amine hydrochloride salt (164 mg, 0.42 mmol, 1 equiv.) and Et$_3$N (0.23 mL, 1.68 mmol, 4 equiv.) in CH$_2$Cl$_2$ (2.3 mL) was added acetic anhydride (0.14 mL, 0.63 mmol, 1.5 equiv.). The reaction mixture was stirred at rt for 2 h, diluted with CH$_2$Cl$_2$ (15 mL) and washed with satd. aq. NaHCO$_3$ (1×20 mL). The organic layer was dried, filtered, and concentrated. Purification using column chromatography (30% MeOH/CH$_2$Cl$_2$) afforded the product as a light pink oil (37 mg, 22%). $^1$H NMR (500 MHz, CDCl$_3$): 8.58-8.56 (m, 1H), 8.03 (ddd, J=7.9, 2.3, 1.7, 1H), 7.36-7.28 (m, 4H), 7.21 (ddd, J=7.9, 4.9, 1.3, 1H), 4.77 (s, 0.5H), 4.24 (s, 0.5H), 3.68 (dd, J=11.4, 1.5, 0.5H), 3.61 (s, 1H), 3.57 (dd, J=9.5, 1.1, 0.5H), 3.33 (dd, J=9.4, 2.2, 0.5H), 3.27 (dd, J=11.4, 1.9, 0.5H), 3.11 (dd, J=9.5, 2.2, 0.5H), 2.96 (dd, J=9.6, 2.2, 0.5H), 2.89-2.70 (m, 4.5H), 2.56 (dd, J=9.5, 1.2, 0.5H), 2.03 (s, 3H), 1.96 (d, J=10.1, 0.5H), 1.89 (d, J=9.9, 0.5H), 1.80 (d, J=9.7, 0.5H), 1.69 (d, J=9.9, 0.5H). MS (ESI): mass calcd. for C$_{21}$H$_{22}$N$_4$O$_2$S, 394.15; m/z found, 395.1 [M+H]$^+$.

Example 80

(1R,4R)-5-{2-[4-([1,3]Thiazolo[4,5-b]pyridin-2-yloxy)phenyl]ethyl}-2,5-diazabicyclo[2.2.1]heptane-2-carboxamide

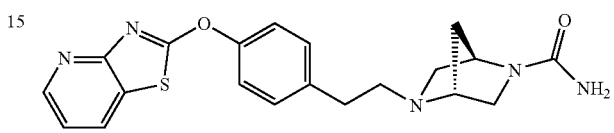

To a solution of 2-[4-([1,3]thiazolo[4,5-b]pyridin-2-yloxy)phenyl]ethyl methanesulfonate (500 mg, 1.42 mmol, 1 equiv.) and K$_2$CO$_3$ (196 mg, 1.42 mmol, 1 equiv.) in CH$_3$CN (14 mL) was added (1R,4R)-2,5-diaza-bicyclo[2.2.1]heptane-2-carboxylic acid tert-butyl ester (340 mg, 1.7 mmol, 1.2 equiv.). The mixture was stirred at 80° C. for 16 h, concentrated, diluted in CH$_2$Cl$_2$ (25 mL), and washed with satd. aq. NaHCO$_3$ (2×25 mL). The organic layer was dried, filtered, and concentrated. Purification using column chromatography (10% MeOH/CH$_2$Cl$_2$) afforded an oil (202 mg, 31%), which was re-dissolved in CH$_2$Cl$_2$. To this solution was added HCl (4 M in dioxane, 1.3 mL, 10 equiv.). The reaction mixture was stirred at rt for 16 h and concentrated to afford the amine hydrochloride salt as a pink solid (100%). To a solution of this amine hydrochloride salt (164 mg, 0.42 mmol, 1 equiv.) and Et$_3$N (0.23 mL, 1.68 mmol, 4 equiv.) in CH$_2$Cl$_2$ (2.3 mL) was added trimethylsilylisocyanate (0.08 mL, 0.63 mmol, 1.5 equiv.). The reaction was stirred at rt for 2 h, diluted with CH$_2$Cl$_2$ (15 mL) and washed with satd. aq. NaHCO$_3$ (1×20 mL). The organic layer was dried, filtered, and concentrated. Purification using column chromatography (40% MeOH/CH$_2$Cl$_2$) afforded the product as an off-white solid (58 mg, 35%). $^1$H NMR (500 MHz, CDCl$_3$): 8.57 (dd, J=4.8, 1.7, 1H), 8.03 (dd, J=7.9, 1.7, 1H), 7.36-7.28 (m, 4H), 7.22 (dd, J=7.9, 4.8, 1H), 4.38 (s, 2H), 3.62 (s, 1H), 3.23 (dd, J=8.9, 2.1, 1H), 3.03 (dd, J=9.6, 1.9z, 1H), 2.88-2.77 (m, 4H), 2.73 (d, J=9.4, 1H), 2.03 (s, 1H), 1.92 (d, J=9.7, 1H), 1.77 (d, J=9.7, 2H). MS (ESI): mass calcd. for C$_{20}$H$_{21}$N$_5$O$_2$S, 395.14; m/z found, 396.1 [M+H]$^+$.

Example 81

1-{2-[4-([1,3]Thiazolo[4,5-b]pyridin-2-yloxy)phenyl]ethyl}piperidine-4-carboxylic Acid

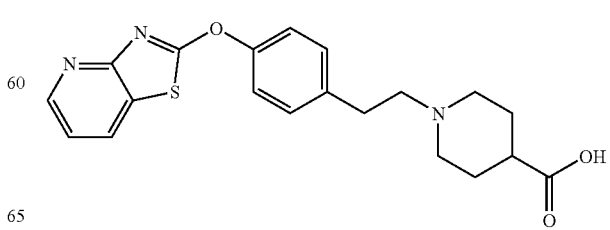

To a solution of ethyl isonipicoate (0.08 mL, 0.57 mmol, 1 equiv.) and 2-[4-([1,3]thiazolo[4,5-b]pyridin-2-yloxy)phenyl]ethyl methanesulfonate (200 mg, 0.57 mmol, 1 equiv.) in tert-amyl alcohol (5 mL) was added K₂CO₃ (78 mg, 0.57 mmol, 1 equiv.). The reaction mixture was heated to 80° C. for 16 h. Purification by preparative reverse phase HPLC afforded the ethyl ester intermediate as an off-white solid (14 mg, 6%). To a solution of this solid in isopropanol (0.6 mL) was added water (0.25 mL) and 1 M KOH (0.6 mL). After stirring at rt for 16 h, the solution was acidified to pH 6 with 6 N HCl, diluted with CH₂Cl₂, and extracted with 25% isopropyl alcohol/CH₂Cl₂ (2×15 mL). The combined organic layers were dried, filtered, and concentrated to afford the product as a white solid (1.3 mg, 10%). ¹H NMR (500 MHz, CDCl₃): 8.57-8.50 (m, 1H), 8.06 (dd, J=7.9, 1.6, 1H), 7.36 (q, J=8.8, 4H), 7.24 (dd, J=7.8, 4.9, 1H), 3.44-3.41 (m, 1H), 3.30-3.15 (m, 6H), 2.39-2.18 (m, 4H), 1.75 (s, 3H). MS (ESI): mass calcd. for C₂₀H₂₁N₃O₃S, 383.13; m/z found, 384.1 [M+H]⁺.

Example 82

{4-[4-([1,3]Thiazolo[4,5-b]pyridin-2-yloxy)benzyl]morpholin-2-yl}methanol

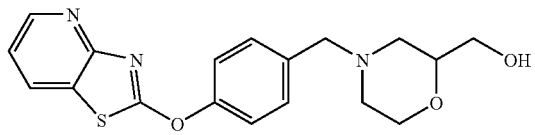

To a solution of 4-([1,3]thiazolo[4,5-b]pyridin-2-yloxy)benzaldehyde (150 mg, 0.585 mmol) and morpholin-2-ylmethanol (82 mg, 0.702 mmol, 1.2 equiv.) in DCE (3.1 mL) was added sodium triacetoxyborohydride (211 mg, 0.995 mmol, 1.7 equiv.) in two portions over 5 min. The mixture was then allowed to stir at rt for 4 h. The mixture was then filtered and purified using preparative reverse phase HPLC to afford the desired product as a light yellow oil (116 mg, 56%). ¹H NMR (600 MHz, CDCl₃): 8.56 (dd, J=4.8, 1.6, 1H), 8.01 (dd, J=7.9, 1.6, 1H), 7.42-7.35 (m, 4H), 7.20 (dd, J=7.9, 4.8, 1H), 3.95-3.87 (m, 1H), 3.75-3.61 (m, 3H), 3.60-3.48 (m, 3H), 2.70 (t, J=12.8, 2H), 2.22 (dt, J=11.5, 3.5, 1H), 2.07-1.99 (m, 1H), 1.93-1.86 (m, 1H). MS (ESI): mass calcd. for C₁₈H₁₉N₃O₃S, 357.12; m/z found, 358.1 [M+H]⁺.

Examples 83-105 were prepared using methods analogous to those described for Example 82.

Example 83

1-{1-[4-([1,3]Thiazolo[4,5-b]pyridin-2-yloxy)benzyl]piperidin-4-yl}pyrrolidin-2-one

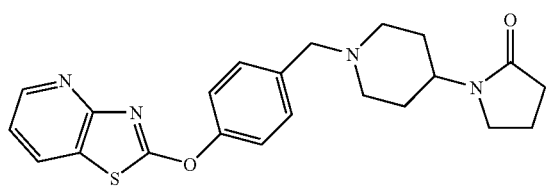

¹H NMR (500 MHz, CDCl₃): 8.58 (dd, J=4.8, 1.6, 1H), 8.04 (dd, J=7.9, 1.6, 1H), 7.44-7.35 (m, 4H), 7.22 (dd, J=7.9, 4.8, 1H), 4.07-3.98 (m, 1H), 3.53 (s, 2H), 3.39 (t, J=7.0, 2H), 3.00-2.93 (m, 2H), 2.44-2.39 (m, 2H), 2.17-2.09 (m, 2H), 2.06-1.98 (m, 2H), 1.82-1.71 (m, 2H), 1.71-1.65 (m, 2H). MS (ESI): mass calcd. for C₂₂H₂₄N₄O₂S, 408.16; m/z found, 409.2 [M+H]⁺.

Example 84

2-[4-(Pyrrolidin-1-ylmethyl)phenoxy][1,3]thiazolo[4,5-b]pyridine

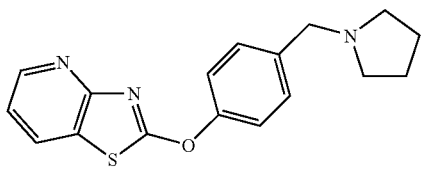

¹H NMR (400 MHz, CDCl₃): 8.57 (dd, J=4.8, 1.7, 1H), 8.01 (dd, J=7.9, 1.7, 1H), 7.44-7.39 (m, 2H), 7.38-7.33 (m, 2H), 7.20 (dd, J=7.9, 4.9, 1H), 3.64 (s, 2H), 2.58-2.48 (m, 4H), 1.85-1.76 (m, 4H). MS (ESI): mass calcd. for C₁₇H₁₇N₃OS, 311.11; m/z found, 312.1 [M+H]⁺.

Example 85

2-[4-(Piperidin-1-ylmethyl)phenoxy][1,3]thiazolo[4,5-b]pyridine

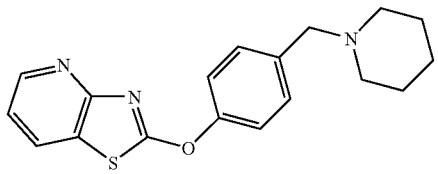

¹H NMR (400 MHz, CDCl₃): 8.56 (dd, J=4.8, 1.7, 1H), 8.01 (dd, J=7.9, 1.7, 1H), 7.43-7.37 (m, 2H), 7.37-7.31 (m, 2H), 7.20 (dd, J=7.9, 4.8, 1H), 3.49 (s, 2H), 2.47-2.32 (m, 4H), 1.65-1.53 (m, 6H). MS (ESI): mass calcd. for C₁₈H₁₉N₃OS, 325.13; m/z found, 326.1 [M+H]⁺.

Example 86

2-[4-(Morpholin-4-ylmethyl)phenoxy][1,3]thiazolo[4,5-b]pyridine

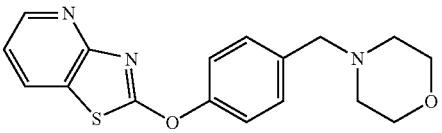

¹H NMR (400 MHz, CDCl₃): 8.56 (dd, J=4.8, 1.7, 1H), 8.02 (dd, J=7.9, 1.7, 1H), 7.44-7.39 (m, 2H), 7.39-7.34 (m, 2H), 7.21 (dd, J=7.9, 4.9, 1H), 3.75-3.69 (m, 4H), 3.52 (s,

2H), 2.52-2.41 (m, 4H). MS (ESI): mass calcd. for C$_{17}$H$_{17}$N$_3$O$_2$S, 327.14; m/z found, 328.1 [M+H]$^+$.

Example 87

2-(4-{[(3R)-3-Fluoropyrrolidin-1-yl]methyl}phenoxy)[1,3]thiazolo[4,5-b]pyridine

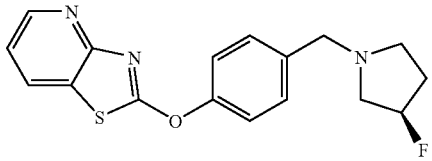

$^1$H NMR (600 MHz, CDCl$_3$): 8.57 (dd, J=4.8, 1.6, 1H), 8.02 (dd, J=7.9, 1.6, 1H), 7.44-7.40 (m, 2H), 7.39-7.34 (m, 2H), 7.21 (dd, J=7.9, 4.8, 1H), 5.28-5.10 (m, 1H), 3.69 (d, J=5.3, 2H), 2.93-2.81 (m, 2H), 2.81-2.69 (m, 1H), 2.51-2.42 (m, 1H), 2.25-2.02 (m, 2H). MS (ESI): mass calcd. for C$_{17}$H$_{16}$FN$_3$OS, 329.10; m/z found, 330.1 [M+H]$^+$.

Example 88

2-(4-{[(3S)-3-Methylmorpholin-4-yl]methyl}phenoxy)[1,3]thiazolo[4,5-b]pyridine

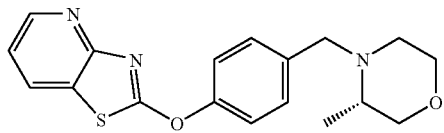

$^1$H NMR (600 MHz, CDCl$_3$): 8.56 (dd, J=4.8, 1.6, 1H), 8.01 (dd, J=7.9, 1.6, 1H), 7.43-7.39 (m, 2H), 7.38-7.34 (m, 2H), 7.20 (dd, J=7.9, 4.8, 1H), 4.06 (d, J=13.4, 1H), 3.77-3.68 (m, 2H), 3.64-3.55 (m, 1H), 3.36-3.28 (m, 1H), 3.17 (d, J=13.4, 1H), 2.65-2.58 (m, 1H), 2.55-2.47 (m, 1H), 2.26-2.15 (m, 1H), 1.08 (d, J=6.3, 3H). MS (ESI): mass calcd. for C$_{18}$H$_{19}$N$_3$O$_2$S, 341.12; m/z found, 342.1 [M+H]$^+$.

Example 89

2-{1-[4-([1,3]Thiazolo[4,5-b]pyridin-2-yloxy)benzyl]piperidin-4-yl}propan-2-ol

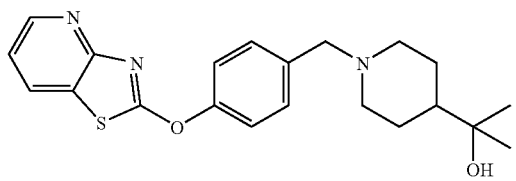

$^1$H NMR (600 MHz, CDCl$_3$): 8.56 (dd, J=4.8, 1.6, 1H), 8.01 (dd, J=7.9, 1.7, 1H), 7.41-7.37 (m, 2H), 7.37-7.33 (m, 2H), 7.19 (dd, J=7.9, 4.8, 1H), 3.51 (s, 2H), 3.01-2.93 (m, 2H), 1.98-1.88 (m, 2H), 1.77-1.69 (m, 2H), 1.45-1.35 (m, 2H), 1.33-1.28 (m, 1H), 1.18 (s, 6H). MS (ESI): mass calcd. for C$_{21}$H$_{25}$N$_3$O$_2$S, 383.17; m/z found, 384.1 [M+H]$^+$.

Example 90

2-(4-{[(2S)-2-Methylpiperidin-1-yl]methyl}phenoxy)[1,3]thiazolo[4,5-b]pyridine

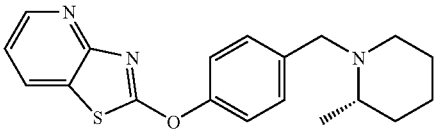

$^1$H NMR (600 MHz, CDCl$_3$): 8.56 (dd, J=4.8, 1.6, 1H), 8.00 (dd, J=7.9, 1.6, 1H), 7.42-7.38 (m, 2H), 7.36-7.31 (m, 2H), 7.19 (dd, J=7.9, 4.8, 1H), 4.05-3.95 (m, 1H), 3.26-3.17 (m, 1H), 2.79-2.71 (m, 1H), 2.41-2.30 (m, 1H), 2.04-1.94 (m, 1H), 1.72-1.61 (m, 2H), 1.52-1.23 (m, 4H), 1.21-1.13 (m, 3H). MS (ESI): mass calcd. for C$_{19}$H$_{21}$N$_3$OS, 339.14; m/z found, 340.1 [M+H]$^+$.

Example 91

2-Piperidin-1-yl-N-[4-([1,3]thiazolo[4,5-b]pyridin-2-yloxy)benzyl]ethanamine

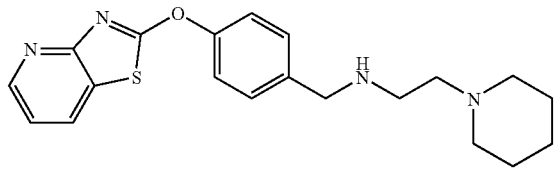

$^1$H NMR (500 MHz, CDCl$_3$): 8.58 (dd, J=4.8, 1.7, 1H), 8.03 (dd, J=7.9, 1.7, 1H), 7.45-7.36 (m, 4H), 7.22 (dd, J=7.9, 4.8, 1H), 3.86 (s, 2H), 2.74 (t, J=6.2, 2H), 2.49 (t, J=6.2, 2H), 2.39 (br s, 4H), 1.82 (br s, 1H), 1.63-1.54 (m, 4H), 1.49-1.41 (m, 2H). MS (ESI): mass calcd. for C$_{20}$H$_{24}$N$_4$OS, 368.17; m/z found, 369.1 [M+H]$^+$.

Example 92

2-(4-{[4-(Trifluoromethyl)piperidin-1-yl]methyl}phenoxy)[1,3]thiazolo[4,5-b]pyridine

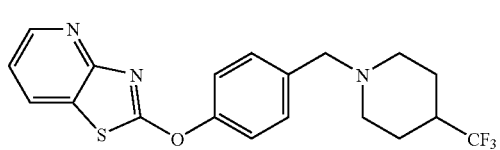

$^1$H NMR (600 MHz, CDCl$_3$): 8.56 (dd, J=4.8, 1.7, 1H), 8.02 (dd, J=7.9, 1.7, 1H), 7.42-7.34 (m, 4H), 7.21 (dd, J=7.9, 4.8, 1H), 3.53 (s, 2H), 2.99 (d, J=11.7, 2H), 2.07-2.00 (m,

1H), 1.97 (dt, J=12.0, 2.3, 2H), 1.87-1.81 (m, 2H), 1.70-1.59 (m, 2H). MS (ESI): mass calcd. for $C_{19}H_{18}F_3N_3OS$, 393.11; m/z found, 394.1 [M+H]$^+$.

Example 93

2-{4-[(3,3-Difluoropyrrolidin-1-yl)methyl]phenoxy}[1,3]thiazolo[4,5-b]pyridine

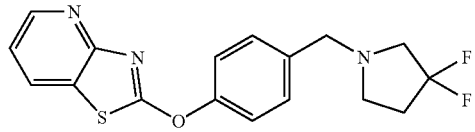

$^1$H NMR (600 MHz, CDCl$_3$): 8.57 (dd, J=4.8, 1.6, 1H), 8.02 (dd, J=7.9, 1.6, 1H), 7.42-7.36 (m, 4H), 7.21 (dd, J=7.9, 4.8, 1H), 3.66 (s, 2H), 2.91 (t, J=13.2, 2H), 2.76 (t, J=6.9, 2H), 2.34-2.26 (m, 2H). MS (ESI): mass calcd. for $C_{17}H_{15}F_2N_3OS$, 347.09; m/z found, 348.1 [M+H]$^+$.

Example 94

(3R)-1-[4-([1,3]Thiazolo[4,5-b]pyridin-2-yloxy)benzyl]pyrrolidin-3-ol

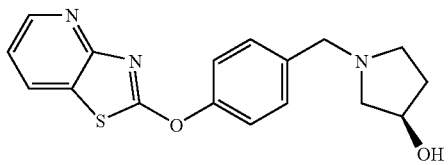

$^1$H NMR (600 MHz, CDCl$_3$): 8.56 (dd, J=4.82, 1.65, 1H), 8.01 (dd, J=7.9, 1.6, 1H), 7.41 (d, J=8.7, 2H), 7.38-7.35 (m, 2H), 7.20 (dd, J=7.9, 4.8, 1H), 4.39-4.33 (m, 1H), 3.67 (s, 2H), 2.92-2.84 (m, 1H), 2.69 (d, J=9.96, 1H), 2.58 (dd, J=10.0, 5.1, 1H), 2.37-2.32 (m, 1H), 2.25-2.15 (m, 1H), 1.90-1.72 (m, 2H). MS (ESI): mass calcd. for $C_{17}H_{17}N_3O_2S$, 327.10; m/z found, 328.1 [M+H]$^+$.

Example 95

{1-[4-([1,3]Thiazolo[4,5-b]pyridin-2-yloxy)benzyl]piperidin-4-yl}methanol

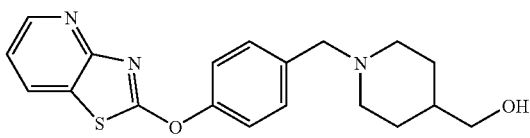

$^1$H NMR (600 MHz, CDCl$_3$): 8.56 (dd, J=4.8, 1.6, 1H), 8.01 (dd, J=7.9, 1.6, 1H), 7.39 (d, J=8.6, 2H), 7.37-7.34 (m, 2H), 7.19 (dd, J=7.9, 4.8, 1H), 3.53-3.50 (m, 4H), 2.96-2.87 (m, 2H), 1.99 (dt, J=11.7, 2.3, 2H), 1.73 (d, J=13.0, 2H), 1.60-1.47 (m, 2H), 1.34-1.26 (m, 2H). MS (ESI): mass calcd. for $C_{19}H_{21}N_3O_2S$, 355.14; m/z found, 356.1 [M+H]$^+$.

Example 96

2-{4-[(4-Fluoropiperidin-1-yl)methyl]phenoxy}[1,3]thiazolo[4,5-b]pyridine

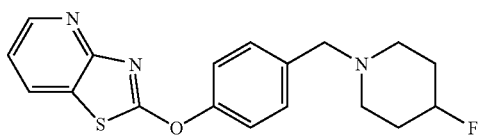

$^1$H NMR (600 MHz, CDCl$_3$): 8.56 (dd, J=4.8, 1.6, 1H), 8.01 (dd, J=7.9, 1.6, 1H), 7.40 (d, J=8.6, 2H), 7.37-7.35 (m, 2H), 7.20 (dd, J=7.9, 4.6, 1H), 4.76-4.61 (m, 1H), 3.52 (s, 2H), 2.65-2.56 (m, 2H), 2.42-2.34 (m, 2H), 1.96-1.83 (m, 4H). MS (ESI): mass calcd. for $C_{18}H_{18}FN_3OS$, 343.12; m/z found, 344.1 [M+H]$^+$.

Example 97

2-{4-[(4-Methylpiperidin-1-yl)methyl]phenoxy}[1,3]thiazolo[4,5-b]pyridine

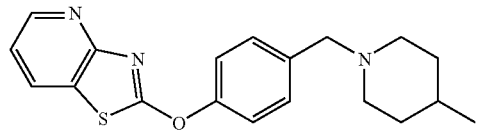

$^1$H NMR (500 MHz, CDCl$_3$): 8.58 (dd, J=4.8, 1.7, 1H), 8.03 (dd, J=7.9, 1.7, 1H), 7.44-7.39 (m, 2H), 7.39-7.34 (m, 2H), 7.22 (dd, J=7.9, 4.8, 1H), 3.52 (s, 2H), 2.92-2.83 (m, 2H), 2.02-1.92 (m, 2H), 1.68-1.58 (m, 3H), 1.33-1.21 (m, 2H), 0.94 (d, J=6.4, 3H). MS (ESI): mass calcd. for $C_{19}H_{21}N_3OS$, 339.14; m/z found, 340.1 [M+H]$^+$.

Example 98

2-(4-{[4-(Pyridin-3-yloxy)piperidin-1-yl]methyl}phenoxy)[1,3]thiazolo[4,5-b]pyridine

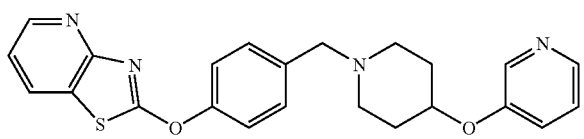

$^1$H NMR (600 MHz, CDCl$_3$): 8.55 (dd, J=4.8, 1.6, 1H), 8.34-8.29 (m, 1H), 8.22-8.17 (m, 1H), 8.02 (dd, J=7.9, 1.6, 1H), 7.44-7.38 (m, 2H), 7.38-7.34 (m, 2H), 7.22-7.17 (m, 3H), 4.45-4.31 (m, 1H), 3.56 (s, 2H), 2.82-2.69 (m, 2H),

Example 99

2-(4-{[4-(Pyrimidin-2-yloxy)piperidin-1-yl]methyl}phenoxy)[1,3]thiazolo[4,5-b]pyridine

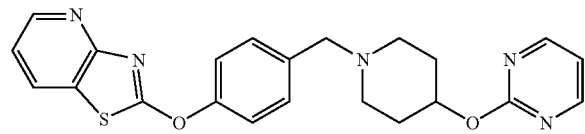

¹H NMR (600 MHz, CDCl₃): 8.56 (dd, J=4.8, 1.6, 1H), 8.50 (d, J=4.8, 2H), 8.01 (dd, J=7.9, 1.6, 1H), 7.46-7.39 (m, 2H), 7.39-7.33 (m, 2H), 7.20 (dd, J=7.9, 4.8, 1H), 6.90 (t, J=4.8, 1H), 5.15-5.03 (m, 1H), 3.56 (s, 2H), 2.88-2.73 (m, 2H), 2.44-2.29 (m, 2H), 2.13-2.01 (m, 2H), 1.99-1.88 (m, 2H). MS (ESI): mass calcd. for C₂₁H₂₁N₅O₂S, 419.15; m/z found, 420.1 [M+H]⁺.

Example 100

1-[4-([1,3]Thiazolo[4,5-b]pyridin-2-yloxy)benzyl]piperidine-4-carboxamide

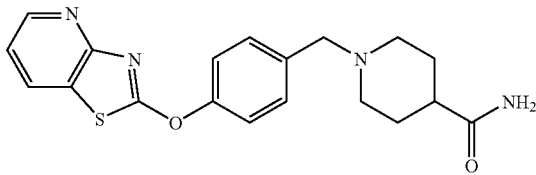

¹H NMR (600 MHz, CDCl₃): 8.56 (dd, J=4.8, 1.7, 1H), 8.01 (dd, J=7.9, 1.7, 1H), 7.42-7.33 (m, 4H), 7.20 (dd, J=7.9, 4.8, 1H), 5.50-5.34 (m, 1H), 5.28-5.14 (m, 1H), 3.52 (s, 2H), 3.00-2.88 (m, 2H), 2.25-2.13 (m, 1H), 2.07-1.98 (m, 2H), 1.94-1.84 (m, 2H), 1.84-1.72 (m, 2H). MS (ESI): mass calcd. for C₁₉H₂₀N₄O₂S, 368.13; m/z found, 369.1 [M+H]⁺.

Example 101

4-Pyridin-2-yl-1-[4-([1,3]thiazolo[4,5-b]pyridin-2-yloxy)benzyl]piperidin-4-ol

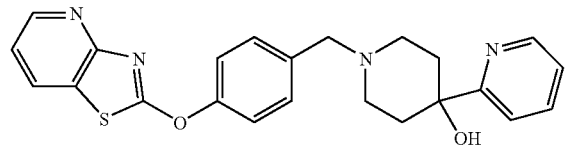

¹H NMR (600 MHz, CDCl₃): 8.55 (dd, J=4.8, 1.6, 1H), 8.53-8.49 (m, 1H), 8.01 (dd, J=7.9, 1.6, 1H), 7.76-7.68 (m, 1H), 7.47 (d, J=8.5, 2H), 7.43 (d, J=8.0, 1H), 7.39-7.35 (m, 2H), 7.23-7.16 (m, 2H), 3.63 (s, 2H), 2.92-2.81 (m, 2H), 2.65-2.53 (m, 2H), 2.20-2.07 (m, 2H), 1.70-1.60 (m, 2H), 2.41-2.27 (m, 2H), 2.06-1.96 (m, 2H), 1.91-1.79 (m, 2H). MS (ESI): mass calcd. for C₂₃H₂₂N₄O₂S, 418.16; m/z found, 419.1 [M+H]⁺.

1.30-1.21 (m, 1H). MS (ESI): mass calcd. for C₂₃H₂₂N₄O₂S, 418.15; m/z found, 419.1 [M+H]⁺.

Example 102

2-{4-[(4-Benzylpiperidin-1-yl)methyl]phenoxy}[1,3]thiazolo[4,5-b]pyridine

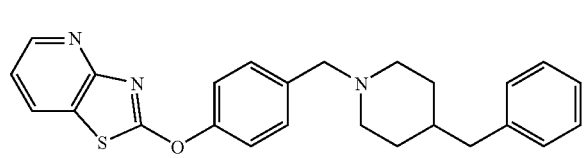

¹H NMR (400 MHz, CDCl₃): 8.56 (dd, J=4.8, 1.6, 1H), 8.00 (dd, J=7.9, 1.6, 1H), 7.41-7.31 (m, 4H), 7.31-7.24 (m, 2H), 7.22-7.17 (m, 2H), 7.17-7.12 (m, 2H), 3.49 (s, 2H), 2.94-2.76 (m, 2H), 2.54 (d, J=7.0, 2H), 1.91 (dt, J=11.6, 2.2, 2H), 1.63-1.56 (m, 3H), 1.32 (ddd, J=15.4, 12.2, 3.8, 2H). MS (ESI): mass calcd. for C₂₅H₂₅N₃OS, 415.17; m/z found, 416.2 [M+H]⁺.

Example 103

1-[4-([1,3]Thiazolo[4,5-b]pyridin-2-yloxy)benzyl]-4-[3-(trifluoromethyl)phenyl]piperidin-4-ol

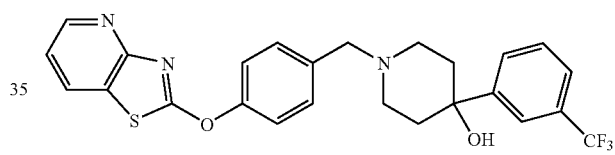

¹H NMR (400 MHz, CDCl₃): 8.56 (dd, J=4.8, 1.7, 1H), 8.02 (dd, J=7.9, 1.7, 1H), 7.82 (s, 1H), 7.72 (d, J=7.6, 1H), 7.55-7.46 (m, 2H), 7.47-7.42 (m, 2H), 7.40-7.35 (m, 2H), 7.21 (dd, J=7.9, 4.8, 1H), 3.61 (s, 2H), 2.92-2.74 (m, 2H), 2.49 (dt, J=12.0, 2.4, 2H), 2.18 (dt, J=13.2, 4.5, 2H), 1.79-1.75 (m, 1H), 1.75-1.72 (m, 2H). MS (ESI): mass calcd. for C₂₅H₂₂F₃N₃O₂S, 485.14; m/z found, 486.1 [M+H]⁺.

Example 104

4-(4-Chlorophenyl)-1-[4-([1,3]thiazolo[4,5-b]pyridin-2-yloxy)benzyl]piperidin-4-ol

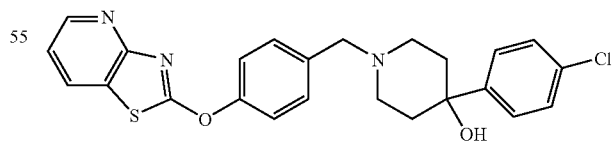

¹H NMR (500 MHz, CDCl₃): 8.55 (dd, J=4.8, 1.7, 1H), 8.03 (dd, J=7.9, 1.7, 1H), 7.50-7.40 (m, 4H), 7.40-7.33 (m, 2H), 7.33-7.29 (m, 2H), 7.21 (dd, J=7.9, 4.8, 1H), 3.65-3.56 (m, 2H), 2.86-2.75 (m, 2H), 2.57-2.43 (m, 2H), 2.20-2.07 (m, 2H), 1.82-1.69 (m, 2H), 0.92-0.75 (m, 1H). MS (ESI): mass calcd. for C₂₄H₂₂N₃O₂SCl, 451.11; m/z found, 452.1 [M+H]⁺.

Example 105

4-Phenyl-1-[4-([1,3]thiazolo[4,5-b]pyridin-2-yloxy)benzyl]piperidin-4-ol

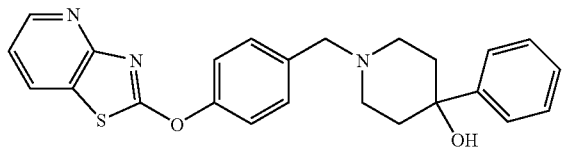

$^1$H NMR (500 MHz, CDCl$_3$): 8.56 (dd, J=4.8, 1.6, 1H), 8.02 (dd, J=7.9, 1.6, 1H), 7.57-7.51 (m, 2H), 7.47-7.43 (m, 2H), 7.40-7.34 (m, 4H), 7.30-7.26 (m, 1H), 7.21 (dd, J=7.9, 4.8, 1H), 3.62 (s, 2H), 2.87-2.75 (m, 2H), 2.59-2.47 (m, 2H), 2.25-2.13 (m, 2H), 1.85-1.72 (m, 2H), 0.93-0.79 (m, 1H). MS (ESI): mass calcd. for C$_{24}$H$_{23}$N$_3$O$_2$S, 417.17; m/z found, 418.2 [M+H]$^+$.

Examples 106-107 were prepared using methods analogous to those described for Example 82, substituting 50° C. for rt.

Example 106

(1S,4S)-5-[4-([1,3]Thiazolo[4,5-b]pyridin-2-yloxy)benzyl]-2,5-diazabicyclo[2.2.1]heptane-2-carboxamide

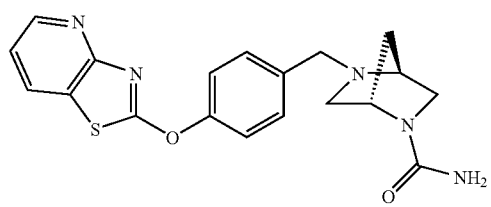

$^1$H NMR (400 MHz, CD$_3$OD): 8.48 (dd, J=4.9, 1.6, 1H), 8.29 (dd, J=8.0, 1.6, 1H), 7.56-7.48 (m, 2H), 7.43-7.36 (m, 2H), 7.33 (dd, J=8.0, 4.9, 1H), 3.81 (s, 2H), 3.67-3.48 (m, 2H), 3.28-3.19 (m, 2H), 2.92-2.87 (m, 1H), 2.78-2.65 (m, 1H), 2.00-1.93 (m, 1H), 1.81-1.73 (m, 1H). MS (ESI): mass calcd for C$_{19}$H$_{19}$N$_5$O$_2$S, 381.13; m/z found, 382.2 [M+H]$^+$.

Example 107 meso-2-(4-{[3-Acetyl-3,8-diazabicyclo[3.2.1]oct-8-yl]methyl}phenoxy)[1,3]thiazolo[4,5-b]pyridine

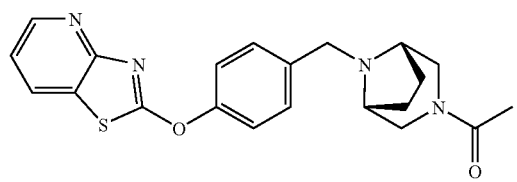

$^1$H NMR (500 MHz, CD$_3$OD): 8.48 (dd, J=4.9, 1.6, 1H), 8.29 (dd, J=8.0, 1.6, 1H), 7.60-7.52 (m, 2H), 7.43-7.38 (m, 2H), 7.34 (dd, J=8.0, 4.9, 1H), 4.11 (d, J=11.8, 1H), 3.63 (s, 2H), 3.61-3.55 (m, 1H), 3.42-3.35 (m, 1H), 3.29-3.21 (m, 2H), 2.89 (d, J=12.8, 1H), 2.08 (s, 3H), 1.73-1.64 (m, 2H), 1.63-1.53 (m, 2H). MS (ESI): mass calcd. for C$_{21}$H$_{22}$N$_4$O$_2$S, 394.15; m/z found, 395.1 [M+H]$^+$.

Example 108

{(2S)-1-[4-([1,3]Thiazolo[4,5-b]pyridin-2-yloxy)benzyl]pyrrolidin-2-yl}methanol

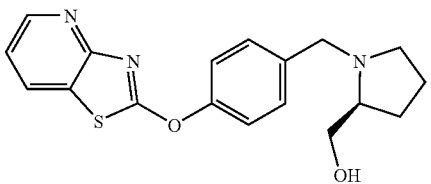

The title compound was prepared using methods analogous to those described for Example 82, substituting the following procedural differences: imine formation was conducted for 8 h at rt followed by heating at 80° C. overnight prior to the addition of sodium triacetoxyborohydride. $^1$H NMR (500 MHz, CDCl$_3$): 8.58 (dd, J=4.8, 1.7, 1H), 8.04 (dd, J=7.9, 1.7, 1H), 7.42-7.37 (m, 4H), 7.22 (dd, J=7.9, 4.8, 1H), 4.03 (d, J=13.2, 1H), 3.71 (dd, J=10.8, 3.5, 1H), 3.52-3.39 (m, 2H), 3.09-2.98 (m, 1H), 2.85-2.72 (m, 1H), 2.37-2.28 (m, 1H), 2.03-1.92 (m, 1H), 1.92-1.83 (m, 1H), 1.80-1.69 (m, 2H), 1.69-1.52 (m, 1H). MS (ESI): mass calcd. for C$_{18}$H$_{19}$N$_3$O$_2$S, 341.12; m/z found, 342.1 [M+H]$^+$.

Examples 109-111 were prepared using methods analogous to those described for Example 82, substituting the following procedural differences: imine formation was conducted for 12 h at rt prior to the addition of sodium triacetoxyborohydride.

Example 109 meso-N-{(3-exo)-8-[4-([1,3]Thiazolo[4,5-b]pyridin-2-yloxy)benzyl]-8-azabicyclo[3.2.1]oct-yl}acetamide

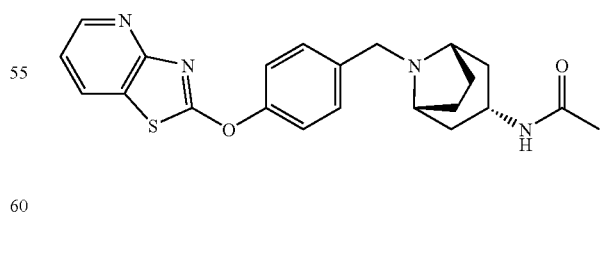

$^1$H NMR (500 MHz, CDCl$_3$): 8.58 (dd, J=4.7, 1.4, 1H), 8.03 (dd, J=7.9, 1.6, 1H), 7.48-7.44 (m, 2H), 7.39-7.35 (m, 2H), 7.22 (dd, J=7.9, 4.8, 1H), 5.28-5.21 (m, 1H), 4.23-4.11 (m, 1H), 3.57 (s, 2H), 3.27-3.20 (m, 2H), 2.09-2.02 (m, 2H), 1.96 (s, 3H), 1.90-1.80 (m, 2H), 1.80-1.72 (m, 2H), 1.58-1.47 (m, 2H). MS (ESI): mass calcd. for $C_{22}H_{24}N_4O_2S$, 408.2; m/z found, 409.2 $[M+H]^+$.

Example 110 meso-1-{(3-exo)-8-[4-([1,3]Thiazolo[4,5-b]pyridin-2-yloxy)benzyl]-8-azabicyclo[3.2.1]oct-yl}urea

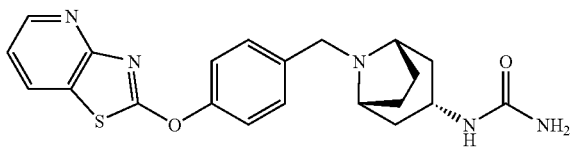

$^1$H NMR (500 MHz, CDCl$_3$): 8.59 (dd, J=4.8, 1.6, 1H), 8.04 (dd, J=7.9, 1.6, 1H), 7.48-7.44 (m, 2H), 7.39-7.34 (m, 2H), 7.23 (dd, J=7.9, 4.8, 1H), 4.49-4.40 (m, 1H), 4.26 (s, 2H), 4.03-3.87 (m, 1H), 3.57 (s, 2H), 3.29-3.20 (m, 2H), 2.10-2.03 (m, 2H), 1.95-1.83 (m, 2H), 1.80-1.71 (m, 2H), 1.55-1.49 (m, 2H). MS (ESI): mass calcd. for $C_{21}H_{23}N_5O_2S$, 409.16; m/z found, 410.1 $[M+H]^+$.

Example 111

N-Ethyl-N-[4-([1,3]thiazolo[4,5-b]pyridin-2-yloxy)benzyl]ethanamine

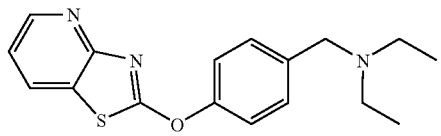

The title compound was prepared using methods analogous to those described for Example 82, with the addition of acetic acid. $^1$H NMR (400 MHz, CDCl$_3$): 8.56 (dd, J=4.8, 1.7, 1H), 8.00 (dd, J=7.9, 1.7, 1H), 7.44-7.32 (m, 4H), 7.19 (dd, J=7.9, 4.8, 1H), 3.59 (s, 2H), 2.54 (q, J=7.1, 4H), 1.06 (t, J=7.1, 6H). MS (ESI): mass calcd. for $C_{17}H_{19}N_3OS$, 313.12; m/z found, 314.1 $[M+H]^+$.

Example 112

1-{1-[4-([1,3]Thiazolo[5,4-b]pyridin-2-yloxy)benzyl]piperidin-4-yl}pyrrolidin-2-one

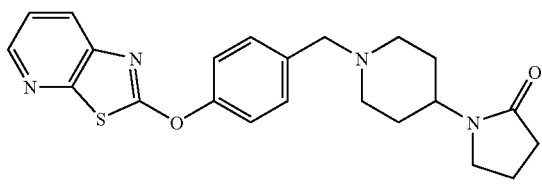

To a solution of 2-[4-(chloromethyl)phenoxy][1,3]thiazolo[5,4-b]pyridine hydrochloride (70 mg, 0.223 mmol) and 1-piperidin-4-yl-pyrrolidin-2-one (64 mg, 0.379 mmol, 1.7 equiv.) in CH$_3$CN (1.3 mL) was added Et$_3$N (110 µL, 0.759 mmol, 3.4 equiv.). The reaction was allowed to stir at 60° C. for 6 h. The solution was cooled to rt, filtered and purified using preparative reverse phase HPLC to afford the desired product as a cream-colored solid (52 mg, 57%). $^1$H NMR (600 MHz, DMSO-d$_6$): 8.45 (dd, J=4.7, 1.5, 1H), 8.09 (dd, J=8.1, 1.5, 1H), 7.50 (dd, J=8.2, 4.8, 1H), 7.47-7.40 (m, 4H), 3.80-3.69 (m, 1H), 3.52 (s, 2H), 3.35-3.29 (m, 2H), 2.91-2.85 (m, 2H), 2.20 (t, J=8.1, 2H), 2.07-2.00 (m, 2H), 1.94-1.85 (m, 2H), 1.73-1.62 (m, 2H), 1.54-1.48 (m, 2H). MS (ESI): mass calcd. for $C_{22}H_{24}N_4O_2S$, 408.16; m/z found, 409.2 $[M+H]^+$.

Examples 113-115 were prepared using methods analogous to those described for Example 112.

Example 113

1-[4-([1,3]Thiazolo[5,4-b]pyridin-2-yloxy)benzyl]piperidine-4-carboxamide

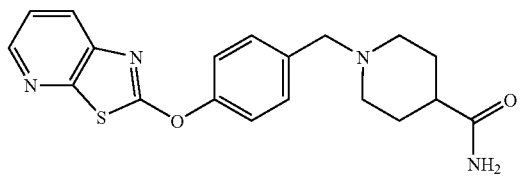

$^1$H NMR (400 MHz, CD$_3$OD): 8.42-8.37 (m, 1H), 7.99 (dd, J=8.2, 1.5, 1H), 7.53-7.42 (m, 3H), 7.41-7.33 (m, 2H), 3.61 (s, 2H), 3.03-2.92 (m, 2H), 2.32-2.05 (m, 3H), 1.86-1.72 (m, 4H). MS (ESI): mass calcd. for $C_{19}H_{20}N_4O_2S$, 368.13; m/z found, 369.1 $[M+H]^+$.

Example 114

2-[4-(Piperidin-1-ylmethyl)phenoxyl][1,3]thiazolo[5,4-c]pyridine

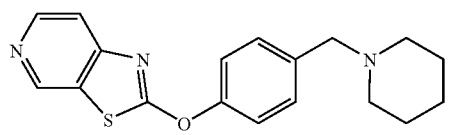

$^1$H NMR (400 MHz, CDCl$_3$): 8.92 (s, 1H), 8.56 (d, J=5.6, 1H), 7.62 (d, J=5.6, 1H), 7.43 (d, J=8.4, 2H), 7.32-7.26 (m, 2H), 3.50 (s, 2H), 2.40 (br s, 4H), 1.62-1.57 (m, 4H), 1.48-1.44 (m, 2H). MS (ESI): mass calcd. for $C_{18}H_{19}N_3OS$, 325.13; m/z found, 326.1 $[M+H]^+$.

Example 115 meso-N-{(3-endo)-8-[4-([1,3]Thiazolo[5,4-c]pyridin-2-yloxy)benzyl]-8-azabicyclo[3.2.1]oct-yl}acetamide

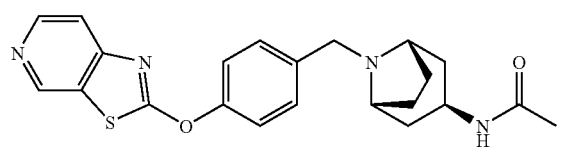

$^1$H NMR (400 MHz, CDCl$_3$): 8.91 (d, J=0.8, 1H), 8.56 (d, J=5.6, 1H), 7.62 (dd, J=5.6, 0.8, 1H), 7.50-7.46 (m, 2H), 7.33-7.29 (m, 2H), 5.79 (br d, J=6.4, 1H), 4.13 (dd, J=7.0, 1H), 3.56 (s, 2H), 3.21 (brs, 2H), 2.26-2.20 (m, 2H), 2.17-2.14 (m, 2H), 1.97 (s, 3H), 1.81-1.75 (m, 2H), 1.62 (br s, 2H). MS (ESI): mass calcd. for C$_{22}$H$_{24}$N$_4$O$_2$S, 408.16; m/z found, 409.2 [M+H]$^+$.

Example 116 meso-N-{(3-endo)-8-[4-([1,3]Thiazolo[4,5-b]pyridin-2-yloxy)benzyl]-8-azabicyclo[3.2.1]oct-yl}acetamide

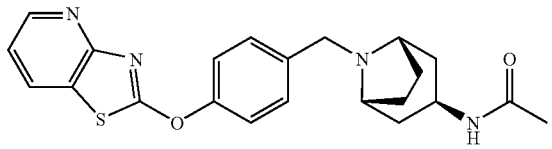

To a suspension of 2-[4-(chloromethyl)phenoxy][1,3]thiazolo[4,5-b]pyridine hydrochloride (14.7 g, 1.0 equiv.) in CH$_3$CN (0.2 M), K$_2$CO$_3$ (13.6 g, powder, 325 mesh; 2.1 equiv.) and meso-N-[(3-endo)-8-azabicyclo[3.2.1]oct-3-yl]acetamide (8.7 g, 51 mmol, 1.1 equiv.) were added sequentially. This latter compound was synthesized as described herein or can be purchased from commercial sources. The reaction mixture was heated at reflux for 3 h and cooled to rt. Some of the desired product precipitated out from the reaction solution, which was dissolved by adding CH$_2$Cl$_2$ (0.2 M relative to starting material). The insoluble inorganic salt was filtered off and washed with CH$_2$Cl$_2$. The filtrate solution was concentrated and the residue was partitioned between CH$_2$Cl$_2$ and satd. aq. NaHCO$_3$ solution (2.0 mol/L) (The aqueous workup was to remove possible inorganic salt residue, which may not be necessary. Filtration of K$_2$CO$_3$ while hot and direct recrystallization may simplify the workup procedure). The organic layer was dried, concentrated, and recrystallized from hot CH$_3$CN (0.4 M relative to starting material) to afford the title product. The mother liquor was concentrated and recrystallized again from hot CH$_3$CN to afford another crop. Combining the two crops provided the title compound (89%).

$^1$H NMR (500 MHz, CDCl$_3$): 8.56 (dd, J=4.8, 1.6, 1H), 8.02 (dd, J=7.9, 1.6, 1H), 7.47-7.42 (m, 2H), 7.37-7.33 (m, 2H), 7.20 (dd, J=7.9, 4.8, 1H), 5.82 (d, J=6.8, 1H), 4.12 (q, J=6.8, 1H), 3.54 (s, 2H), 3.20 (s, 2H), 2.30-2.10 (m, 4H), 1.97 (s, 3H), 1.82-1.74 (m, 2H), 1.62-1.56 (m, 1H). MS (ESI): mass calcd. for C$_{22}$H$_{24}$N$_4$O$_2$S, 408.16; m/z found, 409.2 [M+H]$^+$.

In some embodiments, the title compound was synthesized as follows;

Potassium carbonate (3.096 kg, 22.4 mol) and meso-N-[(3-endo)-8-(4-hydroxy-benzyl)-8-aza-bicyclo[3.2.1]oct-3-yl]acetamide (1.741 kg, 5.60 mol) were added to acetonitrile (23.939 kg). The white suspension was heated to 60° C. and stirred for 90 min. After that 2-chlorothiazolopyridine hydrochloride (1.275 kg, 6.16 mol) were added in one portion, resulting in a color change to reddish pink. After 4 h, the temperature was elevated to 63° C. and the mixture was kept there for 16 h, then at 70° C. for 3 h. The salts were removed by filtration (at 70° C.) and the filter cake was washed with hot acetonitrile (5.0 kg). The filtrate was concentrated by distillation (at 50° C. in vacuo) of 8.1 kg solvent. The resulting suspension was cooled to 20° C. within 90 min, then to 0° C. in 2 h. After 2 h at 0° C., the product was isolated by centrifugation, washed with acetonitrile (5.66 kg) and dried in vacuo at 60° C. Yield: 1.696 kg dusky pink solid (74%).

In some embodiments, succinate salts were prepared as follows. meso-N-{(3-endo)-8-[4-([1,3]Thiazolo[4,5-b]pyridin-2-yloxy)benzyl]-8-azabicyclo[3.2.1]oct-3-yl}acetamide (950 g, 2.08 mol) was dissolved in acetone (22.20 kg) at reflux. The red solution was filtered and stirred at 50-55° C. Succinic acid (261 g, 2.21 mol) was dissolved in acetone (3.905 kg) at 50° C. The resulting clear solution was added to the solution of meso-N-{(3-endo)-8-[4-([1,3]thiazolo[4,5-b]pyridin-2-yloxy)benzyl]-8-azabicyclo[3.2.1]oct-3-yl}acetamide within 10 min. After stirring for 10 min at 50° C., seeding crystals of meso-N-{(3-endo)-8-[4-([1,3]Thiazolo[4,5-b]pyridin-2-yloxy)benzyl]-8-azabicyclo[3.2.1]oct-3-yl}acetamide succinate were added, resulting in the start of crystallization. The mixture was kept at 50° C. for 2 h, then cooled to 0° C. at a rate of 12° C./h and kept at 0° C. overnight. The succinate salt of the title compound was isolated by centrifugation, washed with acetone (5.0 kg, cooled to 0° C.) and dried in vacuo at 50° C. Yield: 1047 g off-white solid (95%).

In some embodiments, salts of the above titled compound were prepared by adding malonic acid (1 equiv.) to the compound in methanol/methyl ethyl ketone; adding benzoic acid (1 equiv.) to the compound in methanol/acetonitrile; or adding succinic acid (1 equiv.) to the compound in acetone to achieve a malonate, benzoate, or succinate salt respectively. Some embodiments of compounds of this invention were prepared in the form of hydrochlorides, phosphates and sulfates, which were identified as solvated salts. Further embodiments were prepared in the form of fumarates, Example 117 meso-8-[4-([1,3]Thiazolo[4,5-b]pyridin-2-yloxy)benzyl]-3,8-diazabicyclo[3.2.1]octane-3-carboxamide

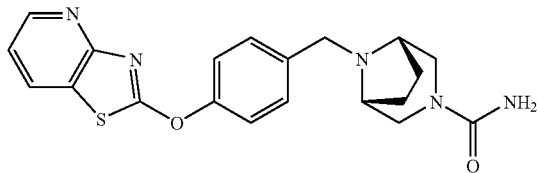

The title compound was prepared using methods analogous to those described for Example 116. $^1$H NMR (400 MHz, CD$_3$OD): 8.48 (dd, J=4.9, 1.6, 1H), 8.29 (dd, J=8.0, 1.6, 1H), 7.60-7.52 (m, 2H), 7.43-7.37 (m, 2H), 7.34 (dd, J=8.0, 4.9, 1H), 3.72-3.47 (m, 4H), 3.27-3.19 (m, 2H), 3.12-3.04 (m, 2H), 2.13-2.03 (m, 2H), 1.75-1.65 (m, 2H). MS (ESI): mass calcd. for C$_{20}$H$_{21}$N$_5$O$_2$S: 395.14; m/z found, 396.1 [M+H]$^+$.

Example 118

2-(4-{[(1S,4S)-5-Acetyl-2,5-diazabicyclo[2.2.1]hept-2-yl]methyl}phenoxy)-5-methyl[1,3]thiazolo[5,4-b]pyridine

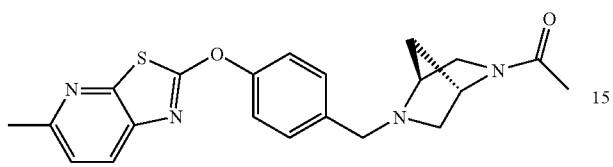

To sodium 4-{[(1S,4S)-5-acetyl-2,5-diazabicyclo[2.2.1]hept-2-yl]methyl}phenolate (170 mg, 0.63 mmol) was added 2-chloro-5-methyl[1,3]thiazolo[5,4-b]pyridine (117 mg, 0.63 mmol) and DMF (6.3 mL). The solution was stirred for 16 h, filtered, and purified by preparative reverse phase HPLC to provide the desired product (140 mg, 56%). $^1$H NMR (400 MHz, CDCl$_3$): 7.81 (d, J=8.2, 1H), 7.46-7.39 (m, 2H), 7.33-7.28 (m, 2H), 7.18 (d, J=8.3, 1H), 4.79 (s, 0.5H), 4.24 (s, 0.5H), 3.82-3.72 (m, 2.5H), 3.60-3.53 (m, 1.5H), 3.30 (ddd, J=13.3, 10.3, 2.1, 1H), 3.02 (dd, J=9.5, 2.1, 0.5H), 2.85 (dd, J=9.7, 2.2, 0.5H), 2.78 (d, J=9.7, 0.5H), 2.61 (s, 3H), 2.57 (dd, J=9.5, 1.2, 0.5H), 2.08 (s, 1.5H), 2.03-1.96 (m, 2H), 1.91 (d, J=9.8, 0.5H), 1.81 (d, J=9.7, 0.5H), 1.67 (d, J=10.0, 0.5H). MS (ESI): mass calcd. for C$_{21}$H$_{22}$N$_4$O$_2$S, 394.15; m/z found, 395.1 [M+H]$^+$.

Examples 119-128 were prepared using methods analogous to those described for Example 118.

Example 119 meso-N-{(3-endo)-8-[4-([1,3]Thiazolo[5,4-b]pyridin-2-yloxy)benzyl]-8-azabicyclo[3.2.1]oct-yl}acetamide

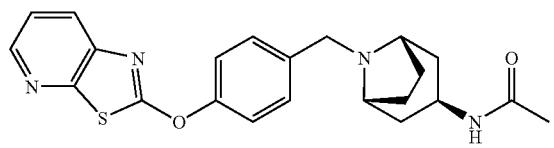

$^1$H NMR (500 MHz, CDCl$_3$): 8.42 (dd, J=4.8, 1.5, 1H), 7.95 (dd, J=8.1, 1.5, 1H), 7.48 (d, J=8.6, 2H), 7.36-7.33 (m, 1H), 7.31 (d, J=8.6, 2H), 5.84 (brs, 1H), 4.16-4.12 (m, 1H), 3.57 (s, 2H), 3.23 (brs, 2H), 2.25-2.21 (m, 2H), 2.18-2.16 (m, 2H), 1.98 (s, 3H), 1.81-1.77 (m, 2H), 1.63-1.61 (m, 2H). MS (ESI): mass calcd. for C$_{22}$H$_{24}$N$_4$O$_2$S, 408.16; m/z found, 409.2 [M+H]$^+$.

Example 120

2-(4-{[(1S,4S)-5-Acetyl-2,5-diazabicyclo[2.2.1]hept-2-yl]methyl}phenoxy)[1,3]thiazolo[4,5-b]pyrazine

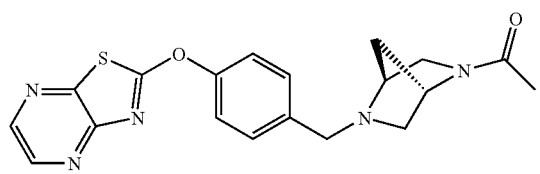

$^1$H NMR (500 MHz, CDCl$_3$): 8.55-8.51 (m, 1H), 8.38-8.34 (m, 1H), 7.49-7.44 (m, 2H), 7.39-7.34 (m, 2H), 4.81 (s, 0.5H), 4.27 (s, 0.5H), 3.83-3.75 (m, 2.5H), 3.62-3.56 (m, 1.5H), 3.35 (dd, J=9.3, 2.2, 0.5H), 3.30 (dd, J=11.5, 1.8, 0.5H), 3.03 (dd, J=9.5, 1.9, 0.5H), 2.87 (dd, J=9.7, 2.0, 0.5H), 2.81 (d, J=9.6, 0.5H), 2.58 (d, J=9.4, 0.5H), 2.11 (s, 1.5H), 2.04-2.00 (m, 2H), 1.93 (d, J=10.2, 0.5H), 1.84 (d, J=10.0, 0.5H), 1.70 (d, J=9.8, 0.5H). MS (ESI): mass calcd. for C$_{19}$H$_{19}$N$_5$O$_2$S, 381.13; m/z found, 382.2 [M+H]$^+$.

Example 121

2-(4-{[(1S,4S)-5-Acetyl-2,5-diazabicyclo[2.2.1]hept-2-yl]methyl}phenoxy)-6-methyl[1,3]thiazolo[4,5-b]pyridine

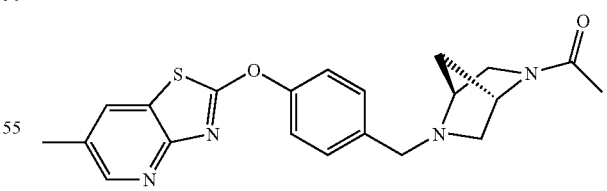

$^1$H NMR (500 MHz, CDCl$_3$): 8.40 (s, 1H), 7.84 (s, 1H), 7.45-7.35 (m, 4H), 4.81 (s, 0.5H), 4.26 (s, 0.5H), 3.81-3.73 (m, 2.5H), 3.61-3.54 (m, 1.5H), 3.34 (dd, J=9.4, 2.3, 0.5H), 3.29 (dd, J=11.4, 1.9, 0.5H), 3.03 (dd, J=9.5, 2.1, 0.5H), 2.86 (dd, J=9.7, 2.1, 0.5H), 2.80 (d, J=9.7, 0.5H), 2.57 (d, J=9.7, 0.5H), 2.45 (s, 3H), 2.11 (s, 1.5H), 2.04-1.99 (m, 2H), 1.93 (d,

J=9.9, 0.5H), 1.83 (d, J=9.4, 0.5H), 1.68 (d, J=9.9, 0.5H). MS (ESI): mass calcd. for $C_{21}H_{22}N_4O_2S$, 394.15; m/z found, 395.1 [M+H]$^+$.

Example 122

2-(4-{[(1S,4S)-5-Acetyl-2,5-diazabicyclo[2.2.1]hept-2-yl]methyl}phenoxy)-6-chloro[1,3]thiazolo[4,5-b]pyridine

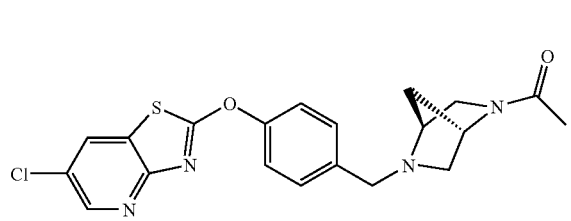

$^1$H NMR (500 MHz, CDCl$_3$): 8.53-8.51 (m, 1H), 8.02 (t, J=2.02, 1H), 7.47-7.41 (m, 2H), 7.39-7.34 (m, 2H), 4.81 (s, 0.5H), 4.26 (s, 0.5H), 3.82-3.74 (m, 2.5H), 3.62-3.54 (m, 1.5H), 3.35 (dd, J=9.3, 2.1, 0.5H), 3.29 (dd, J=11.4, 1.6, 0.5H), 3.03 (dd, J=9.6, 2.0, 0.5H), 2.86 (dd, J=9.7, 2.0, 0.5H), 2.80 (d, J=9.7, 0.5H), 2.57 (d, J=9.6, 0.5H), 2.11 (s, 1.5H), 2.05-1.99 (m, 2H), 1.93 (d, J=9.7, 0.5H), 1.83 (d, J=9.7, 0.5H), 1.69 (d, J=9.9, 0.5H). MS (ESI): mass calcd. for $C_{20}H_{19}ClN_4O_2S$, 414.09; m/z found, 415.1 [M+H]$^+$.

Example 123

2-(4-{[(1S,4S)-5-Acetyl-2,5-diazabicyclo[2.2.1]hept-2-yl]methyl}phenoxy)-6-fluoro[1,3]thiazolo[5,4-b]pyridine

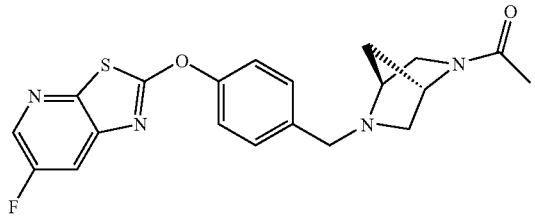

$^1$H NMR (500 MHz, CDCl$_3$): 8.33 (d, J=2.5, 1H), 7.69 (dd, J=9.1, 2.6, 1H), 7.50-7.44 (m, 2H), 7.35-7.30 (m, 2H), 4.81 (s, 0.5H), 4.26 (s, 0.5H), 3.83-3.75 (m, 2.5H), 3.63-3.56 (m, 1.5H), 3.33 (ddd, J=13.2, 10.3, 2.0, 1H), 3.04 (dd, J=9.5, 2.0, 0.5H), 2.86 (dd, J=9.7, 2.1, 0.5H), 2.79 (d, J=9.7, 0.5H), 2.58 (d, J=9.0, 0.5H), 2.12-2.07 (m, 1.75H), 2.04-1.99 (m, 2.25H), 1.94 (d, J=9.9, 0.5H), 1.83 (d, J=9.7, 0.5H). MS (ESI): mass calcd. for $C_{20}H_{19}FN_4O_2S$, 398.12; m/z found, 399.1 [M+H]$^+$.

Example 124

2-(4-{[(1S,4S)-5-Acetyl-2,5-diazabicyclo[2.2.1]hept-2-yl]methyl}phenoxy)[1,3]thiazolo[5,4-b]pyridine

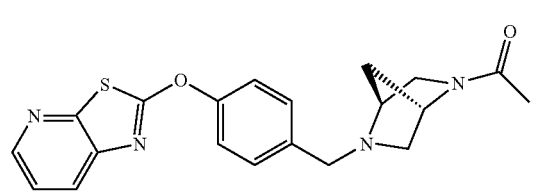

$^1$H NMR (500 MHz, CDCl$_3$): 8.45-8.41 (m, 1H), 7.95 (dd, J=8.1, 1.6, 1H), 7.49-7.44 (m, 2H), 7.37-7.31 (m, 3H), 4.81 (s, 0.5H), 4.26 (s, 0.5H), 3.83-3.75 (m, 2.5H), 3.62-3.56 (m, 1.5H), 3.35 (dd, J=9.3, 2.3, 0.5H), 3.30 (dd, J=11.4, 2.0, 0.5H), 3.04 (dd, J=9.6, 2.1, 0.5H), 2.87 (dd, J=9.7, 2.2, 0.5H), 2.80 (d, J=9.7, 0.5H), 2.58 (dd, J=9.5, 1.2, 0.5H), 2.11 (s, 1.5H), 2.05-2.00 (m, 2H), 1.93 (d, J=10.0, 0.5H), 1.83 (d, J=9.7, 0.5H), 1.69 (d, J=9.9, 0.5H). MS (ESI): mass calcd. for $C_{20}H_{20}N_4O_2S$, 380.13; m/z found, 381.10 [M+H]$^+$.

Example 125

2-(4-{[(1S,4S)-5-Acetyl-2,5-diazabicyclo[2.2.1]hept-2-yl]methyl}phenoxy)-7-methyl[1,3]thiazolo[4,5-b]pyridine

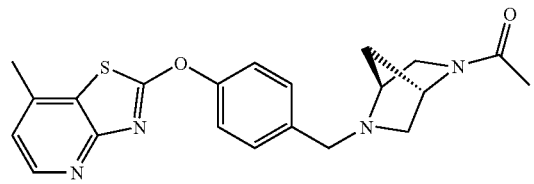

$^1$H NMR (500 MHz, CDCl$_3$): 8.46 (dd, J=5.0, 1.0, 1H), 7.46-7.36 (m, 4H), 7.06-7.03 (m, 1H), 4.81 (s, 0.5H), 4.26 (s, 0.5H), 3.82-3.75 (m, 2.5H), 3.61-3.55 (m, 1.5H), 3.35 (dd, J=9.3, 2.3, 0.5H), 3.30 (dd, J=11.4, 2.0, 0.5H), 3.03 (dd, J=9.6, 2.1, 0.5H), 2.86 (dd, J=9.7, 2.2, 0.5H), 2.81 (d, J=9.9, 0.5H), 2.58 (dd, J=9.5, 1.2, 0.5H), 2.52 (s, 3H), 2.11 (s, 1.5H), 2.05-1.99 (m, 2H), 1.93 (d, J=10.0, 0.5H), 1.83 (d, J=9.9, 0.5H), 1.69 (d, J=10.0, 0.5H). MS (ESI): mass calcd. for $C_{21}H_{22}N_4O_2S$, 394.15; m/z found, 395.10 [M+H]$^+$.

Example 126

2-(4-{[(1S,4S)-5-Acetyl-2,5-diazabicyclo[2.2.1]hept-2-yl]methyl}phenoxy)-5-methyl[1,3]thiazolo[4,5-b]pyridine

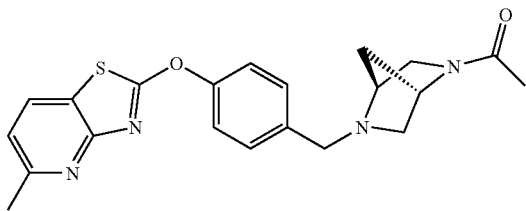

$^1$H NMR (500 MHz, CDCl$_3$): 7.91 (dd, J=8.1, 1.9, 1H), 7.44-7.36 (m, 4H), 7.10 (dd, J=8.1, 1.7, 1H), 4.81 (s, 0.5H), 4.26 (s, 0.5H), 3.77 (d, J=15.5, 2.5H), 3.60-3.54 (m, 1.5H), 3.34 (dd, J=9.3, 2.3, 0.5H), 3.29 (dd, J=11.5, 2.0, 0.5H), 3.02 (dd, J=9.6, 2.1, 0.5H), 2.86 (dd, J=9.7, 2.2, 0.5H), 2.81 (d, J=9.7, 0.5H), 2.64 (s, 3H), 2.57 (dd, J=9.6, 1.2, 0.5H), 2.11 (s, 1.5H), 2.04-1.99 (m, 2H), 1.92 (d, J=9.9, 0.5H), 1.82 (d, J=9.7, 0.5H), 1.68 (d, J=9.8, 0.5H). MS (ESI): mass calcd. for $C_{21}H_{22}N_4O_2S$, 394.15; m/z found, 395.10 [M+H]$^+$.

Example 127

1-{(1S,4S)-5-[4-([1,3]Thiazolo[4,5-b]pyridin-2-yloxy)benzyl]-2,5-diazabicyclo[2.2.1]hept-2-yl}ethanone

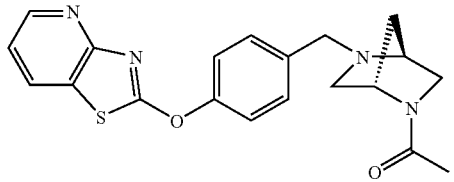

$^1$H NMR (500 MHz, CD$_3$OD): 8.49 (d, J=4.9, 1.6, 1H), 8.29 (d, J=8.0, 1.6, 1H), 7.57-7.48 (m, 2H), 7.43-7.37 (m, 2H), 7.34 (dd, J=8.0, 4.9, 1H), 4.63 (s, 0.5H), 4.48 (s, 0.5H), 3.90-3.77 (m, 2H), 3.71 (dd, J=9.8, 2.3, 1H), 3.67-3.58 (m, 1.5H), 3.44 (dd, J=9.8, 2.3, 0.5H), 3.26 (dd, J=11.4, 2.0, 0.5H), 2.97 (dd, J=9.9, 2.2, 0.5H), 2.88 (dd, J=9.8, 2.2, 0.5H), 2.74-2.63 (m, 1H), 2.11 (s, 1.5H), 2.03 (s, 1.5H), 1.98 (d, J=10.1, 0.5H), 1.84 (d, J=10.1, 0.5H), 1.75 (d, J=10.1, 0.5H). MS (ESI): mass calcd. for $C_{20}H_{20}N_4O_2S$, 380.13; m/z found, 381.1 [M+H]$^+$.

In some methods, the title compound was synthesized using the following procedure;

Step A:
4-(Thiazolo[4,5-b]pyridin-2-yloxy)-benzaldehyde

To a 1-L, round-bottom, 3-necked flask equipped with overhead mechanical stirring, dynamic nitrogen inlet, and thermocouple probe were added 2-chloro-thiazolo[4,5-b]pyridine (51.41 g, 0.248 mol), K$_2$CO$_3$ (38.0 g, 0.275 mol), and CH$_3$CN (400 mL). The resultant slurry was aged at rt for 1 h. The 4-hydroxy-benzaldehyde (30.4 g, 0.248 mol) was then added to the reaction mixture followed by K$_2$CO$_3$ (38.0 g, 0.275 mol). The resultant slurry was diluted with additional CH$_3$CN (100 mL), heated to reflux, and aged for 3.5 h. The solution was cooled to 50° C. and filtered. The inorganic cake was washed with CH$_3$CN (2×100 mL). The washes were added to the filtrate. The filtrate was concentrated until nucleation was observed (removal of ~350 mL of CH$_3$CN was required). The resultant slurry was heated to reflux and slowly cooled to rt during an overnight aging. The resultant slurry was cooled to 2° C. and filtered. The cake was transferred to a vacuum oven and dried at 55° C. for 16 h to yield 4-(thiazolo[4,5-b]pyridin-2-yloxy)-benzaldehyde (51.6 grams, 0.201 mol) as an orange/red powder. The mother liquor was concentrated and an additional crop of 4-(thiazolo[4,5-b]pyridin-2-yloxy)-benzaldehyde (6.2 g, 0.024 mol) was obtained from recrystallization from CH$_3$CN. $^1$H NMR (400 MHz, CDCl$_3$): 10.03 (s, 1H), 8.60 (dd, J=4.8, 1.6 Hz, 1H), 8.09 (dd, J=8.0, 1.6 Hz, 1H), 8.03-7.96 (m, 2H), 7.73-7.65 (m, 2H), 7.32-7.22 (m, 1H). MS (ESI): mass calcd. for $C_{13}H_8N_2O_2S$, 256.03; m/z found, 257.0[M+H]$^+$.

Step B: 1-{(1S,4S)-5-[4-([1,3]Thiazolo[4,5-b]pyridin-2-yloxy)benzyl]-2,5-diazabicyclo[2.2.1]hept-2-yl}ethanone To a 1-L round-bottom, 3-necked flask equipped with magnetic stirring, dynamic nitrogen inlet, and thermocouple probe were added 1-[(1S,4S)-2,5-diazabicyclo[2.2.1]hept-2-yl]ethanone hydrochloride (53.3 g, 0.302 mol), DCE (250 mL), and Et$_3$N (100 mL, 1.006 mol). The flask was warmed to 50° C. and aged for 20 min. An additional 100 mL of DCE was added to facilitate stirring. The solution was cooled to 40° C. and the solution was then added via cannula to a 2-L round-bottom, 3-necked flask equipped with overhead mechanical stirring, dynamic nitrogen inlet, and thermocouple probe containing 4-(thiazolo[4,5-b]pyridin-2-yloxy)-benzaldehyde (51.6 grams, 0.201 mol) dissolved in DCE (100 mL). The 1-L round-bottom flask was rinsed with DCE (100 mL). The rinse solvent was added to the reaction mixture. The resultant deep purple solution was aged at rt for 2.5 h. After such time, the sodium triacetoxyborohydride (72.5 g, 0.342) was added in 4 equal portions over a four-hour period. Once addition was complete, the resultant solution was aged at rt overnight. The reaction was quenched by the slow addition of water (1 L) over a 10-minute period. After 30 additional minutes of stirring, the solution was filtered to remove a fine rag layer of precipitate. The layers were separated and the aqueous layer was extracted with DCE (1×500 mL). The organic layers were combined, washed with brine, dried over MgSO$_4$, filtered and concentrated to yield crude product as a thick brown oil. The crude product was suspended in EtOAc (500 mL), warmed to 70° C., and cooled slowly to rt. The resultant slurry was filtered and the filtrate was concentrated to yield 1-{5-[4-(thiazolo[4,5-b]pyridin-2-yloxy)-benzyl]-2,5-diaza-bicyclo[2.2.1]hept-2-yl}-ethanone (67.2 g, 0.177 mol) as a brown glass. MS (ESI): mass calcd. for $C_{20}H_{20}N_4O_2S$, 380.13; m/z found, 381.1 [M+H]$^+$.

Step C: 1-{(1S,4S)-5-[4-([1,3]Thiazolo[4,5-b]pyridin-2-yloxy)benzyl]-2,5-diazabicyclo[2.2.1]hept-2-yl}ethanone Hydrochloride To a 500-mL round bottom flask equipped with magnetic stirring were added crude 1-{(1S,4S)-5-[4-([1,3]thiazolo[4,5-b]pyridin-2-yloxy)benzyl]-2,5-diazabicyclo[2.2.1]hept-2- yl}ethanone (35.1 g, 0.092 mol) and 1.25 M HCl in EtOH (73.8 mL, 0.092 mol). The resultant solution was diluted with EtOH (25 mL). The solution was heated to 50° C. for 20 min, and then slowly cooled until an unstirrable slurry was obtained. The slurry was diluted with EtOH (100 mL) and warmed to 50° C. The slurry was aged for 30 min, cooled slowly to rt and filtered. The cream colored cake was transferred to a 60° C. vacuum oven where it was dried for 16 h. After drying 1-{(1S,4S)-5-[4-([1,3]thiazolo[4,5-b]pyridin-2-yloxy)benzyl]-2,5-diazabicyclo[2.2.1]hept-2-yl}ethanone hydrochloride (29.2 g, 0.700 mol) was obtained as a tan/red solid. The dry solid was added to a 1-L round-bottom flask equipped with magnetic stirring and diluted with acetone (300 mL). The solution was heated to 55° C. and aged for 30 min. The slurry was then slowly cooled to 2° C. and filtered. The cake was transferred to a 70° C. vacuum oven where it was dried for 18 h. The 1-{(1S,4S)-5-[4-([1,3]thiazolo[4,5-b]pyridin-2-yloxy)benzyl]-2,5-diazabicyclo[2.2.1]hept-2-yl}ethanone hydrochloride (26.1 g, 0.0625 mol) was obtained as a cream colored, free flowing powder. $^1$H NMR (400 MHz, DMSO-$d_6$): 11.82-10.55 (m, 1H), 8.55-8.49 (m, 1H), 8.47-8.41 (m, 1H), 7.94-7.84 (m, 2H), 7.63-7.56 (m, 2H), 7.40-7.33 (m, 1H), 4.77-4.25 (m, 3H), 4.19-3.99 (m, 0.5H), 3.88-3.78 (m, 0.5H), 3.62-3.17 (m, 4H), 2.57-2.35 (m, 2H), 2.13-1.83 (m, 3H). MS (ESI): mass calcd. for $C_{20}H_{20}N_4O_2S$, 380.13; m/z found, 381.1 [M+H]$^+$. Anal. Calcd. For $C_{20}H_{21}ClN_4O_2S$: C, 57.62; H, 5.08; N, 13.44; Cl, 8.50; S, 7.69. Found: C, 54.97; H, 5.25; N, 12.78; Cl, 8.28; S, 7.43 ($C_{20}H_{21}ClN_4O_2S \cdot 1.05H_2O$).

In some embodiments, the title compound was prepared in salt form, such as hydrochlorides, including hydrated hydrochlorides, such as the monohydrate.

Example 128

2-(4-{[(1S,4S)-5-Acetyl-2,5-diazabicyclo[2.2.1]hept-2-yl]methyl}phenoxy)-6-fluoro[1,3]thiazolo[4,5-b]pyridine

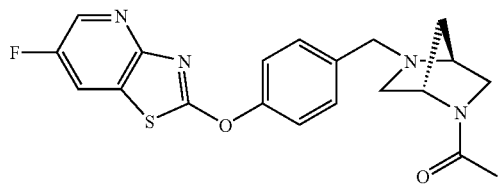

$^1$H NMR (500 MHz, CDCl$_3$): 8.46-8.43 (m, 1H), 7.81-7.76 (m, 1H), 7.47-7.41 (m, 2H), 7.40-7.34 (m, 2H), 4.81 (s, 0.5H), 4.26 (s, 0.5H), 3.82-3.75 (m, 2.5H), 3.61-3.55 (m, 1.5H), 3.34 (dd, J=9.3, 2.3, 0.5H), 3.29 (dd, J=11.4, 2.0, 0.5H), 3.03 (dd, J=9.6, 2.1, 0.5H), 2.86 (dd, J=9.7, 2.1, 0.5H), 2.80 (d, J=9.8, 0.5H), 2.57 (dd, J=9.5, 1.1, 0.5H), 2.11 (s, 1.5H), 2.05-1.99 (m, 2H), 1.93 (d, J=9.8, 0.5H), 1.83 (d, J=9.9, 0.5H), 1.69 (d, J=9.9, 0.5H). MS (ESI): mass calcd. for $C_{20}H_{19}FN_4O_2S$, 398.12; m/z found, 399.10 [M+H]$^+$.

Examples 129-130 were prepared using methods analogous to those described for Example 118, substituting Cs$_2$CO$_3$ and the appropriate phenol for the sodium phenolate starting material.

Example 129

6-Fluoro-2-[4-(piperidin-1-ylmethyl)phenoxy][1,3]thiazolo[4,5-b]pyridine

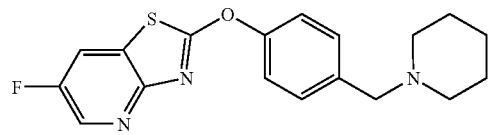

$^1$H NMR (500 MHz, CDCl$_3$): 8.44 (dd, J=2.8, 1.1, 1H), 7.77 (dd, J=7.4, 2.8, 1H), 7.44-7.40 (m, 2H), 7.37-7.33 (m, 2H), 3.50 (s, 2H), 2.41 (s, 4H), 1.66-1.57 (m, 6H). MS (ESI): mass calcd. for $C_{18}H_{18}FN_3OS$, 343.12; m/z found, 344.10 [M+H]$^+$.

Example 130

Ethyl 1-[4-([1,3]thiazolo[4,5-b]pyridin-2-yloxy)benzyl]piperidine-4-carboxylate

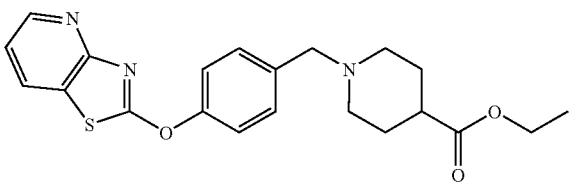

$^1$H NMR (400 MHz, CD$_3$OD): 8.48 (dd, J=4.9, 1.6, 1H), 8.30 (dd, J=8.0, 1.6, 1H), 7.53-7.44 (m, 2H), 7.43-7.37 (m, 2H), 7.34 (dd, J=8.0, 4.9, 1H), 4.19-4.05 (m, 2H), 3.57 (s, 2H), 2.96-2.79 (m, 2H), 2.41-2.29 (m, 1H), 2.19-2.06 (m, 2H), 1.97-1.85 (m, 2H), 1.81-1.67 (m, 2H), 1.24 (t, J=7.1, 3H). MS (ESI): mass calcd for $C_{21}H_{23}N_3O_3S$, 397.15; m/z found, 398.2 [M+H]$^+$.

Example 131

1-[4-([1,3]Thiazolo[4,5-b]pyridin-2-yloxy)benzyl]piperidine-4-carboxylic Acid

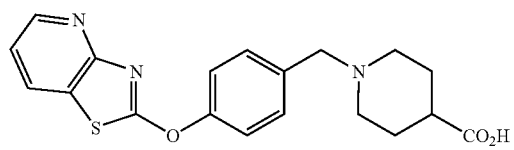

To a solution of ethyl 1-[4-([1,3]thiazolo[4,5-b]pyridin-2-yloxy)benzyl]piperidine-4-carboxylate (97 mg, 0.24 mmol) in isopropyl alcohol (750 µL) was added 1 N KOH (240 µL). The mixture was allowed to stir at rt for 2 h. The reaction mixture was then poured into water (20 mL) and basified to pH 9. The resultant solution was extracted with a 1:1 solution of CHCl$_3$/isopropyl alcohol (2×30 mL). The combined organic extracts were dried, filtered, and concentrated to afford the title compound (38 mg, 43%). $^1$H NMR (400 MHz, CD$_3$OD): 8.49 (d, J=4.8, 1H), 8.32 (dd, J=8.0, 1.6, 1H), 7.61-7.54 (m, 2H), 7.52-7.45 (m, 2H), 7.35 (dd, J=8.0, 4.9, 1H), 3.95 (s, 2H), 3.22-3.09 (m, 2H), 2.65-2.46 (m, 1H), 2.38-2.22 (m, 1H), 2.05-1.92 (m, 2H), 1.91-1.75 (m, 2H), 0.98-0.79 (m, 1H). MS (ESI): mass calcd for $C_{19}H_{19}N_3O_3S$, 369.12; m/z found, 370.2 $[M+H]^+$.

Example 132

1-[4-([1,3]Thiazolo[5,4-b]pyridin-2-yloxy)benzyl]piperidine-4-carboxylic Acid

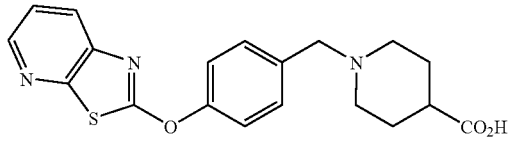

The title compound was prepared using methods analogous to those described for Example 131. $^1$H NMR (400 MHz, DMSO-$d_6$): 8.45 (dd, J=4.8, 1.5, 1H), 8.09 (dd, J=8.2, 1.5, 1H), 7.51 (dd, J=8.2, 4.8, 1H), 7.47-7.38 (m, 4H), 3.55 (s, 2H), 2.85-2.66 (m, 2H), 2.21-2.09 (m, 1H), 2.07-1.90 (m, 2H), 1.86-1.69 (m, 2H), 1.63-1.45 (m, 2H). MS (ESI): mass calcd for $C_{19}H_{19}N_3O_3S$, 369.12; m/z found, 370.2 $[M+H]^+$.

Example 133

2-[4-(Piperidin-1-ylmethyl)phenoxy][1,3]thiazolo[4,5-c]pyridine

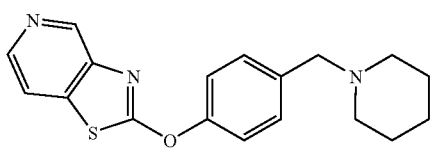

The title compound was prepared using methods analogous to those described for Example 112. $^1$H NMR (500 MHz, CDCl$_3$): 9.02 (s, 1H), 8.45 (d, J=5.0, 1H), 7.65 (d, J=5.0, 1H), 7.45 (d, J=10.0, 2H), 7.33 (d, J=10.0, 2H), 3.53 (s, 2H), 2.43 (br s, 4H), 1.63-1.61 (m, 4H), 1.47 (br s, 2H). MS (ESI): mass calcd. for $C_{18}H_{19}N_3OS$, 325.44; m/z found, 326.1 $[M+H]^+$.

Example 134 meso-N-{(3-endo)-8-[4-([1,3]Thiazolo[4,5-c]pyridin-2-yloxy)benzyl]-8-azabicyclo[3.2.1]oct-yl}acetamide

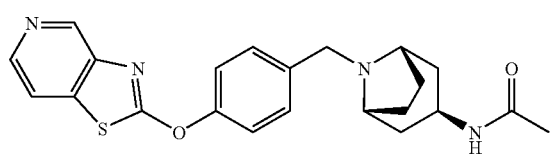

The title compound was prepared using methods analogous to those described for Example 112. $^1$H NMR (500 MHz, CDCl$_3$): 9.02 (s, 1H), 8.45 (d, J=5.0, 1H), 7.65 (d, J=5.0, 1H), 7.50-7.49 (m, 2H), 7.34-7.33 (m, 2H), 5.82 (br d, J=6.5, 1H), 4.15 (dd, J=7.1, 1H), 3.57 (s, 2H), 3.23 (br s, 2H), 2.27-2.22 (m, 2H), 2.18-2.16 (m, 2H), 1.99 (s, 3H), 1.82-1.78 (m, 2H), 1.64 (br s, 2H). MS (ESI): mass calcd. for $C_{22}H_{24}N_4O_2S$, 408.53; m/z found, 409.1 $[M+H]^+$.

Example 135

2-(4-{2-[4-(2-Methoxyphenyl)piperazin-1-yl]ethoxy}phenoxy)[1,3]thiazolo[4,5-b]pyridine

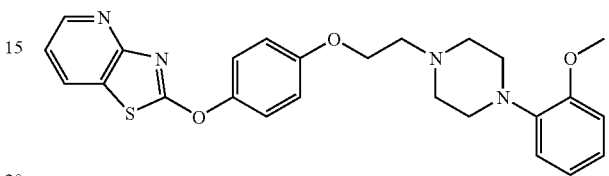

The title compound was prepared using methods analogous to those described for Example 1. $^1$H NMR (500 MHz, CD$_3$OD): 8.49 (dd, J=4.9, 1.6, 1H), 8.30 (dd, J=8.0, 1.6, 1H), 7.42-7.37 (m, 2H), 7.35 (dd, J=8.0, 4.9, 1H), 7.16-7.11 (m, 2H), 7.08-6.96 (m, 3H), 6.95-6.91 (m, 1H), 4.32 (t, J=5.3, 2H), 3.88 (s, 3H), 3.27-3.14 (m, 6H), 3.12-3.02 (m, 4H). MS (ESI): mass calcd. for $C_{25}H_{26}N_4O_3S$, 462.17; m/z found, 463.1 $[M+H]^+$.

Example 136

2-[4-(2-{4-[(4-Chlorophenyl)sulfanyl]piperidin-1-yl}ethoxy)phenoxy][1,3]thiazolo[4,5-b]pyridine

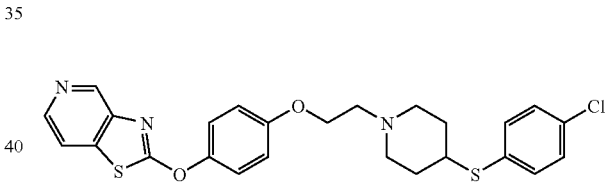

The title compound was prepared using methods analogous to those described for Example 1, using more of N,N-diisopropylethylamine (3.5 equiv.) and more of the appropriate amine (3.2 equiv.). $^1$H NMR (400 MHz, CDCl$_3$): 8.56 (dd, J=4.9, 1.7, 1H), 8.00 (dd, J=7.9, 1.7, 1H), 7.41-7.27 (m, 6H), 7.20 (dd, J=7.9, 4.9, 1H), 6.97-6.90 (m, 2H), 4.15 (t, J=5.6, 2H), 3.09-3.01 (m, 3H), 2.91 (t, J=5.6, 2H), 2.46-2.33 (m, 2H), 2.08-1.96 (m, 2H), 1.81-1.66 (m, 2H). MS (ESI): mass calcd. for $C_{25}H_{24}ClN_3O_2S_2$, 497.1; m/z found, 498.1 $[M+H]^+$.

Example 137

1-[4-([1,3]Thiazolo[4,5-b]pyridin-2-yloxy)benzyl]piperidin-4-ol

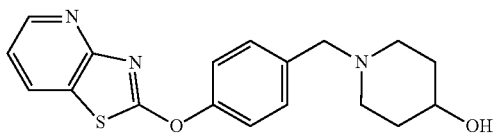

The title compound was prepared using methods analogous to those described for Example 82, using more sodium triacetoxyborohydride (3.2 equiv.) and more of the appropriate amine (1.7 equiv.) as well as adjusting the reaction temperature to 50° C. for 16 h after stirring at rt for 5 h. $^1$H NMR (600 MHz, CDCl$_3$): 8.56 (dd, J=4.8, 1.7, 1H), 8.01 (dd, J=7.9, 1.7, 1H), 7.41-7.37 (m, 2H), 7.37-7.34 (m, 2H), 7.20 (dd, J=7.9, 4.8, 1H), 3.77-3.68 (m, 1H), 3.52 (s, 2H), 2.80-2.73 (m, 2H), 2.23-2.13 (m, 2H), 1.95-1.86 (m, 2H), 1.65-1.56 (m, 2H), 1.37-1.30 (m, 1H). MS (ESI): mass calcd. for C$_{18}$H$_{19}$N$_3$O$_2$S, 341.1; m/z found, 342.1 [M+H]$^+$.

Example 138

7-Methyl-2-[4-(piperidin-1-ylmethyl)phenoxy][1,3]thiazolo[4,5-b]pyridine

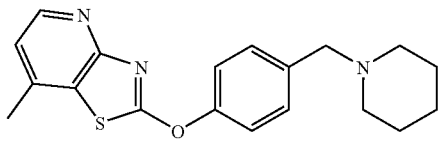

The title compound was prepared using methods analogous to those described for Example 130. $^1$H NMR (500 MHz, CDCl$_3$): 8.46 (d, J=5.0, 1H), 7.44-7.34 (m, 4H), 7.03 (dd, J=5.0, 0.7, 1H), 3.51 (s, 2H), 2.51 (s, 3H), 2.41 (s, 4H), 1.64-1.57 (m, 4H), 1.50-1.43 (m, 2H). MS (ESI): mass calcd. for C$_{19}$H$_{21}$N$_3$OS, 339.14; m/z found, 340.10 [M+H]$^+$.

Example 139

N-{2-[4-([1,3]Thiazolo[4,5-b]pyridin-2-yloxy)phenoxy]ethyl}cyclopropanamine

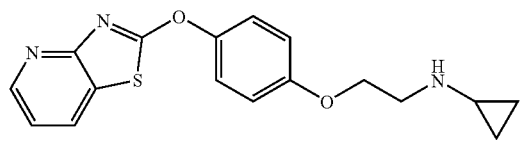

The title compound was prepared using methods analogous to those described for Example 1. $^1$H NMR (500 MHz, CD$_3$OD): 8.48 (dd, J=4.9, 1.6, 1H), 8.28 (dd, J=8.0, 1.6, 1H), 7.38-7.32 (m, 3H), 7.12-7.07 (m, 2H), 4.15 (t, J=5.4, 2H), 3.09 (t, J=5.4, 2H), 2.26 (tt, J=7.2, 3.7, 1H), 0.55-0.51 (m, 2H), 0.45-0.39 (m, 2H). MS (ESI): mass calcd. for C$_{17}$H$_{17}$N$_3$O$_2$S, 327.1; m/z found, 328.1 [M+H]$^+$.

Examples 140-254 were prepared using methods analogous to the previous examples.

Example 140

2-Methyl-N-[1-(2-{4-[(6-methyl[1,3]thiazolo[4,5-b]pyridin-2-yl)oxy]phenoxy}ethyl)piperidin-4-yl]propanamide

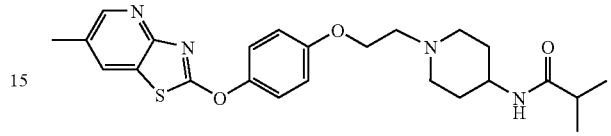

$^1$H NMR (300 MHz, CDCl$_3$): 8.38 (s, 1H), 7.79 (s, 1H), 7.31 (d, J=8.4, 2H), 6.94 (d, J=8.1, 2H), 5.28 (brs, 1H), 4.10 (t, J=5.7, 2H), 3.81 (brs, 1H), 2.93 (d, J=11.1, 2H), 2.81 (t, J=5.7, 2H), 2.42 (s, 3H), 2.31-2.23 (m, 3H), 1.91 d, J=12.0, 2H), 1.52-1.45 (m, 2H), 1.15 (d, J=6.9, 6H). MS (ESI): mass calculated for C$_{24}$H$_{30}$N$_4$O$_3$S, 454.20; m/z found, 455.2 [M+H]$^+$.

Example 141 meso-2-{4-[2-(3-Acetyl-3,8-diazabicyclo[3.2.1]oct-8-yl)ethoxy]phenoxy}[1,3]thiazolo[4,5-b]pyridine

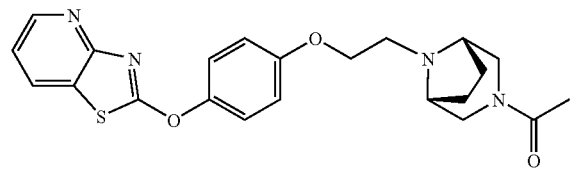

$^1$H NMR (300 MHz, CDCl$_3$): 8.54 (d, J=3.6, 1H), 7.98 (d, J=7.8, 1H), 7.30 (d, J=8.7, 2H), 7.19-7.15 (m, 1H), 6.93 (d, J=8.7, 2H), 4.18-4.14 (m, 3H), 3.40 (br s, 4H), 2.91 (br s, 1H), 2.79 (br s, 2H), 2.05 (s, 3H), 1.98 (br s, 2H), 1.62 (br s, 2H). MS (ESI): mass calculated for C$_{22}$H$_{24}$N$_4$O$_3$S, 424.16; m/z found, 425.1 [M+H]$^+$.

Example 142 meso-1-[(3-exo)-8-{2-[4-([1,3]Thiazolo[4,5-b]pyridin-2-yloxy)phenoxy]ethyl}-8-azabicyclo[3.2.1]oct-3-yl]urea Hydrochloride

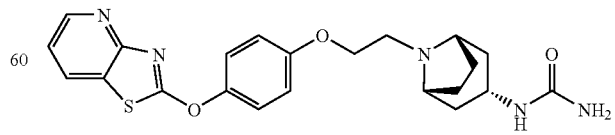

$^1$H NMR (300 MHz, CD$_3$OD): 9.06 (d, J=8.1, 1H), 8.77 (d, J=5.4, 1H), 7.90-7.88 (m, 1H), 7.54 (d, J=8.7, 2H), 7.28 (d, J=8.4, 2H), 4.55 (br s, 2H), 4.25 (br s, 2H), 3.98 (br s, 1H), 3.61 (br s, 2H), 2.62-2.06 (m, 8H). MS (ESI): mass calculated for $C_{22}H_{25}N_5O_3S$, 439.17; m/z found, 440.1 [M+H]$^+$.

Example 143

7-Methyl-2-(4-{2-[4-(pyridin-4-ylcarbonyl)piperazin-1-yl]ethoxy}phenoxy)[1,3]thiazolo[4,5-b]pyridine

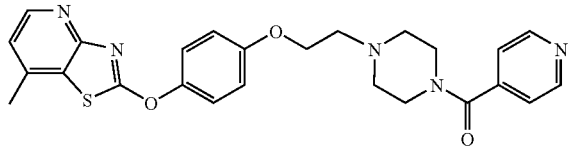

$^1$H NMR (300 MHz, CDCl$_3$): 8.71 (d, J=5.4, 2H), 8.44 (d, J=5.4, 1H), 7.34-7.28 (m, 4H), 7.01 (d, J=4.8, 1H), 6.94 (d, J=6.0, 2H), 4.15-4.10 (m, 2H), 3.84 (br s, 2H), 3.43 (br s, 2H), 2.90 (br s, 2H), 2.71-2.58 (m, 4H), 2.49 (s, 3H). MS (ESI): mass calculated for $C_{25}H_{25}N_5O_3S$, 475.17; m/z found, 476.1 [M+H]$^+$.

Example 144

1-(1-{2-[4-([1,3]Thiazolo[5,4-c]pyridin-2-yloxy)phenoxy]ethyl}piperidin-4-yl)pyrrolidin-2-one

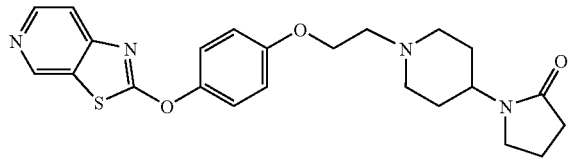

$^1$H NMR (300 MHz, CDCl$_3$): 8.93 (s, 1H), 8.58 (d, J=5.4, 1H), 7.64 (d, J=5.4, 1H), 7.30 (d, J=5.7, 2H), 7.02-6.99 (m, 2H), 4.16-4.01 (m, 3H), 3.36 (t, J=4.2, 2H), 3.14-3.10 (m, 2H), 2.88 (br s, 2H), 2.43 (t, J=4.2, 2H), 2.35-2.28 (m, 2H), 2.08-1.98 (m, 2H), 1.85-1.69 (m, 4H). MS (ESI): mass calculated for $C_{23}H_{26}N_4O_3S$, 438.17; m/z found, 439.0 [M+H]$^+$.

Example 145

6-Methyl-2-(4-{2-[4-(morpholin-4-ylcarbonyl)piperidin-1-yl]ethoxy}phenoxy)[1,3]thiazolo[4,5-b]pyridine

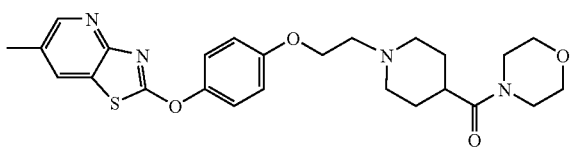

$^1$H NMR (300 MHz, CDCl$_3$): 8.38 (s, 1H), 7.82 (s, 1H), 7.31 (d, J=8.7, 2H), 6.94 (d, J=8.4, 2H), 4.29 (br s, 2H), 3.68-3.53 (m, 7H), 3.24-3.08 (m, 5H), 2.68 (br s, 2H), 2.43 (s, 3H), 1.97 (br s, 3H), 1.42 (t, J=7.50, 2H). MS (ESI): mass calculated for $C_{25}H_{30}N_4O_4S$, 482.20; m/z found, 483.0 [M+H]$^+$.

Example 146

2-(4-{2-[5-(Cyclobutylcarbonyl)hexahydropyrrolo[3,4-c]pyrrol-2(1H)-yl]ethoxy}phenoxy)-7-methyl[1,3]thiazolo[4,5-b]pyridine

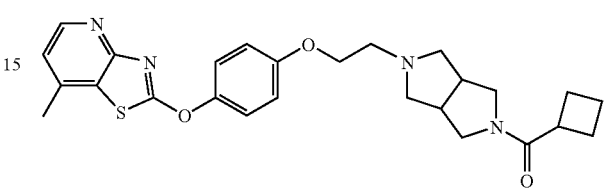

$^1$H NMR (300 MHz, CDCl$_3$): 8.44 (d, J=5.1, 1H), 7.32 (d, J=9.0, 2H), 7.01 (d, J=5.1, 1H), 6.95 (d, J=9.0, 2H), 4.10 (br s, 2H), 3.64-3.50 (m, 3H), 3.28-3.16 (m, 2H), 2.90 (br s, 6H), 2.48 (s, 5H), 2.39-2.29 (m, 2H), 2.18-2.12 (m, 2H), 2.04-1.87 (m, 2H). MS (ESI): mass calculated for $C_{26}H_{30}N_4O_3S$, 478.20; m/z found, 479.0 [M+H]$^+$.

Example 147

6-Chloro-2-(4-{2-[4-(furan-2-ylcarbonyl)piperazin-1-yl]ethoxy}phenoxy)[1,3]thiazolo[4,5-b]pyridine

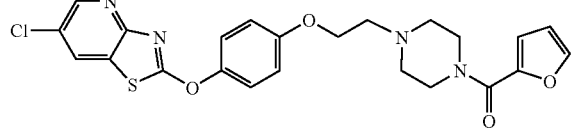

$^1$H NMR (300 MHz, CDCl$_3$): 8.50 (s, 1H), 7.98 (s, 1H), 7.49 (s, 1H), 7.32 (d, J=8.7, 2H), 7.01-6.95 (m, 3H), 6.48 (s, 1H), 4.16 (br s, 2H), 3.87 (br s, 4H), 2.89 (br s, 2H), 2.68 (br s, 4H). MS (ESI): mass calculated for $C_{23}H_{21}ClN_4O_4S$, 484.10; m/z found, 485.1 [M+H]$^+$.

Example 148 meso-N-[(3-endo)-8-{2-[4-([1,3]Thiazolo[4,5-b]pyrazin-2-yloxy)phenoxy]ethyl}-8-azabicyclo[3.2.1]oct-3-yl]acetamide

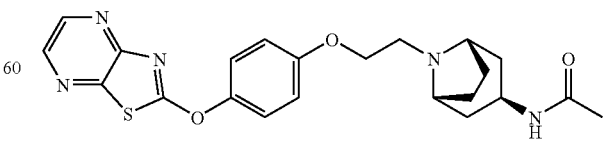

$^1$H NMR (300 MHz, CDCl$_3$): 8.51 (br s, 1H), 8.34 (d, J=1.8, 1H), 7.31 (d, J=8.7, 2H), 6.98 (d, J=8.7, 2H), 5.37 (br s, 1H), 4.26 (br s, 3H), 3.56 (br s, 2H), 2.96 (br s, 2H), 2.09 (br s, 2H), 2.05 (s, 3H), 1.94-1.87 (m, 6H). MS (ESI): mass calculated for C$_{22}$H$_{25}$N$_5$O$_3$S, 439.17; m/z found, 440.1 [M+H]$^+$.

Example 149 meso-3-{2-[4-([1,3]Thiazolo[4,5-b]pyridin-2-yloxy)phenoxy]ethyl}-3,8-diazabicyclo[3.2.1]octane-8-carboxamide

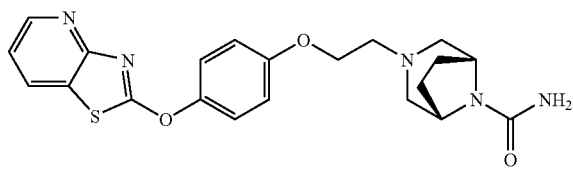

$^1$H NMR (300 MHz, CDCl$_3$): 8.55 (d, J=4.2, 1H), 7.99 (d, J=7.8, 1H), 7.30 (d, J=8.7, 2H), 7.20-7.16 (m, 1H), 6.92 (d, J=9.0, 2H), 4.42 (s, 2H), 4.08 (m, 4H), 2.78-2.70 (m, 4H), 2.51 (d, J=10.2, 2H), 1.90 (s, 4H). MS (ESI): mass calculated for C$_{21}$H$_{23}$N$_5$O$_3$S, 425.152160644531; m/z found, 426.1 [M+H]$^+$.

Example 150

2-[4-(2-Morpholin-4-ylethoxy)phenoxy][1,3]thiazolo[4,5-b]pyrazine

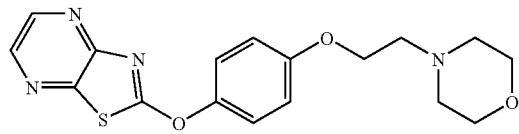

$^1$H NMR (300 MHz, CDCl$_3$): 8.51 (br s, 1H), 8.34 (d, J=1.5, 1H), 7.31 (d, J=8.7, 2H), 6.98 (d, J=8.7, 2H), 4.14 (t, J=5.7, 2H), 3.75 (t, J=5.2, 4H), 2.83 (t, J=5.7, 2H), 2.60 (br s, 4H). MS (ESI): mass calculated for C$_{17}$H$_{18}$N$_4$O$_3$S, 358.11; m/z found, 359.1 [M+H]$^+$.

Example 151

2-(4-{2-[(1R,4R)-5-(Methylsulfonyl)-2,5-diazabicyclo[2.2.1]hept-2-yl]ethoxy}phenoxy)[1,3]thiazolo[5,4-c]pyridine

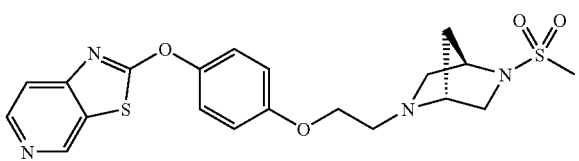

$^1$H NMR (300 MHz, CDCl$_3$): 8.90 (s, 1H), 8.54 (d, J=4.5, 1H), 7.60 (d, J=1.8, 1H), 7.25 (d, J=8.1, 2H), 6.55 (d, J=8.4, 2H), 4.30 (s, 1H), 4.09 (s, 2H), 3.74-3.62 (m, 2H), 3.26 (d, J=9.3, 1H), 3.08 (br s, 3H), 2.87 (s, 4H), 1.78-1.24 (m, 2H). MS (ESI): mass calculated for C$_{20}$H$_{22}$N$_4$O$_4$S$_2$, 446.11; m/z found, 447.1 [M+H]$^+$.

Example 152

2-{4-[2-(4-Methyl-1,4-diazepan-1-yl)ethoxy]phenoxy}[1,3]thiazolo[5,4-b]pyridine

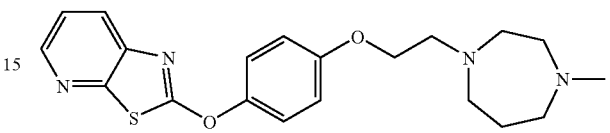

$^1$H NMR (300 MHz, CDCl$_3$): 8.40 (d, J=4.5, 1H), 7.94 (d, J=8.1, 1H), 7.35-7.30 (m, 3H), 6.97 (d, J=8.7, 2H), 4.09 (t, J=6.0, 2H), 2.99 (t, J=6.0, 2H), 2.90 (br s, 4H), 2.67 (br s, 4H), 2.39 (s, 3H), 1.86 (br s, 2H). MS (ESI): mass calculated for C$_{20}$H$_{24}$N$_4$O$_2$S, 384.16; m/z found, 385.1 [M+H]$^+$.

Example 153 meso-N-[(3-exo)-8-{2-[4-([1,3]Thiazolo[5,4-b]pyridin-2-yloxy)phenoxy]ethyl}-8-azabicyclo[3.2.1]oct-3-yl]acetamide

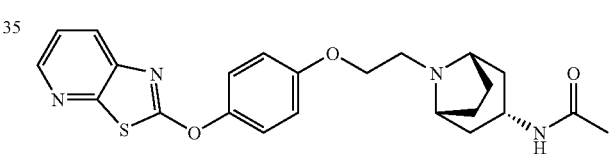

$^1$H NMR (300 MHz, CDCl$_3$): 8.40 (br s, 1H), 7.94 (d, J=7.5, 1H), 7.33-7.27 (m, 3H), 6.97 (d, J=6.6, 2H), 5.83 (br s, 1H), 4.18-4.12 (m, 3H), 3.43 (br s, 2H), 2.88 (br s, 2H), 2.33-2.17 (m, 4H), 1.99 (s, 3H), 1.85 (br s, 2H), 1.71-1.66 (m, 2H). MS (ESI): mass calculated for C$_{23}$H$_{26}$N$_4$O$_3$S, 438.17; m/z found, 439.1 [M+H]$^+$.

Example 154

N-[1-(2-{4-[(6-Methyl[1,3]thiazolo[4,5-b]pyridin-2-yl)oxy]phenoxy}ethyl)piperidin-4-yl]acetamide

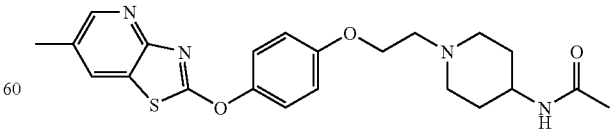

$^1$H NMR (300 MHz, CDCl$_3$): 8.38 (s, 1H), 7.80 (s, 1H), 7.31 (d, J=8.7, 2H), 6.94 (d, J=8.7, 2H), 5.47 (brs, 1H), 4.14 (t, J=5.7, 2H), 3.84-3.82 (m, 1H), 3.01-2.84 (m, 4H), 2.42 (s, 3H), 2.32 (t, J=6.6, 2H), 1.97-1.94 (m, 5H), 1.28-1.25-1.66

(m, 2H). MS (ESI): mass calculated for $C_{22}H_{26}N_4O_3S$, 426.17; m/z found, 427.1 $[M+H]^+$.

Example 155

1-{3-[(2-{4-[(6-Chloro[1,3]thiazolo[4,5-b]pyridin-2-yl)oxy]phenoxy}ethyl)(methyl)amino]propyl}pyrrolidin-2-one

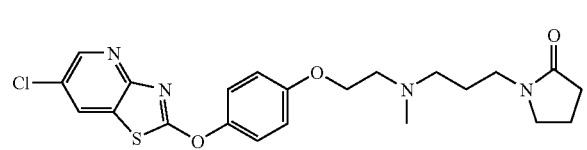

$^1$H NMR (300 MHz, CDCl$_3$): 8.49 (d, J=1.8, 1H), 7.97 (d, J=1.8, 1H), 7.30 (d, J=9.0, 2H), 6.95 (d, J=9.0, 2H), 4.10 (br s, 2H), 3.42-3.30 (m, 4H), 2.85 (br s, 2H), 2.52 (br s, 2H), 2.37-2.34 (m, 5H), 2.05-1.98 (m, 2H), 1.77 (br s, 2H). MS (ESI): mass calculated for $C_{22}H_{25}ClN_4O_3S$, 460.13; m/z found, 461.1 $[M+H]^+$.

Example 156

3-[(Cyclopropylmethyl){2-[4-([1,3]thiazolo[5,4-c]pyridin-2-yloxy)phenoxy]ethyl}amino]propan-1-ol

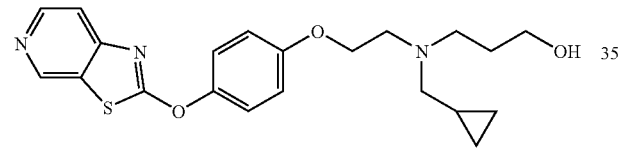

$^1$H NMR (300 MHz, CDCl$_3$): 8.90 (s, 1H), 8.55 (d, J=5.4, 1H), 7.61 (d, J=5.4, 1H), 7.27 (d, J=9.0, 2H), 6.99 (d, J=9.0, 2H), 4.13 (t, J=5.7, 2H), 3.84 (t, J=5.1, 2H), 3.03 (t, J=5.7, 2H), 2.89 (t, J=5.4, 2H), 2.50 (d, J=6.0, 2H), 1.80-1.71 (m, 2H), 0.96-0.91 (m, 1H), 0.59-0.53 (m, 2H), 0.20-0.15 (m, 2H). MS (ESI): mass calculated for $C_{21}H_{25}N_3O_3S$, 399.16; m/z found, 400.1 $[M+H]^+$.

Example 157

2-[(Cyclopropylmethyl){2-[4-([1,3]thiazolo[5,4-b]pyridin-2-yloxy)phenoxy]ethyl}amino]ethanol

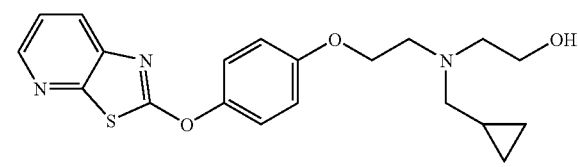

$^1$H NMR (300 MHz, CDCl$_3$): 8.38 (d, J=3.9, 1H), 7.92 (d, J=4.8, 1H), 7.34-7.21 (m, 3H), 6.97 (d, J=9.0, 2H), 4.10 (t, J=5.7, 2H), 3.61 (t, J=5.1, 2H), 3.05 (t, J=5.7, 2H), 2.83 (t, J=5.4, 2H), 2.53 (d, J=6.0, 2H), 0.93-0.87 (m, 1H), 0.57-0.51 (m, 2H), 0.17-0.12 (m, 2H). MS (ESI): mass calculated for $C_{20}H_{23}N_3O_3S$, 385.15; m/z found, 386.1 $[M+H]^+$.

Example 158

1-(2-{4-[(7-Methyl[1,3]thiazolo[4,5-b]pyridin-2-yl)oxy]phenoxy}ethyl)-4-pyridin-2-ylpiperidin-4-ol

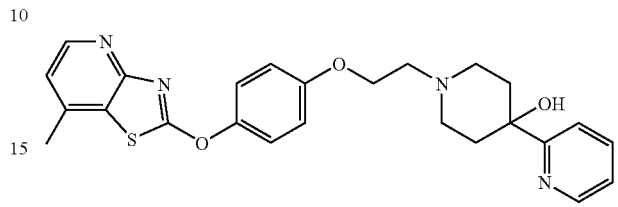

$^1$H NMR (300 MHz, CDCl$_3$): 8.53 (d, J=4.2, 1H), 8.44 (d, J=4.8, 1H), 7.73 (t, J=7.5, 1H), 7.42 (d, J=7.8, 1H), 7.32 (d, J=8.7, 2H), 7.23-7.20 (m, 1H), 6.99 (d, J=9.0, 3H), 5.37 (br s, 1H), 4.22 (br s, 2H), 2.99 (br s, 4H), 2.78 (br s, 2H), 2.48 (s, 3H), 2.19 (br s, 2H), 1.68 (d, J=13.2, 2H). MS (ESI): mass calculated for $C_{25}H_{26}N_4O_3S$, 462.17; m/z found, 463.1 $[M+H]^+$.

Example 159 meso-(3-endo)-8-acetyl-N-{2-[4-([1,3]thiazolo[4,5-b]pyridin-2-yloxy)phenoxy]ethyl}-8-azabicyclo[3.2.1]octan-3-amine

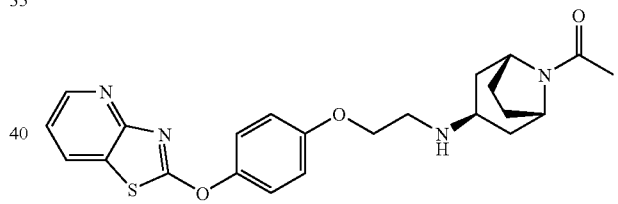

$^1$H NMR (300 MHz, CDCl$_3$): 8.56 (d, J=4.8, 1H), 8.00 (d, J=8.1, 1H), 7.32 (d, J=8.1, 2H), 7.21-7.17 (m, 1H), 6.93 (d, J=8.4, 2H), 4.62 (brs, 1H), 4.14-4.04 (m, 3H), 3.01-3.98 (m, 2H), 2.22-1.54 (m, 12H). MS (ESI): mass calculated for $C_{23}H_{26}N_4O_3S$, 438.17; m/z found, 439.1 $[M+H]^+$.

Example 160

N-Methyl-2-(methyloxy)-N-[2-({4-[(7-methyl[1,3]thiazolo[4,5-b]pyridin-2-yl)oxy]phenyl}oxy)ethyl]ethanamine

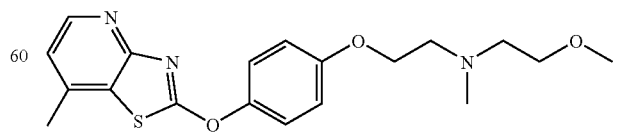

$^1$H NMR (300 MHz, CDCl$_3$): 8.44 (d, J=4.8, 1H), 7.31 (d, J=9.0, 2H), 7.00 (d, J=4.8, 1H), 6.95 (d, J=9.0, 2H), 4.11 (t, J=6.0, 2H), 3.52 (t, J=5.4, 2H), 3.37 (s, 3H), 2.89 (t, J=6.0,

Example 161

N-(2-Hydroxy-1,1-dimethylethyl)-1-(2-{[4-([1,3]thiazolo[4,5-c]pyridin-2-yloxy)phenyl]oxy}ethyl)piperidine-4-carboxamide

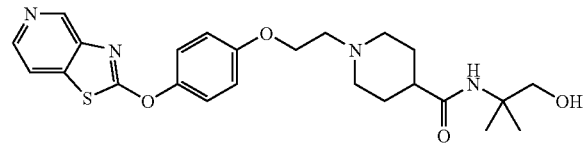

$^1$H NMR (300 MHz, CDCl$_3$): 8.99 (s, 1H), 8.43 (d, J=5.1, 1H), 7.63 (d, J=5.4, 1H), 7.28 (d, J=9.0, 2H), 6.98 (d, J=9.0, 2H), 5.52 (br s, 1H), 4.80 (br s, 1H), 4.13 (br s, 2H), 3.58 (d, J=4.2, 2H), 3.08 (d, J=11.1, 2H), 2.84 (br s, 2H), 2.30-1.60 (m, 7H), 1.29 (s, 6H). MS (ESI): mass calculated for C$_{24}$H$_{30}$N$_4$O$_4$S, 470.20; m/z found, 471.1 [M+H]$^+$.

Example 162 meso-2-{[4-({2-[8-Acetyl-3,8-diazabicyclo[3.2.1]oct-3-yl]ethyl}oxy)phenyl]oxy}[1,3]thiazolo[4,5-b]pyridine

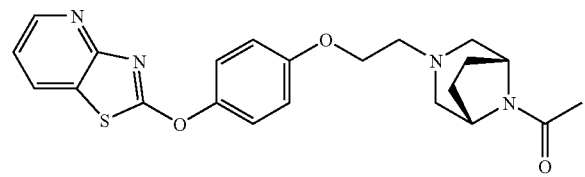

$^1$H NMR (300 MHz, CDCl$_3$): 8.53 (d, J=3.9, 1H), 7.97 (d, J=7.8, 1H), 7.29 (d, J=8.7, 2H), 7.16 (d, J=5.1, 1H), 6.91 (d, J=8.7, 2H), 4.61 (br s, 1H), 4.12-4.10 (m, 3H), 2.83-2.70 (m, 4H), 2.46-2.04 (m, 2H), 2.05 (s, 3H), 2.01-1.76 (m, 4H). MS (ESI): mass calculated for C$_{22}$H$_{24}$N$_4$O$_3$S, 424.16; m/z found, 425.1 [M+H]$^+$.

Example 163

N-[1-(2-{[4-([1,3]Thiazolo[4,5-b]pyridin-2-yloxy)phenyl]oxy}ethyl)piperidin-4-yl]methanesulfonamide

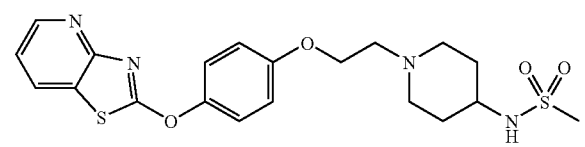

$^1$H NMR (300 MHz, CDCl$_3$): 8.58 (d, J=3.6, 1H), 8.00 (d, J=7.8, 1H), 7.28 (d, J=9.0, 2H), 7.22-7.17 (m, 1H), 6.96 (d, J=9.0, 2H), 4.93 (brs, 1H), 4.13 (t, J=4.8, 2H), 3.35-3.32 (m, 1H), 2.98 (s, 3H), 2.95-2.91 (m, 2H), 2.79 (t, J=5.4, 2H), 2.24 (t, J=5.4, 2H), 2.47 (s, 3H), 2.42 (s, 3H). MS (ESI): mass calculated for C$_{19}$H$_{23}$N$_3$O$_3$S, 373.15; m/z found, 374.1 [M+H]$^+$.

Example 164

2-{[4-({2-[4-(Trifluoromethyl)piperidin-1-yl]ethyl}oxy)phenyl]oxy}[1,3]thiazolo[4,5-c]pyridine

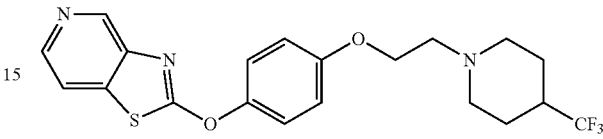

$^1$H NMR (300 MHz, CDCl$_3$): 8.99 (s, 1H), 8.43 (d, J=5.4, 1H), 7.63 (d, J=5.4, 1H), 7.28 (d, J=9.0, 2H), 6.98 (d, J=9.0, 2H), 4.13 (t, J=5.7, 2H), 3.11 (d, J=11.4, 2H), 2.84 (t, J=5.7, 2H), 2.17-1.63 (m, 7H). MS (ESI): mass calculated for C$_{20}$H$_{20}$F$_3$N$_3$O$_2$S, 423.12; m/z found, 424.1 [M+H]$^+$.

Example 165

N-Methyl-1-[2-({4-[(7-methyl[1,3]thiazolo[4,5-b]pyridin-2-yl)oxy]phenyl}oxy)ethyl]piperidine-4-carboxamide

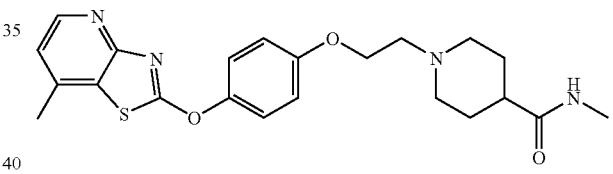

$^1$H NMR (300 MHz, CDCl$_3$): 8.44 (d, J=5.1, 1H), 7.31 (d, J=9.0, 2H), 7.01 (d, J=4.8, 1H), 6.95 (d, J=9.0, 2H), 5.57 (br s 1H), 4.14 (t, J=5.7, 2H), 3.08 (d, J=11.1, 2H), 2.84-2.80 (m, 5H), 2.48 (s, 3H), 2.21-2.10 (m, 3H), 1.88-1.78 (m, 4H). MS (ESI): mass calculated for C$_{22}$H$_{26}$N$_4$O$_3$S, 426.17; m/z found, 427.1 [M+H]$^+$.

Example 166 meso-N-{(3-endo)-8-[2-({4-[(7-Methyl[1,3]thiazolo[4,5-b]pyridin-2-yl)oxy]phenyl}oxy)ethyl]-8-azabicyclo[3.2.1]oct-3-yl}glycinamide Hydrochloride

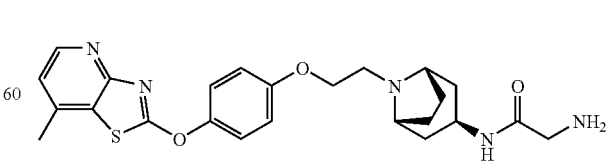

$^1$H NMR (300 MHz, CD$_3$OD): 8.36 (d, J=5.1, 1H), 7.41 (d, J=9.0, 2H), 7.20 (d, J=5.1, 1H), 7.15 (d, J=9.0, 2H), 4.46 (br s, 2H), 4.16 (br s, 2H), 4.06 (t, J=6.0, 1H), 3.76 (s, 2H), 3.59 (t, J=11.4, 2H), 1.98 (d, J=11.7, 2H), 1.64-1.53 (m, 2H). MS (ESI): mass calculated for C$_{20}$H$_{24}$N$_4$O$_4$S$_2$, 448.12; m/z found, 449.1[M+H]$^+$.

(br s, 2H), 2.58-2.40 (m, 9H), 2.20 (d, J=16.2, 2H). MS (ESI): mass calculated for C$_{24}$H$_{29}$N$_{5}$O$_{3}$S, 467.20; m/z found, 468.1 [M+H]$^+$.

Example 167

2-({4-[(4-Pyrimidin-2-ylpiperazin-1-yl)methyl]phenyl}oxy)[1,3]thiazolo[4,5-b]pyrazine

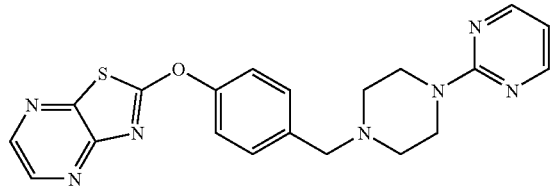

$^1$H NMR (300 MHz, CDCl$_3$): 8.53 (s, 1H), 8.33 (d, J=13.2, 3H), 7.47 (br s, 2H), 7.39 (br s, 2H), 6.49 (br s, 1H), 3.87 (br s, 4H), 3.59 (br s, 2H), 2.54 (br s, 4H). MS (ESI): mass calculated for C$_{20}$H$_{19}$N$_{7}$OS, 405.14; m/z found, 406.1 [M+H]$^+$.

Example 168

7-Methyl-2-({4-[(4-pyridin-4-ylpiperazin-1-yl)methyl]phenyl}oxy)[1,3]thiazolo[4,5-b]pyridine

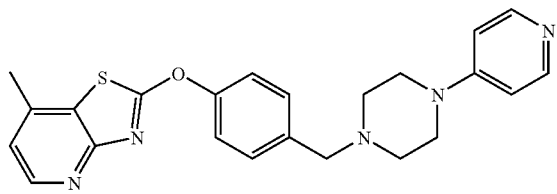

$^1$H NMR (300 MHz, CDCl$_3$): 8.45 (d, J=4.8, 1H), 8.27 (d, J=5.1, 2H), 7.42 (dd, J=13.2, 5.1, 4H), 7.03 (d, J=4.5, 1H), 6.67 (d, J=5.4, 2H), 3.70 (s, 2H), 3.53 (br s, 4H), 2.59 (br s, 4H), 2.51 (s, 3H). MS (ESI): mass calculated for C$_{23}$H$_{23}$N$_{5}$OS, 417.16; m/z found, 418.1 [M+H]$^+$.

Example 169 meso-(3-endo)-8-Acetyl-N-{[4-([1,3]thiazolo[4,5-b]pyridin-2-yloxy)phenyl]methyl}-8-azabicyclo[3.2.1]octan-3-amine

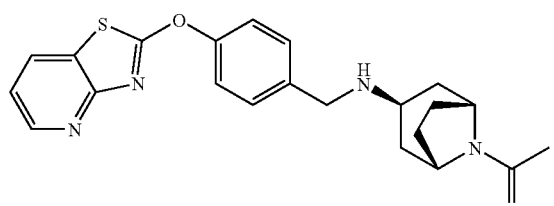

$^1$H NMR (300 MHz, CDCl$_3$): 8.53 (d, J=4.5, 1H), 8.00 (d, J=7.8, 1H), 7.40-7.30 (m, 4H), 7.21-7.15 (m, 1H), 4.61 (br s, 1H), 4.10 (br s, 1H), 3.77 (s, 2H), 3.04 (t, J=5.1, 1H), 2.32-1.85 (m, 9H), 1.77-1.62 (m, 2H). MS (ESI): mass calculated for C$_{22}$H$_{24}$N$_{4}$O$_{2}$S, 408.16; m/z found, 409.0 [M+H]$^+$.

Example 170 meso-(3-exo)-8-Acetyl-N-{[4-([1,3]thiazolo[4,5-b]pyridin-2-yloxy)phenyl]methyl}-8-azabicyclo[3.2.1]octan-3-amine

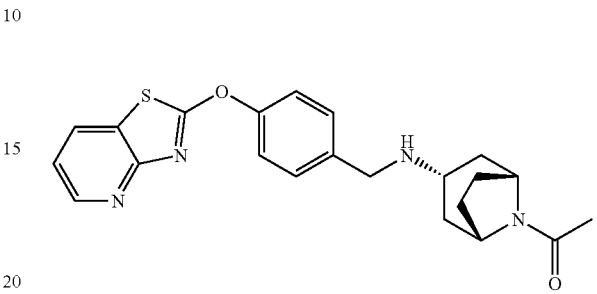

$^1$H NMR (300 MHz, CDCl$_3$): 8.55 (d, J=4.5, 1H), 8.03 (d, J=8.1, 1H), 7.42-7.34 (m, 4H), 7.23-7.18 (m, 1H), 4.71 (br s, 1H), 4.16 (br s, 1H), 3.82 (s, 2H), 3.14-3.10 (m, 1H), 2.07-1.88 (m, 7H), 1.79-1.38 (m, 5H). MS (ESI): mass calculated for C$_{22}$H$_{24}$N$_{4}$O$_{2}$S, 408.16; m/z found, 409.3 [M+H]$^+$.

Example 171 meso-3-{[4-([1,3]Thiazolo[4,5-b]pyridin-2-yloxy)phenyl]methyl}-3,8-diazabicyclo[3.2.1]octane-8-carboxamide

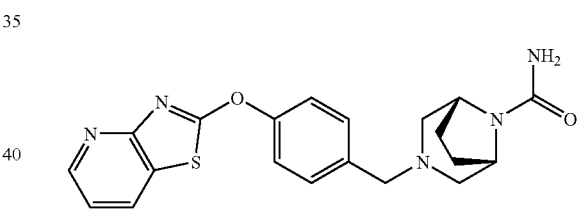

$^1$H NMR (300 MHz, CDCl$_3$): 8.55 (d, J=4.5, 1H), 8.02 (d, J=7.8, 1H), 7.40-7.33 (m, 4H), 7.24-7.18 (m, 1H), 4.44 (brs, 2H), 4.10 (brs, 2H), 3.50 (s, 2H), 2.65 (d, J=10.5, 2H), 2.37 (d, J=10.8, 2H), 1.98-1.91 (m, 4H). MS (ESI): mass calculated for C$_{20}$H$_{21}$N$_{5}$O$_{2}$S, 395.14; m/z found, 396.0 [M+H]$^+$.

Example 172

N,N-Dimethyl-1-({4-[(6-methyl[1,3]thiazolo[4,5-b]pyridin-2-yl)oxy]phenyl}methyl)piperidine-4-carboxamide

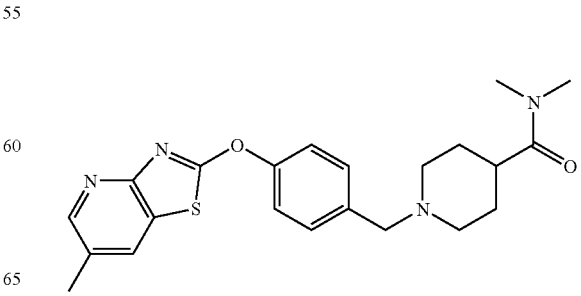

$^1$H NMR (300 MHz, CDCl$_3$): 8.39 (s, 1H), 7.83 (s, 1H), 7.38 (br s, 4H), 3.55 (br s, 2H), 3.06-2.90 (m, 7H), 2.55-2.40 (m, 4H), 2.04-1.88 (m, 4H), 1.72-1.60 (m, 3H). MS (ESI): mass calculated for C$_{22}$H$_{26}$N$_4$O$_2$S, 410.18; m/z found, 411.2 [M+H]$^+$.

Example 173

2-[(4-{[4-(2-Thienylacetyl)piperazin-1-yl]methyl}phenyl)oxy][1,3]thiazolo[4,5-b]pyrazine

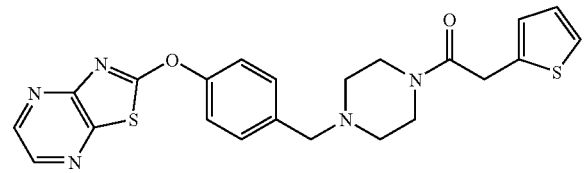

$^1$H NMR (300 MHz, CDCl$_3$): 8.52 (d, J=2.4, 1H), 8.36 (d, J=2.4, 1H), 7.44-7.34 (m, 4H), 7.22-7.20 (m, 1H), 6.98-6.94 (m, 1H), 6.91 (s, 1H), 3.92 (s, 2H), 3.69 (br s, 2H), 3.54 (br s, 4H), 2.50-2.35 (m, 4H). MS (ESI): mass calculated for C$_{22}$H$_{21}$N$_5$O$_2$S$_2$, 451.11; m/z found, 452.0 [M+H]$^+$.

Example 174

N-Ethyl-N-{2-[4-([1,3]thiazolo[5,4-b]pyridin-2-yloxy)phenyl]ethyl}cyclopropanamine

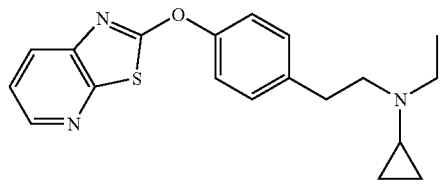

$^1$H NMR (300 MHz, CDCl$_3$): 8.40 (d, J=4.5, 1H), 7.94 (d, J=8.1, 1H), 7.35-7.25 (m, 5H), 2.92-2.70 (m, 6H), 1.56 (br s, 2H), 1.25 (s, 1H), 1.12 (br s, 2H), 0.53-0.44 (m, 3H). MS (ESI): mass calculated for C$_{19}$H$_{21}$N$_3$OS, 339.14; m/z found, 340.5 [M+H]$^+$.

Example 175

N-Methyl-N-[4-([1,3]thiazolo[5,4-c]pyridin-2-yloxy)benzyl]cyclohexanamine

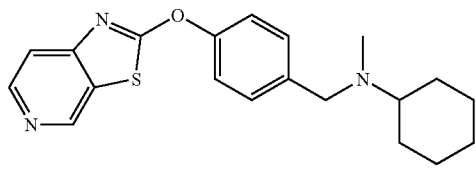

$^1$H NMR (300 MHz, CDCl$_3$): 8.92 (s, 1H), 8.56 (br s, 1H), 7.62 (s, 1H), 7.43-7.31 (m, 4H), 3.61 (s, 2H), 2.51 (br s, 1H), 2.22 (s, 3H), 2.00-1.79 (m, 4H), 1.77-1.55 (m, 2H), 1.40-1.15 (m, 4H). MS (ESI): mass calculated for C$_{20}$H$_{23}$N$_3$OS, 353.16; m/z found, 354.2 [M+H]$^+$.

Example 176

2-{4-[2-(4-Acetylpiperazin-1-yl)ethyl]phenoxy}[1,3]thiazolo[5,4-c]pyridine

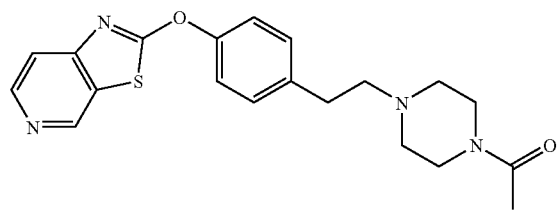

$^1$H NMR (300 MHz, CDCl$_3$): 8.93 (s, 1H), 8.56 (s, 1H), 7.62 (d, J=4.8, 1H), 7.40-7.28 (m, 4H), 3.66 (br s, 2H), 3.51 (br s, 2H), 2.87 (br s, 2H), 2.70-2.50 (m, 6H), 2.11 (s, 3H). MS (ESI): mass calculated for C$_{20}$H$_{22}$N$_4$O$_2$S, 382.15; m/z found, 405.1 [M+Na]$^+$.

Example 177

1-{2-[4-([1,3]Thiazolo[4,5-b]pyrazin-2-yloxy)phenyl]ethyl}-1,4-diazepan-5-one

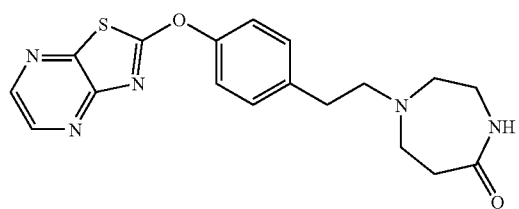

$^1$H NMR (300 MHz, CD$_3$OD): 8.55 (s, 1H), 8.45 (s, 1H), 7.44-7.28 (m, 4H), 3.11-2.67 (m, 12H). MS (ESI): mass calculated for C$_{18}$H$_{19}$N$_5$O$_2$S, 369.13; m/z found, 370.1 [M+H]$^+$.

Example 178

N-Ethyl-N-(2-{4-[(6-methyl[1,3]thiazolo[4,5-b]pyridin-2-yl)oxy]phenyl}ethyl)butan-1-amine

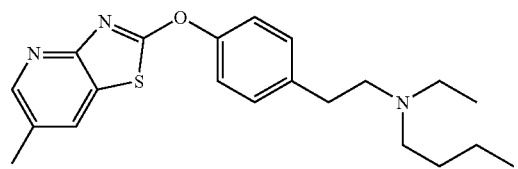

$^1$H NMR (300 MHz, CD$_3$OD): 8.35 (s, 1H), 8.14 (s, 1H), 7.42-7.37 (m, 4H), 2.86-2.69 (m, 6H), 2.69 (t, J=7.8, 2H), 2.48 (s, 3H), 1.56-1.53 (m, 2H), 1.41-1.36 (m, 2H), 1.15 (t,

Example 179

2-{[4-(2-Azepan-1-ylethyl)phenyl]oxy}[1,3]thiazolo[4,5-b]pyrazine

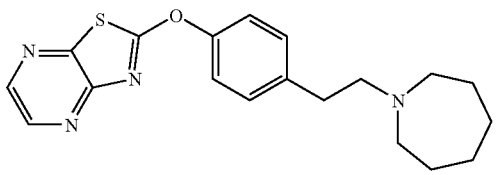

$^1$H NMR (300 MHz, CD$_3$OD): 8.56 (s, 1H), 8.46 (s, 1H), 7.46-7.38 (m, 4H), 2.94-2.82 (m, 8H), 1.77-1.71 (m, 8H). MS (ESI): mass calculated for C$_{19}$H$_{22}$N$_4$OS, 354.15; m/z found, 355.1 [M+H]$^+$.

Example 180

2-({4-[2-(4-Fluoropiperidin-1-yl)ethyl]phenyl}oxy)[1,3]thiazolo[4,5-b]pyrazine

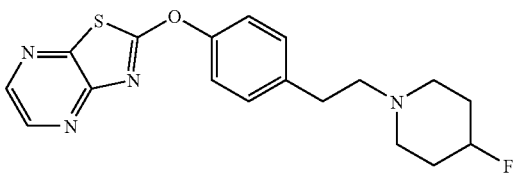

$^1$H NMR (300 MHz, CD$_3$OD): 8.55 (d, J=2.4, 1H), 8.44 (d, J=2.4, 1H), 7.43-7.40 (m, 4H), 4.85-4.65 (m, 1H), 2.94-2.90 (m, 2H), 2.72-2.68 (m, 4H), 2.62-2.55 (m, 2H), 2.09-1.85 (m, 4H). MS (ESI): mass calculated for C$_{18}$H$_{19}$FN$_4$OS, 358.13; m/z found, 359.1 [M+H]$^+$.

Example 181 meso-(3-exo)-8-Acetyl-N-({4-[(6-methyl[1,3]thiazolo[4,5-b]pyridin-2-yl)oxy]phenyl}methyl)-8-azabicyclo[3.2.1]octan-3-amine

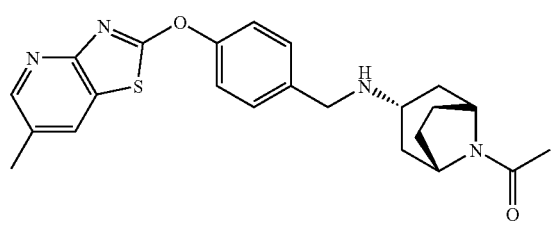

$^1$H NMR (300 MHz, CDCl$_3$): 8.37 (s, 1H), 7.81 (s, 1H), 7.36 (br s, 4H), 4.69 (br s, 1H), 4.14 (br s, 1H), 3.81 (s, 2H), 3.12-3.07 (m, 1H), 2.42 (s, 3H), 2.06-1.87 (m, 7H), 1.77-1.37 (m, 4H). MS (ESI): mass calculated for C$_{23}$H$_{26}$N$_4$O$_2$S, 422.18; m/z found, 423.0 [M+H]$^+$.

Example 182 meso-N-[(3-endo)-8-{[4-([1,3]Thiazolo[4,5-b]pyridin-2-yloxy)phenyl]methyl}-8-azabicyclo[3.2.1]oct-3-yl]methanesulfonamide

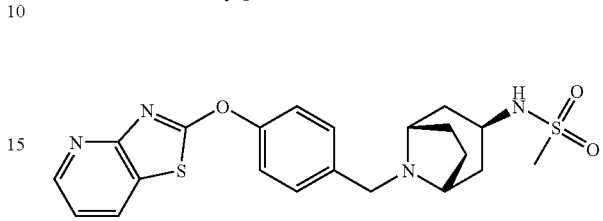

$^1$H NMR (300 MHz, CDCl$_3$): 8.60 (d, J=4.8, 1H), 8.06 (d, J=7.8, 1H), 7.51 (d, J=8.1, 2H), 7.40 (d, J=8.1, 2H), 7.30-7.23 (m, 1H), 4.67 (br, s, 1H), 3.78-3.75 (m, 1H), 3.60 (br s, 2H), 3.23 (br s, 2H), 3.00 (br s, 3H), 2.35-2.16 (m, 4H), 1.97-1.77 (m, 4H). MS (ESI): mass calculated for C$_{21}$H$_{24}$N$_4$O$_3$S$_2$, 444.13; m/z found, 445.0 [M+H]$^+$.

Example 183

2-({4-[(4-Cyclobutylpiperazin-1-yl)methyl]phenyl}oxy)-6-methyl[1,3]thiazolo[4,5-b]pyridine

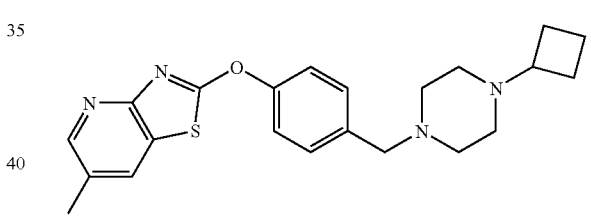

$^1$H NMR (300 MHz, CDCl$_3$): 8.38 (s, 1H), 7.82 (s, 1H), 7.37 (br s, 4H), 3.59 (br s, 2H), 3.05 (br s, 2H), 2.75 (br s, 7H), 2.43-2.35 (m, 5H), 2.13-2.05 (m, 2H), 1.91-1.67 (m, 2H). MS (ESI): mass calculated for C$_{22}$H$_{26}$N$_4$OS, 394.18; m/z found, 395.0 [M+H]$^+$.

Example 184

2-[(4-{[4-(Pyrimidin-2-yloxy)piperidin-1-yl]methyl}phenyl)oxy][1,3]thiazolo[4,5-b]pyrazine

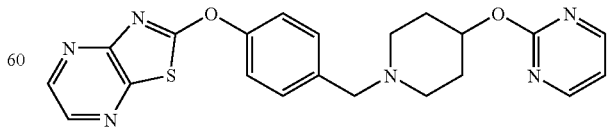

$^1$H NMR (300 MHz, CDCl$_3$): 8.52-8.50 (m, 3H), 8.35 (d, J=2.1, 1H), 7.47 (br s, 2H), 7.37 (d, J=8.1, 2H), 6.92 (t, J=4.5, 1H), 5.12 (br s, 1H), 3.61 (br s, 2H), 2.84 (br s, 2H), 2.41 (br s, 2H), 2.10-1.97 (m, 4H). MS (ESI): mass calculated for $C_{21}H_{20}N_6O_2S$, 420.14; m/z found, 421.1 [M+H]$^+$.

Example 185 meso-2-[(4-{[8-Acetyl-3,8-diazabicyclo[3.2.1]oct-3-yl]methyl}phenyl)oxy][1,3]thiazolo[4,5-b]pyridine

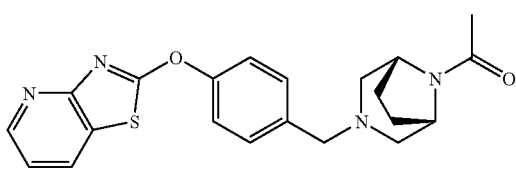

$^1$H NMR (300 MHz, CDCl$_3$): 8.56 (d, J=3.9, 1H), 8.12-8.03 (m, 1H), 7.50 (d, J=7.8, 2H), 7.40 (d, J=8.4, 2H), 7.24-7.20 (m, 1H), 4.71 (br s, 1H), 4.12 (br s, 1H), 3.75-3.71 (m, 2H), 2.95-2.87 (m, 2H), 2.55 (d, J=9.9, 1H), 2.42 (d, J=10.2, 1H), 2.25-1.85 (m, 7H). MS (ESI): mass calculated for $C_{21}H_{22}N_4O_2S$, 394.15; m/z found, 395.1 [M+H]$^+$.

Example 186

N-(Cycloproplylmethyl)-N-{[4-([1,3]thiazolo[4,5-c]pyridin-2-yloxy)phenyl]methyl}propan-1-amine

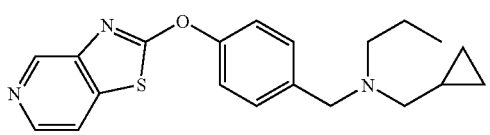

$^1$H NMR (300 MHz, CD$_3$OD): 8.86 (s, 1H), 8.40 (d, J=4.8, 1H), 7.96 (d, J=5.1, 1H), 7.57 (d, J=8.4, 2H), 7.44 (d, J=8.4, 2H), 3.89 (s, 2H), 2.70-2.45 (m, 4H), 1.67-1.59 (m, 2H), 0.95 (t, J=7.2, 4H), 0.60 (d, J=7.8, 2H), 0.19 (d, J=4.5, 2H). MS (ESI): mass calculated for $C_{20}H_{23}N_3OS$, 353.16; m/z found, 354.2 [M+H]$^+$.

Example 187

6-Chloro-2-[(4-{[4-(2-thienylcarbonyl)piperazin-1-yl]methyl}phenyl)oxy][1,3]thiazolo[4,5-b]pyridine

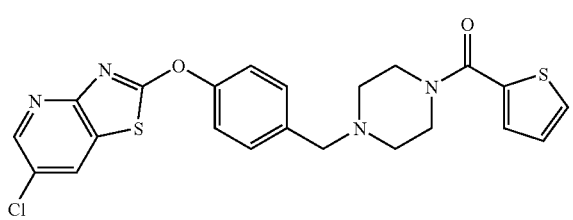

$^1$H NMR (300 MHz, CDCl$_3$): 8.51 (s, 1H), 8.02 (s, 1H), 7.45-7.28 (m, 6H), 7.07-7.04 (m, 1H), 3.80 (br s, 4H), 3.60 (s, 2H), 2.54 (br s, 4H). MS (ESI): mass calculated for $C_{22}H_{19}ClN_4O_2S_2$, 470.06; m/z found, 471.0 [M+H]$^+$.

Example 188

6-Chloro-2-[(4-{[5-(methylsulfonyl)hexahydropyrrolo[3,4-c]pyrrol-2(1H)-yl]methyl}phenyl)oxy][1,3]thiazolo[4,5-b]pyridine

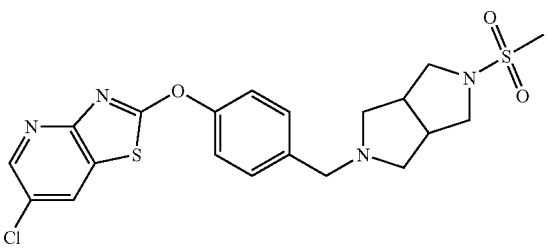

$^1$H NMR (300 MHz, CDCl$_3$): 8.51 (s, 1H), 8.02 (s, 1H), 7.42-7.35 (m, 4H), 3.64 (s, 2H), 3.50-3.45 (m, 2H), 3.12 (d, J=9.9, 2H), 2.92-2.87 (m, 5H), 2.69 (s, 2H), 2.48 (d, J=9.0, 2H). MS (ESI): mass calculated for $C_{20}H_{21}ClN_4O_3S_2$, 464.07; m/z found, 465.1 [M+H]$^+$.

Example 189

6-Chloro-2-{[4-(thiomorpholin-4-ylmethyl)phenyl]oxy}[1,3]thiazolo[4,5-b]pyridine

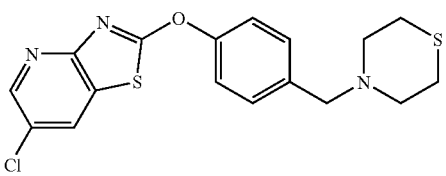

$^1$H NMR (300 MHz, CDCl$_3$): 8.48 (s, 1H), 7.99 (s, 1H), 7.40-7.31 (m, 4H), 3.53 (s, 2H), 2.92-2.69 (m, 8H). MS (ESI): mass calculated for $C_{17}H_{16}ClN_3OS_2$, 377.04; m/z found, 378.9 [M+H]$^+$.

Example 190

2-({4-[(4-pyridin-4-ylpiperidin-1-yl)methyl]phenyl}oxy)[1,3]thiazolo[4,5-c]pyridine

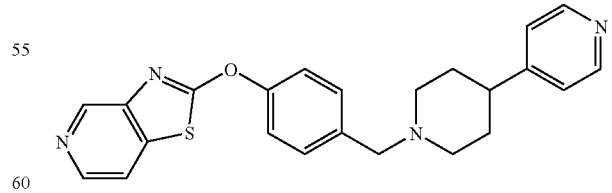

$^1$H NMR (300 MHz, CD$_3$OD): 9.00 (s, 1H), 8.52 (d, J=3.6, 2H), 8.45 (d, J=5.1, 1H), 7.66 (d, J=5.4, 1H), 7.48 (d, J=8.1, 2H), 7.36 (d, J=8.4, 2H), 7.17 (d, J=5.1, 2H), 3.66 (s, 2H), 3.12 (d, J=11.1, 2H), 2.58-2.50 (m, 1H), 2.25-2.16 (m, 2H), 1.88-1.86 (m, 4H). MS (ESI): mass calculated for $C_{23}H_{22}N_4OS$, 402.15; m/z found, 403.1 [M+H]$^+$.

Example 191

(1R,4R)-5-({4-[(6-Chloro[1,3]thiazolo[4,5-b]pyridin-2-yl)oxy]phenyl]methyl)-2,5-diazabicyclo[2.2.1]heptane-2-carboxamide

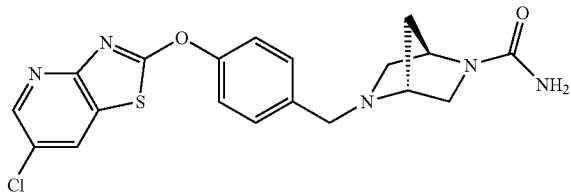

¹H NMR (300 MHz, CD₃OD): 8.45 (s, 1H), 8.37 (s, 1H), 7.55 (d, J=8.4, 2H), 7.41 (d, J=8.4, 2H), 4.42 (s, 1H), 3.92 (s, 2H), 3.72 (s, 1H), 3.57 (d, J=10.2, 1H), 2.97 (d, J=10.2, 1H), 2.83 (d, J=10.2, 1H), 2.02 (d, J=9.0, 1H), 1.84 (d, J=9.9, 1H), 1.28 (br s, 1H). MS (ESI): mass calculated for $C_{19}H_{18}ClN_5O_2S$, 415.09; m/z found, 416.1 [M+H]⁺.

Example 192

N-(1-{2-[4-([1,3]Thiazolo[5,4-c]pyridin-2-yloxy)phenyl]ethyl}piperidin-4-yl)cyclopropanecarboxamide

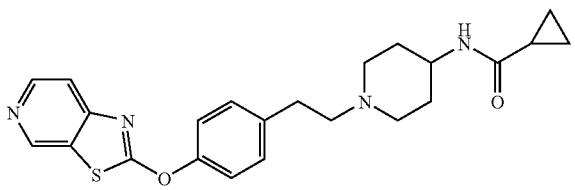

¹H NMR (300 MHz, CD₃OD): 8.97 (s, 1H), 8.48 (s, 1H), 7.66 (s, 1H), 7.39-7.33 (m, 4H), 3.90-3.70 (m, 1H), 3.07-2.99 (m, 2H), 2.91-2.86 (m, 2H), 2.68 (br s, 2H), 2.26 (brs, 2H), 1.96 (d, J=11.7, 2H), 1.80-1.50 (m, 2H), 1.30-1.10 (m, 1H), 0.83-0.72 (m, 4H). MS (ESI): mass calculated for $C_{23}H_{26}N_4O_2S$, 422.18; m/z found, 423.1 [M+H]⁺.

Example 193

(1S,4S)-5-({4-[(6-Chloro[1,3]thiazolo[4,5-b]pyridin-2-yl)oxy]phenyl}methyl)-2,5-diazabicyclo[2.2.1]heptane-2-carboxamide

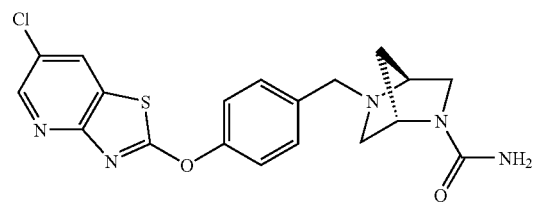

¹H NMR (300 MHz, CD₃OD): 8.51 (d, J=1.8, 1H), 8.42 (d, J=1.8, 1H), 7.63 (d, J=8.4, 2H), 7.49 (d, J=8.1, 2H), 4.53 (s, 1H), 4.20-4.00 (m, 2H), 3.92 (s, 1H), 3.66 (d, J=10.2, 1H), 3.41 (s, 1H), 3.15-2.95 (m, 2H), 2.15 (d, J=7.6, 1H), 1.96 (d, J=9.9, 1H). MS (ESI): mass calculated for $C_{19}H_{18}ClN_5O_2S$, 415.09; m/z found, 416.8 [M+H]⁺.

Example 194 meso-N-[(3-exo)-8-{2-[4-([1,3]Thiazolo[5,4-b]pyridin-2-yloxy)phenyl]ethyl}-8-azabicyclo[3.2.1]oct-3-yl]methanesulfonamide

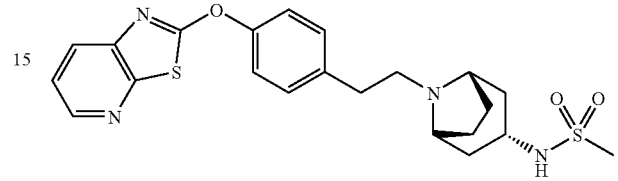

¹H NMR (300 MHz, CDCl₃): 8.40 (s, 1H), 7.93 (d, J=7.8, 1H), 7.35-7.25 (m, 5H), 4.16 (brs, 1H), 3.65 (brs, 1H), 3.36 (brs, 2H), 2.97 (s, 3H), 2.84-2.81 (m, 2H), 2.66-2.61 (m, 2H), 1.99-1.89 (m, 4H), 1.73-1.65 (m, 4H). MS (ESI): mass calculated for $C_{22}H_{26}N_4O_3S_2$, 458.14; m/z found, 459.1 [M+H]⁺.

Example 195

(4-Chlorophenyl)(1-{2-[4-([1,3]thiazolo[4,5-c]pyridin-2-yloxy)phenyl]ethyl}piperidin-4-yl)methanone

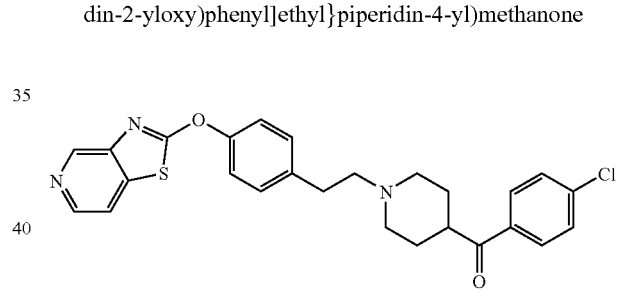

¹H NMR (300 MHz, CD₃OD): 8.85 (s, 1H), 8.39 (d, J=4.5, 1H), 8.0 (d, J=7.5, 2H), 7.94 (d, J=4.5, 1H), 7.54 (d, J=7.8, 2H), 7.43-7.34 (m, 4H), 3.44 (s, 1H), 3.21-3.12 (m, 2H), 2.92 (d, J=7.5, 2H), 2.72-2.67 (m, 2H), 2.37-2.29 (m, 2H), 1.95-1.79 (m, 4H). MS (ESI): mass calculated for $C_{26}H_{24}ClN_3O_2S$, 477.13; m/z found, 478.1 [M+H]⁺.

Example 196

N-Propyl-N-{2-[4-([1,3]thiazolo[4,5-c]pyridin-2-yloxy)phenyl]ethyl}propan-1-amine

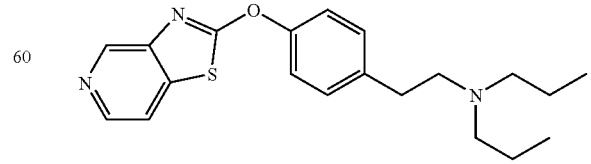

¹H NMR (300 MHz, CD₃OD): 8.97 (s, 1H), 8.49 (d, J=5.7, 1H), 7.65 (d, J=5.4, 1H), 7.41-7.32 (m, 4H), 2.86-2.74 (m,

4H), 2.54 (t, J=7.8, 4H), 1.59-1.51 (m, 4H), 0.96-0.91 (m, 6H). MS (ESI): mass calculated for $C_{20}H_{25}N_3OS$, 355.17; m/z found, 356.1 $[M+H]^+$.

Example 197

6-Chloro-2-[(4-{2-[4-(cyclopropylcarbonyl)piperazin-1-yl]ethyl}phenyl)oxy][1,3]thiazolo[4,5-b]pyridine

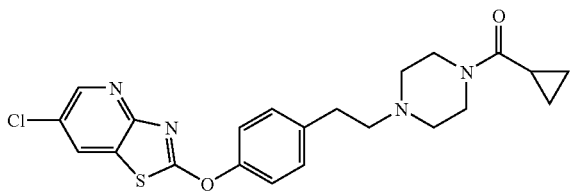

$^1$H NMR (300 MHz, $CDCl_3$): 8.49 (d, J=2.4, 1H), 7.99 (d, J=2., 1H), 7.34-7.24 (m, 4H), 3.69 (br s, 4H), 2.85 (br s, 2H), 2.64 (br s, 2H), 2.56 (br s, 4H), 1.76-1.72 (m, 1H), 1.01-0.99 (m, 2H), 0.78-0.76 (m, 2H). MS (ESI): mass calculated for $C_{22}H_{23}ClN_4O_2S$, 442.12; m/z found, 443.1 $[M+H]^+$.

Example 198

6-Methyl-2-[(4-{2-[4-(pyrrolidin-1-ylcarbonyl)piperidin-1-yl]ethyl}phenyl)oxy][1,3]thiazolo[4,5-b]pyridine

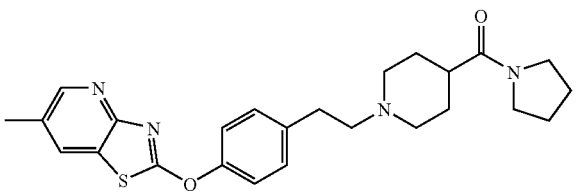

$^1$H NMR (300 MHz, $CDCl_3$): 8.38 (s, 1H), 7.80 (s, 1H), 7.30-7.24 (m, 4H), 3.49-3.44 (m, 5H), 3.08 (br s, 2H), 2.84 (br s, 2H), 2.60 (br s, 2H), 2.42 (s, 3H), 1.97-1.76 (m, 10H). MS (ESI): mass calculated for $C_{25}H_{30}N_4O_2S$, 450.21; m/z found, 451.1 $[M+H]^+$.

Example 199 meso-1-{(3-exo)-8-[4-([1,3]Thiazolo[4,5-b]pyrazin-2-yloxy)benzyl]-8-azabicyclo[3.2.1]oct-3-yl}urea

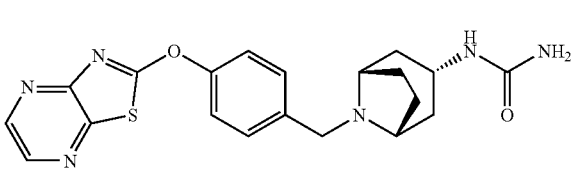

$^1$H NMR (300 MHz, $CD_3OD$): 8.51 (s, 1H), 8.41 (s, 1H), 7.57 (d, J=7.8, 2H), 7.40 (d, J=8.4, 2H), 3.83-3.79 (m, 1H), 3.62 (s, 2H), 3.19 (br s, 2H), 2.16 (br s, 4H), 1.96 (d, J=7.5, 2H), 1.65 (d, J=14.4, 2H). MS (ESI): mass calcd. for $C_{20}H_{22}N_6O_2S$, 410.15; m/z found, 411.1 $[M+H]^+$.

Example 200 meso-1-{(3-exo)-8-[4-([1,3]Thiazolo[5,4-c]pyridin-2-yloxy)benzyl]-8-azabicyclo[3.2.1]oct-3-yl}urea

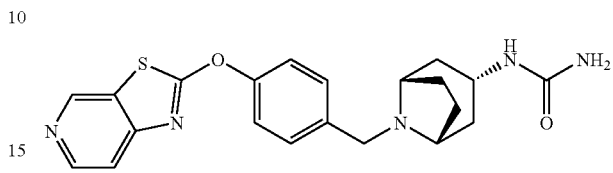

$^1$H NMR (300 MHz, $CD_3OD$): 8.97 (s, 1H), 8.48 (d, J=5.7, 1H), 7.66 (d, J=5.4, 1H), 7.56 (d, J=8.1, 2H), 7.38 (d, J=8.1, 2H), 3.81 (br s, 1H), 3.62 (br s, 2H), 3.20 (br s, 2H), 2.14 (br s, 4H), 1.96 (d, J=7.5, 2H), 1.65 (d, J=14.4, 2H). MS (ESI): mass calcd. for $C_{21}H_{23}N_5O_2S$, 409.16; m/z found, 410.1 $[M+H]^+$.

Example 201 meso-(3-exo)-3-{[4-([1,3]Thiazolo[5,4-b]pyridin-2-yloxy)benzyl]amino}-8-azabicyclo[3.2.1]octane-8-carboxamide

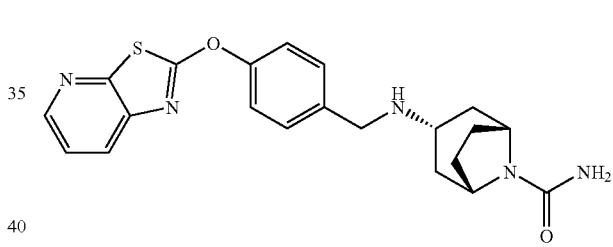

$^1$H NMR (300 MHz, $CD_3OD$): 8.43 (d, J=4.8, 1H), 8.02 (d, J=8.1, 1H), 7.56-7.49 (m, 3H), 7.41 (d, J=8.4, 2H), 4.30 (br s, 2H), 3.85 (s, 2H), 3.22-3.05 (m, 1H), 1.98 (d, J=7.5, 4H), 3.46 (d, J=7.5, 2H), 1.71-1.59 (m, 2H). MS (ESI): mass calcd. for $C_{21}H_{23}N_5O_2S$, 409.16; m/z found, 410.1 $[M+H]^+$.

Example 202 meso-3-[4-([1,3]Thiazolo[4,5-c]pyridin-2-yloxy)benzyl]-3,8-diazabicyclo[3.2.1]octane-8-carboxamide

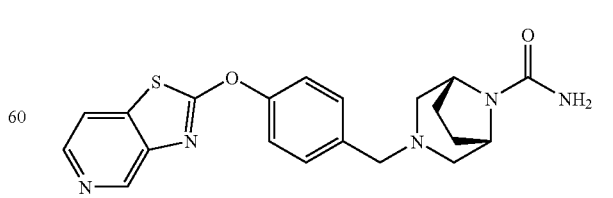

$^1$H NMR (300 MHz, $CDCl_3$): 9.00 (s, 1H), 8.45 (d, J=5.1, 1H), 7.65 (d, J=5.1, 1H), 7.42 (d, J=7.8, 2H), 7.33 (d, J=7.8, 2H), 4.41 (br s, 2H), 4.11 (br s, 2H), 3.53 (s, 2H), 2.67 (d,

J=10.2, 2H), 2.40 (d, J=10.2, 2H), 2.01-1.93 (m, 4H). MS (ESI): mass calcd. for $C_{20}H_{21}N_5O_2S$, 395.14; m/z found, 396.1 $[M+H]^+$.

Example 203 meso-3-{4-[(7-Methyl[1,3]thiazolo[4,5-b]pyridin-2-yl)oxy]benzyl}-3,8-diazabicyclo[3.2.1]octane-8-carboxamide

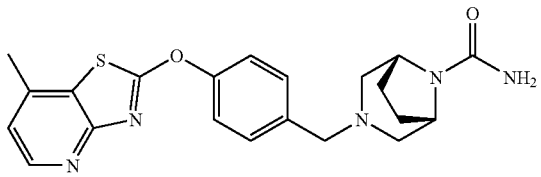

$^1$H NMR (300 MHz, CDCl$_3$): 8.43 (d, J=4.8, 1H), 7.36 (br s, 3H), 7.25 (br s, 1H), 7.02 (s, 1H), 4.39 (br s, 2H), 4.10 (br s, 2H), 3.74-3.71 (m, 1H), 3.50 (br s, 2H), 2.65 (d, J=10.5, 1H), 2.50 (br s, 3H), 2.37 (d, J=10.5, 1H), 2.04-1.91 (m, 3H), 1.26-1.21 (m, 2H). MS (ESI): mass calcd. for $C_{21}H_{23}N_5O_2S$, 409.16; m/z found, 410.1 $[M+H]^+$.

Example 204

N-(Cyclopropylmethyl)-N-[4-([1,3]thiazolo[5,4-c]pyridin-2-yloxy)benzyl]propane-1,3-diamine Hydrochloride

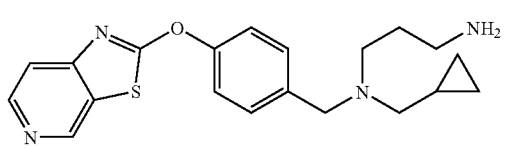

$^1$H NMR (300 MHz, D$_2$O): 9.46 (s, 1H), 8.82 (br s, 1H), 8.21 (br s, 1H), 7.86 (br s, 2H), 7.75 (br s, 2H), 4.73 (br s, 2H), 3.55 (br s, 2H), 3.33-3.23 (m, 4H), 2.37 (br s, 2H), 1.39-1.31 (m, 1H), 0.95 (br s, 2H), 0.54 (br s, 2H). MS (ESI): mass calcd. for $C_{20}H_{24}N_4OS$, 368.17; m/z found, 369.1 $[M+H]^+$.

Example 205 meso-7-Methyl-2-(4-{[3-(methylsulfonyl)-3,8-diazabicyclo[3.2.1]oct-8-yl]methyl}phenoxy)[1,3]thiazolo[4,5-b]pyridine

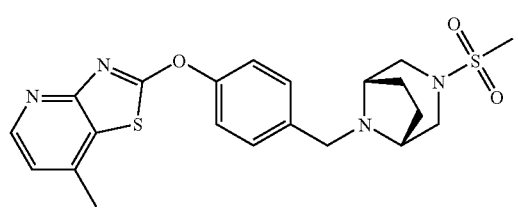

$^1$H NMR (300 MHz, CDCl$_3$): 8.44 (d, J=5.1, 1H), 7.55-7.38 (m, 4H), 7.02 (br s, 1H), 3.53 (br s, 2H), 3.43 (d, J=9.6, 2H), 3.27 (br s, 2H), 2.96 (d, J=10.2, 2H), 2.78 (br s, 3H), 2.51 (br s, 3H), 2.01 (br s, 2H), 1.90 (br s, 2H). MS (ESI): mass calcd. for $C_{21}H_{24}N_4O_3S_2$, 444.13; m/z found, 445.1 $[M+H]^+$.

Example 206

N-(1-{4-[(7-Methyl[1,3]thiazolo[4,5-b]pyridin-2-yl)oxy]benzyl}piperidin-4-yl)pyridine-4-carboxamide

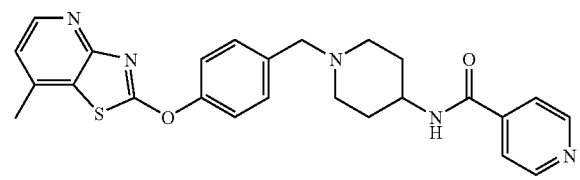

$^1$H NMR (300 MHz, CDCl$_3$): 8.77 (d, J=5.7, 2H), 8.46 (d, J=4.8, 1H), 7.65 (d, J=6.0, 2H), 7.56 (br s, 2H), 7.44 (d, J=8.4, 2H), 7.06 (d, J=4.8, 1H), 6.38 (br s, 1H), 4.13 (br s, 1H), 3.81 (br s, 2H), 3.52-3.48 (m, 1H), 3.15 (br s, 2H), 2.54 (s, 4H), 2.12-1.97 (m, 4H). MS (ESI): mass calcd. for $C_{25}H_{25}N_5O_2S$, 459.17; m/z found, 460.1 $[M+H]^+$.

Example 207

4-Methyl-1-[4-([1,3]thiazolo[5,4-b]pyridin-2-yloxy)benzyl]-1,4-diazepan-5-one

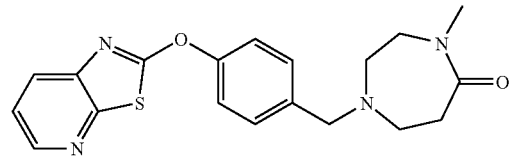

$^1$H NMR (300 MHz, CDCl$_3$): 8.40 (d, J=3.9, 1H), 7.92 (d, J=8.1, 1H), 7.42 (d, J=8.1, 2H), 7.32 (d, J=7.8, 3H), 3.61 (br s, 2H), 3.45 (br s, 2H), 2.98 (s, 3H), 2.68-2.62 (m, 6H). MS (ESI): mass calcd. for $C_{19}H_{20}N_4O_2S$, 368.13; m/z found, 369.2 $[M+H]^+$.

Example 208

3-(Cyclopropyl{2-[4-([1,3]thiazolo[5,4-c]pyridin-2-yloxy)phenoxy]ethyl}amino)propan-1-ol

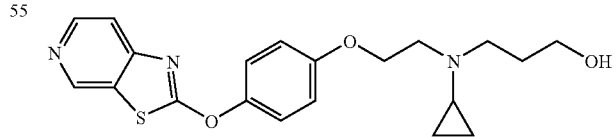

$^1$H NMR (300 MHz, CD$_3$OD): 8.99 (s, 1H), 8.52 (d, J=5.7, 1H), 7.69 (d, J=5.7, 1H), 7.37 (d, J=9.0, 2H), 7.10 (d, J=9.0, 2H), 4.25 (t, J=5.7, 2H), 3.67 (t, J=6.3, 2H), 3.11 (t, J=5.7, 2H), 2.92-2.87 (m, 2H), 1.97-1.87 (m, 1H), 1.85-1.80 (m, 2H), 0.63-0.50 (m, 4H). MS (ESI): mass calcd. for $C_{20}H_{23}N_3O_3S$, 385.15; m/z found, 386.1 $[M+H]^+$.

Example 209 meso-2-(4-{2-[8-Acetyl-3,8-diazabicyclo[3.2.1]oct-3-yl]ethyl}phenoxy)-7-methyl[1,3]thiazolo[4,5-b]pyridine

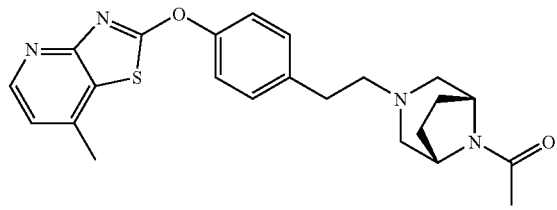

$^1$H NMR (300 MHz, CD$_3$OD): 8.26 (d, J=5.1, 1H), 7.30 (d, J=8.7, 2H), 7.24 (d, J=8.7, 2H), 7.09 (d, J=5.1, 1H), 4.42 (br s, 1H), 4.10 (br s, 1H), 2.76 (d, J=6.9, 2H), 2.70 (d, J=11.1, 2H), 2.59 (d, J=5.1, 1H), 2.54 (d, J=6.9, 1H), 2.42 (s, 3H), 2.21-2.15 (m, 2H), 2.15 (s, 3H), 1.98-1.70 (m, 4H). MS (ESI): mass calcd. for C$_{23}$H$_{26}$N$_4$O$_2$S, 422.18; m/z found, 423.2 [M+H]$^+$.

Example 210 meso-3-{2-[4-([1,3]Thiazolo[4,5-b]pyridin-2-yloxy)phenyl]ethyl}-3,8-diazabicyclo[3.2.1]octane-8-carboxamide Hydrochloride

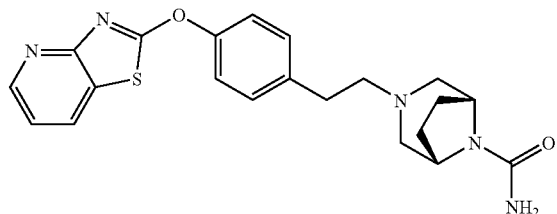

$^1$H NMR (300 MHz, CD$_3$OD): 8.44 (d, J=4.8, 1H), 8.28 (d, J=9.0, 2H), 7.43-7.29 (m, 4H), 3.78 (d, J=14.4, 4H), 3.19 (s, 2H), 3.01 (s, 4H), 2.10 (br s, 2H), 1.82 (d, J=8.1, 2H). MS (ESI): mass calcd. for C$_{21}$H$_{23}$N$_5$O$_2$S, 409.16; m/z found, 410.1 [M+H]$^+$.

Example 211 meso-8-{2-[4-([1,3]Thiazolo[4,5-b]pyridin-2-yloxy)phenoxy]ethyl}-3,8-diazabicyclo[3.2.1]octane-3-carboxamide

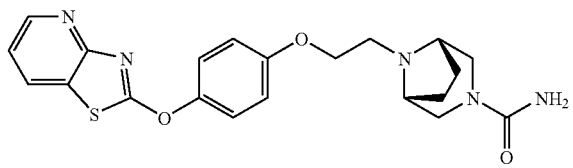

$^1$H NMR (300 MHz, CD$_3$OD): 8.52 (d, J=5.1, 1H), 8.32 (d, J=7.8, 1H), 7.41-7.34 (m, 3H), 7.12 (d, J=9.3, 2H), 4.24 (d, J=5.4, 2H), 3.65-3.57 (m, 2H), 3.46 (brs, 1H), 3.18-3.11 (m, 3H), 2.89 (d, J=5.4, 2H), 2.07 (d, J=9.6, 2H), 1.73 (d, J=7.8, 2H). MS (ESI): mass calcd. for C$_{21}$H$_{23}$N$_5$O$_3$S, 425.15; m/z found, 426.1 [M+H]$^+$.

Example 212 meso-2-(4-{2-[8-Acetyl-3,8-diazabicyclo[3.2.1]oct-3-yl]ethyl}phenoxy)[1,3]thiazolo[4,5-b]pyridine

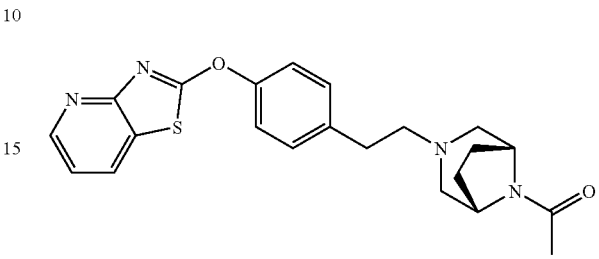

$^1$H NMR (300 MHz, CD$_3$OD): 8.38 (d, J=4.2, 1H), 8.19 (d, J=6.9, 1H), 7.31-7.21 (m, 5H), 4.44 (br s, 1H), 4.11 (br s, 1H), 2.78-2.68 (m, 4H), 2.58-2.52 (m, 2H), 2.21-2.15 (m, 2H), 1.98 (s, 3H), 1.80-1.69 (m, 4H). MS (ESI): mass calcd. for C$_{22}$H$_{24}$N$_4$O$_2$S, 408.16; m/z found, 409.2 [M+H]$^+$.

Example 213 meso-2-(4-{2-[3-(Methylsulfonyl)-3,8-diazabicyclo[3.2.1]oct-8-yl]ethoxy}phenoxy)[1,3]thiazolo[4,5-b]pyridine

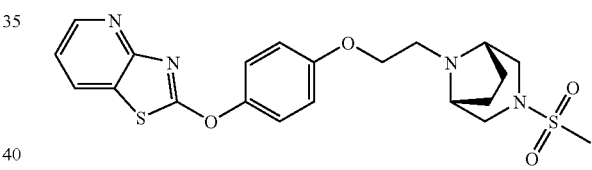

$^1$H NMR (300 MHz, CDCl$_3$): 8.56-8.54 (m, 1H), 8.02-7.99 (m, 1H), 7.32 (d, J=9.0, 2H), 7.22-7.17 (m, 1H), 6.94 (d, J=9.3, 2H), 4.13-4.08 (m, 2H), 3.44-3.40 (m, 2H), 2.99 (d, J=9.3, 2H), 2.69 (br s, 5H), 2.04-1.86 (m, 4H). MS (ESI): mass calcd. for C$_{21}$H$_{24}$N$_4$O$_4$S$_2$, 460.12; m/z found, 461.1 [M+H]$^+$.

Example 214 meso-(3-exo)-8-Acetyl-N-{2-[4-([1,3]thiazolo[4,5-b]pyridin-2-yloxy)phenyl]ethyl}-8-azabicyclo[3.2.1]octan-3-amine

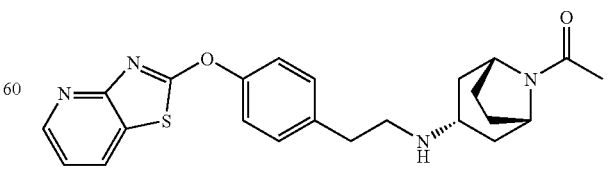

$^1$H NMR (300 MHz, CD$_3$OD): 8.47 (d, J=3.9, 1H), 8.29 (d, J=7.8, 1H), 7.36-7.30 (m, 5H), 4.60 (br s, 1H), 4.30 (br s, 1H), 3.23-3.05 (m, 1H), 2.85-2.69 (m, 4H), 2.28 (s, 1H), 2.28-1.56

Example 215 meso-(3-exo)-8-Acetyl-N-{2-[4-([1,3]thiazolo[4,5-b]pyridin-2-yloxy)phenoxy]ethyl}-8-azabicyclo[3.2.1]octan-3-amine Hydrochloride

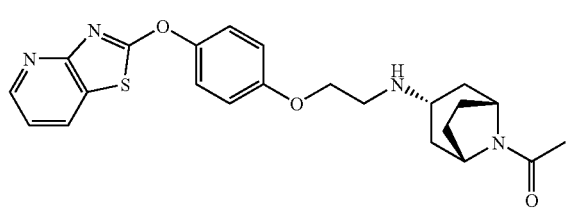

¹H NMR (300 MHz, CD₃OD): 9.05 (dd, J=8.1, 1.5, 1H), 8.76 (dd, J=6.0, 1.5, 1H), 7.90-7.85 (m, 1H), 7.53 (d, J=9.3, 2H), 7.26 (d, J=9.0, 2H), 4.78 (br s, 1H), 4.53 (br s, 1H), 4.43-4.39 (m, 2H), 3.92 (br s, 1H), 3.60-3.58 (m, 2H), 2.23-2.20 (m, 6H), 2.07-1.82 (m, 5H). MS (ESI): mass calcd. for C₂₃H₂₆N₄O₃S, 438.17; m/z found, 439.1 [M+H]⁺.

Example 216

2-Methoxy-N-(1-{4-[(6-methyl[1,3]thiazolo[4,5-b]pyridin-2-yl)oxy]benzyl}piperidin-4-yl)acetamide

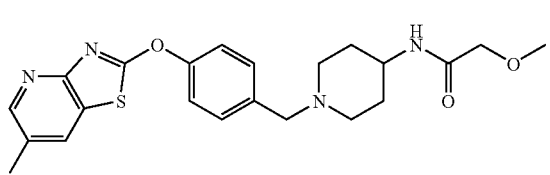

¹H NMR (300 MHz, CD₃OD): 8.30 (s, 1H), 8.10 (s, 1H), 7.47 (d, J=8.4, 2H), 7.37 (d, J=8.4, 2H), 3.86 (s, 1H), 3.77-3.72 (m, 2H), 3.57 (s, 2H), 3.39 (s, 3H), 2.90 (d, J=11.7, 2H), 2.43 (s, 3H), 2.19-2.11 (m, 2H), 1.85-1.82 (m, 2H), 1.63-1.57 (m, 2H). MS (ESI): mass calcd. for C₂₂H₂₆N₄O₃S, 426.17; m/z found, 427.1 [M+H]⁺.

Example 217

2-(4-{[4-(Pyridin-2-ylcarbonyl)piperazin-1-yl]methyl}phenoxy)[1,3]thiazolo[5,4-c]pyridine

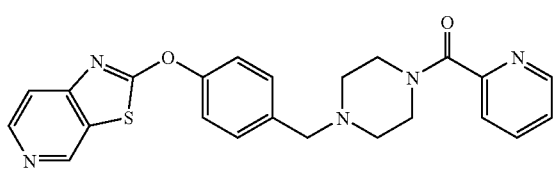

¹H NMR (300 MHz, CD₃OD): 8.99 (s, 1H), 8.61 (d, J=4.5, 1H), 8.50 (d, J=5.7, 1H), 7.98 (t, J=7.8, 1H), 7.68-7.49 (m, 5H), 7.41 (d, J=8.4, 2H), 3.84 (br s, 2H), 3.66 (s, 2H), 3.51 (br s, 2H), 2.63 (br s, 2H), 2.51 (br s, 2H). MS (ESI): mass calcd. for C₂₃H₂₁N₅O₂S, 431.14; m/z found, 432.1 [M+H]⁺.

Example 218

2-{4-[(4-tert-Butylpiperidin-1-yl)methyl]phenoxy}-6-chloro[1,3]thiazolo[4,5-b]pyridine

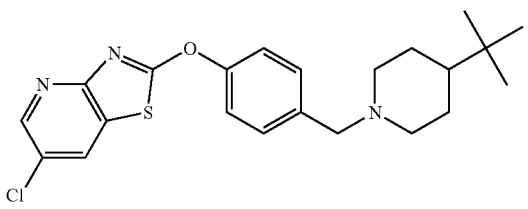

¹H NMR (300 MHz, CDCl₃): 8.50 (s, 1H), 7.99 (s, 1H), 7.40 (br s, 2H), 7.34 (d, J=8.1, 2H), 3.51 (br s, 2H), 2.95 (br s, 2H), 1.91 (br s, 2H), 1.65 (d, J=12.6, 2H), 1.32 (br s, 2H), 0.99 (br s, 1H), 0.86 (s, 9H). MS (ESI): mass calcd. for C₂₂H₂₆ClN₃OS, 415.15; m/z found, 416.2 [M+H]⁺.

Example 219

N-{1-[4-([1,3]Thiazolo[5,4-b]pyridin-2-yloxy)benzyl]piperidin-4-yl}propanamide

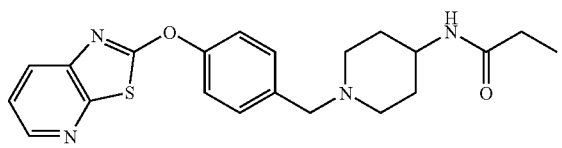

¹H NMR (300 MHz, CD₃OD): 8.39 (br s, 1H), 7.98 (br s, 1H), 7.51-7.35 (m, 5H), 3.58-3.45 (m, 3H), 2.89 (br s, 2H), 2.18-2.12 (m, 4H), 1.83 (br s, 2H), 1.52 (d, J=11.4, 2H), 1.13-1.07 (m, 3H). MS (ESI): mass calcd. for C₂₁H₂₄N₄O₂S, 396.16; m/z found, 397.1 [M+H]⁺.

Example 220

N-(1-{4-[(6-Methyl[1,3]thiazolo[4,5-b]pyridin-2-yl)oxy]benzyl}piperidin-4-yl)thiophene-2-carboxamide

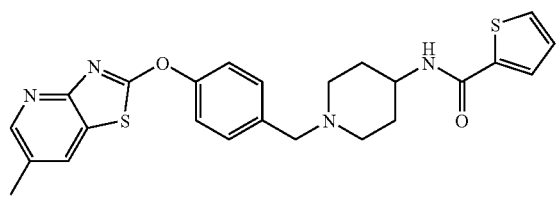

¹H NMR (300 MHz, CD₃OD): 8.27 (s, 1H), 8.08 (s, 1H), 7.67 (d, J=3.3, 1H), 7.59 (d, J=4.8, 1H), 7.46 (d, J=9.0, 2H), 7.36 (d, J=7.8, 2H), 7.07 (t, J=3.9, 1H), 3.86-3.79 (m, 1H), 3.56 (s, 2H), 2.93 (d, J=11.4, 2H), 2.40 (s, 3H), 2.18-2.11 (m,

2H), 1.89 (d, J=11.4, 2H), 1.71-1.60 (m, 2H). MS (ESI): mass calcd. for $C_{24}H_{24}N_4O_2S_2$, 464.13; m/z found, 465.1 [M+H]$^+$.

Example 221

2-[4-(2-Pyrrolidin-1-ylethyl)phenoxy][1,3]thiazolo[4,5-c]pyridine

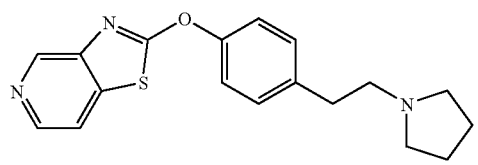

$^1$H NMR (300 MHz, CD$_3$OD): 8.81 (s, 1H), 8.37 (d, J=5.7, 1H), 7.93 (d, J=5.7, 1H), 7.45-7.36 (m, 4H), 3.23-3.01 (m, 8H), 1.97 (br s, 4H). MS (ESI): mass calcd. for $C_{18}H_{19}N_3OS$, 325.12; m/z found, 326.1 [M+H]$^+$.

Example 222

2-(4-{2-[4-(Cyclopropylcarbonyl)-1,4-diazepan-1-yl]ethyl}phenoxy)[1,3]thiazolo[5,4-b]pyridine

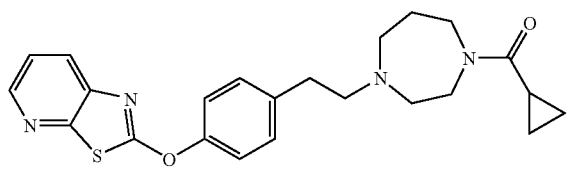

$^1$H NMR (300 MHz, CD$_3$OD): 8.41 (d, J=4.5, 1H), 8.01 (d, J=6.9, 1H), 7.50-7.45 (m, 1H), 7.42-7.31 (m, 4H), 3.89-3.80 (m, 2H), 3.69-3.59 (m, 2H), 2.96-2.75 (m, 8H), 2.01-1.86 (m, 3H), 0.89-0.80 (m, 4H). MS (ESI): mass calcd. for $C_{23}H_{26}N_4O_2S$, 422.18; m/z found, 423.2 [M+H]$^+$.

Example 223

1'-(2-{4-[(6-Chloro[1,3]thiazolo[4,5-b]pyridin-2-yl)oxy]phenyl}ethyl)-1,4'-bipiperidine

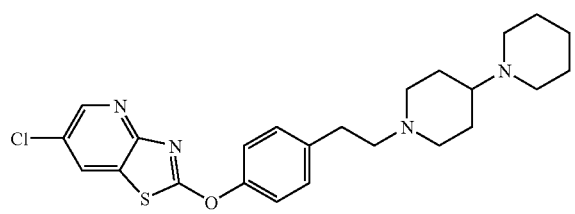

$^1$H NMR (300 MHz, CDCl$_3$): 8.50 (d, J=2.4, 1H), 7.99 (d, J=2.4, 1H), 7.32-7.27 (m, 4H), 3.08 (d, J=11.4, 2H), 2.86-2.80 (m, 2H), 2.61-2.55 (m, 7H), 2.06-1.46 (m, 12H). MS (ESI): mass calcd. for $C_{24}H_{29}ClN_4OS$, 456.18; m/z found, 457.1 [M+H]$^+$.

Example 224

1-Methyl-4-[4-([1,3]thiazolo[4,5-c]pyridin-2-yloxy)benzyl]piperazin-2-one

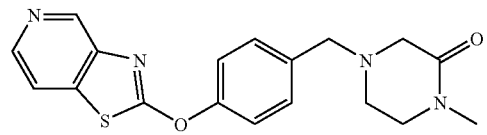

$^1$H NMR (300 MHz, CDCl$_3$): 8.97 (br s, 1H), 8.41 (d, J=3.3, 1H), 7.62 (d, J=5.1, 1H), 7.40 (d, J=8.4, 2H), 7.31 (d, J=8.4, 2H), 3.56 (s, 2H), 3.31 (t, J=5.4, 2H), 3.14 (s, 2H), 2.93 (s, 3H), 2.69 (t, J=5.4, 2H). MS (ESI): mass calcd. for $C_{18}H_{18}N_4O_2S$, 354.12; m/z found, 355.0 [M+H]$^+$.

Example 225

3-(4-{2-[4-([1,3]Thiazolo[4,5-b]pyridin-2-yloxy)phenyl]ethyl}piperazin-1-yl)propanoic Acid Hydrochloride

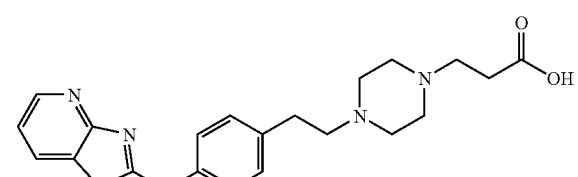

$^1$H NMR (300 MHz, D$_2$O): 8.34-8.29 (m, 1H), 8.18-8.11 (m, 1H), 7.35-7.22 (m, 2H), 7.26 (d, J=7.8, 3H), 3.18-3.07 (m, 12H), 2.95 (d, J=8.1, 2H), 2.53-2.49 (m, 2H). MS (ESI): mass calcd. for $C_{21}H_{24}N_4O_3S$, 412.16; m/z found, 413.2 [M+H]$^+$.

Example 226

2-{4-[(4-Acetyl-1,4-diazepan-1-yl)methyl]phenoxy}[1,3]thiazolo[5,4-c]pyridine

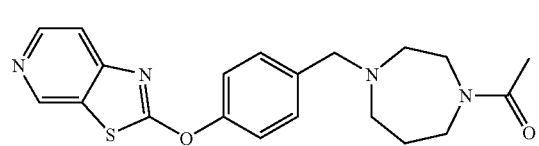

$^1$H NMR (300 MHz, CD$_3$OD): 8.99 (s, 1H), 8.50 (d, J=5.4, 1H), 7.66 (d, J=5.4, 1H), 7.55-7.51 (m, 2H), 7.39 (d, J=8.4, 2H), 3.73 (d, J=6.0, 2H), 3.65-3.60 (m, 4H), 2.79 (d, J=4.8,

2H), 2.71 (d, J=4.8, 2H), 2.12 (s, 3H), 1.95-1.86 (m, 2H). MS (ESI): mass calcd. for $C_{20}H_{22}N_4O_2S$, 382.15; m/z found, 383.2 [M+H]$^+$.

Example 227

2-[4-({4-[(4-Methylpiperazin-1-yl)carbonyl]piperidin-1-yl}methyl)phenoxy][1,3]thiazolo[5,4-c]pyridine

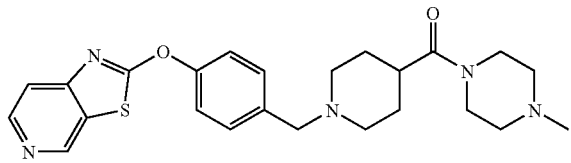

$^1$H NMR (300 MHz, CD$_3$OD): 8.98 (d, J=2.4, 1H), 8.51-8.48 (m, 1H), 7.68-7.65 (m, 1H), 7.51 (d, J=8.4, 2H), 7.40 (d, J=8.4, 2H), 3.60 (s, 6H), 2.98 (d, J=9.9, 2H), 2.69 (br s, 1H), 2.44 (d, J=13.8, 4H), 2.31 (s, 3H), 2.16 (t, J=11.4, 2H), 1.86-1.73 (m, 4H). MS (ESI): mass calcd. for $C_{24}H_{29}N_5O_2S$, 451.20; m/z found, 452.1 [M+H]$^+$.

Example 228 meso-N-Methyl-N-{(3-exo)-8-[4-([1,3]thiazolo[5,4-b]pyridin-2-yloxy)benzyl]-8-azabicyclo[3.2.1]oct-3-yl}acetamide

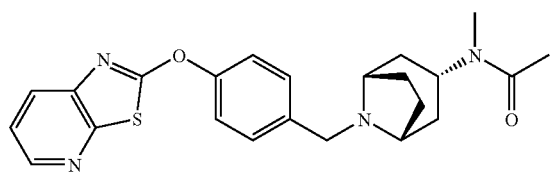

$^1$H NMR (300 MHz, CDCl$_3$): 8.40 (d, J=3.3, 1H), 7.94 (d, J=8.1, 1H), 7.52-7.43 (m, 2H), 7.36-7.25 (m, 3H), 3.49-3.45 (m, 3H), 3.31 (s, 2H), 2.76 (d, J=17.7, 2H), 2.31-2.17 (m, 5H), 2.03 (d, J=15.3, 2H), 1.57-1.51 (m, 3H), 1.36-1.15 (m, 2H). MS (ESI): mass calcd. for $C_{23}H_{26}N_4O_2S$, 422.18; m/z found, 423.1 [M+H]$^+$.

Example 229

6-Methyl-2-(4-{[4-(piperazin-1-ylcarbonyl)piperidin-1-yl]methyl}phenoxy)[1,3]thiazolo[4,5-b]pyridine Hydrochloride

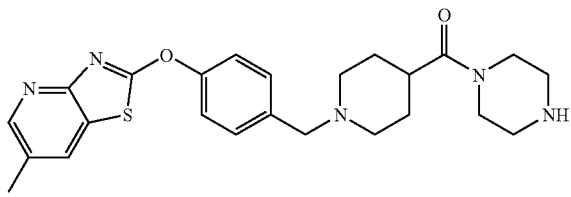

$^1$H NMR (300 MHz, D$_2$O): 8.48 (d, J=3.0, 2H), 7.80 (d, J=8.7, 2H), 7.67 (d, J=8.7, 2H), 4.53 (s, 2H), 4.05 (d, J=5.1, 2H), 3.97 (d, J=4.8, 2H), 3.78 (d, J=12.3, 2H), 3.54-3.41 (m, 5H), 3.31-3.22 (m, 3H), 2.59 (s, 3H), 2.19 (d, J=10.2, 2H), 2.10-2.01 (m, 2H). MS (ESI): mass calcd. for $C_{24}H_{29}N_5O_2S$, 451.20; m/z found, 452.2 [M+H]$^+$.

Example 230 meso-3-(2-{4-[(6-Methyl[1,3]thiazolo[4,5-b]pyridin-2-yl)oxy]phenyl}ethyl)-3,8-diazabicyclo[3.2.1]octane-8-carboxamide

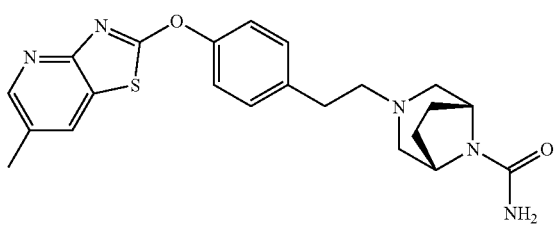

$^1$H NMR (300 MHz, CD$_3$OD): 8.34 (d, J=2.1, 1H), 8.13 (d, J=1.8, 1H), 7.42-7.32 (m, 4H), 4.21 (br s, 2H), 2.88-2.75 (m, 4H), 2.67-2.62 (m, 2H), 2.46 (s, 3H), 2.34 (d, J=10.5, 2H), 1.85 (d, J=1.8, 4H). MS (ESI): mass calcd. for $C_{22}H_{25}N_5O_2S$, 423.17; m/z found, 424.2 [M+H]$^+$.

Example 231 meso-(3-exo)-8-Acetyl-N-[4-([1,3]thiazolo[4,5-c]pyridin-2-yloxy)benzyl]-8-azabicyclo[3.2.1]octan-3-amine

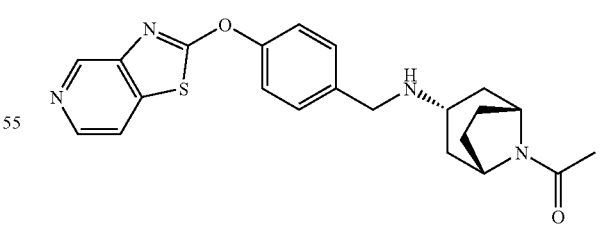

$^1$H NMR (300 MHz, CDCl$_3$): 8.96 (s, 1H), 8.41 (d, J=5.4, 1H), 7.62 (d, J=5.4, 1H), 7.40 (d, J=8.4, 2H), 7.30 (d, J=8.4, 2H), 4.69 (br s, 1H), 4.14 (br s, 1H), 3.85 (s, 2H), 3.81-3.04

(m, 1H), 2.10-1.22 (m, 11H). MS (ESI): mass calcd. for C$_{22}$H$_{24}$N$_4$O$_2$S, 408.16; m/z found, 409.2 [M+H]$^+$.

Example 232 meso-8-{2-[4-([1,3]Thiazolo[4,5-c]pyridin-2-yloxy)phenoxy]ethyl}-3,8-diazabicyclo[3.2.1]octane-3-carboxamide

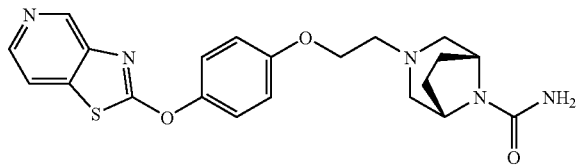

$^1$H NMR (300 MHz, CD$_3$OD): 9.18 (br s, 1H), 8.75 (m, 2H), 7.49 (d, J=9.0, 2H), 7.22 (d, J=9.0, 2H), 4.55-4.51 (m, 2H), 4.31 (br s, 2H), 4.05 (d, J=13.8, 2H), 3.68 (br s, 2H), 3.55 (d, J=13.8, 2H), 2.55-2.35 (m, 2H), 2.20-2.11 (m, 2H). MS (ESI): mass calcd. for C$_{21}$H$_{23}$N$_5$O$_3$S, 425.15; m/z found, 426.2 [M+H]$^+$.

Example 233 meso-(3-exo)-8-Acetyl-N-(2-{4-[(6-methyl[1,3]thiazolo[4,5-b]pyridin-2-yl)oxy]phenyl}ethyl)-8-azabicyclo[3.2.1]octan-3-amine

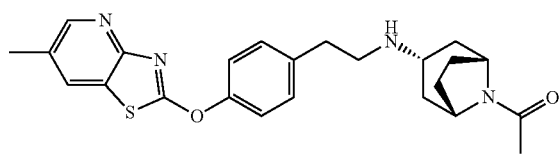

$^1$H NMR (300 MHz, CD$_3$OD): 8.36 (s, 1H), 8.16 (s, 1H), 7.44 (br s, 4H), 4.70-4.68 (m, 1H), 4.43-4.39 (m, 1H), 3.55-3.46 (m, 1H), 3.18-3.13 (m, 2H), 3.01-2.96 (m, 2H), 2.48 (s, 3H), 2.14-1.50 (m, 11H). MS (ESI): mass calcd. for C$_{24}$H$_{28}$N$_4$O$_2$S, 436.19; m/z found, 437.1 [M+H]$^+$.

Example 234 meso-(3-exo)-8-Acetyl-N-methyl-N-(2-{4-[(6-methyl[1,3]thiazolo[4,5-b]pyridin-2-yl)oxy]phenyl}ethyl)-8-azabicyclo[3.2.1]octan-3-amine

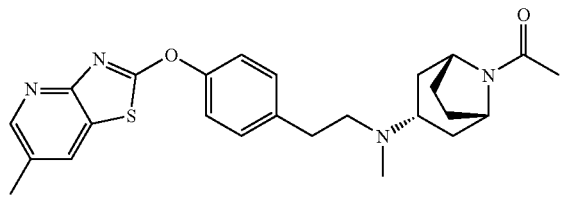

$^1$H NMR (300 MHz, CD$_3$OD): 8.35 (d, J=1.8, 1H), 8.15 (d, J=1.2, 1H), 7.43-7.35 (m, 4H), 4.68-4.66 (m, 1H), 4.37-4.34 (m, 1H), 3.16-3.12 (m, 1H), 2.90-2.84 (m, 2H), 2.80-2.74 (m, 2H), 2.48 (s, 3H), 2.39 (s, 3H), 2.12 (s, 3H), 2.10-1.61 (m, 8H). MS (ESI): mass calcd. for C$_{25}$H$_{30}$N$_4$O$_2$S, 450.21; m/z found, 451.2 [M+H]$^+$.

Example 235

N$^2$-(2-{4-[(6-Chloro[1,3]thiazolo[4,5-b]pyridin-2-yl)oxy]phenoxy}ethyl)-N$^2$-methylglycinamide

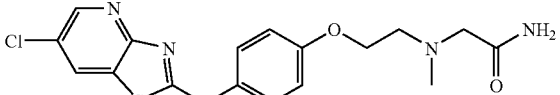

$^1$H NMR (300 MHz, CDCl$_3$) 8.51 (d, J=2.4, 1H), 8.00 (d, J=1.8, 1H), 7.33 (d, J=9.0, 2H), 6.96 (d, J=8.7, 2H), 5.47 (br s, 1H), 4.12 (br s, 2H), 3.22 (br s, 2H), 2.96 (br s, 2H), 2.49 (br s, 3H). MS (ESI): mass calcd. for C$_{17}$H$_{17}$ClN$_4$O$_3$S, 392.07; m/z found, 393.1 [M+H]$^+$.

Example 236

2-[4-(2-Azetidin-1-ylethoxy)phenoxy][1,3]thiazolo[5,4-c]pyridine

$^1$H NMR (300 MHz, CD$_3$OD): 8.95 (s, 1H), 8.47 (d, J=5.7, 1H), 7.64 (d, J=5.4, 1H), 7.32 (d, J=8.7, 2H), 7.04 (d, J=8.7, 2H), 4.05-4.01 (m, 2H), 3.46-3.41 (m, 4H), 2.91 (t, J=5.1, 2H), 2.21-2.10 (m, 2H). MS (ESI): mass calcd. for C$_{17}$H$_{17}$N$_3$O$_2$S, 327.11; m/z found, 328.1 [M+H]$^+$.

Example 237

2-(4-{2-[4-(Pyridin-2-yloxy)piperidin-1-yl]ethyl}phenoxy)[1,3]thiazolo[4,5-b]pyrazine

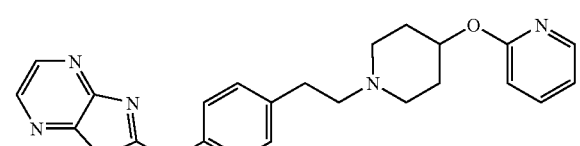

$^1$H NMR (300 MHz, CD$_3$OD): 8.50 (d, J=2.1, 1H), 8.39 (d, J=2.4, 1H), 8.08 (d, J=3.9, 1H), 7.67-7.62 (m, 1H), 7.42-7.34 (m, 4H), 6.92-6.87 (m, 1H), 6.75 (d, J=8.1, 1H), 5.13-5.02 (m, 1H), 2.94-2.88 (m, 4H), 2.70-2.64 (m, 2H), 2.50-2.44 (m,

2H), 2.18-2.05 (m, 2H), 1.87-1.81 (m, 2H). MS (ESI): mass calcd. for C$_{23}$H$_{23}$N$_5$O$_2$S, 433.16; m/z found, 434.1 [M+H]$^+$.

Example 238 meso-8-[4-([1,3]Thiazolo[4,5-b]pyridin-2-yloxy)benzyl]-8-azabicyclo[3.2.1]octane-3-carboxylic Acid Hydrochloride

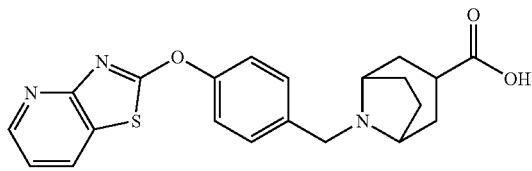

$^1$H NMR (300 MHz, CD$_3$OD): 8.49 (d, J=3.9, 1H), 8.34 (d, J=7.2, 1H), 7.74 (d, J=7.2, 2H), 7.58 (d, J=7.2, 2H), 7.38-7.34 (m, 1H), 4.31 (s, 2H), 4.01 (br s, 2H), 2.93 (br s, 1H), 2.46 (br s, 2H), 2.22-1.95 (m, 6H). MS (ESI): mass calcd. for C$_{21}$H$_{21}$N$_3$O$_3$S, 395.13; m/z found, 396.1 [M+H]$^+$.

Example 239

6-Chloro-2-(4-{2-[5-(1-methylethyl)hexahydropyrrolo[3,4-c]pyrrol-2(1H)-yl]ethoxy}phenoxy)[1,3]thiazolo[4,5-b]pyridine

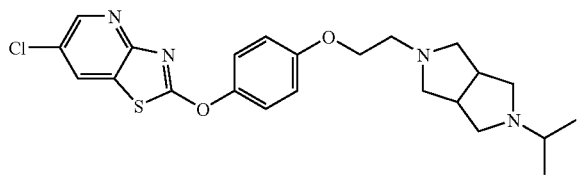

$^1$H NMR (300 MHz, CDCl$_3$): 8.50 (d, J=2.1, 1H), 7.98 (d, J=1.8, 1H), 7.31-7.27 (m, 2H), 6.96 (d, J=9.0, 2H), 4.11 (t, J=5.7, 2H), 2.90-2.82 (m, 4H), 2.71-2.66 (m, 4H), 2.53-2.45 (m, 2H), 2.35-2.26 (m, 3H), 1.09 (d, J=6.3, 6H). MS (ESI): mass calcd. for C$_{23}$H$_{27}$ClN$_4$O$_2$S, 458.15; m/z found, 459.2 [M+H]$^+$.

Example 240

N-(Cyclopropylmethyl)-N-{2-[4-([1,3]thiazolo[4,5-c]pyridin-2-yloxy)phenoxy]ethyl}-beta-alanine

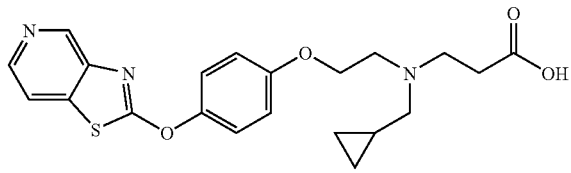

$^1$H NMR (300 MHz, CD$_3$OD): 8.85 (s, 1H), 8.39 (d, J=5.4, 1H), 7.94 (d, J=5.4, 1H), 7.41 (d, J=9.0, 2H), 7.20 (d, J=9.0, 2H), 4.46 (t, J=4.8, 2H), 3.72 (t, J=4.8, 2H), 3.51 (t, J=6.3, 2H), 3.20 (d, J=7.5, 2H), 2.65 (t, J=6.3, 2H), 1.31-1.26 (m, 1H), 0.83-0.75 (m, 2H), 0.58-0.45 (m, 2H). MS (ESI): mass calcd. for C$_{21}$H$_{23}$N$_3$O$_4$S, 413.14; m/z found, 414.1 [M+H]$^+$.

Example 241

N-Methyl-N-(2-{4-[(6-methyl[1,3]thiazolo[4,5-b]pyridin-2-yl)oxy]phenoxy}ethyl)-beta-alanine

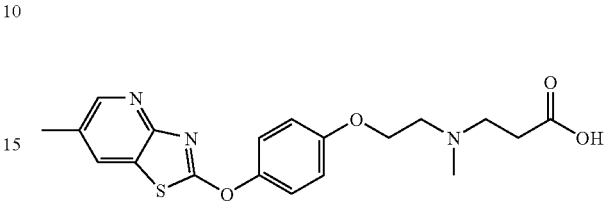

$^1$H NMR (300 MHz, CDCl$_3$): 10.27 (br s, 1H), 8.34 (s, 1H), 7.83 (s, 1H), 7.28 (d, J=5.7, 2H), 6.94 (d, J=8.4, 2H), 4.28 (br s, 2H), 3.35 (br s, 2H), 3.21 (br s, 2H), 2.74 (s, 3H), 2.65 (br s, 2H), 2.41 (s, 3H). MS (ESI): mass calcd. for C$_{19}$H$_{21}$N$_3$O$_4$S, 387.13; m/z found, 388.1 [M+H]$^+$.

Example 242

2-(Cyclopropyl{2-[4-([1,3]thiazolo[5,4-b]pyridin-2-yloxy)phenoxy]ethyl}amino)ethanol

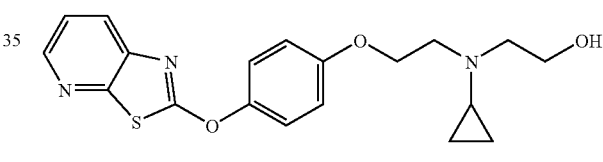

$^1$H NMR (300 MHz, CD$_3$OD): 8.38 (d, J=3.3, 1H), 7.99 (d, J=6.9, 1H), 7.48-7.43 (m, 1H), 7.32 (d, J=9.0, 2H), 7.06 (d, J=9.0, 2H), 4.22-4.18 (m, 2H), 3.72 (t, J=6.3, 2H), 3.11 (t, J=5.7, 2H), 2.93-2.88 (m, 2H), 2.02-1.98 (m, 1H), 0.57-0.47 (m, 4H). MS (ESI): mass calcd. for C$_{19}$H$_{21}$N$_3$O$_3$S, 371.13; m/z found, 372.1 [M+H]$^+$.

Example 243

N-(2-{4-[(6-Chloro[1,3]thiazolo[4,5-b]pyridin-2-yl)oxy]phenyl}ethyl)-N,1-dimethylpiperidin-4-amine

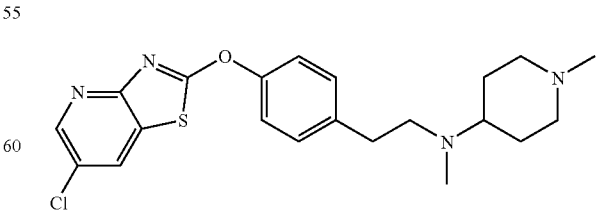

$^1$H NMR (300 MHz, CD$_3$OD): 8.51 (d, J=2.4, 1H), 8.46 (d, J=2.4, 1H), 7.45-7.37 (m, 4H), 3.02-2.83 (m, 7H), 2.43 (s, 3H), 2.33 (s, 3H), 2.20-2.00 (m, 2H), 1.95-1.80 (m, 2H), 1.67-1.62 (m, 2H). MS (ESI): mass calcd. for $C_{21}H_{25}ClN_4OS$, 416.14; m/z found, 417.2 [M+H]$^+$.

Example 244 meso-2-(4-{2-[3-Acetyl-3,8-diazabicyclo[3.2.1]oct-8-yl]ethoxy}phenoxy)[1,3]thiazolo[4,5-c]pyridine

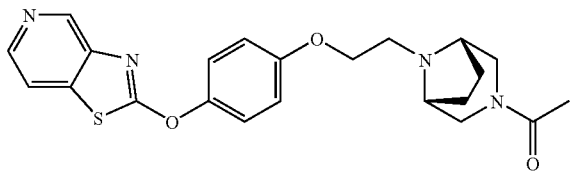

$^1$H NMR (300 MHz, CD$_3$OD): 8.85 (s, 1H), 8.38 (d, J=5.4, 1H), 7.93 (d, J=5.7, 1H), 7.36 (d, J=8.7, 2H), 7.10 (d, J=9.3, 2H), 4.23-4.19 (m, 2H), 4.11 (d, J=12.9, 1H), 3.65-3.55 (m, 1H), 3.50-3.40 (m, 3H), 2.96-2.85 (m, 3H), 2.20-1.95 (m, 5H), 1.69-1.59 (m, 2H). MS (ESI): mass calcd. for $C_{22}H_{24}N_4O_3S$, 424.16; m/z found, 425.2 [M+H]$^+$.

Example 245

6-Methyl-2-{4-[2-(4-pyridin-2-ylpiperidin-1-yl)ethyl]-phenoxy}[1,3]thiazolo[4,5-b]pyridine

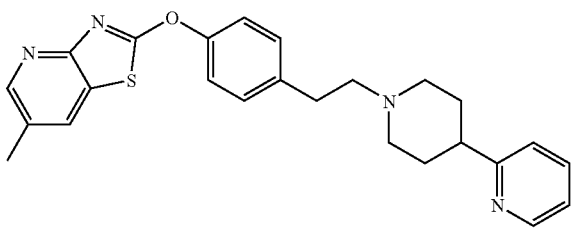

$^1$H NMR (300 MHz, CD$_3$OD): 8.45 (d, J=4.5, 1H), 8.31 (br s, 1H), 8.11 (br s, 1H), 7.81-7.76 (m, 1H), 7.42-7.35 (m, 5H), 7.28-7.23 (m, 1H), 3.40-3.20 (m, 2H), 2.94-2.91 (m, 2H), 2.75-2.71 (m, 3H), 2.43 (s, 3H), 2.35-2.27 (m, 2H), 1.96-1.86 (m, 4H). MS (ESI): mass calcd. for $C_{25}H_{26}N_4OS$, 430.18; m/z found, 431.1 [M+H]$^+$.

Example 246

5-{2-[4-([1,3]Thiazolo[5,4-c]pyridin-2-yloxy)phenyl]ethyl}hexahydropyrrolo[3,4-c]pyrrole-2(1H)-carboxamide

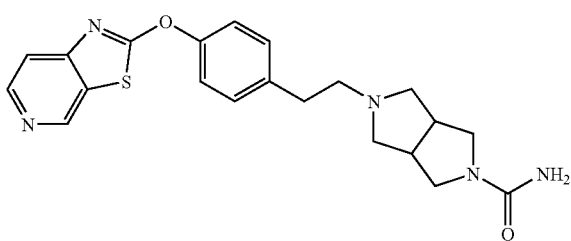

$^1$H NMR (300 MHz, CD$_3$OD): 8.99 (s, 1H), 8.50 (d, J=5.7, 1H), 7.67 (d, J=5.7, 1H), 7.42 (d, J=8.4, 2H), 7.34 (d, J=8.7, 2H), 3.57-3.51 (m, 2H), 3.36-3.15 (m, 2H), 2.91-2.87 (m, 6H), 2.76-2.71 (m, 2H), 2.49 (d, J=6.0, 2H). MS (ESI): mass calcd. for $C_{21}H_{23}N_5O_2S$, 409.16; m/z found, 410.0 [M+H]$^+$.

Example 247

1-(1-Acetylazetidin-3-yl)-N-{4-[(6-chloro[1,3]thiazolo[4,5-b]pyridin-2-yl)oxy]benzyl}-N-methyl-methanamine

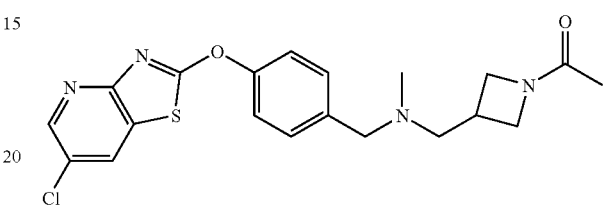

$^1$H NMR (300 MHz, CD$_3$OD): 8.50 (d, J=2.1, 1H), 8.43 (d, J=2.4, 1H), 7.73 (d, J=8.4, 2H), 7.62 (d, J=8.7, 2H), 4.48-4.42 (m, 3H), 4.25-4.04 (m, 2H), 3.83-3.78 (m, 1H), 3.60 (br s, 2H), 3.38-3.26 (m, 1H), 2.86 (s, 3H), 1.89 (s, 3H). MS (ESI): mass calcd. for $C_{20}H_{21}ClN_4O_2S$, 416.11; m/z found, 417.1 [M+H]$^+$.

Example 248

2-(4-{[4-(Pyridin-3-yloxy)piperidin-1-yl]methyl}phenoxy)[1,3]thiazolo[5,4-c]pyridine

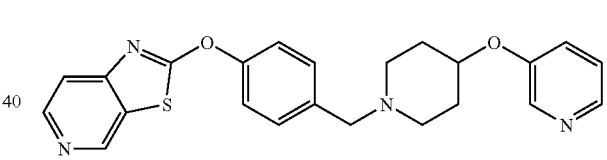

$^1$H NMR (300 MHz, CD$_3$OD): 8.99 (s, 1H), 8.51 (d, J=5.4, 1H), 8.24 (d, J=2.7, 1H), 8.12 (d, J=4.2, 1H), 7.68 (d, J=5.4, 1H), 7.54 (d, J=8.4, 2H), 7.48-7.34 (m, 4H), 4.56-4.53 (m, 1H), 3.65 (s, 2H), 2.90-2.75 (m, 2H), 2.48-2.40 (m, 2H), 2.06-2.05 (m, 2H), 1.89-1.83 (m, 2H). MS (ESI): mass calcd. for $C_{23}H_{22}N_4O_2S$, 418.15; m/z found, 419.1 [M+H]$^+$.

Example 249 meso-N-{(3-exo)-8-[4-([1,3]Thiazolo[5,4-c]pyridin-2-yloxy)benzyl]-8-azabicyclo[3.2.1]oct-3-yl}methanesulfonamide

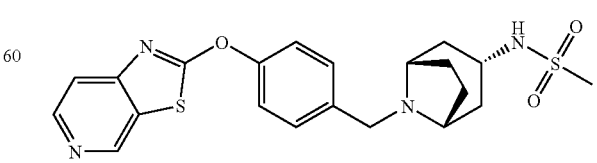

$^1$H NMR (300 MHz, CDCl$_3$): 8.93 (s, 1H), 8.56 (d, J=5.4, 1H), 7.61 (d, J=5.7, 1H), 7.50 (d, J=8.4, 2H), 7.32 (d, J=8.4,

2H), 4.25 (br s, 1H), 3.67-3.58 (m, 3H), 3.28 (brs, 2H), 2.97 (s, 3H), 2.10-2.06 (m, 2H), 1.94-1.89 (m, 2H), 1.90-1.68 (m, 4H). MS (ESI): mass calcd. for $C_{21}H_{24}N_4O_3S_2$, 444.13; m/z found, 445.1 $[M+H]^+$.

Example 250

N-[(1-{2-[4-([1,3]Thiazolo[5,4-c]pyridin-2-yloxy)phenoxy]ethyl}piperidin-4-yl)methyl]acetamide

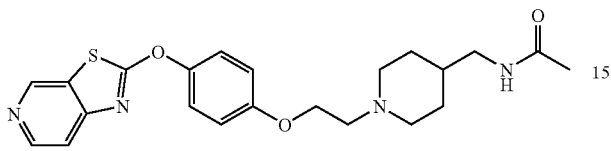

$^1$H NMR (300 MHz, CD$_3$OD): 8.97 (s, 1H), 8.50 (d, J=5.7, 1H), 7.67 (d, J=5.7, 1H), 7.36 (d, J=9.0, 2H), 7.10 (d, J=9.3, 2H), 4.24-4.20 (m, 2H), 3.18-3.08 (m, 4H), 2.95 (br s, 2H), 2.29 (br s, 2H), 1.95 (s, 3H), 1.78 (d, J=12.6, 2H), 1.58 (br s, 1H), 1.39-1.32 (m, 2H). MS (ESI): mass calcd. for $C_{22}H_{26}N_4O_3S$, 426.17; m/z found, 427.2 $[M+H]^+$.

Example 251

2-{4-[(4-Pyridin-2-ylpiperazin-1-yl)methyl]phenoxy}[1,3]thiazolo[5,4-b]pyridine

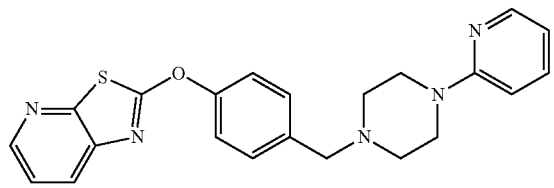

$^1$H NMR (300 MHz, CD$_3$OD): 8.42 (d, J=5.1, 1H), 8.09 (d, J=3.3, 1H), 8.02 (d, J=6.9, 1H), 7.60-7.48 (m, 4H), 7.44 (d, J=12.6, 2H), 6.84 (d, J=8.7, 1H), 6.71-6.67 (m, 1H), 3.66 (s, 2H), 3.57-3.50 (m, 5H), 2.65-2.62 (m, 3H). MS (ESI): mass calcd. for $C_{22}H_{21}N_5OS$, 403.15; m/z found, 404.1 $[M+H]^+$.

Example 252

2-(4-{2-[(1R,4R)-5-Acetyl-2,5-diazabicyclo[2.2.1]hept-2-yl]ethyl}phenoxy)[1,3]thiazolo[5,4-b]pyridine

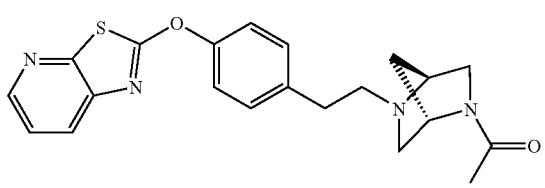

$^1$H NMR (300 MHz, CD$_3$OD): 8.44 (d, J=4.5, 1H), 8.04 (d, J=8.1, 1H), 7.53-7.49 (m, 1H), 7.44 (d, J=8.4, 2H), 7.36 (d, J=8.7, 2H), 4.71 (s, 0.5H), 4.50 (s, 0.5H), 3.76-3.62 (m, 3H), 3.48-3.26 (m, 2H), 3.09-2.95 (m, 1H), 2.89 (s, 3H), 2.77-2.71 (m, 1H), 2.14 (s, 1H), 2.04 (s, 2H), 2.01-1.78 (m, 1H). MS (ESI): mass calcd. for $C_{21}H_{22}N_4O_2S$, 394.15; m/z found, 395.1 $[M+H]^+$.

Example 253

N-Ethyl-N-[4-([1,3]thiazolo[4,5-c]pyridin-2-yloxy)benzyl]cyclohexanamine

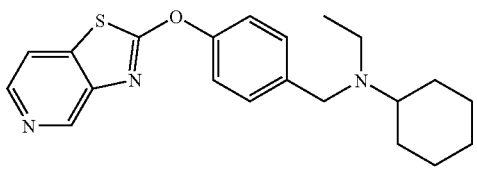

$^1$H NMR (300 MHz, CDCl$_3$): 9.00 (s, 1H), 8.43 (d, J=4.8, 1H), 7.62 (d, J=5.1, 1H), 7.46 (d, J=7.5, 2H), 7.27 (d, J=8.4, 2H), 3.64 (br s, 2H), 2.54 (t, J=6.6, 3H), 1.81 (br s, 4H), 1.63 (d, J=11.4, 1H), 1.27-1.06 (m, 5H), 1.01-0.96 (m, 3H). MS (ESI): mass calcd. for $C_{21}H_{25}N_3OS$, 367.18; m/z found, 368.1 $[M+H]^+$.

Example 254 meso-(3-exo)-3-{[4-([1,3]Thiazolo[4,5-b]pyridin-2-yloxy)benzyl]amino}-8-azabicyclo[3.2.1]octane-8-carboxamide

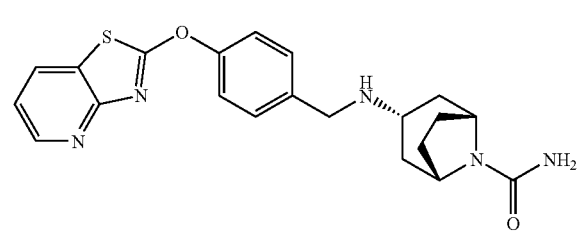

$^1$H NMR (300 MHz, CD$_3$OD): 8.52 (d, J=3.6, 1H), 8.33 (d, J=6.3, 1H), 7.54 (d, J=8.4, 2H), 7.44 (d, J=8.7, 2H), 7.40-7.35 (m, 1H), 4.30 (br s, 2H), 3.85 (s, 2H), 3.16-3.12 (m, 1H), 2.01-1.97 (m, 4H), 1.73 (d, J=7.5, 2H), 1.60 (t, J=10.8, 2H). MS (ESI): mass calcd. for $C_{21}H_{23}N_5O_2S$, 409.16; m/z found, 410.1 $[M+H]^+$.

Example 255

2-[4-(2-{4-[(4-Methylphenyl)sulfanyl]piperidin-1-yl}ethoxy)phenoxyl][1,3]thiazolo[4,5-b]pyridine

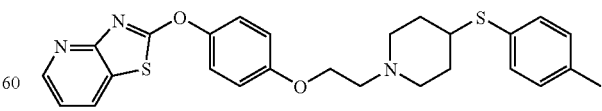

The title compound was prepared using methods analogous to those described for Example 1. $^1$H NMR (400 MHz, CDCl$_3$): 8.56 (dd, J=4.9, 1.7, 1H), 8.00 (dd, J=7.9, 1.7, 1H), 7.36-7.28 (m, 4H), 7.19 (dd, J=7.9, 4.9, 1H), 7.11 (m, 2H), 6.96-6.91 (m, 2H), 4.15 (t, J=5.7, 2H), 3.12-2.99 (m, 3H), 2.90 (t, J=5.6, 2H), 2.44-2.35 (m, 2H), 2.33 (s, 3H), 2.07-1.97 (m, 2H), 1.79-1.66 (m, 2H). MS (ESI): mass calcd. for $C_{26}H_{27}N_3O_2S_2$, 477.2; m/z found, 478.1 $[M+H]^+$.

Examples 256-264 were prepared using methods analogous to those described for Example 82.

Example 256

1'-[4-([1,3]Thiazolo[4,5-b]pyridin-2-yloxy)benzyl]-1,4'-bipiperidine

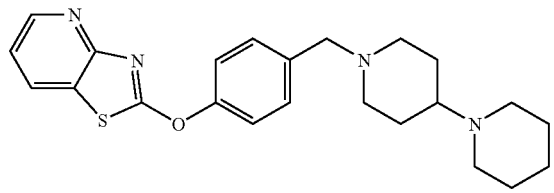

$^1$H NMR (400 MHz, CDCl$_3$): 8.56 (dd, J=4.8, 1.7, 1H), 8.01 (dd, J=7.9, 1.7, 1H), 7.41-7.32 (m, 4H), 7.19 (dd, J=7.9, 4.8, 1H), 3.50 (s, 2H), 2.99-2.89 (m, 2H), 2.55-2.48 (m, 3H), 2.02-1.93 (m, 2H), 1.82-1.74 (m, 2H), 1.62-1.55 (m, 8H), 1.47-1.39 (m, 2H). MS (ESI): mass calcd. for $C_{23}H_{28}N_4OS$, 408.2; m/z found, 409.2 $[M+H]^+$.

Example 257

2-{4-[(4-Morpholin-4-ylpiperidin-1-yl)methyl]phenoxy}[1,3]thiazolo[4,5-b]pyridine

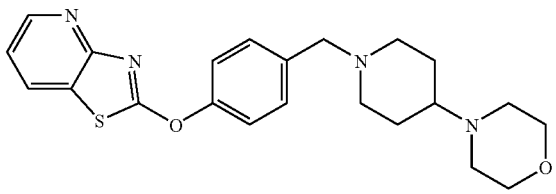

$^1$H NMR (400 MHz, CDCl$_3$): 8.56 (dd, J=4.8, 1.6, 1H), 8.01 (dd, J=7.9, 1.6, 1H), 7.41-7.33 (m, 4H), 7.20 (dd, J=7.9, 4.8, 1H), 3.74-3.69 (m, 4H), 3.51 (s, 2H), 2.98-2.90 (m, 2H), 2.58-2.53 (m, 4H), 2.25-2.15 (m, 1H), 2.04-1.94 (m, 2H), 1.84-1.76 (m, 2H), 1.59-1.55 (m, 2H). MS (ESI): mass calcd. for $C_{22}H_{26}N_4O_2S$, 410.2; m/z found, 411.2 $[M+H]^+$.

Example 258

N,N-Dimethyl-2-{1-[4-([1,3]thiazolo[4,5-b]pyridin-2-yloxy)benzyl]piperidin-2-yl}ethanamine

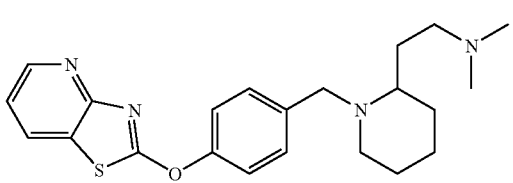

$^1$H NMR (400 MHz, CDCl$_3$): 8.56 (dd, J=4.8, 1.7, 1H), 8.00 (dd, J=7.9, 1.7, 1H), 7.43-7.38 (m, 2H), 7.36-7.31 (m, 2H), 7.19 (dd, J=7.9, 4.8, 1H), 4.02-3.93 (m, 1H), 3.32-3.25 (m, 1H), 2.77-2.69 (m, 1H), 2.45-2.38 (m, 1H), 2.38-2.32 (m, 2H), 2.24 (s, 6H), 2.14-2.02 (m, 1H), 1.86-1.64 (m, 5H), 1.52-1.43 (m, 3H). MS (ESI): mass calcd. for $C_{22}H_{28}N_4OS$, 396.2; m/z found, 397.2 $[M+H]^+$.

Example 259

N,N-Dimethyl-1-[4-([1,3]thiazolo[4,5-b]pyridin-2-yloxy)benzyl]piperidin-4-amine

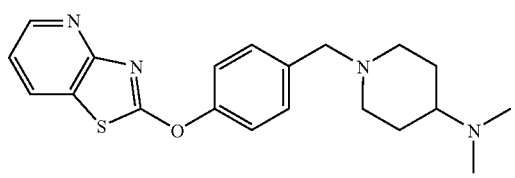

$^1$H NMR (400 MHz, CDCl$_3$): 8.56 (dd, J=4.8, 1.7, 1H), 8.01 (dd, J=7.9, 1.7, 1H), 7.41-7.32 (m, 4H), 7.19 (dd, J=7.9, 4.8, 1H), 3.51 (s, 2H), 2.98-2.87 (m, 2H), 2.28 (s, 6H), 2.19-2.09 (m, 1H), 2.03-1.94 (m, 2H), 1.82-1.75 (m, 2H), 1.61-1.48 (m, 2H). MS (ESI): mass calcd. for $C_{20}H_{24}N_4OS$, 368.2; m/z found, 369.1 $[M+H]^+$.

Example 260

2-{4-[(4-Phenoxypiperidin-1-yl)methyl]phenoxy}[1,3]thiazolo[4,5-b]pyridine

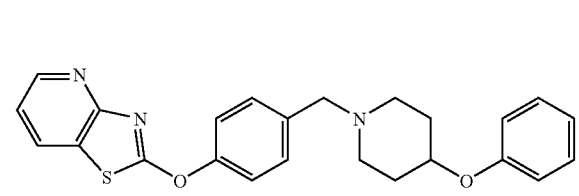

$^1$H NMR (400 MHz, CDCl$_3$): 8.58-8.53 (m, 1H), 8.03-7.97 (m, 1H), 7.44-7.39 (m, 2H), 7.38-7.33 (m, 2H), 7.31-7.24 (m, 2H), 7.19 (dd, J=7.9, 4.9, 1H), 6.96-6.89 (m, 3H), 4.39-4.28 (m, 1H), 3.55 (s, 2H), 2.83-2.71 (m, 2H), 2.38-2.25 (m, 2H), 2.06-1.96 (m, 2H), 1.90-1.78 (m, 2H). MS (ESI): mass calcd. for $C_{24}H_{23}N_3O_2S$, 417.2; m/z found, 418.1 $[M+H]^+$.

Example 261

2-(4-{[4-(Pyridin-2-yloxy)piperidin-1-yl]methyl}phenoxy)[1,3]thiazolo[4,5-b]pyridine

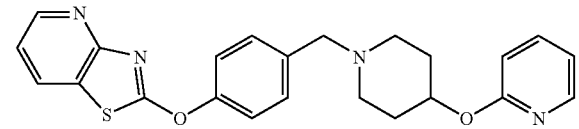

$^1$H NMR (400 MHz, CDCl$_3$): 8.60-8.53 (m, 1H), 8.16-8.10 (m, 1H), 8.05-7.99 (m, 1H), 7.60-7.51 (m, 1H), 7.46-7.40 (m, 2H), 7.40-7.33 (m, 2H), 7.24-7.17 (m, 1H), 6.87-6.78 (m, 1H), 6.75-6.69 (m, 1H), 5.18-5.02 (m, 1H), 3.56 (s, 2H), 2.85-2.71 (m, 2H), 2.43-2.28 (m, 2H), 2.12-1.99 (m, 2H), 1.90-1.80 (m, 2H). MS (ESI): mass calcd. for $C_{23}H_{22}N_4O_2S$, 418.1; m/z found, 419.1 $[M+H]^+$.

Example 262

2-(4-{[4-(Pyridin-4-yloxy)piperidin-1-yl]methyl}phenoxy)[1,3]thiazolo[4,5-b]pyridine

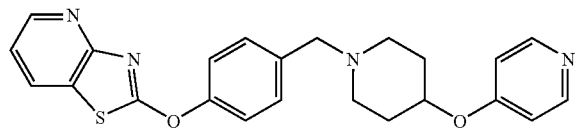

$^1$H NMR (400 MHz, $CDCl_3$): 8.59-8.54 (m, 1H), 8.45-8.38 (m, 2H), 8.06-7.99 (m, 1H), 7.45-7.34 (m, 4H), 7.24-7.17 (m, 1H), 6.82-6.77 (m, 2H), 4.50-4.38 (m, 1H), 3.56 (s, 2H), 2.82-2.68 (m, 2H), 2.42-2.29 (m, 2H), 2.04-1.98 (m, 2H), 1.91-1.79 (m, 2H). MS (ESI): mass calcd. for $C_{23}H_{22}N_4O_2S$, 418.1; m/z found, 419.1 $[M+H]^+$.

Example 263

2-(4-{[4-(Pyridin-2-ylsulfanyl)piperidin-1-yl]methyl}phenoxy)[1,3]thiazolo[4,5-b]pyridine

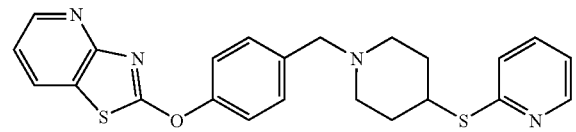

$^1$H NMR (400 MHz, $CDCl_3$): 8.57 (dd, J=4.8, 1.7, 1H), 8.44-8.40 (m, 1H), 8.39-8.37 (m, 1H), 8.04 (dd, J=7.9, 1.7, 1H), 7.46-7.39 (m, 4H), 7.22 (dd, J=7.9, 4.9, 1H), 7.19-7.13 (m, 1H), 7.01-6.95 (m, 1H), 4.03-3.91 (m, 1H), 3.81 (s, 2H), 3.09-2.99 (m, 2H), 2.65-2.52 (m, 2H), 2.27-2.16 (m, 2H), 1.99-1.86 (m, 2H). MS (ESI): mass calcd. for $C_{23}H_{22}N_4OS_2$, 434.1; m/z found, 435.1 $[M+H]^+$.

Example 264

2-(4-{[4-(Phenylsulfanyl)piperidin-1-yl]methyl}phenoxy)[1,3]thiazolo[4,5-b]pyridine

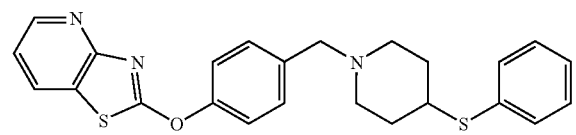

$^1$H NMR (400 MHz, $CDCl_3$): 8.56 (dd, J=4.8, 1.6, 1H), 8.04 (dd, J=8.0, 1.6, 1H), 7.69-7.56 (m, 2H), 7.49-7.43 (m, 2H), 7.43-7.37 (m, 2H), 7.34-7.27 (m, 3H), 7.22 (dd, J=7.9, 4.8, 1H), 4.10-3.84 (m, 2H), 3.49-3.26 (m, 1H), 3.20-3.02 (m, 2H), 2.58-2.17 (m, 3H), 2.02-1.84 (m, 3H). MS (ESI): mass calcd. for $C_{24}H_{23}N_3OS_2$, 433.1; m/z found, 434.1 $[M+H]^+$.

Examples 265-266 were prepared using methods analogous to those described for Example 109.

Example 265

2-(4-{[(1R,4R)-5-Acetyl-2,5-diazabicyclo[2.2.1]hept-2-yl]methyl}phenoxy)[1,3]thiazolo[4,5-b]pyridine

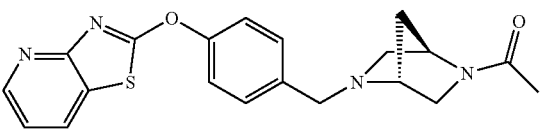

$^1$H NMR (400 MHz, $CDCl_3$): 8.58-8.54 (m, 1H), 8.04-7.99 (m, 1H), 7.45-7.39 (m, 2H), 7.39-7.34 (m, 2H), 7.23-7.17 (m, 1H), 4.81-4.77 (m, 0.5H), 4.26-4.21 (m, 0.5H), 3.80-3.77 (m, 1H), 3.76-3.73 (m, 1H), 3.61-3.52 (m, 2H), 3.35-3.24 (m, 1H), 3.04-2.98 (m, 0.5H), 2.88-2.75 (m, 1H), 2.60-2.53 (m, 0.5H), 2.09 (s, 1.5H), 2.01 (s, 2H), 1.93-1.88 (m, 0.5H), 1.84-1.77 (m, 0.5H), 1.70-1.63 (m, 0.5H). MS (ESI): mass calcd. for $C_{20}H_{20}N_4O_2S$, 380.1; m/z found, 381.1 $[M+H]^+$.

Example 266

(1R,4R)-5-[4-([1,3]Thiazolo[4,5-b]pyridin-2-yloxy)benzyl]-2,5-diazabicyclo[2.2.1]heptane-2-carboxamide

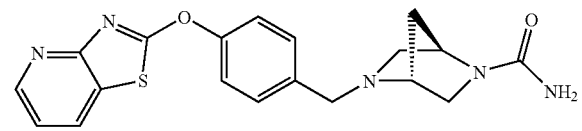

$^1$H NMR (500 MHz, $CDCl_3$): 8.58 (dd, J=4.8, 1.7, 1H), 8.04 (dd, J=7.9, 1.7, 1H), 7.46-7.41 (m, 2H), 7.41-7.35 (m, 2H), 7.23 (dd, J=7.9, 4.8, 1H), 4.33-4.26 (m, 2H), 3.79 (s, 2H), 3.59-3.55 (m, 1H), 3.29-3.22 (m, 1H), 2.97-2.89 (m, 1H), 2.82-2.74 (m, 1H), 1.99-1.92 (m, 1H), 1.82-1.72 (m, 1H). MS (ESI): mass calcd. for $C_{19}H_{19}N_5O_2S$, 381.1; m/z found, 382.1 $[M+H]^+$.

Examples 267-268 were prepared using methods analogous to those described for Example 43.

Example 267

2-(4-{2-[(1R,4R)-5-Acetyl-2,5-diazabicyclo[2.2.1]hept-2-yl]ethoxy}phenoxy)[1,3]thiazolo[4,5-b]pyridine

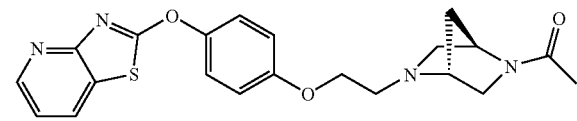

$^1$H NMR (500 MHz, $CDCl_3$): 8.53 (dd, J=4.8, 1.7, 1H), 8.01-7.96 (m, 1H), 7.32-7.26 (m, 2H), 7.20-7.15 (m, 1H), 6.95-6.89 (m, 2H), 4.78-4.70 (m, 0.5H), 4.25-4.19 (m, 0.5H), 4.08-4.02 (m, 2H), 3.74-3.55 (m, 2H), 3.36-3.22 (m, 1H), 3.21-3.14 (m, 0.5H), 3.05-2.92 (m, 3H), 2.83-2.74 (m, 0.5H), 2.68-2.59 (m, 0.5H), 2.07 (s, 1H), 1.99-1.94 (m, 2H), 1.90-1.86 (m, 0.5H), 1.81-1.76 (m, 0.5H), 1.70-1.65 (m, 0.5H). MS (ESI): mass calcd. for $C_{21}H_{22}N_4O_3S$, 410.1; m/z found, 411.1 $[M+H]^+$.

Example 268

(1R,4R)-5-[2-[4-([1,3]Thiazolo[4,5-b]pyridin-2-yloxy)phenoxy]ethyl]-2,5-diazabicyclo[2.2.1]heptane-2-carboxamide

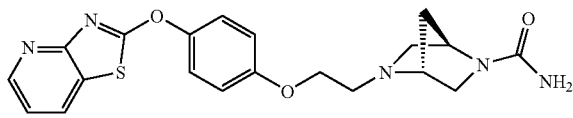

$^1$H NMR (500 MHz, CDCl$_3$): 8.56 (dd, J=4.8, 1.6, 1H), 8.01 (dd, J=7.9, 1.6, 1H), 7.35-7.29 (m, 2H), 7.20 (dd, J=7.9, 4.8, 1H), 6.98-6.92 (m, 2H), 4.51 (s, 2H), 4.47-4.37 (m, 1H), 4.10-4.06 (m, 2H), 3.73-3.67 (m, 1H), 3.59-3.50 (m, 1H), 3.29-3.22 (m, 1H), 3.11-3.06 (m, 1H), 3.06-2.97 (m, 2H), 2.83-2.76 (m, 1H), 1.95-1.89 (m, 1H), 1.80-1.74 (m, 1H). MS (ESI): mass calcd. for $C_{20}H_{21}N_5O_3S$, 411.1; m/z found, 412.1 $[M+H]^+$.

Example 269

(4R)-4-Hydroxy-1-{1-[4-([1,3]thiazolo[4,5-b]pyridin-2-yloxy)benzyl]piperidin-4-yl}pyrrolidin-2-one

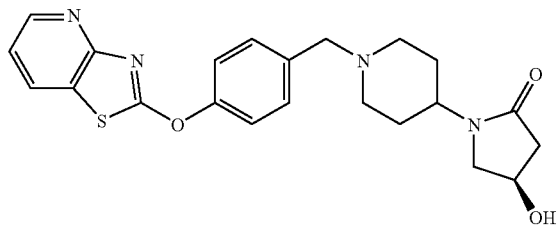

To a solution of (4R)-4-{[tert-butyl(dimethyl)silyl]oxy}-1-(piperidin-4-yl)pyrrolidin-2-one acetate (252 mg, 0.70 mmol, 1.2 equiv.) in DCE (3.1 mL) was added Et$_3$N (98 μL, 0.70 mmol, 1.2 equiv.) and stirred at rt for 30 min to free-base the amine. To this solution was added 4-([1,3]thiazolo[4,5-b]pyridine-2-yloxy)benzaldehyde (150 mg, 0.585 mmol) and sodium triacetoxyborohydride (211 mg, 0.995 mmol, 1.7 equiv.). The mixture was stirred at rt for 17 h. The reaction mixture was then partitioned between sat. aq. NaHCO$_3$ (20 mL) and CH$_2$Cl$_2$ (20 mL). The organic layer was washed with brine (20 mL), dried, filtered, and concentrated to an orange oil. To a solution of this oil (158 mg, 0.293 mmol) in CH$_2$Cl$_2$ (2.9 mL) was added HCl (4 M in dioxane, 1.62 mL, 22.0 equiv.). The reaction was stirred at rt for 2.5 h and then concentrated. The residue was dissolved in water (20 mL), and the pH adjusted to ~pH 7 with 1 M aq. NaOH. The mixture was then extracted with CH$_2$Cl$_2$ (2×15 mL) followed by EtOAc (2×15 mL) and the organic layers (CH$_2$Cl$_2$ and EtOAc) were individually washed with water (30 mL each). The combined organic layers were dried, filtered and concentrated to give the crude product as a white solid. The crude product was purified using preparative reversed phase HPLC to afford the desired product as a white solid (51 mg, 41%). $^1$H NMR (500 MHz, CDCl$_3$): 8.58 (dd, J=4.8, 1.7, 1H), 8.04 (dd, J=7.9, 1.7, 1H), 7.42-7.40 (m, 2H), 7.39-7.37 (m, 2H), 7.22 (dd, J=7.9, 4.8, 1H), 4.38-4.30 (m, 1H), 4.06-3.95 (m, 1H), 3.56-3.51 (m, 2H), 3.45-3.38 (m, 1H), 3.31-3.22 (m, 1H), 3.03-2.94 (m, 2H), 2.82-2.77 (m, 1H), 2.52-2.43 (m, 1H), 2.20-2.07 (m, 2H), 1.98-1.88 (m, 1H), 1.83-1.73 (m, 2H), 1.72-1.66 (m, 2H). MS (ESI): mass calcd. for $C_{22}H_{24}N_4O_3S$, 424.2; m/z found, 425.1 $[M+H]^+$.

Example 270

(4R)-4-Hydroxy-1-(1-{2-[4-([1,3]thiazolo[4,5-b]pyridin-2-yloxy)phenoxy]ethyl}piperidin-4-yl)pyrrolidin-2-one

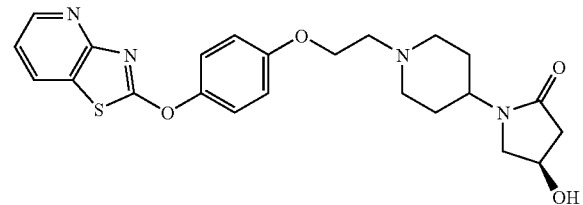

To a solution of (4R)-4-{[tert-butyl(dimethyl)silyl]oxy}-1-(piperidin-4-yl)pyrrolidin-2-one acetate (159 mg, 0.44 mmol, 1.2 equiv.) in MeOH was added Dowex resin (550A ion exchange) to free-base the amine. The resin was filtered and the filtrate was concentrated to an oil. To a solution of this oil in CH$_3$CN (1.9 mL) was added 2-[4-(2-bromoethoxy)phenoxy][1,3]thiazolo[4,5-b]pyridine (130 mg, 0.37 mmol) and N,N-diisopropylethylamine (97 μL, 0.56 mmol, 1.5 equiv.). The resulting solution was stirred at 70° C. for 20 h. The solution was then cooled to rt and partitioned between satd. aq. NaHCO$_3$ (20 mL) and CH$_2$Cl$_2$ (20 mL). The organic layer was washed with brine (20 mL), dried, filtered, and concentrated to give the crude product as a dark orange solid. To a solution of this oil (185 mg, 0.325 mmol) in CH$_2$Cl$_2$ (3.3 mL) was added HCl (4 M in dioxane, 1.79 mL, 22.0 equiv.). The reaction was stirred at rt for 2.5 h and then concentrated. The residue was dissolved in water (20 mL), and the pH adjusted to ~pH 7 with 1 M aq. NaOH. The mixture was then extracted with CH$_2$Cl$_2$ (2×15 mL) followed by EtOAc (2×15 mL) and the organic layers (CH$_2$Cl$_2$ and EtOAc) were individually washed with water (30 mL each). The combined organic layers were dried, filtered and concentrated to give the crude product as a white solid. The crude product was purified using preparative reversed phase HPLC to afford the desired product as a white solid (39 mg, 26%). $^1$H NMR (400 MHz, CDCl$_3$): 8.56 (dd, J=4.8, 1.7, 1H), 8.00 (dd, J=7.9, 1.6, 1H), 7.35-7.30 (m, 2H), 7.19 (dd, J=7.9, 4.9, 1H), 6.97-6.93 (m, 2H), 4.36-4.27 (m, 1H), 4.16-4.07 (m, 2H), 4.05-3.92 (m, 1H), 3.44-3.35 (m, 1H), 3.28-3.19 (m, 1H), 3.13-3.03 (m, 2H), 2.87-2.79 (m, 1H), 2.70-2.64 (m, 1H), 2.51-2.40 (m, 1H), 2.32-2.20 (m, 2H), 1.97-1.75 (m, 3H), 1.74-1.69 (m, 2H). MS (ESI): mass calcd. for $C_{23}H_{26}N_4O_4S$, 454.2; m/z found, 455.1 $[M+H]^+$.

Example 271

N-Methyl-2-piperidin-1-yl-N-[4-([1,3]thiazolo[4,5-b]pyridin-2-yloxy)benzyl]ethanamine

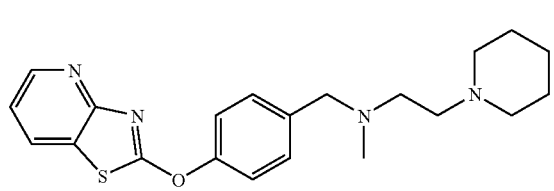

To a solution of 2-(piperidin-1-yl)-N-[4-([1,3]thiazolo[4,5-b]pyridin-2-yloxy)benzyl]ethanamine in DMF (1 mL) at 0° C., sodium hydride (60%) was added (6 mg, 0.158 mmol, 1.1 equiv.). After 30 min, iodomethane was added (11 μL, 0.173 mmol, 1.2 equiv.). After stirring for 1 h, the reaction was diluted with water (5 mL) and extracted with ethyl acetate (3×5 mL). The combined organic layers were concentrated and the residue was purified using preparative reversed phase HPLC to afford the product as a yellow solid (25 mg, 45%). $^1$H NMR (400 MHz, $CD_3OD$): 8.26 (dd, J=5.0, 1.6, 1H), 8.07 (dd, J=7.8, 1.6, 1H), 7.33-7.27 (d, J=8.8, 2H), 7.05 (dd, J=7.8, 5.0, 1H), 6.94-6.89 (m, 2H), 3.78 (s, 3H), 3.72 (d, J=7.1, 2H), 2.63 (d, J=7.1, 2H), 2.52-2.48 (m, 4H), 1.62-1.56 (m, 4H), 1.50-1.45 (m, 2H) (note: two protons missing under solvent or water peak). MS (ESI): mass calcd. for $C_{21}H_{26}N_4OS$, 382.18; m/z found, 383.1 $[M+H]^+$.

Example 272

N-(3-Methoxypropyl)-N-{2-[4-([1,3]thiazolo[4,5-b]pyridin-2-yloxy)phenoxy]ethyl}cyclopropanamine

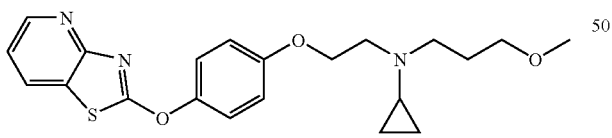

The title compound was prepared from N-{2-[4-([1,3]thiazolo[4,5-b]pyridin-2-yloxy)phenoxy]ethyl}cyclopropanamine using methods analogous to those described for Example 271, using more sodium hydride (2.5 equiv.) and more of the appropriate amine (2 equiv.). $^1$H NMR (500 MHz, $CDCl_3$): 8.58 (dd, J=4.8, 1.6, 1H), 8.01 (dd, J=7.9, 1.7, 1H), 7.35-7.30 (m, 2H), 7.21 (dd, J=7.9, 4.8, 1H), 6.98-6.93 (m, 2H), 4.13 (t, J=6.2, 2H), 3.43 (t, J=6.4, 2H), 3.35 (s, 3H), 3.05 (t, J=6.2, 2H), 2.82-2.77 (m, 2H), 1.92-1.80 (m, 3H), 0.55-0.42 (m, 4H). MS (ESI): mass calcd. for $C_{21}H_{25}N_3O_3S$, 399.16; m/z found, 400.1 $[M+H]^+$.

Example 273

Ethyl N-benzyl-N-[4-([1,3]thiazolo[4,5-b]pyridin-2-yloxy)benzyl]glycinate

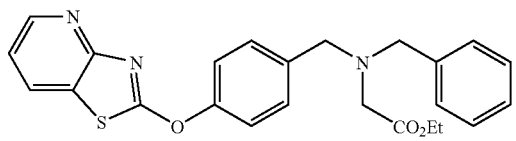

The title compound was prepared using methods analogous to those described for Example 82. $^1$H NMR (400 MHz, $CDCl_3$): 8.56 (dd, J=4.8, 1.7, 1H), 8.00 (dd, J=7.9, 1.7, 1H), 7.50-7.45 (m, 2H), 7.41-7.30 (m, 6H), 7.28-7.23 (m, 1H), 7.19 (dd, J=7.9, 4.8, 1H), 4.21-4.14 (m, 2H), 3.84 (s, 2H), 3.83 (s, 2H), 3.31 (s, 2H), 1.28 (t, J=7.1, 3H). MS (ESI): mass calcd. for $C_{24}H_{23}N_3O_3S$, 433.15; m/z found, 434.1 $[M+H]^+$.

Example 274

N-Benzyl-N-[4-([1,3]thiazolo[4,5-b]pyridin-2-yloxy)benzyl]glycine

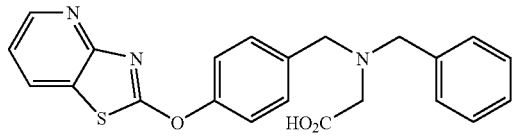

The title compound was prepared from ethyl N-benzyl-N-[4-([1,3]thiazolo[4,5-b]pyridin-2-yloxy)benzyl]glycinate using methods analogous to those described for Example 131. $^1$H NMR (500 MHz, DMSO-$d_6$): 8.52 (dd, J=4.8, 1.7, 1H), 8.40 (dd, J=8.0, 1.7, 1H), 7.53 (d, J=8.6, 2H), 7.46 (d, J=8.6, 2H), 7.39-7.32 (m, 5H), 7.29-7.24 (m, 1H), 3.81 (s, 2H), 3.79 (s, 2H), 3.21 (s, 2H). MS (ESI): mass calcd. for $C_{22}H_{19}N_3O_3S$, 405.11; m/z found, 406.1 $[M+H]^+$.

Example 275

N-[4-([1,3]Thiazolo[4,5-b]pyridin-2-yloxy)benzyl]-beta-alanine

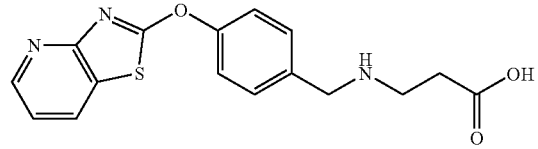

To a mixture of 4-([1,3]thiazolo[4,5-b]pyridin-2-yloxy)benzaldehyde (100 mg, 0.39 mmol) and β-alanine methyl ester (54 mg, 0.39 mmol, 1 equiv.) was added methanol (2 mL) followed by 1 N NaOH (430 μL). The reaction was allowed to stir at rt for 1 h before the addition of sodium triacetoxyborohydride (95 mg, 0.39 mmol, 1 equiv.). Stirring was allowed to continue for 4 h before the reaction was concentrated and purified using preparative reversed phase HPLC to afford the product as white powder (40 mg, 31%). $^1$H NMR (400 MHz, CD$_3$OD): 8.49 (d, J=4.8, 1H), 8.33 (d, J=7.9, 1H), 8.27 (s, 1H), 7.65 (d, J=8.2, 2H), 7.55 (d, J=8.2, 2H), 7.38-7.33 (m, 1H), 4.28 (s, 2H), 3.24 (t, J=6.4, 2H), 2.58 (t, J=6.4, 2H). MS (ESI): Mass calcd for C$_{16}$H$_{15}$N$_3$O$_3$S, 329.08; m/z found, 330.1 [M+H]$^+$.

Examples 276-278 were prepared using methods analogous to those described for Example 116.

Example 276

2-{4-[(5-Acetylhexahydropyrrolo[3,4-c]pyrrol-2 (1H)-yl)methyl]phenoxy}[1,3]thiazolo[4,5-b]pyridine

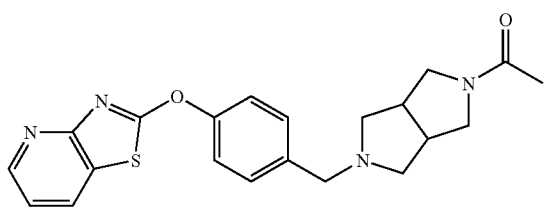

$^1$H NMR (400 MHz, CD$_3$OD): 8.48 (dd, J=4.8, 1.5, 1H), 8.29 (dd, J=8.1, 1.6, 1H), 7.48 (d, J=8.7, 2H), 7.38 (d, J=8.7, 2H), 7.33 (dd, J=7.8, 5.0, 1H), 3.73 (dd, J=11.1, 8.5, 1H), 3.67 (s, 2H), 3.62 (dd, J=12.4, 8.6, 1H), 3.47-3.40 (m, 2H), 3.02-2.84 (m, 2H), 2.74-2.67 (m, 2H), 2.57-2.47 (m, 2H), 2.05 (s, 3H). MS (ESI): Mass calcd for C$_{21}$H$_{22}$N$_4$O$_2$S, 394.15; m/z found, 395.1 [M+H]$^+$.

Example 277

5-[4-([1,3]Thiazolo[4,5-b]pyridin-2-yloxy)benzyl] hexahydropyrrolo[3,4-c]pyrrole-2(1H)-carboxamide

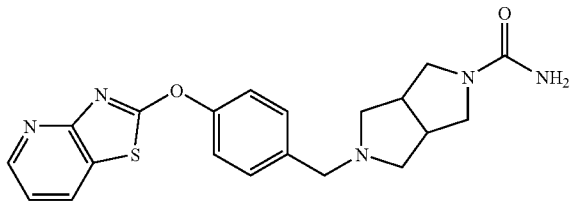

$^1$H NMR (400 MHz, CD$_3$OD): 8.47 (dd, J=4.8, 1.5, 1H), 8.29 (dd, J=8.1, 1.6, 1H), 7.49 (d, J=8.6, 2H), 7.38 (d, J=8.6, 2H), 7.33 (dd, J=7.8, 4.8, 1H), 3.67 (s, 2H), 3.56-3.48 (m, 2H), 3.29-3.26 (m, 2H), 2.95-2.84 (m, 2H), 2.80-2.73 (m, 2H), 2.49-2.42 (m, 2H). MS (ESI): Mass calcd for C$_{20}$H$_{21}$N$_5$O$_2$S, 395.14; m/z found, 396.1 [M+H]$^+$.

Example 278 meso-1-{(3-endo)-8-[4-([1,3]Thiazolo[4,5-b]pyridin-2-yloxy)benzyl]-8-azabicyclo[3.2.1]oct-3-yl}urea

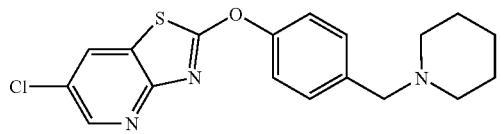

$^1$H NMR (400 MHz, CD$_3$OD): 8.47 (dd, J=5.0, 1.5, 1H), 8.29 (dd, J=8.1, 1.6, 1H), 7.55 (d, J=8.4, 2H), 7.38 (d, J=8.4, 2H), 7.34 (dd, J=8.0, 4.7, 1H), 3.87-3.77 (m, 1H), 3.63 (s, 2H), 3.25-3.14 (m, 2H), 2.26-2.11 (m, 4H), 2.02-1.91 (m, 2H), 1.71-1.58 (m, 2H), 1.39-1.23 (m, 1H). MS (ESI): Mass calcd for C$_{21}$H$_{23}$N$_5$O$_2$S, 409.16; m/z found, 410.1 [M+H]$^+$.

Examples 279-280 were prepared using methods analogous to those described for Example 129.

Example 279

6-Chloro-2-(4-piperidin-1-ylmethyl-phenoxy)[1,3]thiazolo[4,5-b]pyridine

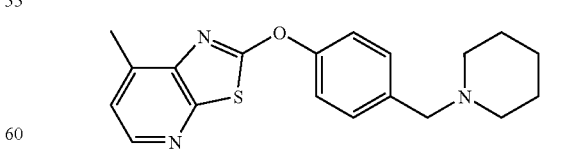

$^1$H NMR (400 MHz, CDCl$_3$): 8.50 (d, J=2.4, 1H), 7.98 (d, J=2.4, 1H), 7.43-7.38 (m, 2H), 7.35-7.30 (m, 2H), 3.49 (s, 2H), 2.46-2.33 (m, 4H), 1.62-1.55 (m, 4H), 1.49-1.40 (m, 2H). MS (ESI): mass calculated for C$_{18}$H$_{18}$ClN$_3$OS, 359.09; m/z found, 360.10 [M+H]$^+$.

Example 280

7-Methyl-2-[4-(piperidin-1-ylmethyl)phenoxyl][1,3]thiazolo[5,4-b]pyridine $^1$H NMR (500 MHz, CDCl$_3$): 8.28 (d, J=4.9, 1H), 7.45-7.41 (m, 2H), 7.35-7.31 (m, 2H), 7.17 (d, J=4.9, 1H), 3.52 (s, 2H), 2.61 (s, 3H), 2.42 (s, 4H), 1.64-1.58 (m, 4H), 1.51-1.43 (m, 2H). MS (ESI): mass calculated for C$_{19}$H$_{21}$N$_3$OS, 339.14; m/z found, 340.10 [M+H]$^+$.

Examples 281-286 were prepared using methods analogous to those described for Example 118.

Example 281

2-(4-{[(1S,4S)-5-Acetyl-2,5-diazabicyclo[2.2.1]hept-2-yl]methyl}phenoxy)-7-methyl[1,3]thiazolo[5,4-b]pyridine

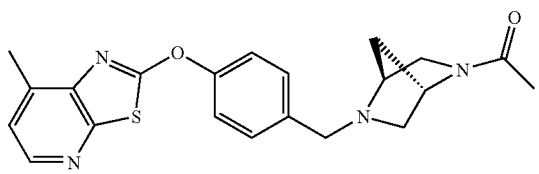

¹H NMR (400 MHz, CDCl₃): 8.26 (d, J=4.9, 1H), 7.43 (dd, J=8.7, 2.8, 2H), 7.35-7.30 (m, 2H), 7.15 (d, J=4.9, 1H), 4.79 (s, 0.5H), 4.24 (s, 0.5H), 3.81-3.73 (m, 2.5H), 3.62-3.53 (m, 1.5H), 3.33 (dd, J=9.3, 2.3, 0.5H), 3.28 (dd, J=11.4, 2.0, 0.5H), 3.02 (dd, J=9.5, 2.1, 0.5H), 2.85 (dd, J=9.7, 2.2, 0.5H), 2.78 (d, J=9.7, 0.5H), 2.61-2.57 (m, 3.5H), 2.08 (s, 1.5H), 2.02-1.97 (m, 2H), 1.92 (d, J=9.9, 0.5H), 1.81 (d, J=9.7, 0.5H), 1.68 (d, J=10.0, 0.5H). MS (ESI): mass calculated for $C_{21}H_{22}N_4O_2S$, 394.15; m/z found, 395.10 [M+H]⁺.

Example 282

1-{4-[(7-Methyl[1,3]thiazolo[4,5-b]pyridin-2-yl)oxy]benzyl}piperidine-4-carboxamide

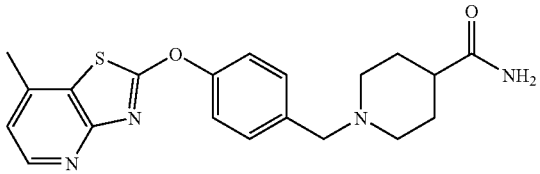

¹H NMR (500 MHz, CDCl₃): 8.46 (d, J=5.0, 1H), 7.43-7.35 (m, 4H), 7.04 (dd, J=5.0, 0.7, 1H), 5.48 (s, 1H), 5.28 (s, 1H), 3.54 (s, 2H), 2.97 (d, J=11.8, 2H), 2.52 (s, 3H), 2.25-2.15 (m, 1H), 2.05 (td, J=11.6, 2.3, 2H), 1.94-1.87 (m, 2H), 1.84-1.74 (m, 2H). MS (ESI): mass calculated for $C_{20}H_{22}N_4O_2S$, 382.15; m/z found, 383.10 [M+H]⁺.

Example 283

1-{4-[(6-Fluoro[1,3]thiazolo[4,5-b]pyridin-2-yl)oxy]benzyl}piperidine-4-carboxamide

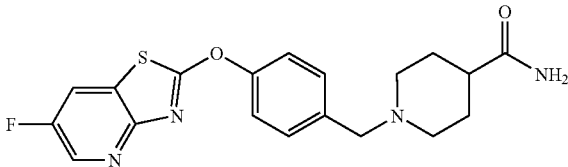

¹H NMR (600 MHz, CDCl₃): 8.42 (dd, J=2.8, 1.0, 1H), 7.76 (dd, J=7.4, 2.8, 1H), 7.41-7.38 (m, 2H), 7.36-7.32 (m, 2H), 5.44 (s, 1H), 5.24 (s, 1H), 3.52 (s, 2H), 2.94 (d, J=11.8, 2H), 2.21-2.14 (m, 1H), 2.07-2.00 (m, 2H), 1.92-1.86 (m, 2H), 1.82-1.72 (m, 2H). MS (ESI): mass calculated for $C_{19}H_{19}FN_4O_2S$, 386.12; m/z found, 387.10 [M+H]⁺.

Example 284

1-{4-[(6-Chloro[1,3]thiazolo[4,5-b]pyridin-2-yl)oxy]benzyl}piperidine-4-carboxamide

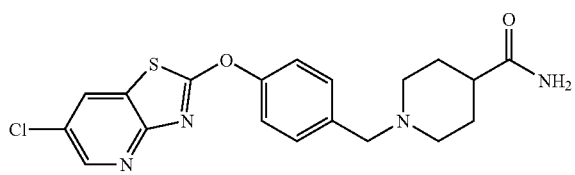

¹H NMR (600 MHz, CDCl₃): 8.50 (d, J=2.4, 1H), 8.00 (d, J=2.4, 1H), 7.41-7.38 (m, 2H), 7.36-7.32 (m, 2H), 5.45 (s, 1H), 5.25 (s, 1H), 3.52 (s, 2H), 2.94 (d, J=11.8, 2H), 2.21-2.14 (m, 1H), 2.03 (td, J=11.6, 2.4, 2H), 1.89 (d, J=12.7, 2H), 1.81-1.72 (m, 2H). MS (ESI): mass calculated for $C_{19}H_{19}ClN_4O_2S$, 402.09; m/z found, 403.10 [M+H]⁺.

Example 285

1-[4-([1,3]Thiazolo[4,5-b]pyrazin-2-yloxy)benzyl]piperidine-4-carboxamide

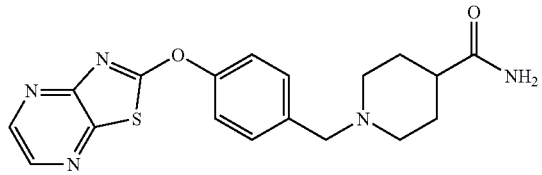

¹H NMR (600 MHz, CDCl₃): 8.51 (d, J=2.6, 1H), 8.34 (d, J=2.6, 1H), 7.44-7.41 (m, 2H), 7.36-7.32 (m, 2H), 5.44 (s, 1H), 5.24 (s, 1H), 3.53 (s, 2H), 2.95 (d, J=11.6, 2H), 2.21-2.15 (m, 1H), 2.04 (td, J=11.6, 2.2, 2H), 1.92-1.86 (m, 2H), 1.82-1.74 (m, 2H). MS (ESI): mass calculated for $C_{18}H_{19}N_5O_2S$, 369.13; m/z found, 370.10 [M+H]⁺.

Example 286

1-{4-[(7-Methyl[1,3]thiazolo[5,4-b]pyridin-2-yl)oxy]benzyl}piperidine-4-carboxamide

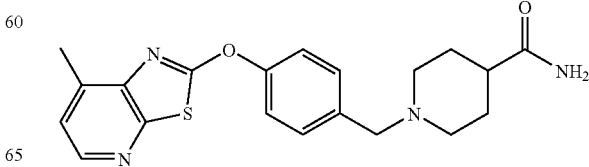

¹H NMR (600 MHz, CDCl₃): 8.26 (d, J=4.9, 1H), 7.42-7.39 (m, 2H), 7.34-7.31 (m, 2H), 7.15 (dd, J=4.9, 0.7, 1H), 5.44 (s, 1H), 5.26 (s, 1H), 3.53 (s, 2H), 2.99-2.91 (m, 2H), 2.60-2.59 (m, 3H), 2.21-2.15 (m, 1H), 2.05 (td, J=11.6, 2.4, 2H), 1.92-1.86 (m, 2H), 1.82-1.74 (m, 2H). MS (ESI): mass calculated for $C_{20}H_{22}N_4O_2S$, 382.15; m/z found, 383.10 [M+H]⁺.

Examples 287-289 were prepared using methods analogous to those described for Example 118, with the addition of $Cs_2CO_3$ (0.6 equiv.).

Example 287 meso-endo-N-[8-{4-[(6-Chloro[1,3]thiazolo[4,5-b]pyridin-2-yl)oxy]benzyl}-8-azabicyclo[3.2.1]oct-3-yl]acetamide

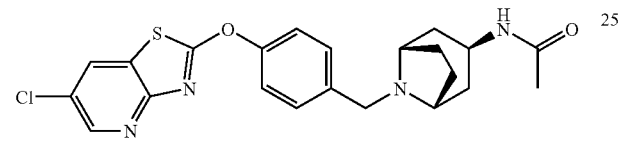

¹H NMR (600 MHz, CDCl₃): 8.50 (d, J=2.4, 1H), 7.99 (d, J=2.4, 1H), 7.47-7.43 (m, 2H), 7.36-7.32 (m, 2H), 5.82-5.77 (m, 1H), 4.13 (q, J=7.0, 1H), 3.55 (s, 2H), 3.22-3.18 (m, 2H), 2.25-2.19 (m, 2H), 2.18-2.12 (m, 2H), 1.97 (s, 3H), 1.80-1.74 (m, 2H), 1.62-1.57 (m, 2H). MS (ESI): mass calculated for $C_{22}H_{23}ClN_4O_2S$, 442.12; m/z found, 443.10 [M+H]⁺.

Example 288 meso-endo-N-[8-{4-[(6-Fluoro[1,3]thiazolo[4,5-b]pyridin-2-yl)oxy]benzyl}-8-azabicyclo[3.2.1]oct-3-yl]acetamide

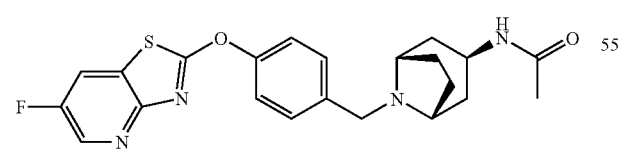

¹H NMR (600 MHz, CDCl₃): 8.42 (dd, J=2.8, 1.0, 1H), 7.76 (dd, J=7.4, 2.8, 1H), 7.50-7.42 (m, 2H), 7.38-7.32 (m, 2H), 5.87-5.76 (m, 1H), 4.12 (dd, J=14.1, 7.0, 1H), 3.55 (s, 2H), 3.20 (s, 2H), 2.26-2.19 (m, 2H), 2.19-2.13 (m, 2H), 1.97 (s, 3H), 1.81-1.74 (m, 2H), 1.67-1.57 (m, 2H). MS (ESI): mass calculated for $C_{22}H_{23}FN_4O_2S$, 426.15; m/z found, 427.10 [M+H]⁺.

Example 289 meso-endo-N-[8-{4-[(7-Methyl[1,3]thiazolo[4,5-b]pyridin-2-yl)oxy]benzyl}-8-azabicyclo[3.2.1]oct-3-yl]acetamide

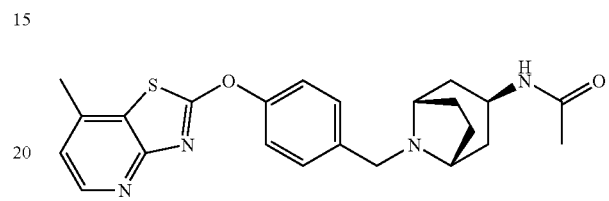

¹H NMR (600 MHz, CDCl₃): 8.37 (d, J=5.0, 1H), 7.39-7.36 (m, 2H), 7.30-7.26 (m, 2H), 6.94 (dd, J=5.0, 0.7, 1H), 5.79-5.71 (m, 1H), 4.05 (q, J=7.1, 1H), 3.48 (s, 2H), 3.17-3.12 (m, 2H), 2.43 (s, 3H), 2.19-2.12 (m, 2H), 2.10-2.05 (m, 2H), 1.90 (s, 3H), 1.74-1.68 (m, 2H), 1.54 (d, J=13.9, 2H). MS (ESI): mass calculated for $C_{23}H_{26}N_4O_2S$, 422.18; m/z found, 423.2 [M+H]⁺.

Example 290

2-(4-{[(1S,4S)-5-Acetyl-2,5-diazabicyclo[2.2.2]oct-2-yl]methyl}phenoxy)[1,3]thiazolo[4,5-b]pyridine

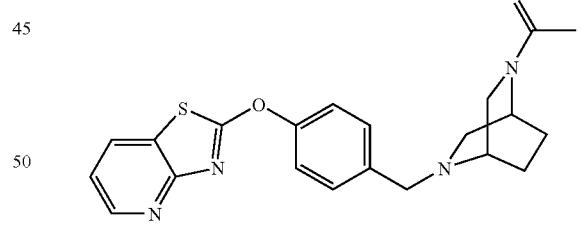

The title compound was prepared using methods analogous to those described for Example 112, substituting $Cs_2CO_3$ for $Et_3N$ and reducing the reaction temperature to rt.
¹H NMR (500 MHz, CDCl₃): 8.56 (dd, J=4.8, 1.6, 1H), 8.02 (dt, J=8.0, 1.3, 1H), 7.44-7.40 (m, 2H), 7.38-7.34 (m, 2H), 7.23-7.18 (m, 1H), 4.58-4.55 (m, 0.5H), 3.90-3.70 (m, 3.5H), 3.45 (d, J=12.7, 0.5H), 3.38 (d, J=10.5, 0.5H), 3.01-2.85 (m, 3H), 2.17-2.00 (m, 4H), 1.96-1.77 (m, 2H), 1.69-1.53 (m, 1H). MS (ESI): mass calculated for $C_{21}H_{22}N_4O_2S$, 394.15; m/z found, 395.10 [M+H]⁺.

Example 291

2-(4-{2-[4-(Pyridin-2-ylsulfanyl)piperidin-1-yl]ethoxy}phenoxy)[1,3]thiazolo[4,5-b]pyridine

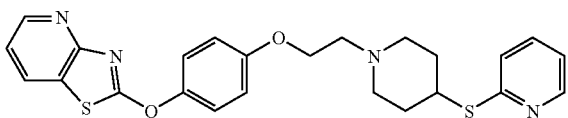

The title compound was prepared using methods analogous to those described for Example 1. $^1$H NMR (400 MHz, CDCl$_3$): 8.56 (dd, J=4.8, 1.7, 1H), 8.45-8.40 (m, 1H), 8.00 (dd, J=7.9, 1.7, 1H), 7.51-7.44 (m, 1H), 7.35-7.29 (m, 2H), 7.23-7.14 (m, 2H), 7.01-6.93 (m, 3H), 4.20 (t, J=5.6, 2H), 4.00-3.88 (m, 1H), 3.13-3.03 (m, 2H), 2.98 (t, J=5.6, 2H), 2.66-2.54 (m, 2H), 2.27-2.14 (m, 2H), 1.96-1.81 (m, 2H). MS (ESI): mass calcd. for C$_{24}$H$_{24}$N$_4$O$_2$S$_2$, 464.1; m/z found, 465.1 [M+H]$^+$.

Example 292

2-(4-{2-[4-(2-Methoxyphenyl)piperazin-1-yl]ethoxy}phenoxy)[1,3]thiazolo[4,5-b]pyridine

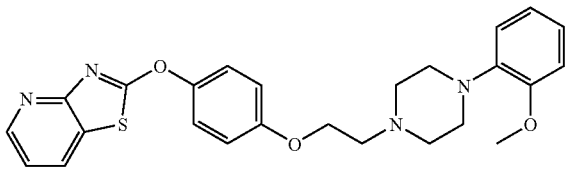

The title compound was prepared using methods analogous to those described for Example 17. $^1$H NMR (500 MHz, CD$_3$OD): 8.58 (dd, J=7.8, 1.1, 0.5H), 8.53-8.44 (m, 2H), 8.30 (dd, J=8.0, 1.6, 0.5H), 7.45-7.31 (m, 1H), 7.16-6.89 (m, 5H), 6.76-6.72 (m, 2H), 6.72-6.66 (m, 1H), 5.07 (t, J=5.0, 1H), 4.53-4.47 (m, 1H), 4.30 (t, J=5.3, 1H), 4.19 (s, 1H), 3.90 (d, J=14.7, 3H), 3.84 (s, 1H), 3.30-3.15 (m, 4H), 3.13 (t, J=5.3, 1H), 3.02 (s, 1H). MS (ESI): mass calcd. for C$_{25}$H$_{26}$N$_4$O$_3$S, 462.17; m/z found, 463.1 [M+H]$^+$.

Example 293

(1S,4S)-5-[4-([1,3]Thiazolo[4,5-b]pyridin-2-yloxy)benzyl]-2,5-diazabicyclo[2.2.2]octane-2-carboxamide formate.

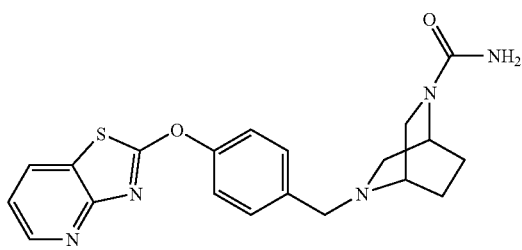

The title compound was prepared using methods analogous to those described for Example 112, substituting Cs$_2$CO$_3$ for Et$_3$N and reducing the reaction temperature to rt. $^1$H NMR (600 MHz, CDCl$_3$): 8.56 (dd, J=4.8, 1.6, 1H), 8.02 (dd, J=7.9, 1.6, 1H), 7.47-7.41 (m, 2H), 7.39-7.34 (m, 2H), 7.21 (dd, J=7.9, 4.8, 1H), 4.45 (s, 2H), 3.82-3.73 (m, 3H), 3.49 (s, 1.5H), 3.33-3.22 (m, 1H), 3.06-2.88 (m, 3H), 2.16-2.09 (m, 1H), 1.94 (d, J=10.9, 1H), 1.86-1.79 (m, 1H), 1.78-1.57 (m, 0.5H). MS (ESI): mass calculated for C$_{20}$H$_{21}$N$_5$O$_2$S, 395.14; m/z found, 396.15 [M+H]$^+$.

Examples 294-295 were prepared using methods analogous to those described for Example 106.

Example 294 meso-2-(4-{[7-Acetyl-3,7-diazabicyclo[3.3.1]non-3-yl]methyl}phenoxy)[1,3]thiazolo[4,5-b]pyridine

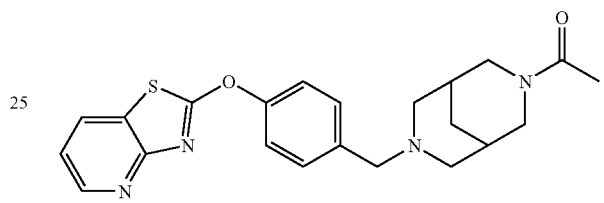

$^1$H NMR (600 MHz, CDCl$_3$): 8.56 (dd, J=4.8, 1.6, 1H), 8.01 (dd, J=7.9, 1.6, 1H), 7.36-7.31 (m, 4H), 7.20 (dd, J=7.9, 4.8, 1H), 4.67 (d, J=13.4, 1H), 3.73 (d, J=13.1, 1H), 3.50 (d, J=13.0, 1H), 3.34 (ddd, J=13.0, 3.3, 1.7, 1H), 3.16 (d, J=13.0, 1H), 3.08 (d, J=10.8, 1H), 2.91-2.84 (m, 2H), 2.33 (d, J=10.9, 1H), 2.21 (d, J=11.1, 1H), 2.03 (s, 3H), 1.96-1.87 (m, 2H), 1.78-1.73 (m, 1H), 1.71-1.67 (m, 1H). MS (ESI): mass calculated for C$_{22}$H$_{24}$N$_4$O$_2$S, 408.16; m/z found, 409.2 [M+H]$^+$.

Example 295

3-Acetyl-9-[4-([1,3]thiazolo[4,5-b]pyridin-2-yloxy)benzyl]-3,9-diazaspiro[5.5]undecane

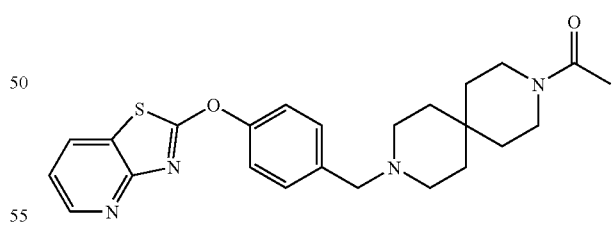

$^1$H NMR (600 MHz, CDCl$_3$): 8.56 (dd, J=4.8, 1.6, 1H), 8.02 (dd, J=7.9, 1.6, 1H), 7.41-7.33 (m, 4H), 7.21 (dd, J=7.9, 4.8, 1H), 3.57-3.51 (m, 4H), 3.41-3.35 (m, 2H), 2.49-2.36 (m, 4H), 2.08 (s, 3H), 1.57-1.53 (m, 4H), 1.50-1.44 (m, 4H). MS (ESI): mass calculated for C$_{24}$H$_{28}$N$_4$O$_2$S, 436.19; m/z found, 437.10 [M+H]$^+$.

Biological Methods:

Compounds of the invention were tested in the following assays in their free base, formate, succinate or hydrochloride salt forms.

Assay 1: Recombinant Human LTA4 Hydrolase Assay for LTA4 Hydrolase Inhibitor Activity Compounds of the present invention were tested for LTA4 hydrolase inhibitor activity against recombinant human LTA4 hydrolase (rhLTA4H). Vectors were prepared and used to express rhLTA4H essentially as follows: LTA4 hydrolase encoding DNA was amplified by polymerase chain reaction (PCR) using a human placental cDNA library as a template. Oligonucleotide primers for the PCR reaction were based on the 5'-end, and the complement of the 3'-end, of the published nucleotide sequence for the coding region of the human LTA4 hydrolase gene (C. D. Funk et al., Proc. Natl. Acad. Sci. USA 1987, 84:6677-6681). The amplified 1.9 kb DNA fragment encoding LTA4 hydrolase was isolated and cloned into the pFastBacl vector (Invitrogen). Recombinant baculovirus was generated as described by the manufacturer, and used to infect *Spodoptera frugiperda* (Sf-9) cells. Recombinant LTA4 hydrolase enzyme was purified from the infected Sf-9 cells essentially as described by J. K. Gierse et al. (Protein Expression and Purification 1993, 4:358-366). The purified enzyme solution was adjusted to contain 0.29 mg/mL LTA4 hydrolase, 50 mM Tris (pH 8.0), 150 mM NaCl, 5 mM dithiothreitol, 50% glycerol, and EDTA-free Complete protease inhibitor cocktail (Roche). The specific activity of the enzyme was about 3.8 μmol/min/mg.

LTA4 substrate was prepared from the methyl ester of LTA4 (Cayman Chemical) by treatment with 67 equiv of NaOH under nitrogen at rt for 40 min. The LTA4 substrate in its free acid form was kept frozen at −80° C. until needed. Each compound was diluted to different concentrations in assay buffer (from Assay Designs) containing 10% DMSO. A 25-μL aliquot of each compound dilution was incubated for 10 min at rt with an equal volume of assay buffer containing 10 ng of recombinant human LTA4H. The solution was then adjusted to 200 μL with assay buffer. LTA4 (free acid) was thawed and diluted in assay buffer to a concentration of 313 ng/mL, and 25 μL (8 ng) of LTA4 substrate was added to the reaction mixture (total volume=225 μL) at time zero. Each reaction was carried out at rt for 30 min. The reaction was stopped by diluting 10 μL of the reaction mixture with 200 μL of assay buffer. LTB4 was quantified in the diluted sample by a commercially available enzyme-linked immunoassay (Cayman Chemical Co.), as recommended by the manufacturer. Positive controls, under essentially identical conditions but without addition of an inhibitor compound, and negative controls, containing all assay components except enzyme, were routinely run in each experiment. $IC_{50}$ values were determined by nonlinear regression of the activity data at different compound concentrations using Graphpad Prism 4.0, one site binding competition.

The $IC_{50}$ values obtained for compounds tested in this assay are presented in Table 1. Such values should be expected to fall within the typical three-fold variability of assays of this type. The values presented here are the result of a single determination or an average of two or more determinations, as indicated in parentheses following each value. For compounds tested three or more times, the average value is followed by the standard deviation.

TABLE 1

| Ex. | $IC_{50}$ (μM) |
|---|---|
| 1 | 0.001 (1) |
| 2 | 0.11 (1) |
| 3 | 0.07 (2) |
| 4 | 0.009 (1) |

TABLE 1-continued

| Ex. | $IC_{50}$ (μM) |
|---|---|
| 5 | 0.014 (1) |
| 6 | 0.009 (1) |
| 7 | 0.31 (1) |
| 8 | 0.13 (1) |
| 9 | 0.006 (1) |
| 10 | 0.005 (1) |
| 11 | 0.098 (1) |
| 12 | 0.011 (1) |
| 13 | 0.013 (1) |
| 14 | 0.0075 ± 0.0046 (6) |
| 15 | 0.029 ± 0.0052 (3) |
| 16 | 0.003 (1) |
| 17 | 0.002 (1) |
| 18 | 0.0055 (2) |
| 19 | 0.017 (1) |
| 20 | 0.13 (1) |
| 21 | 0.16 (1) |
| 22 | 0.062 (1) |
| 23 | 0.16 (1) |
| 24 | 0.052 (1) |
| 25 | 0.16 (1) |
| 26 | 0.2 (2) |
| 27 | 0.032 (1) |
| 28 | 0.052 (1) |
| 29 | 0.013 (1) |
| 30 | 0.03 (1) |
| 31 | 0.029 (1) |
| 32 | 0.0089 (1) |
| 33 | 0.017 (1) |
| 34 | 0.019 (1) |
| 35 | 0.35 (1) |
| 36 | 0.003 (1) |
| 37 | 0.16 (1) |
| 38 | 0.061 (1) |
| 39 | 0.26 (1) |
| 40 | 0.099 (1) |
| 41 | 0.34 (1) |
| 42 | 0.083 (1) |
| 43 | 0.14 (1) |
| 44 | 0.66 (1) |
| 45 | 0.0039 (2) |
| 46 | 0.013 (1) |
| 47 | 0.034 (1) |
| 48 | 0.015 (2) |
| 49 | 0.0007 (1) |
| 50 | 0.002 (1) |
| 51 | 0.11 (1) |
| 52 | 0.001 (1) |
| 53 | 0.058 (1) |
| 54 | 0.0096 (1) |
| 55 | 0.0048 (1) |
| 56 | 0.0019 (1) |
| 57 | 0.003 (1) |
| 58 | 0.008 (1) |
| 59 | 0.009 (1) |
| 60 | 0.003 (2) |
| 61 | 0.004 (1) |
| 62 | 0.0083 (1) |
| 63 | 0.016 (1) |
| 64 | 0.027 (2) |
| 65 | 0.0096 (2) |
| 66 | 0.012 (1) |
| 67 | 0.19 (1) |
| 68 | 0.28 (1) |
| 69 | 0.12 (1) |
| 70 | 0.072 (1) |
| 71 | 0.081 (1) |
| 72 | 0.047 (1) |
| 73 | 0.012 (1) |
| 74 | 0.0065 (2) |
| 75 | 0.012 (2) |
| 76 | 0.0005 (1) |
| 77 | 0.0029 (1) |
| 78 | 0.16 (2) |
| 79 | 0.006 (1) |
| 80 | 0.002 (1) |
| 81 | 0.027 (1) |
| 82 | 0.14 (1) |

TABLE 1-continued

| Ex. | IC$_{50}$ (μM) |
|---|---|
| 83 | 0.0063 (1) |
| 84 | 0.0021 (1) |
| 85 | 0.0029 (1) |
| 86 | 0.012 (1) |
| 87 | 0.03 (1) |
| 88 | 0.008 (1) |
| 89 | 0.042 (1) |
| 90 | 0.0008 (1) |
| 91 | 0.039 (1) |
| 92 | 0.004 (1) |
| 93 | 0.055 (1) |
| 94 | 0.004 (1) |
| 95 | 0.011 (1) |
| 96 | 0.024 (1) |
| 97 | 0.001 (1) |
| 98 | 0.006 (1) |
| 99 | 0.002 (1) |
| 100 | 0.0072 (1) |
| 101 | 0.011 (1) |
| 102 | 0.015 (1) |
| 103 | 0.01 (1) |
| 104 | 0.0019 (1) |
| 105 | 0.00053 (1) |
| 106 | 0.0035 (2) |
| 107 | 0.004 (1) |
| 108 | 0.0024 (1) |
| 109 | 0.00097 (2) |
| 110 | 0.001 (1) |
| 111 | 0.0066 (1) |
| 112 | 0.37 (1) |
| 113 | 0.57 (1) |
| 114 | 0.68 (1) |
| 115 | 0.32 (1) |
| 116 | 0.001 ± 0.00051 (10) |
| 117 | 0.009 (1) |
| 118 | 3.74 (1) |
| 119 | 0.07 (1) |
| 120 | 0.11 ± 0.037 (3) |
| 121 | 0.038 ± 0.017 (3) |
| 122 | 0.048 (2) |
| 123 | 0.18 (1) |
| 124 | 0.220 (1) |
| 125 | 0.012 (1) |
| 126 | 0.92 (1) |
| 127 | 0.005 (2) |
| 128 | 0.023 (1) |
| 129 | 0.042 (1) |
| 130 | 0.0025 (1) |
| 131 | 0.0078 (1) |
| 132 | 1 (1) |
| 133 | 1.87 (1) |
| 134 | 0.038 (1) |
| 135 | 0.072 (1) |
| 136 | 0.427 (1) |
| 137 | 0.008 (1) |
| 138 | 0.029 (1) |
| 139 | 0.041 (1) |
| 140 | 0.138 (1) |
| 141 | 0.002 (1) |
| 142 | 0.008 (2) |
| 143 | 0.193 (1) |
| 144 | 0.350 (1) |
| 145 | 0.275 (1) |
| 146 | 0.097 (1) |
| 147 | 0.252 (1) |
| 148 | 0.043 (1) |
| 149 | 0.063 (1) |
| 150 | 0.602 (1) |
| 151 | 0.367 (1) |
| 152 | 0.498 (1) |
| 153 | 0.035 (1) |
| 154 | 0.049 (1) |
| 155 | 0.329 (1) |
| 156 | 0.494 (1) |
| 157 | 0.114 (1) |
| 158 | 0.194 (1) |
| 159 | 0.009 (1) |
| 160 | 0.099 (1) |
| 161 | 0.535 (1) |
| 162 | 0.003 (1) |
| 163 | 0.006 (1) |
| 164 | 0.045 (1) |
| 165 | 0.053 (1) |
| 166 | 0.114 (1) |
| 167 | 0.432 (1) |
| 168 | 0.647 (1) |
| 169 | 0.018 (1) |
| 170 | 0.029 (1) |
| 171 | 0.042 (1) |
| 172 | 0.026 (1) |
| 173 | 0.388 (1) |
| 174 | 0.094 (1) |
| 175 | 0.791 (1) |
| 176 | 0.835 (1) |
| 177 | 0.624 (1) |
| 178 | 0.011 (1) |
| 179 | 0.038 (1) |
| 180 | 0.071 (1) |
| 181 | 0.332 (1) |
| 182 | 0.0019 (2) |
| 183 | 0.067 (1) |
| 184 | 0.018 (1) |
| 185 | 0.007 (1) |
| 186 | 0.263 (1) |
| 187 | 0.290 (1) |
| 188 | 0.050 (1) |
| 189 | 0.308 (1) |
| 190 | 0.455 (1) |
| 191 | 0.072 (1) |
| 192 | 0.507 (1) |
| 193 | 0.058 (1) |
| 194 | 0.092 (1) |
| 195 | 1.368 (1) |
| 196 | 0.087 (1) |
| 197 | 0.360 (1) |
| 198 | 0.175 (1) |
| 199 | 0.042 (1) |
| 200 | 0.374 (1) |
| 201 | 0.891 (1) |
| 202 | ~8.999 (1) |
| 203 | 0.679 (1) |
| 204 | 0.576 (1) |
| 205 | 0.049 (1) |
| 206 | 0.035 (1) |
| 207 | 1.844 (1) |
| 208 | 3.898 (1) |
| 209 | 0.157 (1) |
| 210 | 0.006 (1) |
| 211 | 0.024 (1) |
| 212 | 0.018 (1) |
| 213 | 0.034 (1) |
| 214 | 0.003 (1) |
| 215 | 0.021 (1) |
| 216 | 0.060 (1) |
| 217 | 2.509 (1) |
| 218 | 0.212 (1) |
| 219 | 0.276 (1) |
| 220 | 0.109 (1) |
| 221 | 0.181 (1) |
| 223 | 0.563 (1) |
| 224 | 4.847 (1) |
| 225 | 0.021 (1) |
| 226 | 1.212 (1) |
| 227 | 0.748 (1) |
| 228 | 0.135 (1) |
| 229 | 1.088 (1) |
| 246 | 0.331 (1) |
| 247 | 0.033 (1) |
| 248 | 1.162 (1) |
| 249 | 0.141 (1) |
| 255 | 0.071 (1) |
| 256 | 0.087 (1) |
| 257 | 0.029 (1) |
| 258 | 0.002 (1) |
| 259 | 0.140 (1) |
| 260 | 0.008 (2) |

TABLE 1-continued

| Ex. | IC$_{50}$ (μM) |
|---|---|
| 261 | 0.007 (2) |
| 262 | 0.003 (2) |
| 263 | 0.004 (1) |
| 264 | 0.030 (1) |
| 265 | 0.011 (1) |
| 266 | 0.002 (1) |
| 267 | 0.003 (1) |
| 268 | 0.032 (1) |
| 269 | 0.003 (1) |
| 270 | 0.010 (1) |
| 271 | 0.293 (1) |
| 272 | 0.037 (1) |
| 273 | 0.176 (1) |
| 274 | 0.919 (1) |
| 275 | 0.047 (1) |
| 276 | 0.003 (1) |
| 277 | 0.007 (1) |
| 278 | 0.002 (1) |
| 279 | 0.032 (1) |
| 280 | >10 (1) |
| 281 | >10 (1) |
| 282 | 0.066 (1) |
| 283 | 0.016 (1) |
| 284 | 0.089 (1) |
| 285 | 0.094 (1) |
| 286 | >10 (1) |
| 287 | 0.003 (1) |
| 288 | 0.015 (1) |
| 289 | 0.009 (1) |
| 290 | 0.006 (1) |
| 291 | 0.082 (1) |
| 292 | 0.072 (1) |
| 293 | 0.003 (1) |
| 294 | 0.023 (1) |
| 295 | 0.006 (1) |

Assay 2: LTB4 Production by Calcium Ionophore-Stimulated Murine Blood for LTA4H Inhibitor Activity CD-1 mice were sacrificed, and blood was collected in heparin-containing syringes by cardiac puncture. The blood was diluted 1 in 15 with RPMI-1640 medium, and 200-μL aliquots of the diluted blood were added to wells of a 96-well microtiter plate. LTA4H inhibitor test compounds were prepared at different concentrations in RPMI-1640 medium containing 1% DMSO, and 20 μL of each test solution was added to a well containing diluted whole blood (final DMSO concentration of 0.1%). After the microtiter plate contents were incubated for 15 min at 37° C. in a humidified incubator, calcium ionophore A23187 (Sigma Chemical Co., St. Louis, Mo.) was added to each sample well (final concentration=7 μg/mL). The incubation was continued under the same conditions for an additional 30 min to allow LTB4 formation. The reaction was terminated by centrifugation (833×g, 10 min at 4° C.), and supernatants were analyzed for LTB4 by a commercially available enzyme-linked immunoassay (Cayman Chemical Co.) according to the manufacturer's instructions. Positive controls, under essentially identical conditions but without addition of an inhibitor compound, and negative unstimulated controls, containing all assay components except calcium ionophore, were routinely run in each experiment. IC$_{50}$ values for compounds tested in this assay were determined by nonlinear regression of the activity data at different compound concentrations using Graphpad Prism 4.0, one site binding competition and are presented in Table 2. The values presented here are the result of a single determination or an average of two or more determinations, as indicated in parentheses following each value. For compounds tested three or more times, the average value is followed by the standard deviation.

TABLE 2

| Ex. | IC$_{50}$ (μM) |
|---|---|
| 1 | 0.15 (1) |
| 3 | 0.38 (1) |
| 4 | 0.054 (1) |
| 5 | 0.14 (1) |
| 6 | 0.064 (1) |
| 9 | 0.017 (1) |
| 10 | 0.019 (1) |
| 11 | 0.19 (1) |
| 12 | 0.16 (1) |
| 13 | 0.12 (1) |
| 14 | 0.018 ± 0.013 (4) |
| 15 | 0.310 (1) |
| 16 | 0.026 (1) |
| 17 | 0.025 (1) |
| 18 | 0.032 ± 0.024 (3) |
| 19 | 0.34 (2) |
| 22 | 0.2 (1) |
| 24 | 0.75 (1) |
| 26 | 0.26 (1) |
| 27 | 0.16 (1) |
| 28 | 0.38 (1) |
| 29 | 0.18 (1) |
| 30 | 0.15 (1) |
| 31 | 0.031 (1) |
| 32 | 0.022 (1) |
| 33 | 0.48 (1) |
| 34 | 0.14 (1) |
| 36 | 0.051 (1) |
| 38 | 0.95 (2) |
| 40 | 0.95 (2) |
| 42 | 0.58 (1) |
| 45 | 0.17 (1) |
| 46 | 0.13 (1) |
| 47 | 0.21 (1) |
| 48 | 0.1 (1) |
| 49 | 0.076 (1) |
| 50 | 2.3 (1) |
| 52 | 0.013 (1) |
| 53 | 2.5 (1) |
| 54 | 0.075 ± 0.071 (3) |
| 55 | 0.055 (1) |
| 56 | 0.005 (1) |
| 57 | 0.016 (1) |
| 58 | 0.045 (1) |
| 59 | 0.019 (1) |
| 60 | 0.015 (2) |
| 61 | 0.011 (1) |
| 64 | 0.22 (1) |
| 65 | 0.1 (1) |
| 66 | 0.04 (1) |
| 70 | 0.35 (1) |
| 71 | 0.28 (1) |
| 72 | 1.04 (1) |
| 73 | 0.05 (1) |
| 74 | 0.23 (1) |
| 75 | 0.044 (1) |
| 76 | 0.065 (2) |
| 77 | 0.19 (1) |
| 79 | 0.02 (1) |
| 80 | 0.08 (1) |
| 81 | 4.25 (1) |
| 83 | 0.055 (1) |
| 84 | 0.039 (1) |
| 85 | 0.037 (1) |
| 86 | 0.06 (1) |
| 87 | 0.024 (1) |
| 88 | 0.05 (1) |
| 89 | 0.11 (1) |
| 90 | 0.023 (1) |
| 91 | 0.68 (1) |
| 92 | 0.067 (1) |
| 93 | 0.52 (1) |
| 94 | 0.035 (1) |
| 95 | 0.029 (1) |
| 96 | 0.037 (1) |
| 97 | 0.013 (1) |
| 98 | 0.009 (1) |
| 99 | 0.008 (1) |

TABLE 2-continued

| Ex. | IC$_{50}$ (μM) |
|---|---|
| 100 | 0.11 (1) |
| 101 | 0.003 (1) |
| 102 | 0.21 (1) |
| 103 | 0.12 (1) |
| 104 | 0.028 (1) |
| 105 | 0.015 (1) |
| 106 | 0.079 (2) |
| 107 | 3.0 (1) |
| 108 | 0.008 (1) |
| 109 | 0.06 (1) |
| 110 | 1.44 (2) |
| 111 | 0.03 (1) |
| 116 | 0.022 ± 0.017 (5) |
| 117 | 0.018 (1) |
| 119 | 0.77 (1) |
| 120 | 0.15 (1) |
| 121 | 0.12 ± 0.042 (3) |
| 122 | 0.27 (2) |
| 124 | 0.700 (1) |
| 125 | 0.019 (1) |
| 127 | 0.0075 (2) |
| 128 | 0.005 (1) |
| 129 | 0.055 (1) |
| 130 | 0.11 (1) |
| 131 | 1.07 (1) |
| 134 | 0.180 (1) |
| 135 | 0.088 (1) |
| 137 | 0.0056 (2) |
| 141 | 0.014 (1) |
| 142 | 1599.930 (1) |
| 146 | 0.450 (1) |
| 148 | 0.036 (1) |
| 149 | 0.180 (1) |
| 153 | 0.360 (1) |
| 154 | 0.330 (1) |
| 159 | 0.082 (1) |
| 160 | 0.180 (1) |
| 162 | 0.012 (1) |
| 163 | 0.031 (1) |
| 169 | 0.054 (1) |
| 178 | 0.260 (1) |
| 182 | 0.024 (1) |
| 184 | 0.110 (1) |
| 185 | 0.850 (1) |
| 255 | 1.300 (1) |
| 256 | 0.178 (1) |
| 257 | 0.097 (1) |
| 258 | 0.047 (1) |
| 260 | 0.043 (2) |
| 261 | 0.038 (2) |
| 262 | 0.097 (2) |
| 263 | 0.462 (1) |
| 264 | 0.159 (1) |
| 265 | 0.023 (1) |
| 266 | 0.140 (1) |
| 267 | 0.110 (1) |
| 268 | 0.091 (1) |
| 269 | 0.077 (1) |
| 270 | 0.120 (1) |
| 272 | 0.097 (1) |
| 275 | 3.300 (1) |
| 276 | 0.010 (1) |
| 277 | 0.900 (1) |
| 278 | 0.280 (1) |
| 279 | 0.550 (1) |
| 282 | 0.155 (1) |
| 283 | 0.068 (1) |
| 284 | 0.640 (1) |
| 285 | 0.300 (1) |
| 287 | 0.110 (1) |
| 288 | 0.104 (1) |
| 289 | 0.542 (1) |
| 290 | 0.005 (1) |
| 291 | 0.280 (1) |
| 292 | 0.088 (1) |
| 293 | 0.029 (1) |
| 294 | 0.079 (1) |
| 295 | 0.015 (1) |

Assay 3: LTB4 Production by Calcium Ionophore-Stimulated Human Blood for LTA4H Inhibitor Activity Human blood was collected from healthy donors in heparin-containing syringes. The blood was diluted 1:1 with RPMI-1640 medium, and 200-μL aliquots of the diluted blood were added to wells of a 96-well microtiter plate. LTA4H inhibitor test compounds were prepared at different concentrations in RPM 1-1640 medium containing 1% DMSO, and 20 μL of each test solution was added to a well containing diluted whole blood (final DMSO concentration of 0.1%). After the microtiter plate contents were incubated for 15 min at 37° C. in a humidified incubator, calcium ionophore A23187 (Sigma Chemical Co., St. Louis, Mo.) was added to each sample well (final concentration=7 μg/mL). The incubation was continued under the same conditions for an additional 30 min to allow LTB4 formation. The reaction was terminated by centrifugation (833×g, 10 min at 4° C.), and supernatants were analyzed for LTB4 by a commercially available enzyme-linked immunoassay (Cayman Chemical Co.) according to the manufacturer's instructions. Positive controls, under essentially identical conditions but without addition of an inhibitor compound, and negative unstimulated controls, containing all assay components except calcium ionophore, were routinely run in each experiment. IC$_{50}$ values for compounds tested in this assay were determined by nonlinear regression of the activity data at different compound concentrations using Graphpad Prism 4.0, one site binding competition, and are presented in Table 3. The number of determinations made is indicated in parentheses following each value.

TABLE 3

| Ex. | IC$_{50}$ (μM) |
|---|---|
| 14 | 0.079 (1) |
| 31 | 0.053 (1) |
| 32 | 0.008 (1) |
| 45 | 0.256 (1) |
| 55 | 0.099 (1) |
| 73 | 0.227 (1) |
| 75 | 0.299 (1) |
| 83 | 0.134 (1) |
| 106 | 0.141 (1) |
| 109 | 0.087 (1) |
| 116 | 0.019 (1) |
| 121 | 0.088 (1) |
| 265 | 0.072 (1) |
| 266 | 0.154 (1) |
| 267 | 0.057 (1) |
| 293 | 0.010 (1) |

Assay 4: Murine Arachidonic Acid-induced Inflammation Model

LTA4H inhibitor compounds of the present invention were dissolved in 20% cyclodextran/H$_2$O at a concentration of 3 mg/mL. The solutions were administered by oral gavage to female Balb/c mice weighing approximately 20 grams each (0.2 mL per mouse, 30 mg of LTA4H inhibitor compound per kg). Sixty minutes after being administered an LTA4 inhibitor, each mouse received topical application of 20 μL of arachidonic acid (100 mg/mL in acetone) to the left ear and 20 μL of acetone only to the right ear. After 3 h, the mice were sacrificed, blood was withdrawn in heparinized syringes, and 8 mm ear biopsies were taken. Ear biopsies were weighed to determine edema and then frozen at −80° C. until needed for determination of neutrophil influx.

One hundred-microliter aliquots of heparinized blood were added to wells of a microtiter plate, along with equal volumes of RPMI-1640 medium, and calcium ionophore A23187 was added to each sample well (final concentration=7 μg/μL). The microtiter plate contents were incubated for 30 min at 37° C. in a humidified incubator. The reaction was terminated by centrifugation (833×g, 10 min at 4° C.). Supernatants were analyzed for LTB4 by a commercially available enzyme-linked immunoassay (Cayman Chemical Co.) in accordance with the manufacturer's instructions. The percent inhibition of ex vivo stimulated LTB4 production (% Inh. LTB4) was determined by comparison to animals treated identically except that the solution administered by oral gavage was devoid of inhibitor compound.

Neutrophil influx was quantified by measuring the activity of myeloperoxidase (MPO), a neutrophil-specific enzyme. The ear biopsies were homogenized in 0.5 mL extraction buffer (0.3 M sucrose, 0.22% (w/v) hexadecyl trimethyl ammonium bromide (CTAB), and 2.5 mM citrate prepared from 0.5 M citrate stock solution (pH 5.0)), in a Fast-Prep-24 (MP™) (40 seconds at 6 mps). Debris was removed by centrifugation at 14000×g for 10 min. Aliquots of 10 μL of the resulting supernatant were added to wells of a microtiter plate, along with 90-μL aliquots of dilution buffer (10 mM citrate, 0.22% CTAB), followed by addition of 20 μL TMB liquid substrate system (Sigma Chemical Co.) to each sample well. The microtiter plate contents were held at room temperature until the sample with the highest concentration of MPO reached an absorbance value of 0.4 at 650 nm. The reaction was stopped by addition of 50 μL 1 M $H_2SO_4$ to each sample well, and the myeloperoxidase activity in each sample was determined from the absorbance at 405 nm. The background value from the right ear, treated only with acetone, was subtracted from that for the left ear, treated with arachidonic acid in acetone, for each animal. The percent inhibition of neutrophil influx (% Inh. MPO) by compounds of the invention was determined by comparison to animals treated identically, except that the solution administered by oral gavage was devoid of inhibitor compound.

Results for compounds tested in this assay are presented in Table 4. The number of determinations is indicated in parentheses following each value.

TABLE 4

| Ex. | % Inh. LTB4 | % Inh. MPO |
|---|---|---|
| 10 | 68 (1) | 62.23 (1) |
| 14 | 84.0 (1) | 72.3 (1) |
| 15 | 61.9 (1) | 47.7 (1) |
| 16 | 84.6 (1) | 73.61 (1) |
| 17 | 81.52 (1) | 63.4 (1) |
| 18 | 80.9 (1) | 86.1 (1) |
| 27 | 78.2 (1) | 83.7 (1) |
| 31 | 79.8 (1) | 70.5 (1) |
| 32 | 89 (1) | 76 (1) |
| 45 | 86.84 (1) | 71.13 (1) |
| 46 | 86.49 (1) | 75.3 (1) |
| 49 | 83.04 (1) | 66.03 (1) |
| 52 | 78.26 (1) | 60.25 (1) |
| 54 | 81.2 (1) | 87.69 (1) |
| 55 | 83.74 (1) | 73.55 (1) |
| 56 | 71.2 (1) | 81.58 (1) |
| 59 | 92.7 (1) | 89.88 (1) |
| 60 | 69.5 (1) | 35.76 (1) |
| 61 | 67.4 (1) | 62.82 (1) |
| 66 | 76.2 (1) | 59.97 (1) |
| 73 | 85.7 (1) | 79.37 (1) |
| 75 | 89.5 (1) | 68.1 (1) |
| 76 | 85.3 (1) | 78.31 (1) |
| 79 | 86.7 (1) | 82.23 (1) |
| 80 | 72.1 (1) | 36.99 (1) |
| 83 | 81 (1) | 88.21 (1) |
| 84 | 53.9 (1) | 72.04 (1) |
| 85 | 66.85 (1) | 48.42 (1) |
| 86 | 70.77 (1) | 51.55 (1) |
| 89 | 79.5 (1) | 79.12 (1) |
| 100 | 85.3 (1) | 88.73 (1) |
| 106 | 90.48 (2) | 95.19 (2) |
| 108 | 79.8 (1) | 71.42 (1) |
| 109 | 84.8 (1) | 71.48 (1) |
| 111 | 56.8 (1) | 66.94 (1) |
| 116 | 81 (2) | 70 (2) |
| 120 | 57.75 (1) | 48.09 (1) |
| 121 | 83 (1) | 83 (1) |
| 122 | 72 (1) | 66.9 (1) |
| 127 | 91.53 (1) | 87.64 (1) |
| 257 | 85.96 (1) | 70.49 (1) |
| 258 | 75.00 (1) | 13.80 (1) |
| 265 | 84.43 (1) | 90.85 (1) |
| 266 | 78.60 (1) | 85.84 (1) |
| 267 | 83.43 (1) | 90.56 (1) |
| 269 | 84.43 (1) | 90.56 (1) |
| 270 | 75.92 (1) | 60.59 (1) |
| 276 | 57.40 (1) | 94.90 (1) |
| 282 | 62.80 (1) | 61.07 (1) |
| 283 | 78.20 (1) | 88.28 (1) |
| 285 | 19.70 (1) | 12.35 (1) |
| 287 | 89.80 (1) | 86.70 (1) |
| 288 | 61.70 (1) | 94.60 (1) |
| 290 | 82.90 (1) | 86.90 (1) |

While the invention has been illustrated by reference to examples, it is understood that the invention is intended not to be limited to the foregoing detailed description.

What is claimed is:

1. A chemical entity selected from compounds of Formula (I), pharmaceutically acceptable salts of compounds of Formula (I), pharmaceutically acceptable prodrugs of compounds of Formula (I), and solvates of compounds of Formula (I)

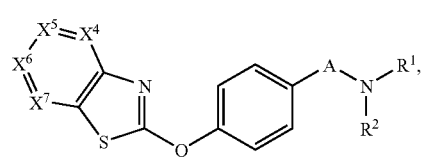

wherein
$X^4$, $X^5$, $X^6$, and $X^7$ are defined as one of the following a) and b):
  a) one of $X^4$, $X^5$, $X^6$ and $X^7$ is N and the others are $CR^a$;
     where each $R^a$ is independently H, methyl, chloro, fluoro, or trifluoromethyl;
  b) each of $X^4$ and $X^7$ is N and each of $X^5$ and $X^6$ is CH;
each of $R^1$ and $R^2$ is independently H, —$(CH_2)_{2-3}OCH_3$, —$CH_2C(O)NH_2$, —$(CH_2)_3NH_2$, —$(CH_2)_{1-2}CO_2H$, —$CH_2CO_2CH_2CH_3$, benzyl, 3-(2-oxo-pyrrolidin-1-yl)-propyl, 1-acetyl-azetidin-3-ylmethyl, monocyclic cycloalkyl, 1-methyl-4-piperidinyl, or —$C_{1-4}$alkyl unsubstituted or substituted with phenyl, monocyclic cycloalkyl, OH, or $NR^bR^c$;

where $R^b$ and $R^c$ are each independently H, —C(O)CH$_3$, or C$_{1-4}$alkyl, or $R^b$ and $R^c$ taken together with the nitrogen to which they are attached form a saturated monocyclic heterocycloalkyl ring; or R$^1$ and R$^2$ taken together with the nitrogen to which they are attached form i) a saturated monocyclic heterocycloalkyl ring, optionally fused to a phenyl ring, and unsubstituted or substituted with one or two R$^d$ substituents;

where each R$^d$ substituent is independently C$_{1-4}$alkyl unsubstituted or substituted with —OH; —OH; =O; —(CH$_2$)$_{0-2}$N(CH$_3$)$_2$; —CF$_3$; halo; —CO$_2$C$_{1-4}$ alkyl; —(CH$_2$)$_{0-2}$CO$_2$H; —C(O)NH$_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —C(O)NR$^f$C$_{1-4}$ alkyl; —C(O)NHC(CH$_3$)$_2$CH$_2$OH; —O-pyridinyl; —O-pyrimidinyl; —S-phenyl; (4-methylphenyl)sulfanyl; —S-pyridinyl; —C(O)—C$_{1-4}$alkyl; —C(O)-saturated monocyclic cycloalkyl; —C(O)—(CH$_2$)$_{1-2}$-thiophene-yl; —C(O)-2-furanyl; —C(O)-4-morpholinyl; —C(O)-pyridyl; —C(O)-1-pyrrolidinyl; —C(O)-phenyl optionally substituted with a chloro; —C(O)-1-piperazinyl optionally substituted with C$_{1-4}$alkyl; —(CH$_2$)$_{0-1}$NHC(O)—C$_{1-4}$alkyl; —NHC(O)-saturated monocyclic cycloalkyl; —NHS(O)(O)CH$_3$; —NHC(O)—CH$_2$OCH$_3$; —NHC(O)-pyridinyl; or —NHC(O)-2-thiophene-yl, where each phenyl in R$^d$ is unsubstituted or substituted with —CF$_3$, halo, or methoxy; or ii) one of the following moieties

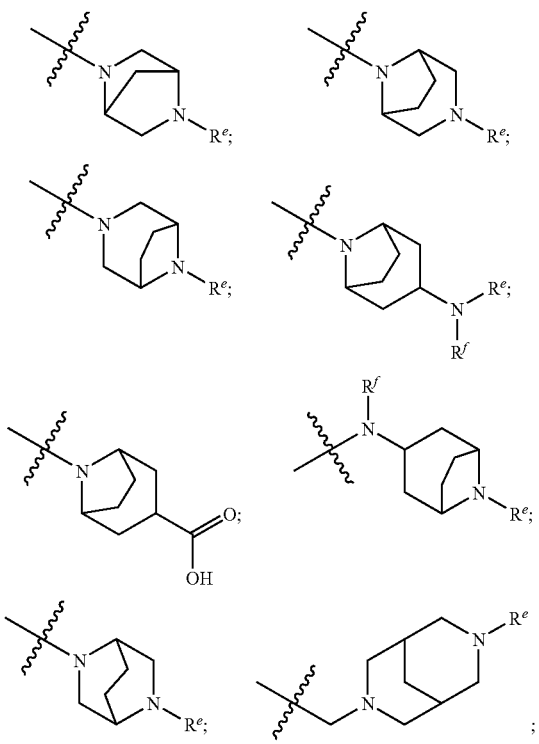

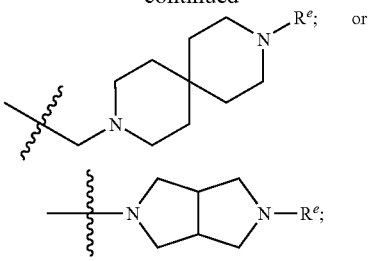

where R$^e$ is —C$_{1-4}$alkyl, —C(O)C$_{1-4}$alkyl, —SO$_2$CH$_3$, —C(O)CH$_2$NH$_2$, or —C(O)NH$_2$;

R$^f$ is H or —CH$_3$; and

A is —CH$_2$—, —CH$_2$CH$_2$—, or —OCH$_2$CH$_2$—.

2. A chemical entity as in claim 1, wherein each of said R$^1$ and R$^2$ is independently H, a monocyclic cycloalkyl, or a —C$_{1-4}$alkyl unsubstituted or substituted with phenyl, monocyclic cycloalkyl, —OH, or —NR$^b$R$^c$;

where R$^b$ and R$^c$ are each independently H or —C$_{1-4}$alkyl, or R$^b$ and R$^c$ taken together with the nitrogen to which they are attached form a saturated monocyclic heterocycloalkyl ring; or R$^1$ and R$^2$ taken together with the nitrogen to which they are attached form i) a saturated monocyclic heterocycloalkyl ring, optionally fused to a phenyl ring, and unsubstituted or substituted with one or two R$^d$ substituents;

where each R$^d$ substituent is independently —C$_{1-4}$alkyl unsubstituted or substituted with —OH; —CF$_3$; halo; —CO$_2$C$_{1-4}$alkyl; —CO$_2$H; —CONH$_2$; phenyl; benzyl; pyridyl; pyrimidinyl; phenoxy; —O-pyridinyl, —O-pyrimidinyl; —S-phenyl; or pyrrolidonyl;

where each phenyl in R$^d$ is unsubstituted or substituted with —CF$_3$, chloro, or methoxy; or ii) one of the following fused or bridged bicyclic structures

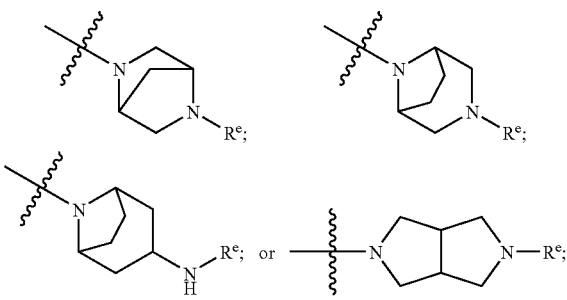

where R$^e$ is —COC$_{1-4}$alkyl or —CONH$_2$.

3. A chemical entity as in claim 2, wherein X$^4$ is N and each of X$^5$, X$^6$, and X$^7$ is CR$^a$, with R$^a$ independently chosen for X$^5$, X$^6$, and X$^7$, where R$^a$ is H, methyl, chloro, or fluoro.

4. A chemical entity as in claim 2, wherein X$^5$ is N and each of X$^4$, X$^6$, and X$^7$ is CH.

5. A chemical entity as in claim 2, wherein each of X$^4$, X$^5$, and X$^7$ is CH and X$^6$ is N.

6. A chemical entity as in claim 2, wherein each of X$^4$ and X$^7$ is N and each of X$^5$ and X$^6$ is CH.

7. A chemical entity as in claim 2, wherein $R^a$ is H.

8. A chemical entity as in claim 2, wherein each of $R^1$ and $R^2$ is independently H, cyclopropyl, methyl, ethyl, propyl, hydroxyethyl, cyclopropylmethyl, benzyl, 1-phenylethyl, or 2-piperidin-1-yl-ethylamino.

9. A chemical entity as in claim 2, wherein $R^1$ and $R^2$ taken together with the nitrogen to which they are attached form pyrrolidine, piperidine, morpholine, piperazine, dihydroisoindole, tetrahydroquinoline, or tetrahydroisoquinoline, unsubstituted or substituted with one or two $R^d$ substituents.

10. A chemical entity as in claim 2, wherein each $R^d$ substituent is independently hydroxy, methyl, trifluoromethyl, hydroxymethyl, 1-hydroxy-1-methyl-ethyl, fluoro, ethoxycarbonyl, carboxy, carbamoyl, phenyl, 3-trifluoromethylphenyl, 2-methoxyphenyl, 4-chlorophenyl, benzyl, pyridin-4-yl, pyridin-2-yl, pyrimidin-2-yloxy, pyridin-3-yloxy, phenoxy, phenylsulfanyl, 4-chlorophenylsulfanyl, pyridin-2-yloxy, pyridin-4-yloxy, or pyrrolidin-2-onyl.

11. A chemical entity as in claim 2, wherein $R^1$ and $R^2$ taken together with the nitrogen to which they are attached form 2,5-diaza-bicyclo[2.2.1]hept-2-yl, hexahydro-pyrrolo[3,4-c]pyrrol-2(1H)-yl, 3,8-diaza-bicyclo[3.2.1]oct-8-yl, or 3-amino-8-aza-bicyclo[3.2.1]oct-8-yl, each substituted with $R^e$.

12. A chemical entity as in claim 2, wherein $R^e$ is acetyl or carbamoyl.

13. A chemical entity as in claim 2, wherein A is —CH$_2$—.

14. A chemical entity as in claim 2, wherein A is —CH$_2$CH$_2$—.

15. A chemical entity as in claim 2, wherein A is —OCH$_2$CH$_2$—.

16. A chemical entity selected from the group consisting of
2-(4-{2-[4-(Pyrimidin-2-yloxy)piperidin-1-yl]ethoxy}phenoxy)[1,3]thiazolo[4,5-b]pyridine;
2-{4-[2-(1,3-Dihydro-2H-isoindol-2-yl)ethoxy]phenoxy}[1,3]thiazolo[4,5-b]pyridine;
2-(4-{2-[4-(Phenylsulfanyl)piperidin-1-yl]ethoxy}phenoxy)[1,3]thiazolo[4,5-b]pyridine;
2-(4-{2-[4-(Pyridin-3-yloxy)piperidin-1-yl]ethoxy}phenoxy)[1,3]thiazolo[4,5-b]pyridine;
4-Pyridin-2-yl-1-{2-[4-([1,3]thiazolo[4,5-b]pyridin-2-yloxy)phenoxy]ethyl}piperidin-4-ol;
2-{2-[4-([1,3]Thiazolo[4,5-b]pyridin-2-yloxy)phenoxy]ethyl}-1,2,3,4-tetrahydroisoquinoline;
1-{2-[4-([1,3]Thiazolo[4,5-b]pyridin-2-yloxy)phenoxy]ethyl}-1,2,3,4-tetrahydroquinoline;
2-{4-[2-(4-Phenoxypiperidin-1-yl)ethoxy]phenoxy}[1,3]thiazolo[4,5-b]pyridine;
2-[4-(2-Pyrrolidin-1-ylethoxy)phenoxy][1,3]thiazolo[4,5-b]pyridine;
2-[4-(2-Piperidin-1-ylethoxy)phenoxy][1,3]thiazolo[4,5-b]pyridine;
2-[4-(2-Morpholin-4-ylethoxy)phenoxy][1,3]thiazolo[4,5-b]pyridine;
2-(4-{2-[4-(Pyridin-2-yloxy)piperidin-1-yl]ethoxy}phenoxy)[1,3]thiazolo[4,5-b]pyridine;
2-(4-{2-[4-(Pyridin-4-yloxy)piperidin-1-yl]ethoxy}phenoxy)[1,3]thiazolo[4,5-b]pyridine;
2-(4-{2-[(1S,4S)-5-Acetyl-2,5-diazabicyclo[2.2.1]hept-2-yl]ethoxy}phenoxy)[1,3]thiazolo[4,5-b]pyridine;
(1S,4S)-5-{2-[4-([1,3]Thiazolo[4,5-b]pyridin-2-yloxy)phenoxy]ethyl}-2,5-diazabicyclo[2.2.1]heptane-2-carboxamide;
meso-N-[(3-endo)-8-{2-[4-([1,3]Thiazolo[4,5-b]pyridin-2-yloxy)phenoxy]ethyl}-8-azabicyclo[3.2.1]oct-3-yl]acetamide;
meso-N-[(3-exo)-8-{2-[4-([1,3]Thiazolo[4,5-b]pyridin-2-yloxy)phenoxy]ethyl}-8-azabicyclo[3.2.1]oct-3-yl]acetamide;
2-{4-[2-(5-Acetylhexahydropyrrolo[3,4-c]pyrrol-2(1H)-yl)ethoxy]phenoxy}[1,3]thiazolo[4,5-b]pyridine;
5-{2-[4-([1,3]Thiazolo[4,5-b]pyridin-2-yloxy)phenoxy]ethyl}hexahydropyrrolo[3,4-c]pyrrole-2(1H)-carboxamide;
4-Phenyl-1-{2-[4-([1,3]thiazolo[4,5-b]pyridin-2-yloxy)phenoxy]ethyl}piperidin-4-ol;
2-{4-[2-(4-Benzylpiperidin-1-yl(ethoxy]phenoxy}[1,3]thiazolo[4,5-b]pyridine;
2-{4-[2-(4-Pyridin-4-ylpiperidin-1-yl(ethoxy]phenoxy}[1,3]thiazolo[4,5-b]pyridine;
4-(4-Chlorophenyl)-1-{2-[4-([1,3]thiazolo[4,5-b]pyridin-2-yloxy)phenoxy]ethyl}piperidin-4-ol;
1-{2-[4-([1,3]Thiazolo[4,5-b]pyridin-2-yloxy)phenoxy]ethyl}piperidine-4-carboxamide;
1-(1-{2-[4-([1,3]Thiazolo[4,5-b]pyridin-2-yloxy)phenoxy]ethyl}piperidin-4-yl)pyrrolidin-2-one;
1-{2-[4-([1,3]Thiazolo[4,5-b]pyridin-2-yloxy)phenoxy]ethyl}-4-[3-(trifluoromethyl)phenyl]piperidin-4-ol;
2-{4-[2-(4-Pyridin-2-ylpiperidin-1-yl(ethoxy]phenoxy}[1,3]thiazolo[4,5-b]pyridine;
N-Benzyl-N-methyl-2-[4-([1,3]thiazolo[4,5-b]pyridin-2-yloxy)phenoxy]ethanamine;
(1S,4S)-5-{2-[4-([1,3]Thiazolo[4,5-b]pyridin-2-yloxy)phenyl]ethyl}-2,5-diazabicyclo[2.2.1]heptane-2-carboxamide;
1-(1-{2-[4-([1,3]Thiazolo[4,5-b]pyridin-2-yloxy)phenyl]ethyl}piperidin-4-yl)pyrrolidin-2-one;
4-(4-Chlorophenyl)-1-{2-[4-([1,3]thiazolo[4,5-b]pyridin-2-yloxy)phenyl]ethyl}piperidin-4-ol;
2-{4-[2-(4-Pyridin-2-ylpiperidin-1-yl)ethyl]phenoxy}[1,3]thiazolo[4,5-b]pyridine;
meso-N-[(3-exo)-8-{2-[4-([1,3]Thiazolo[4,5-b]pyridin-2-yloxy)phenyl]ethyl}-8-azabicyclo[3.2.1]oct-3-yl]acetamide;
meso-1-[(3-exo)-8-{2-[4-([1,3]Thiazolo[4,5-b]pyridin-2-yloxy)phenyl]ethyl}-8-azabicyclo[3.2.1]oct-3-yl]urea;
meso-8-{2-[4-([1,3]Thiazolo[4,5-b]pyridin-2-yloxy)phenyl]ethyl}-3,8-diazabicyclo[3.2.1]octane-3-carboxamide;
meso-2-(4-{2-[3-Acetyl-3,8-diazabicyclo[3.2.1]oct-8-yl]ethyl}phenoxy)[1,3]thiazolo[4,5-b]pyridine;
2-(Ethyl{2-[4-([1,3]thiazolo[4,5-b]pyridin-2-yloxy)phenyl]ethyl}amino)ethanol;
N-(Cyclopropylmethyl)-N-{2-[4-([1,3]thiazolo[4,5-b]pyridin-2-yloxy)phenyl]ethyl}propan-1-amine;
(1R)-N-Methyl-1-phenyl-N-{2-[4-([1,3]thiazolo[4,5-b]pyridin-2-yloxy)phenyl]ethyl}ethanamine;
2-[4-(2-Morpholin-4-ylethyl)phenoxy][1,3]thiazolo[4,5-b]pyridine;
2-[4-(2-Piperidin-1-ylethyl)phenoxy][1,3]thiazolo[4,5-b]pyridine;
2-[4-(2-Pyrrolidin-1-ylethyl)phenoxy][1,3]thiazolo[4,5-b]pyridine;
4-Phenyl-1-{2-[4-([1,3]thiazolo[4,5-b]pyridin-2-yloxy)phenyl]ethyl}piperidin-4-ol;
2-{4-[2-(4-Benzylpiperidin-1-yl)ethyl]phenoxy}[1,3]thiazolo[4,5-b]pyridine;
1-{2-[4-([1,3]Thiazolo[4,5-b]pyridin-2-yloxy)phenyl]ethyl}-4-[3-(trifluoromethyl)phenyl]piperidin-4-ol;
2-{4-[2-(4-Pyridin-4-ylpiperidin-1-yl)ethyl]phenoxy}[1,3]thiazolo[4,5-b]pyridine;
1-{2-[4-([1,3]Thiazolo[4,5-b]pyridin-2-yloxy)phenyl]ethyl}piperidine-4-carboxamide;

2-{4-[2-(5-Acetylhexahydropyrrolo[3,4-c]pyrrol-2(1H)-yl)ethyl]phenoxy}[1,3]thiazolo[4,5-b]pyridine;
5-{2-[4-([1,3]Thiazolo[4,5-b]pyridin-2-yloxy)phenyl]ethyl}hexahydropyrrolo[3,4-c]pyrrole-2(1H)-carboxamide;
2-(4-{2-[(1S,4S)-5-Acetyl-2,5-diazabicyclo[2.2.1]hept-2-yl]ethyl}phenoxy)[1,3]thiazolo[4,5-b]pyridine;
meso-N-[(3-endo)-8-{2-[4-([1,3]Thiazolo[4,5-b]pyridin-2-yloxy)phenyl]ethyl}-8-azabicyclo[3.2.1]oct-3-yl]acetamide;
meso-1-[(3-endo)-8-{2-[4-([1,3]Thiazolo[4,5-b]pyridin-2-yloxy)phenyl]ethyl}-8-azabicyclo[3.2.1]oct-3-yl]urea;
2-(4-{2-[(1R,4R)-5-Acetyl-2,5-diazabicyclo[2.2.1]hept-2-yl]ethyl}phenoxy)[1,3]thiazolo[4,5-b]pyridine;
(1R,4R)-5-{2-[4-([1,3]Thiazolo[4,5-b]pyridin-2-yloxy)phenyl]ethyl}-2,5-diazabicyclo[2.2.1]heptane-2-carboxamide;
1-{2-[4-([1,3]Thiazolo[4,5-b]pyridin-2-yloxy)phenyl]ethyl}piperidine-4-carboxylic acid;
{-4-[4-([1,3]Thiazolo[4,5-b]pyridin-2-yloxy)benzyl]morpholin-2-yl}methanol;
1-{1-[4-([1,3]Thiazolo[4,5-b]pyridin-2-yloxy)benzyl]piperidin-4-yl}pyrrolidin-2-one;
2-[4-(Pyrrolidin-1-ylmethyl)phenoxy][1,3]thiazolo[4,5-b]pyridine;
2-[4-(Piperidin-1-ylmethyl)phenoxy][1,3]thiazolo[4,5-b]pyridine;
2-[4-(Morpholin-4-ylmethyl)phenoxy][1,3]thiazolo[4,5-b]pyridine;
2-(4-{[(3R)-3-Fluoropyrrolidin-1-yl]methyl}phenoxy)[1,3]thiazolo[4,5-b]pyridine;
2-(4-{[(3S)-3-Methylmorpholin-4-yl]methyl}phenoxy)[1,3]thiazolo[4,5-b]pyridine;
2-{1-[4-([1,3]Thiazolo[4,5-b]pyridin-2-yloxy)benzyl]piperidin-4-yl}propan-2-ol;
2-(4-{[(2S)-2-Methylpiperidin-1-yl]methyl}phenoxy)[1,3]thiazolo[4,5-b]pyridine;
2-Piperidin-1-yl-N-[4-([1,3]thiazolo[4,5-b]pyridin-2-yloxy)benzyl]ethanamine;
2-(4-{[4-(Trifluoromethyl)piperidin-1-yl]methyl}phenoxy)[1,3]thiazolo[4,5-b]pyridine;
2-{4-[(3,3-Difluoropyrrolidin-1-yl)methyl]phenoxy}[1,3]thiazolo[4,5-b]pyridine;
(3R)-1-[4-([1,3]Thiazolo[4,5-b]pyridin-2-yloxy)benzyl]pyrrolidin-3-ol;
{1-[4-([1,3]Thiazolo[4,5-b]pyridin-2-yloxy)benzyl]piperidin-4-yl}methanol;
2-{4-[(4-Fluoropiperidin-1-yl)methyl]phenoxy}[1,3]thiazolo[4,5-b]pyridine;
2-{4-[(4-Methylpiperidin-1-yl)methyl]phenoxy}[1,3]thiazolo[4,5-b]pyridine;
2-(4-{[4-(Pyridin-3-yloxy)piperidin-1-yl]methyl}phenoxy)[1,3]thiazolo[4,5-b]pyridine;
2-(4-{[4-(Pyrimidin-2-yloxy)piperidin-1-yl]methyl}phenoxy)[1,3]thiazolo[4,5-b]pyridine;
1-[4-([1,3]Thiazolo[4,5-b]pyridin-2-yloxy)benzyl]piperidine-4-carboxamide;
4-Pyridin-2-yl-1-[4-([1,3]Thiazolo[4,5-b]pyridin-2-yloxy)benzyl]piperidin-4-ol;
2-{4-[(4-Benzylpiperidin-1-yl)methyl]phenoxy}[13]thiazolo[4,5-b]pyridine;
1-[4-([1,3]Thiazolo[4,5-b]pyridin-2-yloxy)benzyl]-4-[3-(trifluoromethyl)phenyl]piperidin-4-ol;
4-(4-Chlorophenyl)-1-[4-([1,3]thiazolo[4,5-b]pyridin-2-yloxy)benzyl]piperidin-4-ol;
4-Phenyl-1-[4-([1,3]thiazolo[4,5-b]pyridin-2-yloxy)benzyl]piperidin-4-ol;
(1S,4S)-5-[4-([1,3]Thiazolo[4,5-b]pyridin-2-yloxy)benzyl]-2,5-diazabicyclo[2.2.1]heptane-2-carboxamide;
meso-2-(4-{[3-Acetyl-3,8-diazabicyclo[3.2.1]oct-8-yl]methyl}phenoxy)[1,3]thiazolo[4,5-b]pyridine;
{(2S)-1-[4-([1,3]Thiazolo[4,5-b]pyridin-2-yloxy)benzyl]pyrrolidin-2-yl}methanol;
meso-N-{(3-exo)-8-[4-([1,3]Thiazolo[4,5-b]pyridin-2-yloxy)benzyl]-8-azabicyclo[3.2.1]oct-3-yl}acetamide;
meso-1-{(3-exo)-8-[4-([1,3]Thiazolo[4,5-b]pyridin-2-yloxy)benzyl]-8-azabicyclo[3.2.1]oct-3-yl}urea;
N-Ethyl-N-[4-([1,3]thiazolo[4,5-b]pyridin-2-yloxy)benzyl]ethanamine;
meso-N-{(3-endo)-8-[4-([1,3]Thiazolo[4,5-b]pyridin-2-yloxy)benzyl]-8-azabicyclo[3.2.1]oct-3-yl}acetamide;
meso-8-[4-([1,3]Thiazolo[4,5-b]pyridin-2-yloxy)benzyl]-3,8-diazabicyclo[3.2.1]octane-3-carboxamide;
2-(4-{[(1S,4S)-5-Acetyl-2,5-diazabicyclo[2.2.1]hept-2-yl]methyl}phenoxy)-6-methyl[1,3]thiazolo[4,5-b]pyridine;
2-(4-{[(1S,4S)-5-Acetyl-2,5-diazabicyclo[2.2.1]hept-2-yl]methyl}phenoxy)-6-chloro[1,3]thiazolo[4,5-b]pyridine;
2-(4-{[(1S,4S)-5-Acetyl-2,5-diazabicyclo[2.2.1]hept-2-yl]methyl}phenoxy)-7-methyl[1,3]thiazolo[4,5-b]pyridine;
2-(4-{[(1S,4S)-5-Acetyl-2,5-diazabicyclo[2.2.1]hept-2-yl]methyl}phenoxy)-5-methyl[1,3]thiazolo[4,5-b]pyridine;
1-{(1S,4S)-5-[4-([1,3]Thiazolo[4,5-b]pyridin-2-yloxy)benzyl]-2,5-diazabicyclo[2.2.1]hept-2-yl}ethanone;
2-(4-{[(1S,4S)-5-Acetyl-2,5-diazabicyclo[2.2.1]hept-2-yl]methyl}phenoxy)-6-fluoro[1,3]thiazolo[4,5-b]pyridine;
6-Fluoro-2-[4-(piperidin-1-ylmethyl)phenoxy][1,3]thiazolo[4,5-b]pyridine;
Ethyl 1-[4-([1,3]thiazolo[4,5-b]pyridin-2-yloxy)benzyl]piperidine-4-carboxylate;
1-[4-([1,3]Thiazolo[4,5-b]pyridin-2-yloxy)benzyl]piperidine-4-carboxylic acid;
2-(4-{2-[4-(2-Methoxyphenyl)piperazin-1-yl]ethoxy}phenoxy)[1,3]thiazolo[4,5-b]pyridine;
2-[4-(2-{4-[(4-Chlorophenyl)sulfanyl]piperidin-1-yl}ethoxy)phenoxy][1,3]thiazolo[4,5-b]pyridine;
1-[4-([1,3]Thiazolo[4,5-b]pyridin-2-yloxy)benzyl]piperidin-4-ol;
7-Methyl-2-[4-(piperidin-1-ylmethyl)phenoxy][1,3]thiazolo[4,5-b]pyridine;
N-{2-[4-([1,3]Thiazolo[4,5-b]pyridin-2-yloxy)phenoxy]ethyl}cyclopropanamine;
2-Methyl-N-[1-(2-{4-[(6-methyl[1,3]thiazolo[4,5-b]pyridin-2-yl)oxy]phenoxy}ethyl)piperidin-4-yl]propanamide;
meso-2-{4-[2-(3-Acetyl-3,8-diazabicyclo[3.2.1]oct-8-yl)ethoxy]phenoxy}[1,3]thiazolo[4,5-b]pyridine;
meso-1-[(3-exo)-8-{2-[4-([1,3]Thiazolo[4,5-b]pyridin-2-yloxy)phenoxy]ethyl}-8-azabicyclo[3.2.1]oct-3-yl]urea;
7-Methyl-2-(4-{2-[4-(pyridin-4-ylcarbonyl)piperazin-1-yl]ethoxy}phenoxy)[1,3]thiazolo[4,5-b]pyridine;
6-Methyl-2-(4-{2-[4-(morpholin-4-ylcarbonyl)piperidin-1-yl]ethoxy}phenoxy)[1,3]thiazolo[4,5-b]pyridine;
2-(4-{2-[5-(Cyclobutylcarbonyl)hexahydropyrrolo[3,4-c]pyrrol-2(1H)-yl]ethoxy}phenoxy)-7-methyl[1,3]thiazolo[4,5-b]pyridine;

6-Chloro-2-(4-{2-[4-(furan-2-ylcarbonyl)piperazin-1-yl]ethoxy}phenoxy)[1,3]thiazolo[4,5-b]pyridine;

meso-3-{2-[4-([1,3]Thiazolo[4,5-b]pyridin-2-yloxy)phenoxy]ethyl}-3,8-diazabicyclo[3.2.1]octane-8-carboxamide;

N-[1-(2-{4-[(6-Methyl[1,3]thiazolo[4,5-b]pyridin-2-yl)oxy]phenoxy}ethyl)piperidin-4-yl]acetamide;

1-{3-[(2-{4-[(6-Chloro[1,3]thiazolo[4,5-b]pyridin-2-yl)oxy]phenoxy}ethyl)(methyl)amino]propyl}pyrrolidin-2-one;

1-(2-{4-[(7-Methyl[1,3]thiazolo[4,5-b]pyridin-2-yl)oxy]phenoxy}ethyl)-4-pyridin-2-ylpiperidin-4-ol;

meso-(3-endo)-8-acetyl-N-{2-[4-([1,3]thiazolo[4,5-b]pyridin-2-yloxy)phenoxy]ethyl}-8-azabicyclo[3.2.1]octan-3-amine;

N-Methyl-2-(methyloxy)-N-[2-({4-[(7-methyl[1,3]thiazolo[4,5-b]pyridin-2-yl)oxy]phenyl}oxy)ethyl]ethanamine;

meso-2-{[4-({2-[8-Acetyl-3,8-diazabicyclo[3.2.1]oct-3-yl]ethyl}oxy)phenyl]oxy}[1,3]thiazolo[4,5-b]pyridine;

N-[1-(2-{[4-[1,3]Thiazolo[4,5-b]pyridin-2-yloxy)phenyl]oxy}ethyl)piperidin-4-yl]methanesulfonamide;

N-Methyl-1-[2-({4-[(7-methyl[1,3]thiazolo[4,5-b]pyridin-2-yl)oxy]phenyl}oxy)ethyl]piperidine-4-carboxamide;

meso-N-{(3-endo)-8-[2-({4-[(7-Methyl[1,3]thiazolo[4,5-b]pyridin-2-yl)oxy]phenyl}oxy)ethyl]-8-azabicyclo[3.2.1]oct-3-yl}glycinamide;

meso-3-{[4-([1,3]Thiazolo[4,5-b]pyridin-2-yloxy)phenyl]methyl}-3,8-diazabicyclo[3.2.1]octane-8-carboxamide;

N,N-Dimethyl-1-({4-[(6-methyl[1,3]thiazolo[4,5-b]pyridin-2-yl)oxy]phenyl}methyl)piperidine-4-carboxamide;

N-Ethyl-N-(2-{4-[(6-methyl[1,3]thiazolo[4,5-b]pyridin-2-yl)oxy]phenyl}ethyl)butan-1-amine;

meso-(3-exo)-8-Acetyl-N-({4-[(6-methyl[1,3]thiazolo[4,5-b]pyridin-2-yl)oxy]phenyl}methyl)-8-azabicyclo[3.2.1]octan-3-amine;

meso-N-[(3-endo)-8-{[4-([1,3]Thiazolo[4,5-b]pyridin-2-yloxy)phenyl]methyl}-8-azabicyclo[3.2.1]oct-3-yl]methanesulfonamide;

2-({4-[(4-Cyclobutylpiperazin-1-yl)methyl]phenyl}oxy)-6-methyl[1,3]thiazolo[4,5-b]pyridine;

meso-2-[(4-{[8-Acetyl-3,8-diazabicyclo[3.2.1]oct-3-yl]methyl}phenyl)oxy][1,3]thiazolo[4,5-b]pyridine;

6-Chloro-2-[(4-{[4-(2-thienylcarbonyl)piperazin-1-yl]methyl}phenyl)oxy][1,3]thiazolo[4,5-b]pyridine;

6-Chloro-2-[(4-{[5-(methylsulfonyl)hexahydropyrrolo[3,4-c]pyrrol-2(1H)-yl]methyl}phenyl)oxy][1,3]thiazolo[4,5-b]pyridine;

6-Chloro-2-{[4-(thiomorpholin-4-ylmethyl)phenyl]oxy}[1,3]thiazolo[4,5-b]pyridine;

(1R,4R)-5-({4-[(6-Chloro[1,3]thiazolo[4,5-b]pyridin-2-yl)oxy]phenyl}methyl)-2,5-diazabicyclo[2.2.1]heptane-2-carboxamide;

(1S,4S)-5-({4-[(6-Chloro[1,3]thiazolo[4,5-b]pyridin-2-yl)oxy]phenyl}methyl)-2,5-diazabicyclo[2.2.1]heptane-2-carboxamide;

6-Chloro-2-[(4-{2-[4-(cyclopropylcarbonyl)piperazin-1-yl]ethyl}phenyl)oxy][1,3]thiazolo[4,5-b]pyridine;

6-Methyl-2-[(4-{2-[4-(pyrrolidin-1-ylcarbonyl)piperazin-1-yl]ethyl}phenyl)oxy][1,3]thiazolo[4,5-b]pyridine;

meso-3-{4-[(7-Methyl[1,3]thiazolo[4,5-b]pyridin-2-yl)oxy]benzyl}-3,8-diazabicyclo[3.2.1]octane-8-carboxamide;

meso-7-Methyl-2-(4-{[3-(methylsulfonyl)-3,8-diazabicyclo[3.2.1]oct-8-yl]methyl}phenoxy)[1,3]thiazolo[4,5-b]pyridine;

N-(1-{4-[(7-Methyl[1,3]thiazolo[4,5-b]pyridin-2-yl)oxy]benzyl}piperidin-4-yl)pyridine-4-carboxamide;

meso-2-(4-{2-[8-Acetyl-3,8-diazabicyclo[3.2.1]oct-3-yl]ethyl}phenoxy)-7-methyl[1,3]thiazolo[4,5-b]pyridine;

meso-3-{2-[4-([1,3]Thiazolo[4,5-b]pyridin-2-yloxy)phenyl]ethyl}-3,8-diazabicyclo[3.2.1]octane-8-carboxamide;

meso-8-{2-[4-([1,3]Thiazolo[4,5-b]pyridin-2-yloxy)phenoxy]ethyl}-3,8-diazabicyclo[3.2.1]octane-3-carboxamide;

meso-2-(4-{2-[8-Acetyl-3,8-diazabicyclo[3.2.1]oct-3-yl]ethyl}phenoxy)[1,3]thiazolo[4,5-b]pyridine;

meso-2-(4-{2-[3-(Methylsulfonyl)-3,8-diazabicyclo[3.2.1]oct-8-yl]ethoxy}phenoxy)[1,3]thiazolo[4,5-b]pyridine;

meso-(3-exo)-8-Acetyl-N-{2-[4-([1,3]thiazolo[4,5-b]pyridin-2-yloxy)phenyl]ethyl}-8-azabicyclo[3.2.1]octan-3-amine;

meso-(3-exo)-8-Acetyl-N-{2-[4-([1,3]thiazolo[4,5-b]pyridin-2-yloxy)phenoxy]ethyl}-8-azabicyclo[3.2.1]octan-3-amine;

2-Methoxy-N-(1-{4-[(6-methyl[1,3]thiazolo[4,5-b]pyridin-2-yl)oxy]benzyl}piperidin-4-yl)acetamide;

2-{4-[(4-tert-Butylpiperidin-1-yl)methyl]phenoxy}-6-chloro[1,3]thiazolo[4,5-b]pyridine;

N-(1-{4-[(6-Methyl[1,3]thiazolo[4,5-b]pyridin-2-yl)oxy]benzyl}piperidin-4-yl)thiophene-2-carboxamide;

1'-(2-{4-[(6-Chloro[1,3]thiazolo[4,5-b]pyridin-2-yl)oxy]phenyl}ethyl)-1,4'-bipiperidine;

3-(4-{2-[4-([1,3]Thiazolo[4,5-b]pyridin-2-yloxy)phenyl]ethyl}piperazin-1-yl)propanoic acid;

6-Methyl-2-(4-{[4-(piperazin-1-ylcarbonyl)piperidin-1-yl]methyl}phenoxy)[1,3]thiazolo[4,5-b]pyridine;

meso-3-(2-{4-[(6-Methyl[1,3]thiazolo[4,5-b]pyridin-2-yl)oxy]phenyl}ethyl)-3,8-diazabicyclo[3.2.1]octane-8-carboxamide;

meso-(3-exo)-8-Acetyl-N-(2-{4-[(6-methyl[1,3]thiazolo[4,5-b]pyridin-2-yl)oxy]phenyl}ethyl)-8-azabicyclo[3.2.1]octan-3-amine;

meso-(3-exo)-8-Acetyl-N-methyl-N-(2-{4-[(6-methyl[1,3]thiazolo[4,5-b]pyridin-2-yl)oxy]phenyl}ethyl)-8-azabicyclo[3.2.1]octan-3-amine;

$N^2$-(2-{4-[(6-Chloro[1,3]thiazolo[4,5-b]pyridin-2-yl)oxy]phenoxy}ethyl)-N2-methylglycinamide;

meso-8-[4-([1,3]Thiazolo[4,5-b]pyridin-2-yloxy)benzyl]-8-azabicyclo[3.2.1]octane-3-carboxylic acid;

6-Chloro-2-(4-{2-[5-(1-methylethyl)hexahydropyrrolo[3,4-c]pyrrol-2(1H)-yl]ethoxy}phenoxy)[1,3]thiazolo[4,5-b]pyridine;

N-Methyl-N-(2-{4-[(6-methyl[1,3]thiazolo[4,5-b]pyridin-2-yl)oxy]phenoxy}ethyl)-beta-alanine;

N-(2-{4-[(6-Chloro[1,3]thiazolo[4,5-b]pyridin-2-yl)oxy]phenyl}ethyl)-N,1-dimethylpiperidin-4-amine;

6-Methyl-2-{4-[2-(4-pyridin-2-ylpiperidin-1-yl)ethyl]phenoxy}[1,3]thiazolo[4,5-b]pyridine;

1-(1-Acetylazetidin-3-yl)-N-{4-[(6-chloro[1,3]thiazolo[4,5-b]pyridin-2-yl)oxy]benzyl}-N-methylmethanamine;

meso-(3-exo)-3-{[4-([1,3]Thiazolo[4,5-b]pyridin-2-yloxy)benzyl]amino}-8-azabicyclo[3.2.1]octane-8-carboxamide;

2-[4-(2-{4-[(4-Methylphenyl)sulfanyl]piperidin-1-yl}ethoxy)phenoxy][1,3]thiazolo[4,5-b]pyridine;

1'-[4-([1,3]Thiazolo[4,5-b]pyridin-2-yloxy)benzyl]-1,4'-bipiperidine;
2-{4-[(4-Morpholin-4-ylpiperidin-1-yl)methyl]phenoxy}[1,3]thiazolo[4,5-b]pyridine;
N,N-Dimethyl-2-{1-[4-([1,3]thiazolo[4,5-b]pyridin-2-yloxy)benzyl]piperidin-2-yl}ethanamine;
N,N-Dimethyl-1-[4-([1,3]thiazolo[4,5-b]pyridin-2-yloxy)benzyl]piperidin-4-amine;
2-{4-[(4-Phenoxypiperidin-1-yl)methyl]phenoxy}[1,3]thiazolo[4,5-b]pyridine;
2-(4-{[4-(Pyridin-2-yloxy)piperidin-1-yl]methyl}phenoxy)[1,3]thiazolo[4,5-b]pyridine;
2-(4-{[4-(Pyridin-4-yloxy)piperidin-1-yl]methyl}phenoxy)[1,3]thiazolo[4,5-b]pyridine;
2-(4-{[4-(Pyridin-2-ylsulfanyl)piperidin-1-yl]methyl}phenoxy)[1,3]thiazolo[4,5-b]pyridine;
2-(4-{[4-(Phenylsulfanyl)piperidin-1-yl]methyl}phenoxy)[1,3]thiazolo[4,5-b]pyridine;
2-(4-{[(1R,4R)-5-Acetyl-2,5-diazabicyclo[2.2.1]hept-2-yl]methyl}phenoxy)[1,3]thiazolo[4,5-b]pyridine;
(1R,4R)-5-[4-([1,3]Thiazolo[4,5-b]pyridin-2-yloxy)benzyl]-2,5-diazabicyclo[2.2.1]heptane-2-carboxamide;
2-(4-{2-[(1R,4R)-5-Acetyl-2,5-diazabicyclo[2.2.1]hept-2-yl]ethoxy}phenoxy)[1,3]thiazolo[4,5-b]pyridine;
(1R,4R)-5-{2-[4-([1,3]Thiazolo[4,5-b]pyridin-2-yloxy)phenoxy]ethyl}-2,5-diazabicyclo[2.2.1]heptane-2-carboxamide;
(4R)-4-Hydroxy-1-{1-[4-([1,3]thiazolo[4,5-b]pyridin-2-yloxy)benzyl]piperidin-4-yl}pyrrolidin-2-one;
(4R)-4-Hydroxy-1-{1-[4-([1,3]thiazolo[4,5-b]pyridin-2-yloxy)phenoxy]ethyl}piperidin-4-yl)pyrrolidin-2-one;
N-Methyl-2-piperidin-1-yl-N-[4-([1,3]thiazolo[4,5-b]pyridin-2-yloxy)benzyl]ethanamine;
N-(3-Methoxypropyl)-N-{2-[4-([1,3]thiazolo[4,5-b]pyridin-2-yloxy)phenoxy]ethyl}cyclopropanamine;
Ethyl N-benzyl-N-[4-([1,3]thiazolo[4,5-b]pyridin-2-yloxy)benzyl]glycinate;
N-Benzyl-N-[4-([1,3]thiazolo[4,5-b]pyridin-2-yloxy)benzyl]glycine;
N-[4-([1,3]Thiazolo[4,5-b]pyridin-2-yloxy)benzyl]-beta-alanine;
2-{4-[(5-Acetylhexahydropyrrolo[3,4-c]pyrrol-2(1H)-yl)methyl]phenoxy}[1,3]thiazolo[4,5-b]pyridine;
5-[4-([1,3]Thiazolo[4,5-b]pyridin-2-yloxy)benzyl]hexahydropyrrolo[3,4-c]pyrrole-2(1H)-carboxamide;
meso-1-{(3-endo)-8-[4-([1,3]Thiazolo[4,5-b]pyridin-2-yloxy)benzyl]-8-azabicyclo[3.2.1]oct-3-yl}urea;
6-Chloro-2-(4-piperidin-1-ylmethyl-phenoxy)[1,3]thiazolo[4,5-b]pyridine;
1-{4-[(7-Methyl[1,3]thiazolo[4,5-b]pyridin-2-yl)oxy]benzyl}piperidine-4-carboxamide;
1-{4-[(6-Fluoro[1,3]thiazolo[4,5-b]pyridin-2-yl)oxy]benzyl}piperidine-4-carboxamide;
1-{4-[(6-Chloro[1,3]thiazolo[4,5-b]pyridin-2-yl)oxy]benzyl}piperidine-4-carboxamide;
meso-endo-N-[8-{4-[(6-Chloro[1,3]thiazolo[4,5-b]pyridin-2-yl)oxy]benzyl}-8-azabicyclo[3.2.1]oct-3-yl]acetamide;
meso-endo-N-[8-{4-[(6-Fluoro[1,3]thiazolo[4,5-b]pyridin-2-yl)oxy]benzyl}-8-azabicyclo[3.2.1]oct-3-yl]acetamide;
meso-endo-N-[8-{4-[(7-Methyl[1,3]thiazolo[4,5-b]pyridin-2-yl)oxy]benzyl}-8-azabicyclo[3.2.1]oct-3-yl]acetamide;
2-(4-{[(1S,4S)-5-Acetyl-2,5-diazabicyclo[2.2.2]oct-2-yl]methyl}phenoxy)[1,3]thiazolo[4,5-b]pyridine;
meso-N-{(3-endo)-8-[4-([1,3]Thiazolo[4,5-b]pyridin-2-ylmethyl)benzyl]-8-azabicyclo[3.2.1]oct-3-yl}acetamide;
2-(4-{[(1S,4S)-5-Acetyl-2,5-diazabicyclo[2.2.1]hept-2-yl]methyl}benzyl)[1,3]thiazolo[4,5-b]pyridine;
meso-N-[(3-endo)-8-{2-[4-([1,3]Thiazolo[4,5-b]pyridin-2-ylmethyl)phenoxy]ethyl}-8-azabicyclo[3.2.1]oct-3-yl]acetamide;
2-(4-{2-[(1S,4S)-5-Acetyl-2,5-diazabicyclo[2.2.1]hept-2-yl]ethoxy}benzyl)[1,3]thiazolo[4,5-b]pyridine;
2-[4-(Piperidin-1-ylmethyl)phenoxy][1,3]thiazolo[4,5-c]pyridine;
meso-N-{(3-endo)-8-[4-([1,3]Thiazolo[4,5-c]pyridin-2-yloxy)benzyl]-8-azabicyclo[3.2.1]oct-3-yl}acetamide;
N-(2-Hydroxy-1,1-dimethylethyl)-1-(2-{[4-([1,3]thiazolo[4,5-c]pyridin-2-yloxy)phenyl]oxy}ethyl)piperidine-4-carboxamide;
2-{[4-({2-[4-(Trifluoromethyl)piperidin-1-yl]ethyl}oxy)phenyl]oxy}[1,3]thiazolo[4,5-c]pyridine;
N-(Cyclopropylmethyl)-N-{[4-([1,3]thiazolo[4,5-c]pyridin-2-yloxy)phenyl]methyl}propan-1-amine;
2-({4-[(4-Pyridin-4-ylpiperidin-1-yl)methyl]phenyl}oxy)[1,3]thiazolo[4,5-c]pyridine;
N-{1-[4-([1,3]Thiazolo[5,4-c]pyridin-2-yloxy)phenyl]ethyl}piperidin-4-yl)cyclopropanecarboxamide;
(4-Chlorophenyl)(1-{2-[4-([1,3]thiazolo[4,5-c]pyridin-2-yloxy)phenyl]ethyl}piperidin-4-yl)methanone;
N-Propyl-N-{2-[4-([1,3]thiazolo[4,5-c]pyridin-2-yloxy)phenyl]ethyl}propan-1-amine;
meso-3-[4-([1,3]Thiazolo[4,5-c]pyridin-2-yloxy)benzyl]-3,8-diazabicyclo[3.2.1]octane-8-carboxamide;
2-[4-(2-Pyrrolidin-1-ylethyl)phenoxy][1,3]thiazolo[4,5-c]pyridine;
1-Methyl-4-[4-([1,3]thiazolo[4,5-c]pyridin-2-yloxy)benzyl]piperazin-2-one;
meso-(3-exo)-8-Acetyl-N-[4-([1,3]thiazolo[4,5-c]pyridin-2-yloxy)benzyl]-8-azabicyclo[3.2.1]octan-3-amine;
meso-8-{2-[4-([1,3]Thiazolo[4,5-c]pyridin-2-yloxy)phenoxy]ethyl}-3,8-diazabicyclo[3.2.1]octane-3-carboxamide;
N-(Cyclopropylmethyl)-N-{2-[4-([1,3]thiazolo[4,5-c]pyridin-2-yloxy)phenoxy]ethyl}-beta-alanine;
meso-2-(4-{2-[3-Acetyl-3,8-diazabicyclo[3.2.1]oct-8-yl]ethoxy}phenoxy)[1,3]thiazolo[4,5-c]pyridine;
N-Ethyl-N-[4-([1,3]thiazolo[4,5-c]pyridin-2-yloxy)benzyl]cyclohexanamine;
2-[4-(Piperidin-1-ylmethyl)phenoxy][1,3]thiazolo[5,4-c]pyridine;
meso-N-{(3-endo)-8-[4-([1,3]Thiazolo[5,4-c]pyridin-2-yloxy)benzyl]-8-azabicyclo[3.2.1]oct-3-yl}acetamide;
1-(1-{2-[4-([1,3]Thiazolo[5,4-c]pyridin-2-yloxy)phenoxy]ethyl}piperidin-4-yl)pyrrolidin-2-one;
2-(4-{2-[(1R,4R)-5-(Methylsulfonyl)-2,5-diazabicyclo[2.2.1]hept-2-yl]ethoxy}phenoxy)[1,3]thiazolo[5,4-c]pyridine;
3-[(Cyclopropylmethyl){2-[4-([1,3]thiazolo[5,4-c]pyridin-2-yloxy)phenoxy]ethyl}amino]propan-1-ol;
N-Methyl-N-[4-([1,3]thiazolo[5,4-c]pyridin-2-yloxy)benzyl]cyclohexanamine;
2-{4-[2-(4-Acetylpiperazin-1-yl)ethyl]phenoxy}[1,3]thiazolo[5,4-c]pyridine;
meso-1-{(3-exo)-8-[4-([1,3]Thiazolo[5,4-c]pyridin-2-yloxy)benzyl]-8-azabicyclo[3.2.1]oct-3-yl}urea;
N-(Cyclopropylmethyl)-N-[4-([1,3]thiazolo[5,4-c]pyridin-2-yloxy)benzyl]propane-1,3-diamine;

3-(Cyclopropyl{2-[4-([1,3]thiazolo[5,4-c]pyridin-2-yloxy)phenoxy]ethyl}amino)propan-1-ol;
2-(4-{[4-(Pyridin-2-ylcarbonyl)piperazin-1-yl]methyl}phenoxy)[1,3]thiazolo[5,4-c]pyridine;
2-{4-[(4-Acetyl-1,4-diazepan-1-yl)methyl]phenoxy}[1,3]thiazolo[5,4-c]pyridine;
2-[4-({4-[(4-Methylpiperazin-1-yl)carbonyl]piperidin-1-yl}methyl)phenoxy][1,3]thiazolo[5,4-c]pyridine;
2-[4-(2-Azetidin-1-ylethoxy)phenoxy][1,3]thiazolo[5,4-c]pyridine;
5-{2-[4-([1,3]Thiazolo[5,4-c]pyridin-2-yloxy)phenyl]ethyl}hexahydropyrrolo[3,4-c]pyrrole-2(1H)-carboxamide;
2-(4-{[4-(Pyridin-3-yloxy)piperidin-1-yl]methyl}phenoxy)[1,3]thiazolo[5,4-c]pyridine;
meso-N-{(3-exo)-8-[4-([1,3]Thiazolo[5,4-c]pyridin-2-yloxy)benzyl]-8-azabicyclo[3.2.1]oct-3-yl}methanesulfonamide;
N-[(1-{2-[4-([1,3]Thiazolo[5,4-c]pyridin-2-yloxy)phenoxy]ethyl}piperidin-4-yl)methyl]acetamide;
2-(4-{2-[(1S,4S)-5-Acetyl-2,5-diazabicyclo[2.2.1]hept-2-yl]ethoxy}phenoxy)[1,3]thiazolo[5,4-b]pyridine;
(1S,4S)-5-{2-[4-([1,3]Thiazolo[5,4-b]pyridin-2-yloxy)phenoxy]ethyl}-2,5-diazabicyclo[2.2.1]heptane-2-carboxamide;
1-{2-[4-([1,3]Thiazolo[5,4-b]pyridin-2-yloxy)phenoxy]ethyl}piperidine-4-carboxamide;
1-{2-[4-([1,3]Thiazolo[5,4-b]pyridin-2-yloxy)phenoxy]ethyl}-4-[3-(trifluoromethyl)phenyl]piperidin-4-ol;
2-{4-[2-(4-Pyridin-2-ylpiperidin-1-yl)ethoxy]phenoxy}[1,3]thiazolo[5,4-b]pyridine;
4-(4-Chlorophenyl)-1-{2-[4-([1,3]thiazolo[5,4-b]pyridin-2-yloxy)phenoxy]ethyl}piperidin-4-ol;
4-Phenyl-1-{2-[4-([1,3]thiazolo[5,4-b]pyridin-2-yloxy)phenoxy]ethyl}piperidin-4-ol;
2-(4-{2-[4-(2-Methoxyphenyl)piperidin-1-yl]ethoxy}phenoxy)[1,3]thiazolo[5,4-b]pyridine;
2-{4-[2-(4-Pyridin-4-ylpiperidin-1-yl)ethoxy]phenoxy}[1,3]thiazolo[5,4-b]pyridine;
1-(1-{2-[4-([1,3]Thiazolo[5,4-b]pyridin-2-yloxy)phenoxy]ethyl}piperidin-4-yl)pyrrolidin-2-one;
1-{2-[4-([1,3]Thiazolo[5,4-b]pyridin-2-yloxy)phenoxy]ethyl}piperidine-4-carboxylic acid;
2-(4-{2-[(1S,4S)-5-Acetyl-2,5-diazabicyclo[2.2.1]hept-2-yl]ethyl}phenoxy)[1,3]thiazolo[5,4-b]pyridine;
meso-N-[(3-endo)-8-{2-[4-([1,3]Thiazolo[5,4-b]pyridin-2-yloxy)phenyl]ethyl}-8-azabicyclo[3.2.1]oct-3-yl]acetamide;
meso-2-(4-{2-[3-Acetyl-3,8-diazabicyclo[3.2.1]oct-8-yl]ethyl}phenoxy)[1,3]thiazolo[5,4-b]pyridine;
1-{2-[4-([1,3]Thiazolo[5,4-b]pyridin-2-yloxy)phenyl]ethyl}piperidine-4-carboxamide;
1-(1-{2-[4-([1,3]Thiazolo[5,4-b]pyridin-2-yloxy)phenyl]ethyl}piperidin-4-yl)pyrrolidin-2-one;
2-{4-[2-(5-Acetylhexahydropyrrolo[3,4-c]pyrrol-2(1H)-yl)ethyl]phenoxy}[1,3]thiazolo[5,4-b]pyridine;
5-{2-[4-([1,3]Thiazolo[5,4-b]pyridin-2-yloxy)phenyl]ethyl}hexahydropyrrolo[3,4-c]pyrrole-2(1H)-carboxamide;
meso-8-{2-[4-([1,3]Thiazolo[5,4-b]pyridin-2-yloxy)phenyl]ethyl}-3,8-diazabicyclo[3.2.1]octane-3-carboxamide;
meso-1-[(3-endo)-8-{2-[4-([1,3]Thiazolo[5,4-b]pyridin-2-yloxy)phenyl]ethyl}-8-azabicyclo[3.2.1]oct-3-yl]urea;
(1S,4S)-5-{2-[4-([1,3]Thiazolo[5,4-b]pyridin-2-yloxy)phenyl]ethyl}-2,5-diazabicyclo[2.2.1]heptane-2-carboxamide;
1-{1-[4-([1,3]Thiazolo[5,4-b]pyridin-2-yloxy)benzyl]piperidin-4-yl}pyrrolidin-2-one;
1-[4-([1,3]Thiazolo[5,4-b]pyridin-2-yloxy)benzyl]piperidine-4-carboxamide;
2-(4-{[(1S,4S)-5-Acetyl-2,5-diazabicyclo[2.2.1]hept-2-yl]methyl}phenoxy)-5-methyl[1,3]thiazolo[5,4-b]pyridine;
meso-N-{(3-endo)-8-[4-([1,3]Thiazolo[5,4-b]pyridin-2-yloxy)benzyl]-8-azabicyclo[3.2.1]oct-3-yl}acetamide;
2-(4-{[(1S,4S)-5-Acetyl-2,5-diazabicyclo[2.2.1]hept-2-yl]methyl}phenoxy)-6-fluoro[1,3]thiazolo[5,4-b]pyridine;
2-(4-{[(1S,4S)-5-Acetyl-2,5-diazabicyclo[2.2.1]hept-2-yl]methyl}phenoxy)[1,3]thiazolo[5,4-b]pyridine;
1-[4-([1,3]Thiazolo[5,4-b]pyridin-2-yloxy)benzyl]piperidine-4-carboxylic acid;
2-{4-[2-(4-Methyl-1,4-diazepan-1-yl)ethoxy]phenoxy}[1,3]thiazolo[5,4-b]pyridine;
meso-N-[(3-exo)-8-{2-[4-([1,3]Thiazolo[5,4-b]pyridin-2-yloxy)phenoxy]ethyl}-8-azabicyclo[3.2.1]oct-3-yl]acetamide;
2-[(Cyclopropylmethyl){2-[4-([1,3]thiazolo[5,4-b]pyridin-2-yloxy)phenoxy]ethyl}amino]ethanol;
7-Methyl-2-({4-[(4-pyridin-4-ylpiperazin-1-yl)methyl]phenyl}oxy)[1,3]thiazolo[4,5-b]pyridine;
meso-(3-endo)-8-Acetyl-N-{[4-([1,3]thiazolo[4,5-b]pyridin-2-yloxy)phenyl]methyl}-8-azabicyclo[3.2.1]octan-3-amine;
meso-(3-exo)-8-Acetyl-N-{[4-([1,3]thiazolo[4,5-b]pyridin-2-yloxy)phenyl]methyl}-8-azabicyclo[3.2.1]octan-3-amine;
N-Ethyl-N-{2-[4-([1,3]thiazolo[5,4-b]pyridin-2-yloxy)phenyl]ethyl}cyclopropanamine;
meso-N-[(3-exo)-8-{2-[4-([1,3]Thiazolo[5,4-b]pyridin-2-yloxy)phenyl]ethyl}-8-azabicyclo[3.2.1]oct-3-yl]methanesulfonamide;
meso-(3-exo)-3-{[4-([1,3]Thiazolo[5,4-b]pyridin-2-yloxy)benzyl]amino}-8-azabicyclo[3.2.1]octane-8-carboxamide;
4-Methyl-1-[4-([1,3]thiazolo[5,4-b]pyridin-2-yloxy)benzyl]-1,4-diazepan-5-one;
N-{1-[4-([1,3]Thiazolo[5,4-b]pyridin-2-yloxy)benzyl]piperidin-4-yl}propanamide;
2-(4-{2-[4-(Cyclopropylcarbonyl)-1,4-diazepan-1-yl]ethyl}phenoxy)[1,3]thiazolo[5,4-b]pyridine;
meso-N-Methyl-N-{(3-exo)-8-[4-([1,3]thiazolo[5,4-b]pyridin-2-yloxy)benzyl]-8-azabicyclo[3.2.1]oct-3-yl}acetamide;
2-(Cyclopropyl{2-[4-([1,3]thiazolo[5,4-b]pyridin-2-yloxy)phenoxy]ethyl}amino)ethanol;
2-{4-[(4-Pyridin-2-ylpiperazin-1-yl)methyl]phenoxy}[1,3]thiazolo[5,4-b]pyridine;
2-(4-{2-[(1R,4R)-5-Acetyl-2,5-diazabicyclo[2.2.1]hept-2-yl]ethyl}phenoxy)[1,3]thiazolo[5,4-b]pyridine;
7-Methyl-2-[4-(piperidin-1-ylmethyl)phenoxy][1,3]thiazolo[5,4-b]pyridine;
2-(4-{[(1S,4S)-5-Acetyl-2,5-diazabicyclo[2.2.1]hept-2-yl]ethyl}phenoxy)-7-methyl[1,3]thiazolo[5,4-b]pyridine;
1-{4-[(7-Methyl[1,3]thiazolo[5,4-b]pyridin-2-yl)oxy]benzyl}piperidine-4-carboxamide;
4-Phenyl-1-{2-[4-([1,3]thiazolo[4,5-b]pyrazin-2-yloxy)phenoxy]ethyl}piperidin-4-ol;

2-{4-[2-(4-Benzylpiperidin-1-yl(ethoxy]phenoxy}[1,3]thiazolo[4,5-b]pyrazine;
1-{2-[4-([1,3]Thiazolo[4,5-b]pyrazin-2-yloxy)phenoxy]ethyl}-4-[3-(trifluoromethyl)phenyl]piperidin-4-ol;
4-(4-Chlorophenyl)-1-{2-[4-([1,3]thiazolo[4,5-b]pyrazin-2-yloxy)phenoxy]ethyl}piperidin-4-ol;
1-{2-[4-([1,3]Thiazolo[4,5-b]pyrazin-2-yloxy)phenoxy]ethyl}piperidine-4-carboxamide;
2-(4-{[(1S,4S)-5-Acetyl-2,5-diazabicyclo[2.2.1]hept-2-yl]methyl}phenoxy)[1,3]thiazolo[4,5-b]pyrazine;
meso-N-[(3-endo)-8-{2-[4-([1,3]Thiazolo[4,5-b]pyrazin-2-yloxy)phenoxy]ethyl}-8-azabicyclo[3.2.1]oct-3-yl]acetamide;
2-[4-(2-Morpholin-4-ylethoxy)phenoxy][1,3]thiazolo[4,5-b]pyrazine;
2-({4-[(4-Pyrimidin-2-ylpiperazin-1-yl)methyl]phenyl}oxy)[1,3]thiazolo[4,5-b]pyrazine;
2-[(4-{[4-(2-Thienylacetyl)piperazin-1-yl]methyl}phenyl)oxy][1,3]thiazolo[4,5-b]pyrazine;
1-{2-[4-([1,3]Thiazolo[4,5-b]pyrazin-2-yloxy)phenyl]ethyl}-1,4-diazepan-5-one;
2-{[4-(2-Azepan-1-ylethyl)phenyl]oxy}[1,3]thiazolo[4,5-b]pyrazine;
2-({4-[2-(4-Fluoropiperidin-1-yl)ethyl]phenyl}oxy)[1,3]thiazolo[4,5-b]pyrazine;
2-[(4-{[4-(Pyrimidin-2-yloxy)piperidin-1-yl]methyl}phenyl)oxy][1,3]thiazolo[4,5-b]pyrazine;
meso-1-{(3-exo)-8-[4-([1,3]Thiazolo[4,5-b]pyrazin-2-yloxy)benzyl]-8-azabicyclo[3.2.1]oct-3-yl}urea;
2-(4-{2-[4-(Pyridin-2-yloxy)piperidin-1-yl]ethyl}phenoxy)[1,3]thiazolo[4,5-b]pyrazine;
3-Acetyl-9-[4-([1,3]thiazolo[4,5-b]pyridin-2-yloxy)benzyl]-3,9-diazaspiro[5.5]undecane; and
1-[4-([1,3]Thiazolo[4,5-b]pyrazin-2-yloxy)benzyl]piperidine-4-carboxamide;

and pharmaceutically acceptable salts, prodrugs, and solvates thereof of any of the foregoing compounds.

17. A pharmaceutical composition comprising an effective amount of at least one chemical entity selected from the group consisting of compounds of Formula (I), pharmaceutically acceptable salts of compounds of Formula (I), pharmaceutically acceptable prodrugs of compounds of Formula (I), and solvates of compounds of Formula (I)

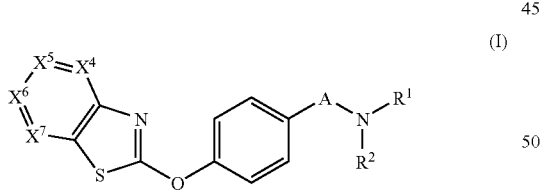

(I)

wherein
$X^4$, $X^5$, $X^6$, and $X^7$ are defined as one of the following a) and b)
  a) one of $X^4$, $X^5$, $X^6$ and $X^7$ is N and the others are $CR^a$;
     where each $R^a$ is independently H, methyl, chloro, fluoro, or trifluoromethyl;
  b) each of $X^4$ and $X^7$ is N and each of $X^5$ and $X^6$ is CH;
each of $R^1$ and $R^2$ is independently H, —$(CH_2)_{2-3}OCH_3$, —$CH_2C(O)NH_2$, —$(CH_2)_3NH_2$, —$(CH_2)_{1-2}CO_2H$, —$CH_2CO_2CH_2CH_3$, benzyl, 3-(2-oxo-pyrrolidin-1-yl)-propyl, 1-acetyl-azetidin-3ylmethyl, monocyclic cycloalkyl, 1-methyl-4-piperidinyl, or —$C_{1-4}$alkyl unsubstituted or substituted with phenyl, monocyclic cycloalkyl, OH, or $NR^bR^c$;

where $R^b$ and $R^c$ are each independently H, —$C(O)CH_3$, or $C_{1-4}$alkyl, or $R^b$ and $R^c$ taken together with the nitrogen to which they are attached form a saturated monocyclic heterocycloalkyl ring; or $R^1$ and $R^2$ taken together with the nitrogen to which they are attached form i) a saturated monocyclic heterocycloalkyl ring, optionally fused to a phenyl ring, and unsubstituted or substituted with one or two $R^d$ substituents;

where each $R^d$ substituent is independently $C_{1-4}$alkyl unsubstituted or substituted with —OH; —OH; =O; —$(CH_2)_{0-2}N(CH_3)_2$; —$CF_3$; halo; —$CO_2C_{1-4}$ alkyl; —$(CH_2)_{0-2}CO_2H$; —$C(O)NH_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —$C(O)NR^fC_{1-4}$ alkyl; —$C(O)NHC(CH_3)_2CH_2OH$; —O-pyridinyl; —O-pyrimidinyl; —S-phenyl; (4-methylphenyl)sulfanyl; —S-pyridinyl; —C(O)—$C_{1-4}$alkyl; —C(O)-saturated monocyclic cycloalkyl; —C(O)—$(CH_2)_{0-1}$-2-thiophene-yl; —C(O)-2-furanyl; —C(O)-4-morpholinyl; —C(O)-pyridyl; —C(O)-1-pyrrolidinyl; —C(O)-phenyl optionally substituted with a chloro; —C(O)-1-piperazinyl optionally substituted with $C_{1-4}$alkyl; —$(CH_2)_{0-1}$NHC(O)—$C_{1-4}$alkyl; —NHC(O)-saturated monocyclic cycloalkyl; —NHS(O)(O)CH_3; —NHC(O)—$CH_2OCH_3$; —NHC(O)-pyridinyl; or —NHC(O)-2-thiophene-yl, where each phenyl in $R^d$ is unsubstituted or substituted with —$CF_3$, halo, or methoxy; or ii) one of the following moieties

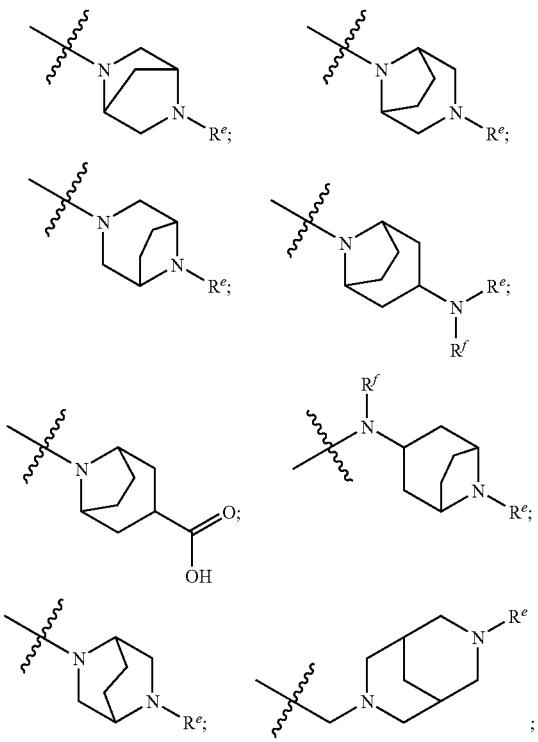

-continued

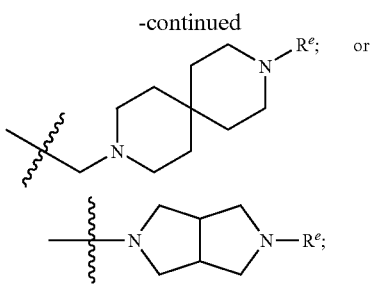

where $R^e$ is —$C_{1-4}$alkyl, C(O)$C_{1-4}$alkyl, —$SO_2CH_3$, —C(O)$CH_2NH_2$, or C(O)$NH_2$;
$R^f$ is H or —$CH_3$; and
A is —$CH_2$—, —$CH_2CH_2$—, or —$OCH_2CH_2$—.

18. A pharmaceutical composition as in claim 17, wherein said chemical entity is selected from the group consisting of 2-(4-{2-[4-(Pyrimidin-2-yloxy)piperidin-1-yl]ethoxy}phenoxy)[1,3]thiazolo[4,5-b]pyridine;
2-{4-[2-(1,3-Dihydro-2H-isoindol-2-yl(ethoxy]phenoxy}[1,3]thiazolo[4,5-b]pyridine;
2-(4-{2-[4-(Phenylsulfanyl)piperidin-1-yl]ethoxy}phenoxy)[1,3]thiazolo[4,5-b]pyridine;
2-(4-{2-[4-(Pyridin-3-yloxy)piperidin-1-yl]ethoxy}phenoxy)[1,3]thiazolo[4,5-b]pyridine;
4-Pyridin-2-yl-1-{2-[4-([1,3]thiazolo[4,5-b]pyridin-2-yloxy)phenoxy]ethyl}piperidin-4-ol;
2-{2-[4-([1,3]Thiazolo[4,5-b]pyridin-2-yloxy)phenoxy]ethyl}-1,2,3,4-tetrahydroisoquinoline;
1-{2-[4-([1,3]Thiazolo[4,5-b]pyridin-2-yloxy)phenoxy]ethyl}-1,2,3,4-tetrahydroquinoline;
2-{4-[2-(4-Phenoxypiperidin-1-yl(ethoxy]phenoxy}[1,3]thiazolo[4,5-b]pyridine;
2-[4-(2-Pyrrolidin-1-ylethoxy)phenoxy][1,3]thiazolo[4,5-b]pyridine;
2-[4-(2-Piperidin-1-ylethoxy)phenoxy][1,3]thiazolo[4,5-b]pyridine;
2-[4-(2-Morpholin-4-ylethoxy)phenoxy][1,3]thiazolo[4,5-b]pyridine;
2-(4-{2-[4-(Pyridin-2-yloxy)piperidin-1-yl]ethoxy}phenoxy)[1,3]thiazolo[4,5-b]pyridine;
2-(4-{2-[4-(Pyridin-4-yloxy)piperidin-1-yl]ethoxy}phenoxy)[1,3]thiazolo[4,5-b]pyridine;
2-(4-{2-[(1S,4S)-5-Acetyl-2,5-diazabicyclo[2.2.1]hept-2-yl]ethoxy}phenoxy)[1,3]thiazolo[4,5-b]pyridine;
(1S,4S)-5-{2-[4-([1,3]Thiazolo[4,5-b]pyridin-2-yloxy)phenoxy]ethyl}-2,5-diazabicyclo[2.2.1]heptane-2-carboxamide;
meso-N-[(3-endo)-8-{2-[4-([1,3]Thiazolo[4,5-b]pyridin-2-yloxy)phenoxy]ethyl}-8-azabicyclo[3.2.1]oct-3-yl]acetamide;
meso-N-[(3-exo)-8-{2-[4-([1,3]Thiazolo[4,5-b]pyridin-2-yloxy)phenoxy]ethyl}-8-azabicyclo[3.2.1]oct-3-yl]acetamide;
2-{4-[2-(5-Acetylhexahydropyrrolo[3,4-c]pyrrol-2(1H)-yl)ethoxy]phenoxy}[1,3]thiazolo[4,5-b]pyridine;
5-{2-[4-([1,3]Thiazolo[4,5-b]pyridin-2-yloxy)phenoxy]ethyl}hexahydropyrrolo[3,4-c]pyrrole-2(1H)-carboxamide;
4-Phenyl-1-{2-[4-([1,3]thiazolo[4,5-b]pyridin-2-yloxy)phenoxy]ethyl}piperidin-4-ol;
2-{4-[2-(4-Benzylpiperidin-1-yl)ethoxy]phenoxy}[1,3]thiazolo[4,5-b]pyridine;
2-{4-[2-(4-Pyridin-4-ylpiperidin-1-yl(ethoxy]phenoxy}[1,3]thiazolo[4,5-b]pyridine;
4-(4-Chlorophenyl)-1-{2-[4-([1,3]thiazolo[4,5-b]pyridin-2-yloxy)phenoxy]ethyl}piperidin-4-ol;
1-{2-[4-([1,3]Thiazolo[4,5-b]pyridin-2-yloxy)phenoxy]ethyl}piperidine-4-carboxamide;
1-(1-{2-[4-([1,3]Thiazolo[4,5-b]pyridin-2-yloxy)phenoxy]ethyl}piperidin-4-yl)pyrrolidin-2-one;
1-{2-[4-([1,3]Thiazolo[4,5-b]pyridin-2-yloxy)phenoxy]ethyl}-4-[3-(trifluoromethyl)phenyl]piperidin-4-ol;
2-{4-[2-(4-Pyridin-2-ylpiperidin-1-yl(ethoxy]phenoxy}[1,3]thiazolo[4,5-b]pyridine;
N-Benzyl-N-methyl-2-[4-([1,3]thiazolo[4,5-b]pyridin-2-yloxy)phenoxy]ethanamine;
(1S,4S)-5-{2-[4-([1,3]Thiazolo[4,5-b]pyridin-2-yloxy)phenyl]ethyl}-2,5-diazabicyclo[2.2.1]heptane-2-carboxamide;
1-(1-{2-[4-([1,3]Thiazolo[4,5-b]pyridin-2-yloxy)phenyl]ethyl}piperidin-4-yl)pyrrolidin-2-one;
4-(4-Chlorophenyl)-1-{2-[4-([1,3]Thiazolo[4,5-b]pyridin-2-yloxy)phenyl]ethyl}piperidin-4-ol;
2-{4-[2-(4-Pyridin-2-ylpiperidin-1-yl)ethyl]phenoxy}[1,3]thiazolo[4,5-b]pyridine;
meso-N-[(3-exo)-8-{2-[4-([1,3]Thiazolo[4,5-b]pyridin-2-yloxy)phenyl]ethyl}-8-azabicyclo[3.2.1]oct-3-yl]acetamide;
meso-1-[(3-exo)-8-{2-[4-([1,3]Thiazolo[4,5-b]pyridin-2-yloxy)phenyl]ethyl}-8-azabicyclo[3.2.1]oct-3-yl]urea;
meso-8-{2-[4-([1,3]Thiazolo[4,5-b]pyridin-2-yloxy)phenyl]ethyl}-3,8-diazabicyclo[3.2.1]octane-3-carboxamide;
meso-2-(4-{2-[3-Acetyl-3,8-diazabicyclo[3.2.1]oct-8-yl]ethyl}phenoxy)[1,3]thiazolo[4,5-b]pyridine;
2-(Ethyl{2-[4-([1,3]thiazolo[4,5-b]pyridin-2-yloxy)phenyl]ethyl}amino)ethanol;
N-(Cyclopropylmethyl)-N-{2-[4-([1,3]thiazolo[4,5-b]pyridin-2-yloxy)phenyl]ethyl}propan-1-amine;
(1R)-N-Methyl-1-phenyl-N-{2-[4-([1,3]thiazolo[4,5-b]pyridin-2-yloxy)phenyl]ethyl}ethanamine;
2-[4-(2-Morpholin-4-ylethyl)phenoxy][1,3]thiazolo[4,5-b]pyridine;
2-[4-(2-Piperidin-1-ylethyl)phenoxy][1,3]thiazolo[4,5-b]pyridine;
2-[4-(2-Pyrrolidin-1-ylethyl)phenoxy][1,3]thiazolo[4,5-b]pyridine;
4-Phenyl-1-{2-[4-([1,3]thiazolo[4,5-b]pyridin-2-yloxy)phenyl]ethyl}piperidin-4-ol;
2-{4-[2-(4-Benzylpiperidin-1-yl)ethyl]phenoxy}[1,3]thiazolo[4,5-b]pyridine;
1-{2-[4-([1,3]Thiazolo[4,5-b]pyridin-2-yloxy)phenyl]ethyl}-4-[3-(trifluoromethyl)phenyl]piperidin-4-ol;
2-{4-[2-(4-Pyridin-4-ylpiperidin-1-yl)ethyl]phenoxy}[1,3]thiazolo[4,5-b]pyridine;
1-{2-[4-([1,3]Thiazolo[4,5-b]pyridin-2-yloxy)phenyl]ethyl}piperidine-4-carboxamide;
2-{4-[2-(5-Acetylhexahydropyrrolo[3,4-c]pyrrol-2(1H)-yl)ethyl]phenoxy}[1,3]thiazolo[4,5-b]pyridine;
5-{2-[4-([1,3]Thiazolo[4,5-b]pyridin-2-yloxy)phenyl]ethyl}hexahydropyrrolo[3,4-c]pyrrole-2(1H)-carboxamide;
2-(4-{2-[(1S,4S)-5-Acetyl-2,5-diazabicyclo[2.2.1]hept-2-yl]ethyl}phenoxy)[1,3]thiazolo[4,5-b]pyridine;
meso-N-[(3-endo)-8-{2-[4-([1,3]Thiazolo[4,5-b]pyridin-2-yloxy)phenyl]ethyl}-8-azabicyclo[3.2.1]oct-3-yl]acetamide;
meso-1-[(3-endo)-8-{2-[4-([1,3]Thiazolo[4,5-b]pyridin-2-yloxy)phenyl]ethyl}-8-azabicyclo[3.2.1]oct-3-yl]urea;

2-(4-{2-[(1R,4R)-5-Acetyl-2,5-diazabicyclo[2.2.1]hept-2-yl]ethyl}phenoxy)[1,3]thiazolo[4,5-b]pyridine;
(1R,4R)-5-{2-[4-([1,3]Thiazolo[4,5-b]pyridin-2-yloxy)phenyl]ethyl}-2,5-diazabicyclo[2.2.1]heptane-2-carboxamide;
1-{2-[4-([1,3]Thiazolo[4,5-b]pyridin-2-yloxy)phenyl]ethyl}piperidine-4-carboxylic acid;
{4-[4-([1,3]Thiazolo[4,5-b]pyridin-2-yloxy)benzyl]morpholin-2-yl}methanol;
1-{1-[4-([1,3]Thiazolo[4,5-b]pyridin-2-yloxy)benzyl]piperidin-4-yl}pyrrolidin-2-one;
2-[4-(Pyrrolidin-1-ylmethyl)phenoxy][1,3]thiazolo[4,5-b]pyridine;
2-[4-(Piperidin-1-ylmethyl)phenoxy][1,3]thiazolo[4,5-b]pyridine;
2-[4-(Morpholin-4-ylmethyl)phenoxy][1,3]thiazolo[4,5-b]pyridine;
2-(4-{[(3R)-3-Fluoropyrrolidin-1-yl]methyl}phenoxy)[1,3]thiazolo[4,5-b]pyridine;
2-(4-{[(3S)-3-Methylmorpholin-4-yl]methyl}phenoxy)[1,3]thiazolo[4,5-b]pyridine;
2-{1-[4-([1,3]Thiazolo[4,5-b]pyridin-2-yloxy)benzyl]piperidin-4-yl}propan-2-ol;
2-(4-{[(2S)-2-Methylpiperidin-1-yl]methyl}phenoxy)[1,3]thiazolo[4,5-b]pyridine;
2-Piperidin-1-yl-N-[4-([1,3]thiazolo[4,5-b]pyridin-2-yloxy)benzyl]ethanamine;
2-(4-{[4-(Trifluoromethyl)piperidin-1-yl]methyl}phenoxy)[1,3]thiazolo[4,5-b]pyridine;
2-{4-[(3,3-Difluoropyrrolidin-1-yl)methyl]phenoxy}[1,3]thiazolo[4,5-b]pyridine;
(3R)-1-[4-([1,3]Thiazolo[4,5-b]pyridin-2-yloxy)benzyl]pyrrolidin-3-ol;
{1-[4-([1,3]Thiazolo[4,5-b]pyridin-2-yloxy)benzyl]piperidin-4-yl}methanol;
2-{4-[(4-Fluoropiperidin-1-yl)methyl]phenoxy}[1,3]thiazolo[4,5-b]pyridine;
2-{4-[(4-Methylpiperidin-1-yl)methyl]phenoxy}[1,3]thiazolo[4,5-b]pyridine;
2-(4-{[4-(Pyridin-3-yloxy)piperidin-1-yl]methyl}phenoxy)[1,3]thiazolo[4,5-b]pyridine;
2-(4-{[4-(Pyrimidin-2-yloxy)piperidin-1-yl]methyl}phenoxy)[1,3]thiazolo[4,5-b]pyridine;
1-[4-([1,3]Thiazolo[4,5-b]pyridin-2-yloxy)benzyl]piperidine-4-carboxamide;
4-Pyridin-2-yl-1-[4-[1,3]Thiazolo[4,5-b]pyridin-2-yloxy)benzyl]piperidin-4-ol;
2-{4-[(4-Benzylpiperidin-1-yl)methyl]phenoxy}[1,3]thiazolo[4,5-b]pyridine;
1-[4-[1,3]Thiazolo[4,5-b]pyridin-2-yloxy)benzyl]-4-[3-(trifluoromethyl)phenyl]piperidin-4-ol;
4-(4-Chlorophenyl)-1-[4-([1,3]Thiazolo[4,5-b]pyridin-2-yloxy)benzyl]piperidin-4-ol;
4-Phenyl-1-[4-([1,3]Thiazolo[4,5-b]pyridin-2-yloxy)benzyl]piperidin-4-ol;
(1S,4S)-5-[4-([1,3]Thiazolo[4,5-b]pyridin-2-yloxy)benzyl]-2,5-diazabicyclo[2.2.1]heptane-2-carboxamide;
meso-2-(4-{[3-Acetyl-3,8-diazabicyclo[3.2.1]oct-8-yl]methyl}phenoxy)[1,3]thiazolo[4,5-b]pyridine;
{(2S)-1-[4-([1,3]Thiazolo[4,5-b]pyridin-2-yloxy)benzyl]pyrrolidin-2-yl}methanol;
meso-N-{(3-exo)-8-[4-([1,3]Thiazolo[4,5-b]pyridin-2-yloxy)benzyl]-8-azabicyclo[3.2.1]oct-3-yl}acetamide;
meso-1-{(3-exo)-8-[4-([1,3]Thiazolo[4,5-b]pyridin-2-yloxy)benzyl]-8-azabicyclo[3.2.1]oct-3-yl}urea;
N-Ethyl-N-[4-([1,3]Thiazolo[4,5-b]pyridin-2-yloxy)benzyl]ethanamine;
meso-N-{(3-endo)-8-[4-([1,3]Thiazolo[4,5-b]pyridin-2-yloxy)benzyl]-8-azabicyclo[3.2.1]oct-3-yl}acetamide;
meso-8-[4-([1,3]Thiazolo[4,5-b]pyridin-2-yloxy)benzyl]-3,8-diazabicyclo[3.2.1]octane-3-carboxamide;
2-(4-{[(1S,4S)-5-Acetyl-2,5-diazabicyclo[2.2.1]hept-2-yl]methyl}phenoxy)-6-methyl[1,3]thiazolo[4,5-b]pyridine;
2-(4-{[(1S,4S)-5-Acetyl-2,5-diazabicyclo[2.2.1]hept-2-yl]methyl}phenoxy)-6-chloro[1,3]thiazolo[4,5-b]pyridine;
2-(4-{[(1S,4S)-5-Acetyl-2,5-diazabicyclo[2.2.1]hept-2-yl]methyl}phenoxy)-7-methyl[1,3]thiazolo[4,5-b]pyridine;
2-(4-{[(1S,4S)-5-Acetyl-2,5-diazabicyclo[2.2.1]hept-2-yl]methyl}phenoxy)-5-methyl[1,3]thiazolo[4,5-b]pyridine;
1-{(1S,4S)-5-[4-([1,3]Thiazolo[4,5-b]pyridin-2-yloxy)benzyl]-2,5-diazabicyclo[2.2.1]hept-2-yl}ethanone;
2-(4-{[(1S,4S)-5-Acetyl-2,5-diazabicyclo[2.2.1]hept-2-yl]methyl}phenoxy)-6-fluoro[1,3]thiazolo[4,5-b]pyridine;
6-Fluoro-2-[4-(piperidin-1-ylmethyl)phenoxy][1,3]thiazolo[4,5-b]pyridine;
Ethyl 1-[4-([1,3]thiazolo[4,5-b]pyridin-2-yloxy)benzyl]piperidine-4-carboxylate;
1-[4-([1,3]Thiazolo[4,5-b]pyridin-2-yloxy)benzyl]piperidine-4-carboxylic acid;
2-(4-{2-[4-(2-Methoxyphenyl)piperazin-1-yl]ethoxy}phenoxy)[1,3]thiazolo[4,5-b]pyridine;
2-[4-(2-{4-[(4-Chlorophenyl)sulfanyl]piperidin-1-yl}ethoxy)phenoxy][1,3]thiazolo[4,5-b]pyridine;
1-[4-([1,3]Thiazolo[4,5-b]pyridin-2-yloxy)benzyl]piperidin-4-ol;
7-Methyl-2-[4-(piperidin-1-ylmethyl)phenoxy][1,3]thiazolo[4,5-b]pyridine;
N-{2-[4-([1,3]Thiazolo[4,5-b]pyridin-2-yloxy)phenoxy]ethyl}cyclopropanamine;
2-Methyl-N-[1-(2-{4-[(6-methyl[1,3]thiazolo[4,5-b]pyridin-2-yl)oxy]phenoxy}ethyl)piperidin-4-yl]propanamide;
meso-2-{4-[2-(3-Acetyl-3,8-diazabicyclo[3.2.1]oct-8-yl)ethoxy]phenoxy}[1,3]thiazolo[4,5-b]pyridine;
meso-1-[(3-exo)-8-{2-[4-([1,3]Thiazolo[4,5-b]pyridin-2-yloxy)phenoxy]ethyl}-8-azabicyclo[3.2.1]oct-3-yl]urea;
7-Methyl-2-(4-{2-[4-(pyridin-4-ylcarbonyl)piperazin-1-yl]ethoxy}phenoxy)[1,3]thiazolo[4,5-b]pyridine;
6-Methyl-2-(4-{2-[4-(morpholin-4-ylcarbonyl)piperidin-1-yl]ethoxy}phenoxy)[1,3]thiazolo[4,5-b]pyridine;
2-(4-{2-[5-(Cyclobutylcarbonyl)hexahydropyrrolo[3,4-c]pyrrol-2(1H)-yl]ethoxy}phenoxy)-7-methyl[1,3]thiazolo[4,5-b]pyridine;
6-Chloro-2-(4-{2-[4-(furan-2-ylcarbonyl)piperazin-1-yl]ethoxy}phenoxy)[1,3]thiazolo[4,5-b]pyridine;
meso-3-{2-[4-([1,3]Thiazolo[4,5-b]pyridin-2-yloxy)phenoxy]ethyl}-3,8-diazabicyclo[3.2.1]octane-8-carboxamide;
N-[1-(2-{4-[(6-Methyl[1,3]thiazolo[4,5-b]pyridin-2-yl)oxy]phenoxy}ethyl)piperidin-4-yl]acetamide;
1-{3-[(2-{4-[(6-Chloro[1,3]thiazolo[4,5-b]pyridin-2-yl)oxy]phenoxy}ethyl)(methyl)amino]propyl}pyrrolidin-2-one;
1-(2-{4-[(7-Methyl[1,3]thiazolo[4,5-b]pyridin-2-yl)oxy]phenoxy}ethyl)-4-pyridin-2-ylpiperidin-4-ol;
meso-(3-endo)-8-acetyl-N-{2-[4-([1,3]thiazolo[4,5-b]pyridin-2-yloxy)phenoxy]ethyl}-8-azabicyclo[3.2.1]octan-3-amine;

N-Methyl-2-(methyloxy)-N-[2-({4-[(7-methyl[1,3]thiazolo[4,5-b]pyridin-2-yl)oxy]phenyl}oxy)ethyl]ethanamine;

meso-2-{[4-({2-[8-Acetyl-3,8-diazabicyclo[3.2.1]oct-3-yl]ethyl}oxy)phenyl]oxy}[1,3]thiazolo[4,5-b]pyridine;

N-[1-(2-{[4-([1,3]Thiazolo[4,5-b]pyridin-2-yloxy)phenyl]oxy}ethyl)piperidin-4-yl]methanesulfonamide;

N-Methyl-1-[2-({4-[(7-methyl[1,3]thiazolo[4,5-b]pyridin-2-yl)oxy]phenyl}oxy)ethyl]piperidine-4-carboxamide;

meso-N-{(3-endo)-8-[2-({4-[(7-Methyl[1,3]thiazolo[4,5-b]pyridin-2-yl)oxy]phenyl}oxy)ethyl]-8-azabicyclo[3.2.1]oct-3-yl}glycinamide;

meso-3-{[4-([1,3]Thiazolo[4,5-b]pyridin-2-yloxy)phenyl]methyl}-3,8-diazabicyclo[3.2.1]octane-8-carboxamide;

N,N-Dimethyl-1-({4-[(6-methyl[1,3]thiazolo[4,5-b]pyridin-2-yl)oxy]phenyl}methyl)piperidine-4-carboxamide;

N-Ethyl-N-(2-{4-[(6-methyl[1,3]thiazolo[4,5-b]pyridin-2-yl)oxy]phenyl}ethyl)butan-1-amine;

meso-(3-exo)-8-Acetyl-N-({4-[(6-methyl[1,3]thiazolo[4,5-b]pyridin-2-yl)oxy]phenyl}methyl)-8-azabicyclo[3.2.1]octan-3-amine;

meso-N-[(3-endo)-8-{[4-([1,3]Thiazolo[4,5-b]pyridin-2-yloxy)phenyl]methyl}-8-azabicyclo[3.2.1]oct-3-yl]methanesulfonamide;

2-({4-[(4-Cyclobutylpiperazin-1-yl)methyl]phenyl}oxy)-6-methyl[1,3]thiazolo[4,5-b]pyridine;

meso-2-[(4-{[8-Acetyl-3,8-diazabicyclo[3.2.1]oct-3-yl]methyl}phenyl)oxy][1,3]thiazolo[4,5-b]pyridine;

6-Chloro-2-[(4-{[4-(2-thienylcarbonyl)piperazin-1-yl]methyl}phenyl)oxy][1,3]thiazolo[4,5-b]pyridine;

6-Chloro-2-[(4-{[5-(methylsulfonyl)hexahydropyrrolo[3,4-c]pyrrol-2(1H)-yl]methyl}phenyl)oxy][1,3]thiazolo[4,5-b]pyridine;

6-Chloro-2-{[4-(thiomorpholin-4-ylmethyl)phenyl]oxy}[1,3]thiazolo[4,5-b]pyridine;

(1R,4R)-5-({4-[(6-Chloro[1,3]thiazolo[4,5-b]pyridin-2-yl)oxy]phenyl}methyl)-2,5-diazabicyclo[2.2.1]heptane-2-carboxamide;

(1S,4S)-5-({4-[(6-Chloro[1,3]thiazolo[4,5-b]pyridin-2-yl)oxy]phenyl}methyl)-2,5-diazabicyclo[2.2.1]heptane-2-carboxamide;

6-Chloro-2-[(4-{2-[4-(cyclopropylcarbonyl)piperazin-1-yl]ethyl}phenyl)oxy][1,3]thiazolo[4,5-b]pyridine;

6-Methyl-2-[(4-{2-[4-(pyrrolidin-1-ylcarbonyl)piperidin-1-yl]ethyl}phenyl)oxy][1,3]thiazolo[4,5-b]pyridine;

meso-3-{4-[(7-Methyl[1,3]thiazolo[4,5-b]pyridin-2-yl)oxy]benzyl}-3,8-diazabicyclo[3.2.1]octane-8-carboxamide;

meso-7-Methyl-2-(4-{[3-(methylsulfonyl)-3,8-diazabicyclo[3.2.1]oct-8-yl]methyl}phenoxy)[1,3]thiazolo[4,5-b]pyridine;

N-(1-{4-[(7-Methyl[1,3]thiazolo[4,5-b]pyridin-2-yl)oxy]benzyl}piperidin-4-yl)pyridine-4-carboxamide;

meso-2-(4-{2-[8-Acetyl-3,8-diazabicyclo[3.2.1]oct-3-yl]ethyl}phenoxy)-7-methyl[1,3]thiazolo[4,5-b]pyridine;

meso-3-{2-[4-([1,3]Thiazolo[4,5-b]pyridin-2-yloxy)phenyl]ethyl}-3,8-diazabicyclo[3.2.1]octane-8-carboxamide;

meso-8-{2-[4-([1,3]Thiazolo[4,5-b]pyridin-2-yloxy)phenoxy]ethyl}-3,8-diazabicyclo[3.2.1]octane-3-carboxamide;

meso-2-(4-{2-[8-Acetyl-3,8-diazabicyclo[3.2.1]oct-3-yl]ethyl}phenoxy)[1,3]thiazolo[4,5-b]pyridine;

meso-2-(4-{2-[3-(Methylsulfonyl)-3,8-diazabicyclo[3.2.1]oct-8-yl]ethoxy}phenoxy)[1,3]thiazolo[4,5-b]pyridine;

meso-(3-exo)-8-Acetyl-N-{2-[4-([1,3]thiazolo[4,5-b]pyridin-2-yloxy)phenyl]ethyl}-8-azabicyclo[3.2.1]octan-3-amine;

meso-(3-exo)-8-Acetyl-N-{2-[4-([1,3]thiazolo[4,5-b]pyridin-2-yloxy)phenoxy]ethyl}-8-azabicyclo[3.2.1]octan-3-amine;

2-Methoxy-N-(1-{4-[(6-methyl[1,3]thiazolo[4,5-b]pyridin-2-yl)oxy]benzyl}piperidin-4-yl)acetamide;

2-{4-[(4-tert-Butylpiperidin-1-yl)methyl]phenoxy}-6-chloro[1,3]thiazolo[4,5-b]pyridine;

N-(1-{4-[(6-Methyl[1,3]thiazolo[4,5-b]pyridin-2-yl)oxy]benzyl}piperidin-4-yl)thiophene-2-carboxamide;

1'-(2-{4-[(6-Chloro[1,3]thiazolo[4,5-b]pyridin-2-yl)oxy]phenyl}ethyl)-1,4'-bipiperidine;

3-(4-{2-[4-([1,3]Thiazolo[4,5-b]pyridin-2-yloxy)phenyl]ethyl}piperazin-1-yl)propanoic acid;

6-Methyl-2-(4-{[4-(piperazin-1-ylcarbonyl)piperidin-1-yl]methyl}phenoxy)[1,3]thiazolo[4,5-b]pyridine;

meso-3-(2-{4-[(6-Methyl[1,3]thiazolo[4,5-b]pyridin-2-yl)oxy]phenyl}ethyl)-3,8-diazabicyclo[3.2.1]octane-8-carboxamide;

meso-(3-exo)-8-Acetyl-N-(2-{4-[(6-methyl[1,3]thiazolo[4,5-b]pyridin-2-yl)oxy]phenyl}ethyl)-8-azabicyclo[3.2.1]octan-3-amine;

meso-(3-exo)-8-Acetyl-N-methyl-N-(2-{4-[(6-methyl[1,3]thiazolo[4,5-b]pyridin-2-yl)oxy]phenyl}ethyl)-8-azabicyclo[3.2.1]octan-3-amine;

$N^2$-(2-{4-[(6-Chloro[1,3]thiazolo[4,5-b]pyridin-2-yl)oxy]phenoxy}ethyl)-N2-methylglycinamide;

meso-8-[4-([1,3]Thiazolo[4,5-b]pyridin-2-yloxy)benzyl]-8-azabicyclo[3.2.1]octane-3-carboxylic acid;

6-Chloro-2-(4-{2-[5-(1-methylethyl)hexahydropyrrolo[3,4-c]pyrrol-2(1H)-yl]ethoxy}phenoxy)[1,3]thiazolo[4,5-b]pyridine;

N-Methyl-N-(2-{4-[(6-methyl[1,3]thiazolo[4,5-b]pyridin-2-yl)oxy]phenoxy}ethyl)-beta-alanine;

N-(2-{4-[(6-Chloro[1,3]thiazolo[4,5-b]pyridin-2-yl)oxy]phenyl}ethyl)-N,1-dimethylpiperidin-4-amine;

6-Methyl-2-{4-[2-(4-pyridin-2-ylpiperidin-1-yl)ethyl]phenoxy}[1,3]thiazolo[4,5-b]pyridine;

1-(1-Acetylazetidin-3-yl)-N-{4-[(6-chloro[1,3]thiazolo[4,5-b]pyridin-2-yl)oxy]benzyl}-N-methylmethanamine;

meso-(3-exo)-3-{[4-([1,3]Thiazolo[4,5-b]pyridin-2-yloxy)benzyl]amino}-8-azabicyclo[3.2.1]octane-8-carboxamide;

2-[4-(2-{4-[(4-Methylphenyl)sulfanyl]piperidin-1-yl}ethoxy)phenoxy][1,3]thiazolo[4,5-b]pyridine;

1'-[4-([1,3]Thiazolo[4,5-b]pyridin-2-yloxy)benzyl]-1,4'-bipiperidine;

2-{4-[(4-Morpholin-4-ylpiperidin-1-yl)methyl]phenoxy}[1,3]thiazolo[4,5-b]pyridine;

N,N-Dimethyl-2-{1-[4-([1,3]thiazolo[4, 5-1D]pyridin-2-yloxy)benzyl]piperidin-2-yl}ethanamine;

N,N-Dimethyl-1-[4-([1,3]thiazolo[4,5-b]pyridin-2-yloxy)benzyl]piperidin-4-amine;

2-{4-[(4-Phenoxypiperidin-1-yl)methyl]phenoxy}[1,3]thiazolo[4,5-b]pyridine;

2-(4-{[4-(Pyridin-2-yloxy)piperidin-1-yl]methyl}phenoxy)[1,3]thiazolo[4,5-b]pyridine;

2-(4-{[4-(Pyridin-4-yloxy)piperidin-1-yl]methyl}phenoxy)[1,3]thiazolo[4,5-b]pyridine;

2-(4-{[4-(Pyridin-2-ylsulfanyl)piperidin-1-yl]methyl}phenoxy)[1,3]thiazolo[4,5-b]pyridine;

2-(4-{[4-(Phenylsulfanyl)piperidin-1-yl]methyl}phenoxy)[1,3]thiazolo[4,5-b]pyridine;
2-(4-{[(1R,4R)-5-Acetyl-2,5-diazabicyclo[2.2.1]hept-2-yl]methyl}phenoxy)[1,3]thiazolo[4,5-b]pyridine;
(1R,4R)-5-[4-([1,3]Thiazolo[4,5-b]pyridin-2-yloxy)benzyl]-2,5-diazabicyclo[2.2.1]heptane-2-carboxamide;
2-(4-{2-[(1R,4R)-5-Acetyl-2,5-diazabicyclo[2.2.1]hept-2-yl]ethoxy}phenoxy)[1,3]thiazolo[4,5-b]pyridine;
(1R,4R)-5-{2-[4-([1,3]Thiazolo[4,5-b]pyridin-2-yloxy)phenoxy]ethyl}-2,5-diazabicyclo[2.2.1]heptane-2-carboxamide;
(4R)-4-Hydroxy-1-{1-[4-([1,3]thiazolo[4,5-b]pyridin-2-yloxy)benzyl]piperidin-4-yl}pyrrolidin-2-one;
(4R)-4-Hydroxy-1-(1-{2-[4-([1,3]thiazolo[4,5-b]pyridin-2-yloxy)phenoxy]ethyl}piperidin-4-yl)pyrrolidin-2-one;
N-Methyl-2-piperidin-1-yl-N-[4-([1,3]thiazolo[4,5-b]pyridin-2-yloxy)benzyl]ethanamine;
N-(3-Methoxypropyl)-N-{2-[4-([1,3]thiazolo[4,5-b]pyridin-2-yloxy)phenoxy]ethyl}cyclopropanamine;
Ethyl N-benzyl-N-[4-([1,3]thiazolo[4,5-b]pyridin-2-yloxy)benzyl]glycinate;
N-Benzyl-N-[4-([1,3]thiazolo[4,5-b]pyridin-2-yloxy)benzyl]glycine;
N-[4-([1,3]Thiazolo[4,5-b]pyridin-2-yloxy)benzyl]-beta-alanine;
2-{4-[(5-Acetylhexahydropyrrolo[3,4-c]pyrrol-2(1H)-yl)methyl]phenyl}[1,3]thiazolo[4,5-b]pyridine;
5-[4-([1,3]Thiazolo[4,5-b]pyridin-2-yloxy)benzyl]hexahydropyrrolo[3,4-c]pyrrole-2(1H)-carboxamide;
meso-1-{(3-endo)-8-[4-([1,3]Thiazolo[4,5-b]pyridin-2-yloxy)benzyl]-8-azabicyclo[3.2.1]oct-3-yl}urea;
6-Chloro-2-(4-piperidin-1-ylmethyl-phenoxy)[1,3]thiazolo[4,5-b]pyridine;
1-{4-[(7-Methyl[1,3]thiazolo[4,5-b]pyridin-2-yl)oxy]benzyl}piperidine-4-carboxamide;
1-{4-[(6-Fluoro[1,3]thiazolo[4,5-b]pyridin-2-yl)oxy]benzyl}piperidine-4-carboxamide;
1-{4-[(6-Chloro[1,3]thiazolo[4,5-b]pyridin-2-yl)oxy]benzyl}piperidine-4-carboxamide;
meso-endo-N-[8-{4-[(6-Chloro[1,3]thiazolo[4,5-b]pyridin-2-yl)oxy]benzyl}-8-azabicyclo[3.2.1]oct-3-yl]acetamide;
meso-endo-N-[8-{4-[(6-Fluoro[1,3]thiazolo[4,5-b]pyridin-2-yl)oxy]benzyl}-8-azabicyclo[3.2.1]oct-3-yl]acetamide;
meso-endo-N-[8-{4-[(7-Methyl[1,3]thiazolo[4,5-b]pyridin-2-yl)oxy]benzyl}-8-azabicyclo[3.2.1]oct-3-yl]acetamide;
2-(4-{[(1S,4S)-5-Acetyl-2,5-diazabicyclo[2.2.2]oct-2-yl]methyl}phenoxy)[1,3]thiazolo[4,5-b]pyridine;
meso-N-{(3-endo)-8-[4-([1,3]Thiazolo[4,5-b]pyridin-2-ylmethyl)benzyl]-8-azabicyclo[3.2.1]oct-3-yl}acetamide;
2-(4-{[(1S,4S)-5-Acetyl-2,5-diazabicyclo[2.2.1]hept-2-yl]methyl}benzyl)[1,3]thiazolo[4,5-b]pyridine;
meso-N-[(3-endo)-8-{2-[4-([1,3]Thiazolo[4,5-b]pyridin-2-ylmethyl)phenoxy]ethyl}-8-azabicyclo[3.2.1]oct-3-yl]acetamide;
2-(4-{2-[(1S,4S)-5-Acetyl-2,5-diazabicyclo[2.2.1]hept-2-yl]ethoxy}benzyl)[1,3]thiazolo[4,5-b]pyridine;
2-[4-(Piperidin-1-ylmethyl)phenoxy][1,3]thiazolo[4,5-c]pyridine;
meso-N-{(3-endo)-8-[4-([1,3]Thiazolo[4,5-c]pyridin-2-yloxy)benzyl]-8-azabicyclo[3.2.1]oct-3-yl}acetamide;
N-(2-Hydroxy-1,1-dimethylethyl)-1-(2-{[4-([1,3]thiazolo[4,5-c]pyridin-2-yloxy)phenyl]oxy}ethyl)piperidine-4-carboxamide;
2-{[4-({2-[4-(Trifluoromethyl)piperidin-1-yl]ethyl}oxy)phenyl]oxy}[1,3]thiazolo[4,5-c]pyridine;
N-(Cyclopropylmethyl)-N-{[4-([1,3]thiazolo[4,5-c]pyridin-2-yloxy)phenyl]methyl}propan-1-amine;
2-({4-[(4-Pyridin-4-ylpiperidin-1-yl)methyl]phenyl}oxy)[1,3]thiazolo[4,5-c]pyridine;
N-(1-{2-[4-([1,3]Thiazolo[5,4-c]pyridin-2-yloxy)phenyl]ethyl}piperidin-4-yl)cyclopropanecarboxamide;
(4-Chlorophenyl)(1-{2-[4-([1,3]thiazolo[4,5-c]pyridin-2-yloxy)phenyl]ethyl}piperidin-4-yl)methanone;
N-Propyl-N-{2-[4-([1,3]thiazolo[4,5-c]pyridin-2-yloxy)phenyl]ethyl}propan-1-amine;
meso-3-[4-([1,3]Thiazolo[4,5-c]pyridin-2-yloxy)benzyl]-3,8-diazabicyclo[3.2.1]octane-8-carboxamide;
2-[4-(2-Pyrrolidin-1-ylethyl)phenoxy][1,3]thiazolo[4,5-c]pyridine;
1-Methyl-4-[4-([1,3]thiazolo[4,5-c]pyridin-2-yloxy)benzyl]piperazin-2-one;
meso-(3-exo)-8-Acetyl-N-[4-([1,3]thiazolo[4,5-c]pyridin-2-yloxy)benzyl]-8-azabicyclo[3.2.1]octan-3-amine;
meso-8-{2-[4-([1,3]Thiazolo[4,5-c]pyridin-2-yloxy)phenoxy]ethyl}-3,8-diazabicyclo[3.2.1]octane-3-carboxamide;
N-(Cyclopropylmethyl)-N-{2-[4-([1,3]thiazolo[4,5-c]pyridin-2-yloxy)phenoxy]ethyl}-beta-alanine;
meso-2-(4-{2-[3-Acetyl-3,8-diazabicyclo[3.2.1]oct-8-yl]ethoxy}phenoxy)[1,3]thiazolo[4,5-c]pyridine;
N-Ethyl-N-[4-([1,3]thiazolo[4,5-c]pyridin-2-yloxy)benzyl]cyclohexanamine;
2-[4-(Piperidin-1-ylmethyl)phenoxy][1,3]thiazolo[5,4-c]pyridine;
meso-N-{(3-endo)-8-[4-([1,3]Thiazolo[5,4-c]pyridin-2-yloxy)benzyl]-8-azabicyclo[3.2.1]oct-3-yl}acetamide;
1-(1-{2-[4-([1,3]Thiazolo[5,4-c]pyridin-2-yloxy)phenoxy]ethyl}piperidin-4-yl)pyrrolidin-2-one;
2-(4-{2-[(1R,4R)-5-(Methylsulfonyl)-2,5-diazabicyclo[2.2.1]hept-2-yl]ethoxy}phenoxy)[1,3]thiazolo[5,4-c]pyridine;
3-[(Cyclopropylmethyl){2-[4-([1,3]thiazolo[5,4-c]pyridin-2-yloxy)phenoxy]ethyl}amino]propan-1-ol;
N-Methyl-N-[4-([1,3]thiazolo[5,4-c]pyridin-2-yloxy)benzyl]cyclohexanamine;
2-{4-[2-(4-Acetylpiperazin-1-yl)ethyl]phenoxy}[1,3]thiazolo[5,4-c]pyridine;
meso-1-{(3-exo)-8-[4-([1,3]Thiazolo[5,4-c]pyridin-2-yloxy)benzyl]-8-azabicyclo[3.2.1]oct-3-yl}urea;
N-(Cyclopropylmethyl)-N-[4-([1,3]thiazolo[5,4-c]pyridin-2-yloxy)benzyl]propane-1,3-diamine;
3-(Cyclopropyl{2-[4-([1,3]thiazolo[5,4-c]pyridin-2-yloxy)phenoxy]ethyl}amino)propan-1-ol;
2-(4-{[4-(Pyridin-2-ylcarbonyl)piperazin-1-yl]methyl}phenoxy)[1,3]thiazolo[5,4-c]pyridine;
2-{4-[(4-Acetyl-1,4-diazepan-1-yl)methyl]phenoxy}[1,3]thiazolo[5,4-c]pyridine;
2-[4-({4-[(4-Methylpiperazin-1-yl)carbonyl]piperidin-1-yl}methyl)phenoxy][1,3]thiazolo[5,4-c]pyridine;
2-[4-(2-Azetidin-1-ylethoxy)phenoxy][1,3]thiazolo[5,4-c]pyridine;
5-{2-[4-([1,3]Thiazolo[5,4-c]pyridin-2-yloxy)phenyl]ethyl}hexahydropyrrolo[3,4-c]pyrrole-2(1H)-carboxamide;
2-(4-{[4-(Pyridin-3-yloxy)piperidin-1-yl]methyl}phenoxy)[1,3]thiazolo[5,4-c]pyridine;

meso-N-{(3-exo)-8-[4-([1,3]Thiazolo[5,4-c]pyridin-2-yloxy)benzyl]-8-azabicyclo[3.2.1]oct-3-yl}methanesulfonamide;
N-[4-(1-{2-[4-([1,3]Thiazolo[5,4-c]pyridin-2-yloxy)phenoxy]ethyl}piperidin-4-yl)methyl]acetamide;
2-(4-{2-[(1S,4S)-5-Acetyl-2,5-diazabicyclo[2.2.1]hept-2-yl]ethoxy}phenoxy)[1,3]thiazolo[5,4-b]pyridine;
(1S,4S)-5-{2-[4-([1,3]Thiazolo[5,4-b]pyridin-2-yloxy)phenoxy]ethyl}-2,5-diazabicyclo[2.2.1]heptane-2-carboxamide;
1-{2-[4-([1,3]Thiazolo[5,4-b]pyridin-2-yloxy)phenoxy]ethyl}piperidine-4-carboxamide;
1-{2-[4-([1,3]Thiazolo[5,4-b]pyridin-2-yloxy)phenoxy]ethyl}-4-[3-(trifluoromethyl)phenyl]piperidin-4-ol;
2-{4-[2-(4-Pyridin-2-ylpiperidin-1-yl)ethoxy]phenoxy}[1,3]thiazolo[5,4-b]pyridine;
4-(4-Chlorophenyl)-1-{2-[4-([1,3]thiazolo[5,4-b]pyridin-2-yloxy)phenoxy]ethyl}piperidin-4-ol;
4-Phenyl-1-{2-[4-([1,3]Thiazolo[5,4-b]pyridin-2-yloxy)phenoxy]ethyl}piperidin-4-ol;
2-(4-{2-[4-(2-Methoxyphenyl)piperidin-1-yl]ethoxy}phenoxy)[1,3]thiazolo[5,4-b]pyridine;
2-{4-[2-(4-Pyridin-4-ylpiperidin-1-yl)ethoxy]phenoxy}[1,3]thiazolo[5,4-b]pyridine;
1-(1-{2-[4-([1,3]Thiazolo[5,4-b]pyridin-2-yloxy)phenoxy]ethyl}piperidin-4-yl)pyrrolidin-2-one;
1-{2-[4-([1,3]Thiazolo[5,4-b]pyridin-2-yloxy)phenoxy]ethyl}piperidine-4-carboxylic acid;
2-(4-{2-[(1S,4S)-5-Acetyl-2,5-diazabicyclo[2.2.1]hept-2-yl]ethyl}phenoxy)[1,3]thiazolo[5,4-b]pyridine;
meso-N-[(3-endo)-8-{2-[4-([1,3]Thiazolo[5,4-b]pyridin-2-yloxy)phenyl]ethyl}-8-azabicyclo[3.2.1]oct-3-yl]acetamide;
meso-2-(4-{2-[3-Acetyl-3,8-diazabicyclo[3.2.1]oct-8-yl]ethyl}phenoxy)[1,3]thiazolo[5,4-b]pyridine;
1-{2-[4-([1,3]Thiazolo[5,4-b]pyridin-2-yloxy)phenyl]ethyl}piperidine-4-carboxamide;
1-(1-{2-[4-([1,3]Thiazolo[5,4-b]pyridin-2-yloxy)phenyl]ethyl}piperidin-4-yl)pyrrolidin-2-one;
2-{4-[2-(5-Acetylhexahydropyrrolo[3,4-c]pyrrol-2(1H)-yl)ethyl]phenoxy}[1,3]thiazolo[5,4-b]pyridine;
5-{2-[4-([1,3]Thiazolo[5,4-b]pyridin-2-yloxy)phenyl]ethyl}hexahydropyrrolo[3,4-c]pyrrole-2(1H)-carboxamide;
meso-8-{2-[4-([1,3]Thiazolo[5,4-b]pyridin-2-yloxy)phenyl]ethyl}-3,8-diazabicyclo[3.2.1]octane-3-carboxamide;
meso-1-[(3-endo)-8-{2-[4-([1,3]Thiazolo[5,4-b]pyridin-2-yloxy)phenyl]ethyl}-8-azabicyclo[3.2.1]oct-3-yl]urea;
(1S,4S)-5-{2-[4-([1,3]Thiazolo[5,4-b]pyridin-2-yloxy)phenyl]ethyl}-2,5-diazabicyclo[2.2.1]heptane-2-carboxamide;
1-{1-[4-([1,3]Thiazolo[5,4-b]pyridin-2-yloxy)benzyl]piperidin-4-yl}pyrrolidin-2-one;
1-[4-([1,3]Thiazolo[5,4-b]pyridin-2-yloxy)benzyl]piperidine-4-carboxamide;
2-(4-{[(1S,4S)-5-Acetyl-2,5-diazabicyclo[2.2.1]hept-2-yl]methyl}phenoxy)-5-methyl[1,3]thiazolo[5,4-b]pyridine;
meso-N-{(3-endo)-8-[4-([1,3]Thiazolo[5,4-b]pyridin-2-yloxy)benzyl]-8-azabicyclo[3.2.1]oct-3-yl}acetamide;
2-(4-{[(1S,4S)-5-Acetyl-2,5-diazabicyclo[2.2.1]hept-2-yl]methyl}phenoxy)-6-fluoro[1,3]thiazolo[5,4-b]pyridine;
2-(4-{[(1S,4S)-5-Acetyl-2,5-diazabicyclo[2.2.1]hept-2-yl]methyl}phenoxy)[1,3]thiazolo[5,4-b]pyridine;

1-[4-([1,3]Thiazolo[5,4-b]pyridin-2-yloxy)benzyl]piperidine-4-carboxylic acid;
2-{4-[2-(4-Methyl-1,4-diazepan-1-yl(ethoxy]phenoxy}[1,3]thiazolo[5,4-b]pyridine;
meso-N-[(3-exo)-8-{2-[4-([1,3]Thiazolo[5,4-b]pyridin-2-yloxy)phenoxy]ethyl}-8-azabicyclo[3.2.1]oct-3-yl]acetamide;
2-[(Cyclopropylmethyl){2-[4-([1,3]thiazolo[5,4-b]pyridin-2-yloxy)phenoxy]ethyl}amino]ethanol;
7-Methyl-2-({4-[(4-pyridin-4-ylpiperazin-1-yl)methyl]phenyl}oxy)[1,3]thiazolo[4,5-b]pyridine;
meso-(3-endo)-8-Acetyl-N-{[4-([1,3]thiazolo[4,5-b]pyridin-2-yloxy)phenyl]methyl}-8-azabicyclo[3.2.1]octan-3-amine;
meso-(3-exo)-8-Acetyl-N-{[4-([1,3]thiazolo[4,5-b]pyridin-2-yloxy)phenyl]methyl}-8-azabicyclo[3.2.1]octan-3-amine;
N-Ethyl-N-{2-[4-([1,3]thiazolo[5,4-b]pyridin-2-yloxy)phenyl]ethyl}cyclopropanamine;
meso-N-[(3-exo)-8-{2-[4-([1,3]Thiazolo[5,4-b]pyridin-2-yloxy)phenyl]ethyl}-8-azabicyclo[3.2.1]oct-3-yl]methanesulfonamide;
meso-(3-exo)-3-{[4-([1,3]Thiazolo[5,4-b]pyridin-2-yloxy)benzyl]amino}-8-azabicyclo[3.2.1]octane-8-carboxamide;
4-Methyl-1-[4-([1,3]thiazolo[5,4-b]pyridin-2-yloxy)benzyl]-1,4-diazepan-5-one;
N-{1-[4-([1,3]Thiazolo[5,4-b]pyridin-2-yloxy)benzyl]piperidin-4-yl}propanamide;
2-(4-{2-[4-(Cyclopropylcarbonyl)-1,4-diazepan-1-yl]ethyl}phenoxy)[1,3]thiazolo[5,4-b]pyridine;
meso-N-Methyl-N-{(3-exo)-8-[4-([1,3]thiazolo[5,4-b]pyridin-2-yloxy)benzyl]-8-azabicyclo[3.2.1]oct-3-yl}acetamide;
2-(Cyclopropyl{2-[4-([1,3]thiazolo[5,4-b]pyridin-2-yloxy)phenoxy]ethyl}amino)ethanol;
2-{4-[(4-Pyridin-2-ylpiperazin-1-yl)methyl]phenoxy}[1,3]thiazolo[5,4-b]pyridine;
2-(4-{2-[(1R,4R)-5-Acetyl-2,5-diazabicyclo[2.2.1]hept-2-yl]ethyl}phenoxy)[1,3]thiazolo[5,4-b]pyridine;
7-Methyl-2-[4-(piperidin-1-ylmethyl)phenoxy][1,3]thiazolo[5,4-b]pyridine;
2-(4-{[(1S,4S)-5-Acetyl-2,5-diazabicyclo[2.2.1]hept-2-yl]methyl}phenoxy)-7-methyl[1,3]thiazolo[5,4-b]pyridine;
1-{4-[(7-Methyl[1,3]thiazolo[5,4-b]pyridin-2-yl)oxy]benzyl}piperidine-4-carboxamide;
4-Phenyl-1-{2-[4-([1,3]thiazolo[4,5-b]pyrazin-2-yloxy)phenoxy]ethyl}piperidin-4-ol;
2-{4-[2-(4-Benzylpiperidin-1-yl)ethoxy]phenoxy}[1,3]thiazolo[4,5-b]pyrazine;
1-{2-[4-([1,3]Thiazolo[4,5-b]pyrazin-2-yloxy)phenoxy]ethyl}-4-[3-(trifluoromethyl)phenyl]piperidin-4-ol;
4-(4-Chlorophenyl)-1-{2-[4-([1,3]thiazolo[4,5-b]pyrazin-2-yloxy)phenoxy]ethyl}piperidin-4-ol;
1-{2-[4-([1,3]Thiazolo[4,5-b]pyrazin-2-yloxy)phenoxy]ethyl}piperidine-4-carboxamide;
2-(4-{[(1S,4S)-5-Acetyl-2,5-diazabicyclo[2.2.1]hept-2-yl]methyl}phenoxy)[1,3]thiazolo[4,5-b]pyrazine;
meso-N-[(3-endo)-8-{2-[4-([1,3]Thiazolo[4,5-b]pyrazin-2-yloxy)phenoxy]ethyl}-8-azabicyclo[3.2.1]oct-3-yl]acetamide;
2-[4-(2-Morpholin-4-ylethoxy)phenoxy][1,3]thiazolo[4,5-b]pyrazine;
2-({4-[(4-Pyrimidin-2-ylpiperazin-1-yl)methyl]phenyl}oxy)[1,3]thiazolo[4,5-b]pyrazine;

2-[(4-{[4-(2-Thienylacetyl)piperazin-1-yl]methyl}phenyl)oxy][1,3]thiazolo[4,5-b]pyrazine;
1-{2-[4-([1,3]Thiazolo[4,5-b]pyrazin-2-yloxy)phenyl]ethyl}-1,4-diazepan-5-one;
2-{[4-(2-Azepan-1-ylethyl)phenyl]oxy}[1,3]thiazolo[4,5-b]pyrazine;
2-({4-[2-(4-Fluoropiperidin-1-yl)ethyl]phenyl}oxy)[1,3]thiazolo[4,5-b]pyrazine;
2-[(4-{[4-(Pyrimidin-2-yloxy)piperidin-1-yl]methyl}phenyl)oxy][1,3]thiazolo[4,5-b]pyrazine;
meso-1-{(3-exo)-8-[4-([1,3]Thiazolo[4,5-b]pyrazin-2-yloxy)benzyl]-8-azabicyclo[3.2.1]oct-3-yl}urea;
2-(4-{2-[4-(Pyridin-2-yloxy)piperidin-1-yl]ethyl}phenoxy)[1,3]thiazolo[4,5-b]pyrazine;
3-Acetyl-9-[4-([1,3]thiazolo[4,5-b]pyridin-2-yloxy)benzyl]-3,9-diazaspiro[5.5]undecane; and
1-[4-([1,3]Thiazolo[4,5-b]pyrazin-2-yloxy)benzyl]piperidine-4-carboxamide;
and pharmaceutically acceptable salts, prodrugs, and solvates thereof of any of the foregoing compounds.

19. A method for inhibiting leukotriene A4 hydrolase activity, comprising exposing leukotriene A4 hydrolase to an effective amount of at least one chemical entity selected from the group consisting of compounds of Formula (I), pharmaceutically acceptable salts of compounds of Formula (I), pharmaceutically acceptable prodrugs of compounds of Formula (I), and solvates of compounds of Formula (I)

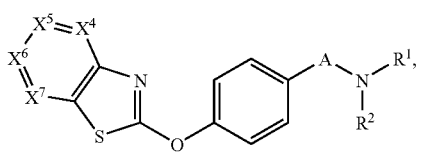

(I)

wherein
$X^4$, $X^5$, $X^6$, and $X^7$ are defined as one of the following a) and b):
   a) one of $X^4$, $X^5$, $X^6$ and $X^7$ is N and the others are $CR^a$; where each $R^a$ is independently H, methyl, chloro, fluoro, or trifluoromethyl;
   b) each of $X^4$ and $X^7$ is N and each of $X^5$ and $X^6$ is CH;
each of $R^1$ and $R^2$ is independently H, —$(CH_2)_{2-3}OCH_3$, —$CH_2C(O)NH_2$, —$(CH_2)_3NH_2$, —$(CH_2)_{1-2}CO_2H$, —$CH_2CO_2CH_2CH_3$, benzyl, 3-(2-oxo-pyrrolidin-1-yl)-propyl, 1-acetyl-azetidin-3ylmethyl, monocyclic cycloalkyl, 1-methyl-4-piperidinyl, or —$C_{1-4}$alkyl unsubstituted or substituted with phenyl, monocyclic cycloalkyl, OH, or $NR^bR^c$;
   where $R^b$ and $R^c$ are each independently H, —C(O)CH$_3$, or C$_{1-4}$alkyl, or $R^b$ and $R^c$ taken together with the nitrogen to which they are attached form a saturated monocyclic heterocycloalkyl ring; or
$R^1$ and $R^2$ taken together with the nitrogen to which they are attached form
   i) a saturated monocyclic heterocycloalkyl ring, optionally fused to a phenyl ring, and unsubstituted or substituted with one or two $R^d$ substituents;
      where each $R^d$ substituent is independently C$_{1-4}$alkyl unsubstituted or substituted with —OH; —OH; =O; —(CH$_2$)$_{0-2}$N(CH$_3$)$_2$; —CF$_3$; halo; —CO$_2$C$_{1-4}$alkyl; —(CH$_2$)$_{0-2}$CO$_2$H; —C(O)NH$_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —C(O)NR$^f$C$_{1-4}$alkyl; —C(O)NHC(CH$_3$)$_2$CH$_2$OH; —O-pyrimidinyl; —S-phenyl; (4-methylphenyl)sulfanyl; —S-pyridinyl; —C(O)—C$_{1-4}$alkyl; —C(O)-saturated monocyclic cycloalkyl; —C(O)—(CH$_2$)$_{0-1}$-2-thiophene-yl; —C(O)-2-furanyl; —C(O)-4-morpholinyl; —C(O)-pyridyl; —C(O)-1-pyrrolidinyl; —C(O)-phenyl optionally substituted with a chloro; —C(O)-1-piperazinyl optionally substituted with C$_{1-4}$alkyl; —(CH$_2$)$_{0-1}$NHC(O)—C$_{1-4}$alkyl; —NHC(O)-saturated monocyclic cycloalkyl; —NHS(O)(O)CH$_3$; —NHC(O)—CH$_2$OCH$_3$; —NHC(O)-pyridinyl; or —NHC(O)-2-thiophene-yl,
      where each phenyl in $R^d$ is unsubstituted or substituted with —CF$_3$, halo, or methoxy; or
   ii) one of the following moieties

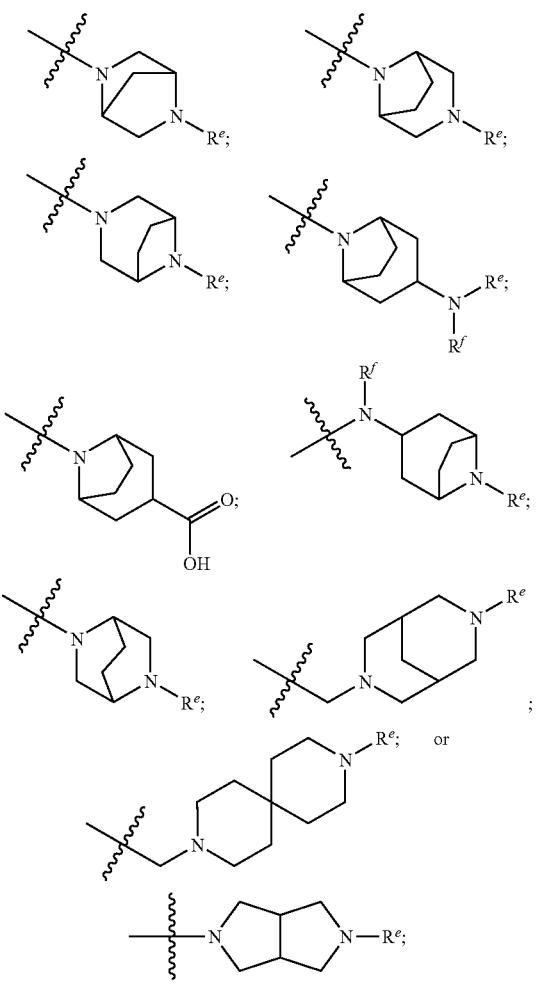

where $R^e$ is —C$_{1-4}$alkyl, —C(O)C$_{1-4}$alkyl, —SO$_2$CH$_3$, —C(O)CH$_2$NH$_2$, —C(O)NH$_2$;
$R^f$ is H or —CH$_3$; and
A is —CH$_2$—, —CH$_2$CH$_2$—, or —OCH$_2$CH$_2$—.

20. A method of making a compound of Formula (I), a pharmaceutically acceptable salt of a compound of Formula (I), a pharmaceutically acceptable prodrug of a compound of Formula (I), or a solvate of a compound of Formula (I)

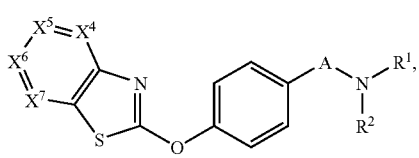
(I)

wherein $X^4$, $X^5$, $X^6$, and $X^7$ are defined as one of the following a) and b):

a) one of $X^4$, $X^5$, $X^6$ and $X^7$ is N and the others are $CR^a$;

where each $R^a$ is independently H, methyl, chloro, fluoro, or trifluoromethyl;

b) each of $X^4$ and $X^7$ is N and each of $X^5$ and $X^6$ is CH;

each of $R^1$ and $R^2$ is independently H, —(CH$_2$)$_{2-3}$OCH$_3$, —CH$_2$C(O)NH$_2$, —(CH$_2$)$_3$NH$_2$, —(CH$_2$)$_{1-2}$CO$_2$H, —CH$_2$CO$_2$CH$_2$CH$_3$, benzyl, 3-(2-oxo-pyrrolidin-1-yl)-propyl, 1-acetyl-azetidin-3ylmethyl, monocyclic cycloalkyl, 1-methyl-4-piperidinyl, or —C$_{1-4}$alkyl unsubstituted or substituted with phenyl, monocyclic cycloalkyl, OH, or NR$^b$R$^c$;

where $R^b$ and $R^c$ are each independently H, —C(O)CH$_3$, or C$_{1-4}$alkyl, or $R^b$ and $R^c$ taken together with the nitrogen to which they are attached form a saturated monocyclic heterocycloalkyl ring; or $R^1$ and $R^2$ taken together with the nitrogen to which they are attached form i) a saturated monocyclic heterocycloalkyl ring, optionally fused to a phenyl ring, and unsubstituted or substituted with one or two $R^d$ substituents;

where each $R^d$ substituent is independently C$_{1-4}$alkyl unsubstituted or substituted with —OH; —OH; =O; —(CH$_2$)$_{0-2}$N(CH$_3$)$_2$; —CF$_3$; halo; —CO$_2$C$_{1-4}$ alkyl; —(CH$_2$)$_{0-2}$CO$_2$H; —C(O)NH$_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —C(O)NR$^f$C$_{1-4}$ alkyl; —C(O)NHC(CH$_3$)$_2$CH$_2$OH; —O-pyridinyl, —O-pyrimidinyl; —S-phenyl; (4-methylphenyl)sulfanyl; —S-pyridinyl; —C(O)—C$_{1-4}$alkyl; —C(O)-saturated monocyclic cycloalkyl; —C(O)—(CH$_2$)$_{0-1}$-2-thiophene-yl; —C(O)-2-furanyl; —C(O)-4-morpholinyl; —C(O)-pyridyl; —C(O)-1-pyrrolidinyl; —C(O)-phenyl optionally substituted with a chloro; —C(O)-1-piperazinyl optionally substituted with C$_{1-4}$alkyl; —(CH$_2$)$_{0-1}$NHC(O)—C$_{1-4}$-alkyl; —NHC(O)-saturated monocyclic cycloalkyl; —NHS(O)(O)CH$_3$; —NHC(O)—CH$_2$OCH$_3$; —NHC(O)-pyridinyl; or —NHC(O)-2-thiophene-yl, where each phenyl in $R^d$ is unsubstituted or substituted with —CF$_3$, halo, or methoxy; or ii) one of the following moieties

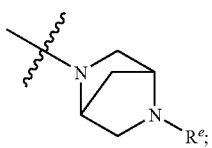

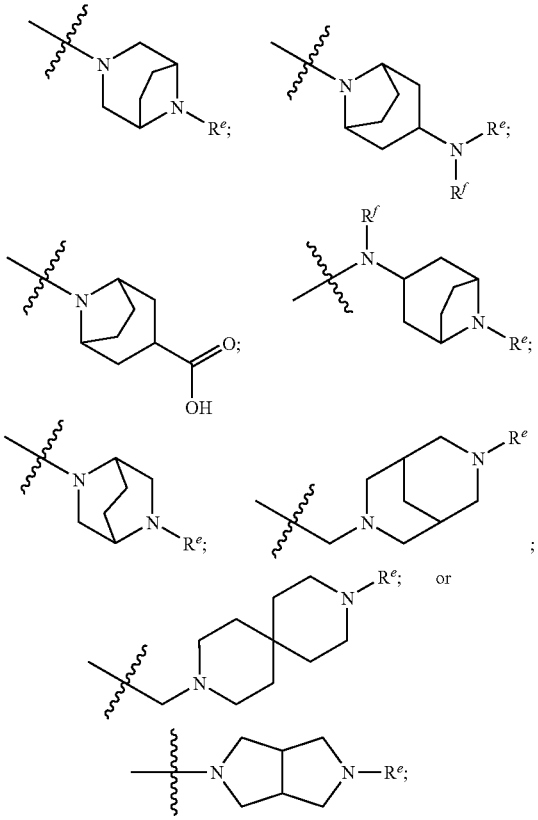

where $R^e$ is —C$_{1-4}$alkyl, —C(O)C$_{1-4}$alkyl, —SO$_2$CH$_3$, —C(O)CH$_2$NH$_2$, or —C(O)NH$_2$;

$R^f$ is H or —CH$_3$; and

A is —CH$_2$—, —CH$_2$CH$_2$—, or —OCH$_2$CH$_2$—, comprising reacting compound D4

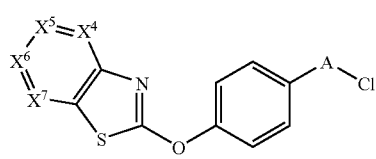

D4 with an amine HNR$^1$R$^2$.

21. A method as in claim 20, wherein each of said $R^1$ and $R^2$ is independently H, a monocyclic cycloalkyl, or a —C$_{1-4}$alkyl unsubstituted or substituted with phenyl, monocyclic cycloalkyl, —OH, or —NR$^b$R$^c$;

where $R^b$ and $R^c$ are each independently H or —C$_{1-4}$alkyl, or $R^b$ and $R^c$ taken together with the nitrogen to which they are attached form a saturated monocyclic heterocycloalkyl ring; or $R^1$ and $R^2$ taken together with the nitrogen to which they are attached form i) a saturated monocyclic heterocycloalkyl ring, optionally fused to a phenyl ring, and unsubstituted or substituted with one or two $R^d$ substituents;

where each $R^d$ substituent is independently —C$_{1-4}$ alkyl unsubstituted or substituted with —OH; —CF$_3$; halo; —CO$_2$C$_{1-4}$alkyl; —CO$_2$H; —CONH$_2$; phenyl; benzyl; pyridyl; pyrimidinyl;

phenoxy; —O-pyridinyl, —O-pyrimidinyl; —S-phenyl; or pyrrolidonyl;

where each phenyl in $R^d$ is unsubstituted or substituted with —$CF_3$, chloro, or methoxy; or ii) one of the following fused or bridged bicyclic structures

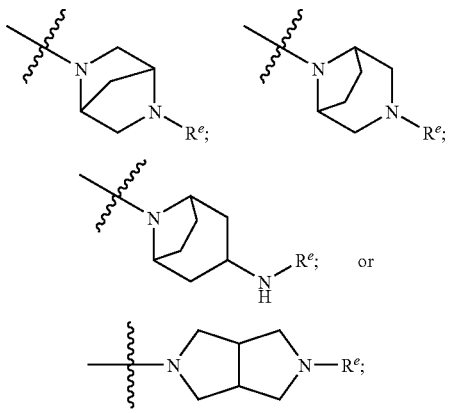

where $R^e$ is —$COC_{1-4}$alkyl or —$CONH_2$.

22. A method as in claim 20, further comprising chlorinating compound D3

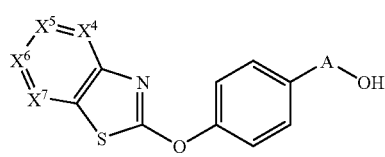

to form compound D4.

23. A method as in claim 22, further comprising reacting compound D1

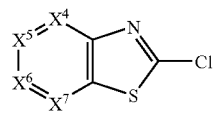

with compound D2

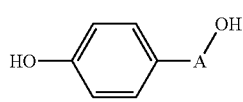

to form compound D3.

24. A method as in claim 21, wherein the amine $HNR^1R^2$ is N-[(3-endo)-8-azabicyclo[3.2.1]oct-3-yl]acetamide.

25. A method as in claim 24, further comprising a) reacting compound E4

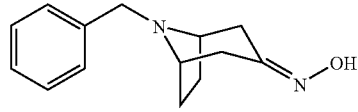

with hydrogen in the presence of acetic anhydride to form compound E5

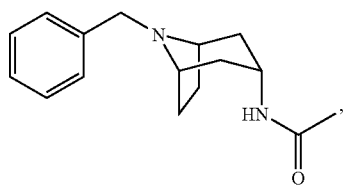

and b) reacting compound E5 to form N-[(3-endo)-8-azabicyclo[3.2.1]oct-3-yl]acetamide.

26. A method for synthesizing a compound of Formula ($I^x$),

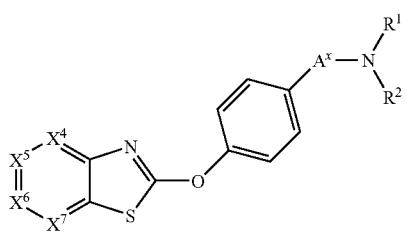

comprising reacting compound of formula BX

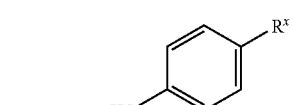

with $HNR^1R^2$ to form compound of formula F1,

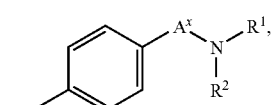

and reacting the compound of formula F1 with a compound of formula A3

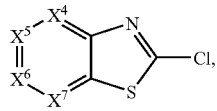

(A3)

to form a compound of formula I$^x$,
wherein
R$^x$ is one of —CHO and —CH$_2$CHO;
A$^x$ is one of —CH$_2$— and —CH$_2$CH$_2$—;
X$^4$, X$^5$, X$^6$, and X$^7$ are defined as one of the following a) and b)
  a) one of X$^4$, X$^5$, X$^6$ and X$^7$ is N and the others are CR$^a$;
    where each R$^a$ is independently H, methyl, chloro, fluoro, or trifluoromethyl;
  b) each of X$^4$ and X$^7$ is N and each of X$^5$ and X$^6$ is CH;
each of R$^1$ and R$^2$ is independently H, —(CH$_2$)$_{2-3}$OCH$_3$, —CH$_2$C(O)NH$_2$, —(CH$_2$)$_3$NH$_2$, —(CH$_2$)$_{1-2}$CO$_2$H, —CH$_2$CO$_2$CH$_2$CH$_3$, benzyl, 3-(2-oxo-pyrrolidin-1-yl)-propyl, 1-acetyl-azetidin-3ylmethyl, monocyclic cycloalkyl, 1-methyl-4-piperidinyl, or —C$_{1-4}$alkyl unsubstituted or substituted with phenyl, monocyclic cycloalkyl, OH, or NR$^b$R$^c$;
  where R$^b$ and R$^c$ are each independently H, —C(O)CH$_3$, or C$_{1-4}$alkyl, or R$^b$ and R$^c$ taken together with the nitrogen to which they are attached form a saturated monocyclic heterocycloalkyl ring; or
R$^1$ and R$^2$ taken together with the nitrogen to which they are attached form
  i) a saturated monocyclic heterocycloalkyl ring, optionally fused to a phenyl ring, and unsubstituted or substituted with one or two R$^d$ substituents;
    where each R$^d$ substituent is independently C$_{1-4}$alkyl unsubstituted or substituted with —OH; —OH; =O; —(CH$_2$)$_{0-2}$N(CH$_3$)$_2$; —CF$_3$; halo; —CO$_2$C$_{1-4}$ alkyl; —(CH$_2$)$_{0-2}$CO$_2$H; —C(O)NH$_2$; phenyl; benzyl; morpholin-4-yl; pyridyl; pyrimidinyl; 1-piperidyl; phenoxy; 2-oxo-pyrrolidin-1-yl; 4-hydroxy-2-oxo-pyrrolidin-1-yl; —C(O)NR$^f$C$_{1-4}$ alkyl; —C(O)NHC(CH$_3$)$_2$CH$_2$OH; —O-pyridinyl, —O-pyrimidinyl; —S-phenyl; (4-methylphenyl)sulfanyl; —S-pyridinyl; —C(O)—C$_{1-4}$alkyl; —C(O)-saturated monocyclic cycloalkyl; —C(O)—(CH$_2$)$_{0-1}$-2-thiophene-yl; —C(O)-2-furanyl; —C(O)-4-morpholinyl; —C(O)-pyridyl; —C(O)-1-pyrrolidinyl; —C(O)-phenyl optionally substituted with a chloro; —C(O)-1-piperazinyl optionally substituted with C$_{1-4}$alkyl; —(CH$_2$)$_{0-1}$NHC(O)—C$_{1-4}$alkyl; —NHC(O)-saturated monocyclic cycloalkyl; —NHS(O)(O)CH$_3$; —NHC(O)—CH$_2$OCH$_3$; —NHC(O)-pyridinyl; or —NHC(O)-2-thiophene-yl, where each phenyl in R$^d$ is unsubstituted or substituted with —CF$_3$, halo, or methoxy; or
ii) one of the following moieties

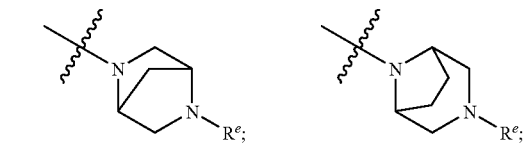

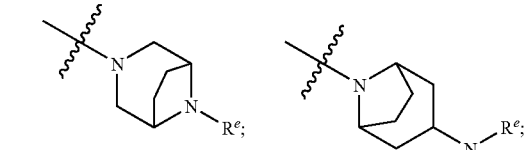

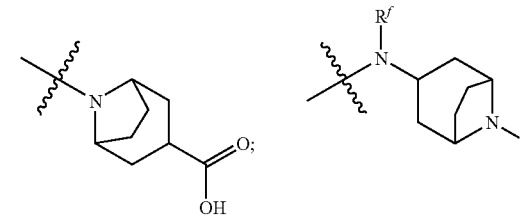

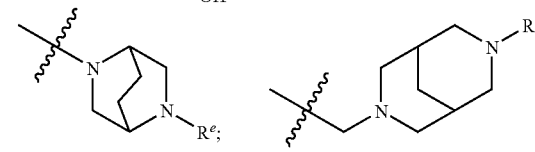

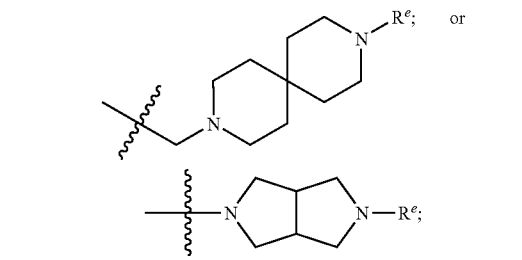

where R$^e$ is —C$_{1-4}$alkyl, C(O)C$_{1-4}$alkyl, —SO$_2$CH$_3$, —C(O)CH$_2$NH$_2$, or C(O)NH$_2$; and
R$^f$ is H or —CH$_3$.

27. A method as in claim 26, wherein said reacting compound of formula BX with HNR$^1$R$^2$ is made in the presence of a reducing agent.

28. A method as in claim 27, wherein said reducing agent is selected from the group consisting of NaB(OAc)$_3$H, NaCNBH$_3$, and mixtures thereof.

29. A method as in claim 28, wherein said reacting compound of formula BX with HNR$^1$R$^2$ is made in the presence of an acid catalyst.

30. A method as in claim 29, wherein said acid catalyst comprises acetic acid.

31. A method as in claim 26, wherein said amine HNR$^1$R$^2$ is in salt form.

32. A method as in claim 26, wherein said reacting compound of formula F1 with compound of formula A3 is made in the presence of a base.

33. A method as in claim 32, wherein said base is selected from the group consisting of K$_2$CO$_3$, Cs$_2$CO$_3$, Na$_2$CO$_3$, NaHCO$_3$, K$_3$PO$_4$, and mixtures thereof.

34. A chemical entity as in claim 16, wherein said pharmaceutically acceptable salt is one of succinate, hydrochloride, maleate, acetate, formate, fumarate, citrate, tartrate, sulfate, phosphate, malate, malonate and benzoate.

35. A chemical entity as in claim 34, wherein said pharmaceutically acceptable salt is one of succinate, and hydrochloride.

36. A pharmaceutical composition as in claim 18, wherein said pharmaceutically acceptable salts are succinate, hydrochloride, formate, maleate, acetate, fumarate, citrate, tartrate, sulfate, phosphate, malate, malonate and benzoate.

37. A pharmaceutical composition as in claim 36, wherein said pharmaceutically acceptable salts are succinate and hydrochloride.

* * * * *

UNITED STATES PATENT AND TRADEMARK OFFICE
CERTIFICATE OF CORRECTION

PATENT NO.        : 7,939,527 B2
APPLICATION NO.   : 12/421406
DATED             : May 10, 2011
INVENTOR(S)       : Genesis M. Bacani et al.

It is certified that error appears in the above-identified patent and that said Letters Patent is hereby corrected as shown below:

In column 112, line 47 the recitation "yl}-acetamide" should be changed to: --3-yl}acetamide--

In column 113, line 8 the recitation "2-yloxy)benzyl]-8-azabicyclo[3.2.1]oct-yl}urea" should be changed to: --2-yloxy)benzyl]-8-azabicyclo[3.2.1]oct-3-yl}urea--

In column 115, line 13 the recitation "yl}-acetamide" should be changed to: --3-yl}acetamide--

In column 136, line 54 the recitation "cyclo[3.2.1]oct-3-yl}qlycinamide Hydrochloride" should be changed to: --cyclo[3.2.1]oct-3-yl}glycinamide Hydrochloride--

In column 125, line 54 the recitation "yl}-acetamide" should be changed to: --3-yl}acetamide--

In column 114, line 57 the recitation "yl}acetamide" should be changed to: --3-yl}acetamide--

In column 117, line 46 the recitation "yl}-acetamide" should be changed to: --3-yl}acetamide--

Signed and Sealed this
Third Day of July, 2012

David J. Kappos
*Director of the United States Patent and Trademark Office*

UNITED STATES PATENT AND TRADEMARK OFFICE
CERTIFICATE OF CORRECTION

PATENT NO. : 7,939,527 B2
APPLICATION NO. : 12/421406
DATED : May 10, 2011
INVENTOR(S) : Genesis M. Bacani et al.

It is certified that error appears in the above-identified patent and that said Letters Patent is hereby corrected as shown below:

In the Claims

In column 193, line 23:

"–(CO)–(CH$_2$)$_{1-2}$-2-thiophenyl" should be changed to -- –(CO)–(CH$_2$)$_{0-1}$-2-thiophenyl --

Signed and Sealed this
Twelfth Day of November, 2013

Teresa Stanek Rea
*Deputy Director of the United States Patent and Trademark Office*